US008552022B2

(12) United States Patent
Wood et al.

(10) Patent No.: US 8,552,022 B2
(45) Date of Patent: Oct. 8, 2013

(54) SUBSTITUTED CYCLOPROPYL COMPOUNDS, COMPOSITIONS CONTAINING SUCH COMPOUNDS AND METHODS OF TREATMENT

(75) Inventors: Harold B. Wood, Westfield, NJ (US); Alan D. Adams, Holland, NY (US); Jason W. Szewczyk, New York, NY (US); Yong Zhang, West Windsor, NJ (US); Meng Yang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 72 days.

(21) Appl. No.: 13/390,147

(22) PCT Filed: Aug. 3, 2010

(86) PCT No.: PCT/US2010/044181
§ 371 (c)(1),
(2), (4) Date: Feb. 13, 2012

(87) PCT Pub. No.: WO2011/019538
PCT Pub. Date: Feb. 17, 2011

(65) Prior Publication Data
US 2012/0142706 A1 Jun. 7, 2012

Related U.S. Application Data

(60) Provisional application No. 61/233,690, filed on Aug. 13, 2009.

(51) Int. Cl.
*A61K 31/505* (2006.01)
*C07D 239/02* (2006.01)
*C07D 403/04* (2006.01)

(52) U.S. Cl.
USPC ............ 514/275; 544/330; 544/295; 544/331

(58) Field of Classification Search
None
See application file for complete search history.

(56) References Cited

U.S. PATENT DOCUMENTS 7,470,699 B2 12/2008 Jones et al.

FOREIGN PATENT DOCUMENTS

| WO | 2005/007647 | 1/2005 |
|---|---|---|
| WO | 2005/121121 | 12/2005 |
| WO | 2006/067531 | 6/2006 |
| WO | 2008/081205 | 7/2008 |
| WO | 2009/034388 | 3/2009 |
| WO | 2009/038974 | 3/2009 |
| WO | 2009/129036 | 10/2009 |
| WO | 2012/138845 | 10/2012 |
| WO | 2012/173917 | 12/2012 |

OTHER PUBLICATIONS

Costanzi et al., "Seven transmembrane-snanning receptors for free fatty acids . . . ", J. Biol. Chem. (2008), vol. 283, p. 16269-16273.
Int'l Search Report of PCT/US2010/044181, mailed Sep. 20, 2010.
Int'l Preliminary Report on Patentability of PCT/US2010/044181, dated Feb. 14, 2012.
Suppl. EP Search Report of EP 10808529, mailed Dec. 20, 2012.
Stevens, et al. "Synthesis of two novel regioisomeric oxospiropyrazole . . . ", Tetrahedron Letters (2011), vol. 52, pp. 1949-1951.
Kalgutkar et al., "Intrinsic electrophilicity of a 4-substituted-5-cyano- . . . ", Chem. Res. Toxicol. (2011), vol. 24, 269-278.
Zhu et al., "The first pharmacophore model for potent G protein-coupled . . . ", Eur. J. of Med. Chemistry (2011), vol. 46, pp. 2901-2907.
McClure et al., "Activation of the G-protein-coupled receptor 119 . . . ", J. Med. Chem. (2011), vol. 54, pp. 1948-1952.
Szewczyk et al., "Design of potent and selective GPR119 agonists . . . ", Bioorg. & Med. Chem. Letters (2011), vol. 21, pp. 2665-2669.
Xia et al., "Discovery of a nortropanol derivative as a potent and orally active GPR119 . . . ", Bioorg. & Med. Chem. Letters (2011), vol. 21, pp. 3290-3296.
Semple et al., "Discovery of fused bicyclic agonists of the orphan G-protein . . . ", Bioorg. & Med. Chem. Letters (2011), vol. 21, pp. 3134-3141.
Brocklehurst et al., "Discovery, optimisation and in vivo evaluation . . . ", Bioorg. & Med. Chem. Letters (2011), vol. 21, pp. 7310-7316.
Mascitti et al., "Design and evaluation of a 2-(2,3,6-trifluorophenyl)acetamide . . . ", Bioorg. & Med. Chem. Letters (2011), vol. 21, pp. 1306-1309. Wu et al., "2,5-Disubstituted pyridines as potent GPR119 agonists", Bioorg. & Med. Chem. Letters (2010), vol. 20, 2577-2581.
Semple et al., "Discovery of a second generation agonist of the orphan G-protein . . . ", Bioorg. & Med. Chem. Letters (2012), vol. 22, pp. 1750-1755.

*Primary Examiner* — Noble Jarrell
*Assistant Examiner* — Valerie Rodriguez-Garcia
(74) *Attorney, Agent, or Firm* — Anna L. Cocuzzo; Catherine D. Fitch

(57) ABSTRACT

Substituted cyclopropyl compounds of the formula I: are disclosed as useful for treating or preventing type 2 diabetes and similar conditions. Pharmaceutically acceptable salts are included as well. The compounds are useful as agonists of the g-protein coupled receptor GPR-119.

20 Claims, No Drawings

SUBSTITUTED CYCLOPROPYL COMPOUNDS, COMPOSITIONS CONTAINING SUCH COMPOUNDS AND METHODS OF TREATMENT

BACKGROUND OF THE INVENTION

The present invention relates to G-protein coupled receptor agonists. In particular, the present invention is directed to agonists of GPR 119 that are useful for the treatment of diabetes, especially type 2 diabetes, obesity, the metabolic syndrome and related diseases and conditions.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Obesity is characterized by excessive adiposity relative to body mass. Clinically, obesity is defined by the body mass index [BMI=weight (kg)/height (m)$^2$], corresponding to BMI values ≥30. Obesity and being overweight increases the risk of developing conditions such as high blood pressure, type 2 diabetes, heart disease, stroke, osteoarthritis, sleep apnea, gallbladder disease and cancer of the breast, prostate and colon. Higher body weights are also associated with increases in all-cause mortality.

There is renewed focus on pancreatic islet-based insulin secretion that is controlled by glucose-dependent insulin secretion. In this regard, several orphan G-protein coupled receptors (GPCR's) have recently been identified that are preferentially expressed in the β-cell and are implicated in glucose dependent insulin secretion (GDIS). GPR119 is a cell-surface Gs-coupled GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. GPR119 agonists therefore have the potential to function as anti-hyperglycemic agents that produce weight loss.

WO2005/007647 published on 27 Jan. 2005, WO2005/121121 published on 22 Dec. 2005 and WO2006/067531 published on 29 Jun. 2006 relate to GPR 119 agonist compounds.

SUMMARY OF THE INVENTION

A compound represented by the any one of the following formulas:

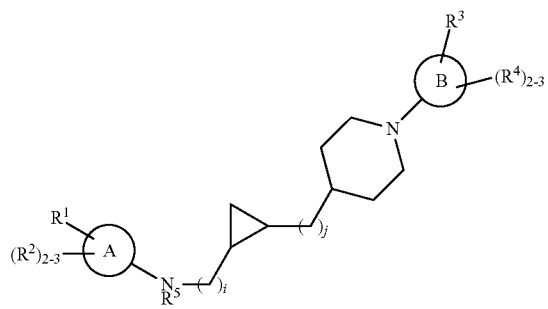

I or a pharmaceutically acceptable salt thereof, wherein:

ring A represents an aryl or heteroaryl group containing 1 nitrogen atom, and optionally 1-3 additional nitrogen atoms and optionally 0-1 oxygen or sulfur atoms;

ring B represents a heteroaryl ring containing 1-2 nitrogen atoms;

i and j independently represent integers selected from 0, 1 and 2, such that i plus j is 1 or 2;

$R^1$ represents a member selected from the group consisting of H, oxo, OH, halo, $C_{1-6}$alkyl, $C_{1-6}$alkylhalo, $C_{1-6}$alkoxy, $C_{1-6}$alkoxyhalo, $C(O)C_{1-6}$alkyl, $C(O)$—$C_{1-6}$alkylhalo, $C(O)$—NH—$C_{1-6}$alkyl, NH—$C(O)$—$C_{1-6}$alkyl optionally substituted with $C_{1-6}$alkyl, $C_{1-6}$alkyl-$C(O)$—NH—$C_{1-6}$alkyl optionally substituted with $C_{1-6}$alkyl, $S(O)$—$C_{1-6}$alkyl, $SO_2$—$C_{1-6}$alkyl, $SC_{1-6}$alkyl, $SO_2$, $NH_2$, $SO_2$—NH—$C_{1-6}$alkyl, $SO_2N$—$(C_{1-6}$alkyl$)_2$, CN, and heteroaryl ring or heteroalkyl ring optionally substituted with 1-3 $C_{1-6}$alkyl, oxo, halo or $C_{1-6}$alkylhalo groups;

each $R^2$, $R^3$ and $R^4$ is independently selected from H, oxo, halo, $C_{1-6}$alkyl and $C_{1-6}$alkylhalo, wherein the total number of oxo groups does not exceed two; and $R^5$ is selected from H, $C_{1-6}$alkylhalo and $C_{1-6}$alkyl; and

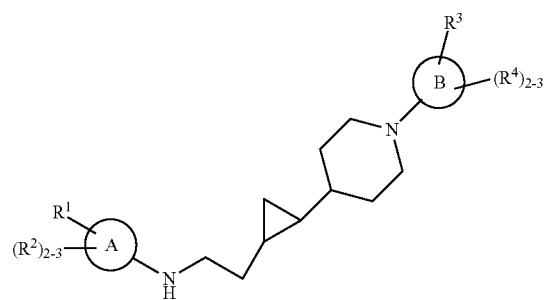

II or a pharmaceutically acceptable salt thereof, wherein:

ring A represents an aryl or heteroaryl group containing 1 nitrogen atom, and optionally 1-3 additional nitrogen atoms and optionally 0-1 oxygen or sulfur atoms;

ring B represents a heteroaryl ring containing 1-2 nitrogen atoms;

$R^1$ represents a member selected from the group consisting of H, oxo, OH, halo, $C_{1-6}$alkyl, $C_{1-6}$alkylhalo, $C_{1-6}$alkoxy, $C_{1-6}$alkoxyhalo, $C(O)C_{1-6}$alkyl, $C(O)$—$C_{1-6}$alkylhalo, $C(O)$—NH—$C(O)$—$C_{1-6}$alkyl optionally substituted with $C_{1-6}$ alkyl, $C_{1-6}$alkyl-$C(O)$—NH—$C_{1-6}$alkyl optionally substituted with $C_{1-6}$ alkyl, $S(O)$—$C_{1-6}$alkyl, $SC_{1-6}$alkyl, $SO_2$—$NH_2$, $SO_2$—NH—$C_{1-6}$alkyl, $SO_2N$—$(C_{1-6}$alkyl$)_2$, CN, and heteroaryl ring or heteroalkyl ring optionally substituted with 1-3 $C_{1-6}$alkyl, oxo, halo or $C_{1-6}$alkylhalo groups;

and each $R^2$, $R^3$ and $R^4$ is independently selected from H, oxo, halo, $C_{1-6}$ alkyl, and $C_{1-6}$alkylhalo, wherein the total number of oxo groups does not exceed two.

DETAILED DESCRIPTION OF THE INVENTION

The invention is described herein in detail using the terms defined below unless otherwise specified.

Definitions

"Alkyl", as well as other groups having the prefix "alk", such as alkoxy, and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkoxy" refers to an alkyl group linked to oxygen.

"Alkoxyhalo" and "haloOalkyl" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Alkylhalo" include mono-substituted as well as multiple halo substituted alkyl groups, up to perhalo substituted alkyl. For example, trifluoromethyl is included.

"Aryl" (Ar) unless otherwise specified, means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl. "Aryl" also includes an aryl group fused to nonaromatic rings in which the point of attachment is on the aromatic portion.

"Heteroalyl" (HAR) unless otherwise specified, means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofuran, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 3-15 atoms are included, forming 1-3 rings.

"Halogen" (Halo) includes fluorine, chlorine, bromine and iodine.

"Oxo" means the functional group "=O", such as, for example, (1) "C=(O)", that is a carbonyl group; (2) "S=(O)", that is, a sulfoxide group; and (3) "N=(O)", that is, an N-oxide group, such as pyridyl-N-oxide.

Compounds

One aspect of the invention that is of interest relates to a compound represented by the formula:

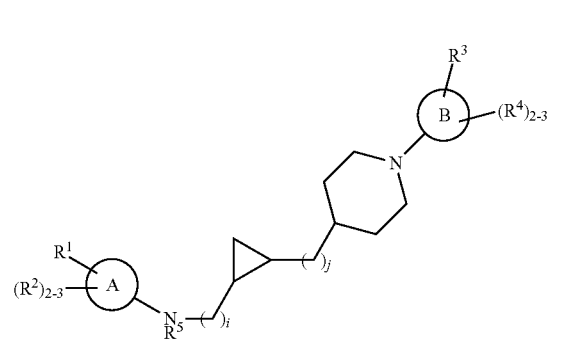

or a pharmaceutically acceptable salt thereof.

An aspect of the invention that is of interest relates to compounds of formula I, or a pharmaceutically acceptable salt thereof, wherein ring A represents an aryl or heteroaryl group containing 1 nitrogen atom, and optionally 1-3 additional nitrogen atoms and optionally 0-1 oxygen or sulfur atoms. In certain embodiments, ring A represents an aryl or heteroaryl group containing 1 nitrogen atom, and optionally 1-3 additional nitrogen atoms. In certain embodiments A is a monocyclic aryl or heteroaryl ring. In other embodiments, A is a bicyclic aryl or heteroaryl ring. For example, ring A is selected from the group consisting of aryl which is phenyl, and heteroaryl selected from the group consisting of pyrrole, pyrazine, pyrazole, pyridine, pyrimidine, imidazole, triazole, tetrazole, triazine, indoline, pyridazine, indazole, isoindole, indolizine, cinnoline, phthalazine, quinazoline, naphthyridine, quinoxaline, purine, benzimidazole, quinolone, indole, oxindole, oxo-dihydroquinoline, and isoquinoline. In certain embodiments, ring A is selected from the group consisting of phenyl, indole, oxindole and pyrimidine. In one embodiment ring A is a pyrimidine ring. In another embodiment, ring A is a pyridine ring. In another embodiment ring A is an oxindole ring.

Additionally, in certain embodiments, ring A is selected from the group consisting of:

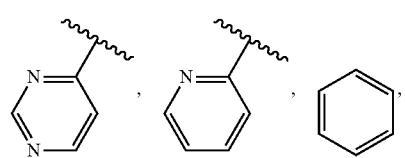

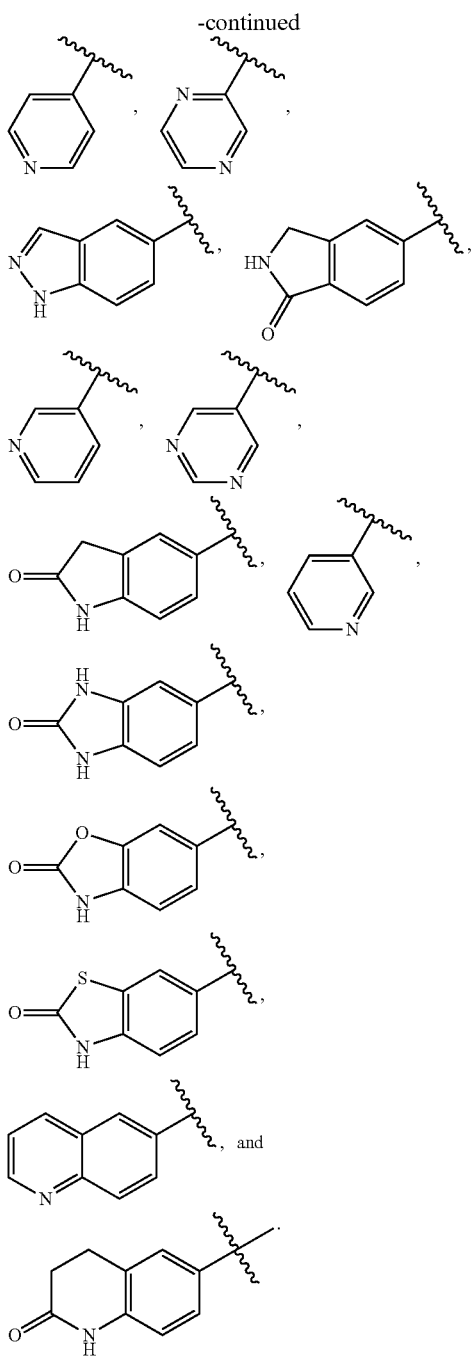

Another aspect of the invention that is of interest relates to compounds of formula I, or a pharmaceutically acceptable salt thereof, wherein ring B represents a heteroaryl ring containing 1-2 nitrogen atoms. For example, ring B is selected from the group consisting of pyridine, pyrimidine, thiazole, oxadiazole and pyrazine. In certain embodiments, ring B represents pyrimidine.

Another aspect of the invention that is of interest relates to compounds of formula I, or a pharmaceutically acceptable salt thereof, wherein i and j independently represent integers selected from 0, 1 and 2, such that i plus j is 1 or 2. For example, i and j can represent 0, 1 or 2, such that the sum of i and j is 2. In certain embodiments, i and j are both 1 or i is 2 and j is 0.

Yet another aspect of the invention that is of interest relates to compounds of formula I, or a pharmaceutically acceptable salt thereof, wherein $R^1$ represents a member selected from the group consisting of H, oxo, halo, $C_{1-6}$alkyl, $C_{1-6}$alkylhalo, $C(O)C_{1-6}$alkyl, $C(O)—C_{1-6}$alkylhalo, $C_{1-6}$alkoxy, $C_{1-6}$alkoxyhalo, $C(O)—NH—C_{1-6}$alkyl, $NH—C(O)—C_{1-6}$alkyl optionally substituted with $C_{1-6}$alkyl, $C_{1-6}$alkyl-$C(O)—NH—C_{1-6}$alkyl optionally substituted with $C_{1-6}$alkyl, $S(O)—C_{1-6}$alkyl, $SC_{1-6}$alkyl, $SO_2—C_{1-6}$alkyl, $SO_2—NH_2$, $SO_2NH—C_{1-6}$alkyl, $SO_2N—(C_{1-6}$alkyl$)_2$, CN, and heteroaryl ring or heteroalkyl ring optionally substituted with 1-3 $C_{1-6}$alkyl, oxo, halo or $C_{1-6}$alkylhalo groups. For example, $R^1$ is selected from the group consisting of: H, oxo, halo which is F, Cl or Br, $C_{1-3}$alkyl, $NH—C(O)—C_{1-4}$alkyl, $S(O)—C_{1-3}$alkyl, $SO_2—C_{1-3}$alkyl, $SO_2NH—C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with oxo or $C_{1-3}$alkyl group. In certain embodiments, $R^1$ is selected from the group consisting of: oxo, halo which is F or Cl, $CF_3$, $NH—C(O)$-cyclopropyl, $S(O)CH_3$, $SO_2CH_3$, $SO_2—NH$-cyclopropyl, CN and heteroaryl ring which is selected from the group consisting of: oxadiazole, triazole, pyrazole and tetrazole, said group being optionally substituted with methyl, oxo or cyclopropyl.

Yet another aspect of the invention that is of interest relates to compounds of formula I, or a pharmaceutically acceptable salt thereof, wherein each $R^2$, $R^3$ and $R^4$ is independently selected from H, oxo, halo, $C_{1-6}$alkyl and $C_{1-6}$alkylhalo, wherein the total number of oxo groups does not exceed two. Unless otherwise indicated "total number of oxo groups does not exceed two" means taken together as a group $(R^2)_{2-3}$, $R^3$ and $(R^4)_{2-3}$ includes no more that two oxo groups. In certain embodiments, each $R^2$, $R^3$ and $R^4$ is independently selected from H, halo, $C_{1-6}$alkyl and $C_{1-6}$alkylhalo.

Yet another aspect of the invention that is of interest relates to compounds of formula I, or a pharmaceutically acceptable salt thereof, wherein $R^5$ is selected from H, $C_{1-6}$alkylhalo and $C_{1-6}$alkyl.

One aspect of the invention described herein includes a compound of formula I, or a pharmaceutically acceptable salt thereof, wherein:

ring A is selected from the group consisting of aryl which is phenyl, and heteroaryl selected from the group consisting of indole, pyridine, pyrimidine and pyrazine;

ring B is selected from the group consisting of pyridine, pyrimidine and pyrazine;

i is 2 and j is 0;

$R^1$ is selected from the group consisting of: H, oxo, halo which is F or $C_1$, $C_{1-3}$alkylhalo, $C(O)—NH—C_{2-4}$alkyl, $S(O)—C_{1-3}$alkyl, $SO_2—C_{1-3}$alkyl, $SO_2—NH—C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with one $C_{1-3}$alkyl group;

$R^2$ represents H, halo selected from F and Cl, $CH_3$ and $CF_3$;

$R^3$ and $R^4$ represent H, halo selected from F and Cl, $CH_3$ and $CF_3$;

and $R^5$ represents H.

The compounds described herein can also be represented by the formula:

II

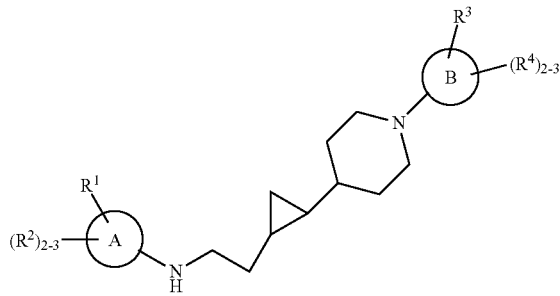

or a pharmaceutically acceptable salt thereof.

An aspect of the invention that is of interest relates to compounds of formula II, or a pharmaceutically acceptable salt thereof, wherein ring A represents an aryl or heteroaryl group containing 1 nitrogen atom, and optionally 1-3 additional nitrogen atoms and optionally 0-1 oxygen or sulfur atoms. In certain embodiments, ring A represents an aryl or heteroaryl group containing 1 nitrogen atom, and optionally 1-3 additional nitrogen atoms. In certain embodiments A is a monocyclic aryl or heteroaryl ring. In other embodiments, A is a bicyclic heteroaryl ring. For example, ring A is selected from the group consisting of aryl which is phenyl, and heteroaryl selected from the group consisting of pyrrole, pyrazine, pyrazole, pyridine, pyrimidine, imidazole, triazole, tetrazole, triazine, indoline, pyridazine, indazole, isoindole, indolizine, cinnoline, phthalazine, quinazoline, naphthyridine, quinoxaline, purine, benzimidazole, quinolone, indole, oxindole and isoquinoline. In certain embodiments, ring A is selected from the group consisting of phenyl, indole, oxodihydroquinoline, oxindole and pyrimidine. In one embodiment ring A is a pyrimidine ring. In another embodiment, ring A is a pyridine ring. In another embodiment ring A is an oxindole ring.

Additionally, in certain embodiments, ring A is selected from the group consisting of:

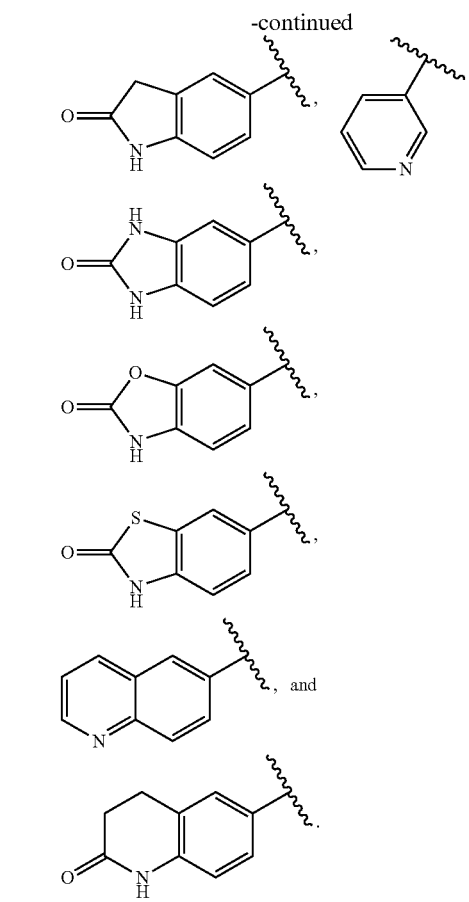

Another aspect of the invention that is of interest relates to compounds of formula II, or a pharmaceutically acceptable salt thereof, wherein ring B represents a heteroaryl ring containing 1-2 nitrogen atoms. For example, ring B is selected from the group consisting of pyridine, pyrimidine, triazole, oxadiazole and pyrazine. In certain embodiments, ring B represents pyrimidine.

Yet another aspect of the invention that is of interest relates to compounds of formula II, or a pharmaceutically acceptable salt thereof, wherein $R^1$ represents a member selected from the group consisting of H, oxo, halo, $C_{1-6}$alkyl, $C_{1-6}$alkylhalo, $C(O)C_{1-6}$alkyl, $C(O)—C_{1-6}$alkylhalo, $C_{1-6}$alkoxy, $C_{1-6}$alkoxyhalo, $C(O)—NH—C_{1-6}$alkyl, $NH—C(O)—C_{1-6}$alkyl optionally substituted with $C_{1-6}$ alkyl, $C_{1-6}$alkyl-C(O)—NH—C_{1-6}$alkyl optionally substituted with $C_{1-6}$ alkyl, $S(O)—C_{1-6}$alkyl, $SC_{1-6}$alkyl, $SO_2—C_{1-6}$alkyl, $SO_2—NH_2$, $SO_2N—(C_{1-6}$alkyl$)_2$, CN, and heteroaryl ring or heteroalkyl ring optionally substituted with 1-3 $C_{1-6}$alkyl, oxo, halo or $C_{1-6}$-alkylhalo groups. For example, $R^1$ is selected from the group consisting of: H, oxo, halo which is F, Cl or Br, $C_{1-3}$alkyl, $NH—C(O)—C_{1-4}$alkyl, $S(O)—C_{1-3}$alkyl, $SO_2—C_{1-3}$alkyl, $SO_2—NH—C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with oxo or $C_{1-3}$alkyl group. In certain embodiments, $R^1$ is selected from the group consisting of oxo, halo which is F or $C_1$, $CF_3$, $NH—C(O)$-cyclopropyl, $S(O)CH_3$, $SO_2CH_3$, $SO_2—NH$-cyclopropyl, CN and heteroaryl ring which is selected from the group consisting of oxadiazole, triazole, pyrazole and tetrazole, said group being optionally substituted with methyl, oxo or cyclopropyl.

Yet another aspect of the invention that is of interest relates to compounds of formula II, or a pharmaceutically acceptable salt thereof, wherein each $R^2$, $R^3$ and $R^4$ is independently selected from H, oxo, halo, $C_{1-6}$alkyl, and $C_{1-6}$ alkylhalo, wherein the total number of oxo groups does not exceed two. In certain embodiments, each $R^2$, $R^3$ and $R^4$ is independently selected from H, halo, $C_{1-6}$ alkyl and $C_{1-6}$ alkylhalo.

In certain embodiments of formula II, $R^3$ and $R^4$ are selected from the group consisting of: H, halo selected from F and Cl, oxo, $CH_3$ and $CF_3$.

In certain embodiments of formulas I and II, $R^3$ and $R^4$ are selected from the group consisting of: H, halo selected from F and Cl, $CH_3$ and $CF_3$.

One aspect of the invention described herein includes a compound of formula II, or a pharmaceutically acceptable salt thereof, wherein:

ring A is selected from the group consisting of aryl which is phenyl, and heteroaryl selected from the group consisting of indole, pyridine, pyrimidine and pyrazine;

ring B is selected from the group consisting of pyridine, pyrimidine and pyrazine;

$R^1$ is selected from the group consisting of: H, oxo, halo which is F or Cl, $C_{1-3}$alkylhalo, NH—C(O)—$C_{2-4}$alkyl, S(O)—$C_{1-3}$alkyl, $SO_2$—NH—$C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with one $C_{1-3}$alkyl group;

$R^2$ represents H, halo selected from F and Cl, $CH_3$ and $CF_3$; and $R^3$ and $R^4$ represent H, halo selected from F and Cl, $CH_3$ and $CF_3$.

The compounds described herein can also be represented by the formula:

III

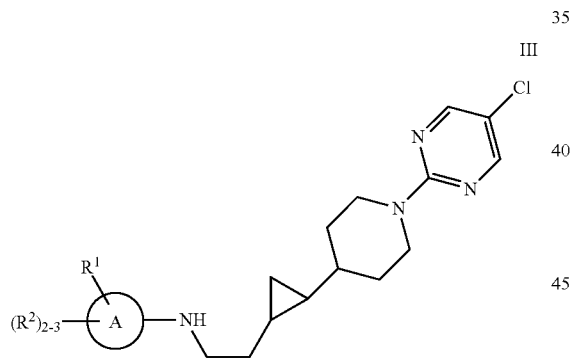

or a pharmaceutically acceptable salt thereof.

An aspect of the invention that is of interest relates to compounds of formula III, or a pharmaceutically acceptable salt thereof, wherein ring A represents an aryl or heteroaryl group containing 1 nitrogen atom, and optionally 1-3 additional nitrogen atoms and optionally 0-1 oxygen or sulfur atoms. In certain embodiments, ring A represents an aryl or heteroaryl group containing 1 nitrogen atom, and optionally 1-3 additional nitrogen atoms. In certain embodiments A is a monocyclic aryl or heteroaryl ring. In other embodiments, A is a bicyclic aryl or heteroaryl ring. For example, ring A is selected from the group consisting of aryl which is phenyl, and heteroaryl selected from the group consisting of pyrrole, pyrazine, pyrazole, pyridine, pyrimidine, imidazole, triazole, tetrazole, triazine, indoline, pyridazine, indazole, isoindole, indolizine, cinnoline, phthalazine, quinazoline, naphthyridine, quinoxaline, purine, benzimidazole, quinolone, indole, oxindole and isoquinoline. In certain embodiments, ring A is selected from the group consisting of phenyl, indole, oxindole, oxo-dihydroquinoline, and pyrimidine. In one embodiment ring A is a pyrimidine ring. In another embodiment, ring A is a pyridine ring. In another embodiment ring A is an oxindole ring.

Additionally, in certain embodiments, ring A is selected from the group consisting of:

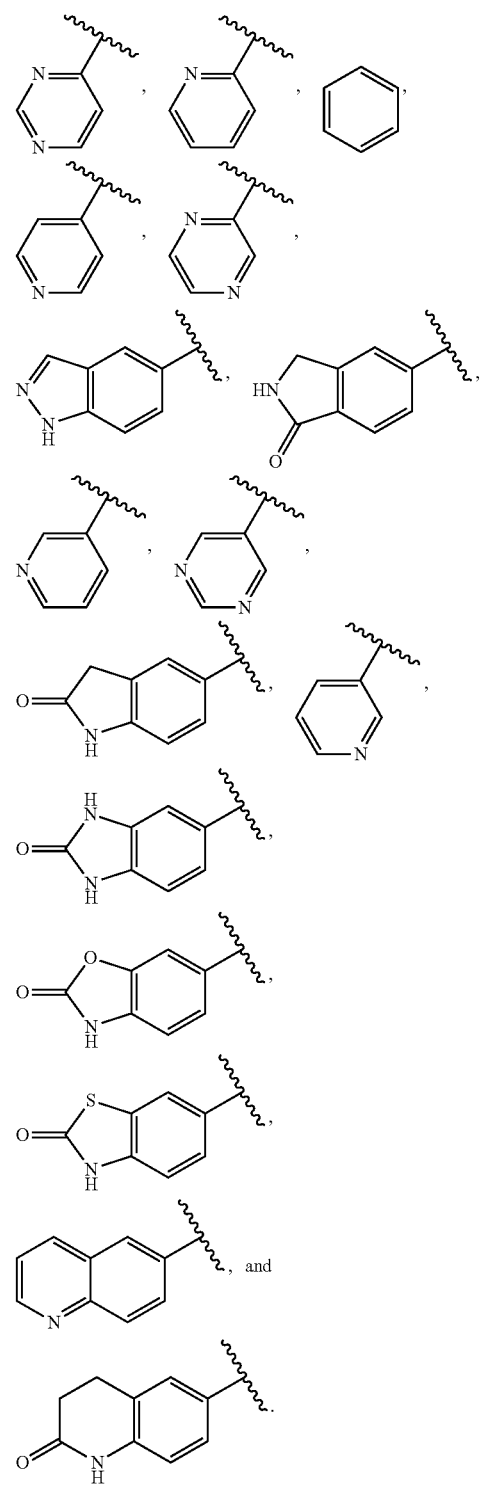

Yet another aspect of the invention that is of interest relates to compounds of formula III, or a pharmaceutically acceptable salt thereof, wherein $R^1$ represents a member selected from the group consisting of H, oxo, halo, $C_{1-6}$alkyl, $C_{1-6}$alkylhalo, $C(O)C_{1-6}$alkyl, $C(O)$—$C_{1-6}$alkylhalo, $C_{1-6}$alkoxy, $C_{1-6}$alkoxyhalo, $C(O)$—NH—$C_{1-6}$alkyl, NH—C(O)—$C_{1-6}$alkyl optionally substituted with $C_{1-6}$alkyl, $C_{1-6}$alkyl-C(O)—NH—$C_{1-6}$alkyl optionally substituted with $C_{1-6}$alkyl, $S(O)$—$C_{1-6}$alkyl, $SC_{1-6}$alkyl, $SO_2$—$C_{1-6}$alkyl, $SO_2$—$NH_2$, $SO_2N$—$(C_{1-6}alkyl)_2$, CN, and heteroaryl ring or heteroalkyl ring optionally substituted with 1-3 $C_{1-6}$alkyl, oxo, halo or $C_{1-6}$alkylhalo groups. For example, $R^1$ is selected from the group consisting of: H, oxo, halo which is F, Cl or Br, $C_{1-3}$alkyl, NH—C(O)—$C_{1-4}$allyl, $S(O)$—$C_{1-3}$alkyl, $SO_2$—$C_{1-3}$alkyl, $SO_2$—NH—$C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with oxo or $C_{1-3}$alkyl group. In certain embodiments, $R^1$ is selected from the group consisting of: oxo, halo which is F or $C_1$, $CF_3$, NH—C(O)-cyclopropyl, $S(O)CH_3$, $SO_2CH_3$, $SO_2$—NH-cyclopropyl, CN and heteroaryl ring which is selected from the group consisting of: oxadiazole, triazole, pyrazole and tetrazole, said group being optionally substituted with methyl, oxo or cyclopropyl.

Yet another aspect of the invention that is of interest relates to compounds of formula III, or a pharmaceutically acceptable salt thereof, wherein $R^2$ is selected from H, halo, $C_{1-6}$ alkyl and $C_{1-6}$alkylhalo.

In certain embodiments of formulas I-III, ring A represents a pyridine or pyrimidine ring and $R^1$ represents CN, $CF_3$, $SO_2$—$C_{1-3}$alkyl, NH—C(O)—$C_{1-6}$alkyl, or a five membered heteroaryl ring selected from the group consisting of oxadiazole, triazole and tetrazole, said ring being optionally substituted with methyl or cyclopropyl.

One aspect of the invention described herein includes a compound of formula III, or a pharmaceutically acceptable salt thereof, wherein:

ring A is selected from the group consisting of aryl which is phenyl, and heteroaryl selected from the group consisting of indole, pyridine, pyrimidine and pyrazine;

$R^1$ is selected from the group consisting of: H, oxo, halo which is F or $C_1$, $C_{1-3}$alkylhalo, NH—C(O)—$C_{1-4}$alkyl, $S(O)$—$C_{1-3}$alkyl, $SO_2$—$C_{1-3}$alkyl, $SO_2$—NH—$C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with one $C_{1-3}$alkyl group;

$R^2$ represents H, halo selected from F and Cl, $CH_3$ and $CF_3$; as well as the pharmaceutically acceptable salts thereof.

In certain embodiments, the compounds described herein can be represented by the formula:

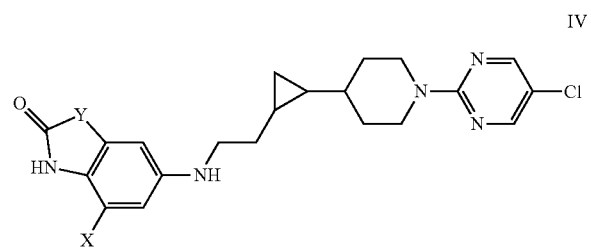

IV or a pharmaceutically acceptable salt thereof.

An aspect of the invention that is of interest relates to compounds of formula IV, or a pharmaceutically acceptable salt thereof, wherein Y represents a member selected from the group consisting of C, N, S, or O.

An aspect of the invention that is of interest relates to compounds of formula IV, or a pharmaceutically acceptable salt thereof, wherein X represents a member selected from the group consisting of H, halo or $C_{1-6}$alkyl. For example, X represents a halo, wherein halo is F, Cl or Br.

In certain embodiments, the compounds described herein can be represented by the formula:

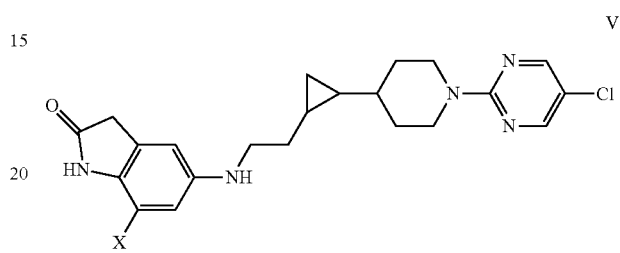

V or a pharmaceutically acceptable salt thereof.

An aspect of the invention that is of interest relates to compounds of formula V, or a pharmaceutically acceptable salt thereof, wherein X represents a member selected from the group consisting of H, halo or $C_{1-6}$alkyl. For example, X represents a halo, wherein halo is F, Cl or Br.

In certain embodiments of formulas I-V, the cyclopropyl ring is the cis cyclopropyl isomer. In other embodiments of formulas I-V, the cyclopropyl ring is the trans cyclopropyl isomer. For example formula V can be cis as follows:

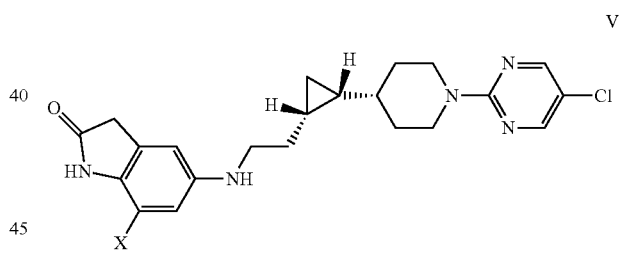

V

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Examples of compounds that are of interest are provided below in Table A.

TABLE A

| No. | Structure | Name |
| --- | --- | --- |
| 1 | 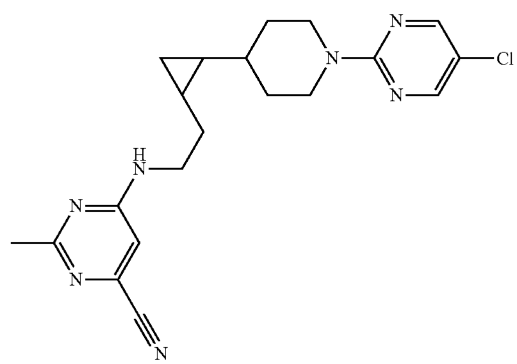 [SMILES: Cc1nc(C#N)cc(NCCC2CC2C2CCN(c3ncc(Cl)cn3)CC2)n1] | 6-[(2-{2-[1-(5-chloropyrimidin-2-yl)piperidin-4-yl]cyclopropyl}ethyl)amino]-2-methylpyrimidine-4-carbonitrile |
| 2 | 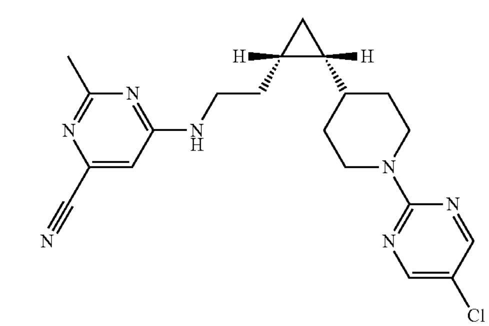 [SMILES: Cc1nc(C#N)cc(NCC[C@@H]2C[C@@H]2C2CCN(c3ncc(Cl)cn3)CC2)n1] | 6-[(2-{(1S,2S)-2-[1-(5-chloropyrimidin-2-yl)piperidin-4-yl]cyclopropyl}ethyl)amino]-2-methylpyrimidine-4-carbonitrile |

TABLE A-continued

| No. | Structure | Name |
|---|---|---|
| 3 | 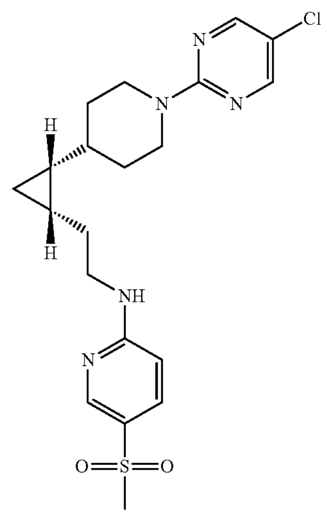 | N-(2-{(1S,2S)-2-[1-(5-chloropyrimidin-2-yl)piperidin-4-yl]cyclopropyl}ethyl)-5-(methylsulfonyl)pyridin-2-amine |
| 4 | 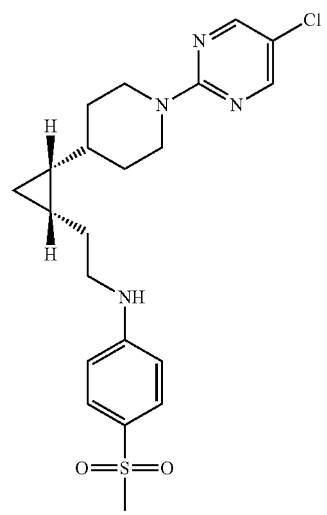 [SMILES: CS(=O)(=O)c1ccc(NCC[C@@H]2C[C@@H]2C2CCN(c3ncc(Cl)cn3)CC2)nc1] | N-(2-{(1S,2S)-2-[1-(5-chloropyrimidin-2-yl)piperidin-4-yl]cyclopropyl}ethyl)-5-(methylsulfonyl)aniline |
| 5 | 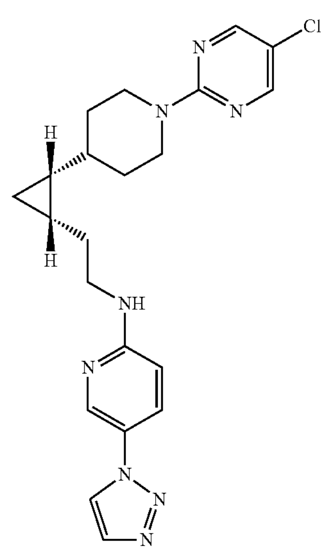 [SMILES: Clc1cnc(N2CCC([C@H]3C[C@H]3CCNc3ccc(-n4ccnn4)cn3)CC2)nc1] | N-(2-{(1S,2S)-2-[1-chloropyrimidin-2-yl)piperidin-4-yl]cyclopropyl}ethyl)-5-(1H-1,2,3-triazol-1-yl)pyridin-2-amine |

TABLE A-continued

| No. | Structure | Name |
|-----|-----------|------|
| 6 | 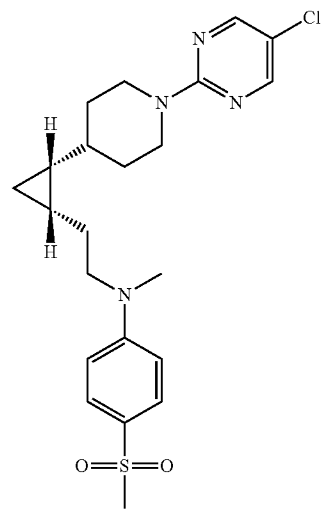 [SMILES: CN(CC[C@@H]1C[C@@H]1C1CCN(c2ncc(Cl)cn2)CC1)c1ccc(S(C)(=O)=O)cc1] | N-(2-{(1S,2S)-2-[1-(5-chloropyrimidin-2-yl)piperidin-4-yl]cyclopropyl}ethyl)-N-methyl-4-(methylsulfonyl)aniline |
| 7 | 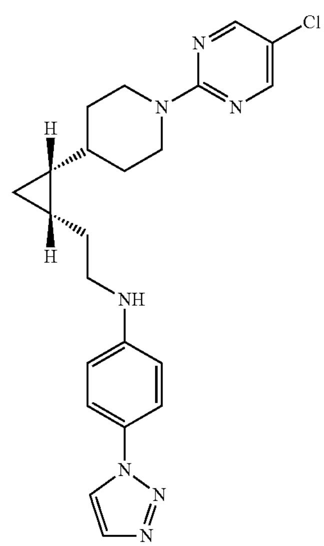 [SMILES: Clc1cnc(N2CCC([C@H]3C[C@H]3CCNc3ccc(-n4ccnn4)cc3)CC2)nc1] | N-(2-{(1S,2S)-2-[1-(5-chloropyrimidin-2-yl)piperidin-4-yl]cyclopropyl}ethyl)-4-(1H-1,2,3-triazol-1-yl)aniline |
| 8 | 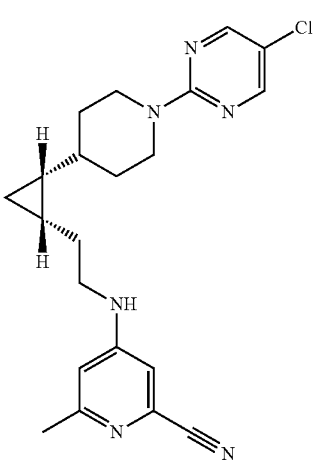 [SMILES: Cc1cc(NCC[C@@H]2C[C@@H]2C2CCN(c3ncc(Cl)cn3)CC2)cc(C#N)n1] | 4-[(2-{(1S,2S)-2-[1-(5-chloropyrimidin-2-yl)piperidin-4-yl]cyclopropyl}ethyl)amino]-6-methylpyrimidine-2-carbonitrile |

TABLE A-continued

| No. | Structure | Name |
|---|---|---|
| 9 | 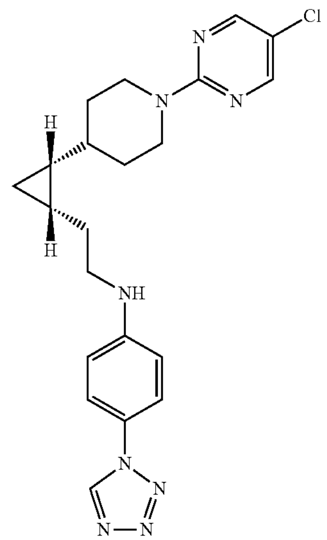 [SMILES: Clc1cnc(N2CCC([C@H]3C[C@H]3CCNc3ccc(-n4cnnn4)cc3)CC2)nc1] | N-(2-{(1S,2S)-2-[1-(5-chloropyrimidin-2-yl)piperidin-4-yl]cyclopropyl}ethyl)-4-(1H-tetrazol-1-yl)aniline |
| 10 | 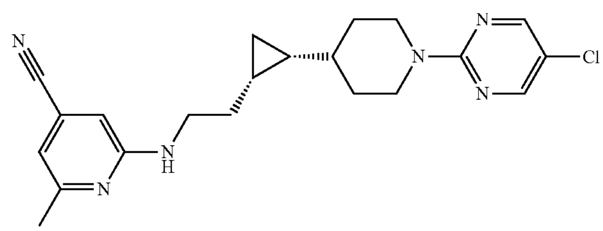 [SMILES: Cc1cc(C#N)cc(NCC[C@@H]2C[C@@H]2C2CCN(c3ncc(Cl)cn3)CC2)n1] | 2-[(2-{(1S,2S)-2-[1-(5-chloropyrimidin-2-yl)piperidin-4-yl]cyclopropyl}ethyl)amino]-6-methylisonicotinonitrile |
| 11 | 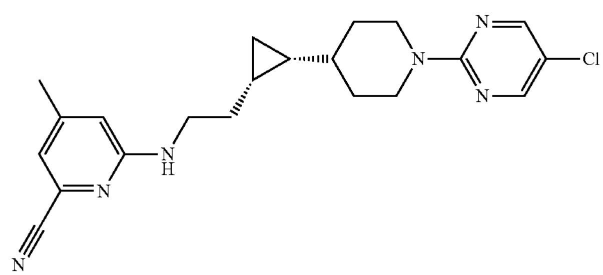 [SMILES: Cc1cc(C#N)nc(NCC[C@@H]2C[C@@H]2C2CCN(c3ncc(Cl)cn3)CC2)c1] | 6-[(2-{(1S,2S)-2-[1-(5-chloropyrimidin-2-yl)piperidin-4-yl]cyclopropyl}ethyl)amino]-4-methylpyridine-2-carbonitrile |
| 12 | 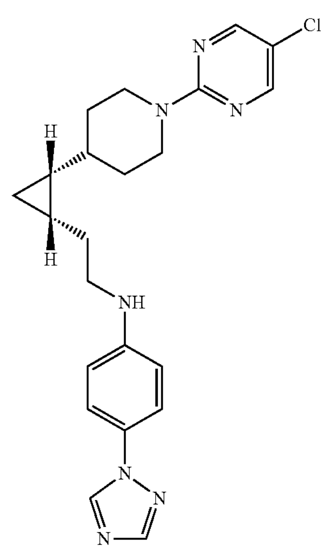 [SMILES: Clc1cnc(N2CCC([C@H]3C[C@H]3CCNc3ccc(-n4cncn4)cc3)CC2)nc1] | N-(2-{(1S,2S)-2-[1-(5-chloropyrimidin-2-yl)piperidin-4-yl]cyclopropyl}ethyl)-4-(1H-1,2,4-triazol-1-yl)aniline |

TABLE A-continued

| No. | Structure | Name |
|---|---|---|
| 13 | 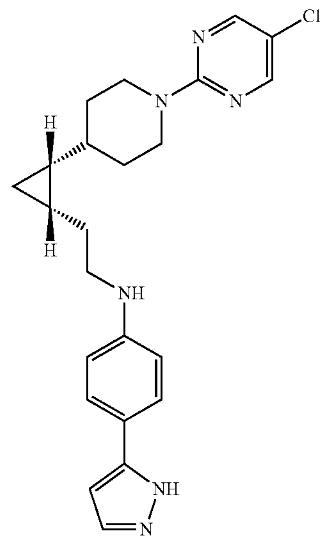 [SMILES: Clc1cnc(N2CCC([C@H]3C[C@H]3CCNc3ccc(-c4ccn[nH]4)cc3)CC2)nc1] | N-(2-{(1S,2S)-2-[1-(5-chloropyrimidin-2-yl)piperidin-4-yl]cyclopropyl}ethyl)-4-(1H-pyrazol-5-yl)aniline |
| 14 | 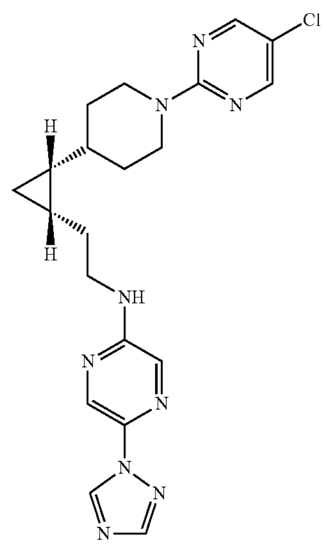 [SMILES: Clc1cnc(N2CCC([C@H]3C[C@H]3CCNc3cnc(-n4cncn4)cn3)CC2)nc1] | N-(2-{(1S,2S)-2-[1-(5-chloropyrimidin-2-yl)piperidin-4-yl]cyclopropyl}ethyl)-5-(1H-1,2,4-triazol-1-yl)pyrazin-2-amine |
| 15 | 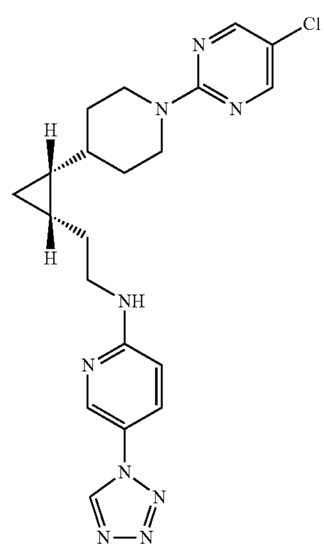 [SMILES: Clc1cnc(N2CCC([C@H]3C[C@H]3CCNc3ccc(-n4cnnn4)cn3)CC2)nc1] | N-(2-{(1S,2S)-2-[1-((5-chloropyrimidin-2-yl)piperidin-4-yl]cyclopropyl}ethyl)-5-(1H-tetrazol-1-yl)pyridin-2-amine |

TABLE A-continued
| No. | Structure | Name |
|---|---|---|
| 16 | 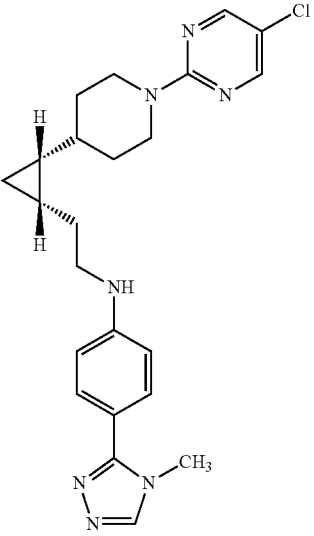 [SMILES: Cn1cnnc1-c1ccc(NCC[C@@H]2C[C@@H]2C2CCN(c3ncc(Cl)cn3)CC2)cc1] | N-(2-{(1S,2S)-2-[1-(5-chloropyrimidin-2-yl)piperidin-4-yl]cyclopropyl}ethyl)-4-(4-methyl-4H-1,2,4-triazol-3-yl)aniline |
| 17 | 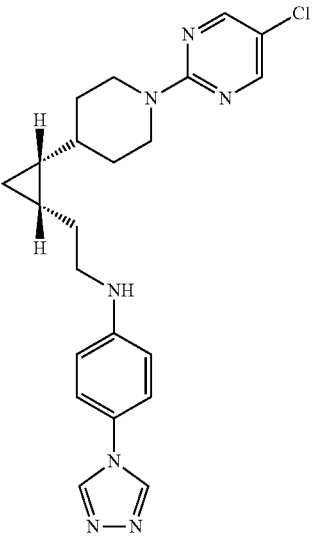 [SMILES: Clc1cnc(N2CCC([C@H]3C[C@H]3CCNc3ccc(-n4cnnc4)cc3)CC2)nc1] | N-(2-{(1S,2S)-2-[1-(5-chloropyrimidin-2-yl)piperidin-4-yl]cyclopropyl}ethyl)-4-(4H-1,2,4-triazol-4-yl)aniline |
| 18 | 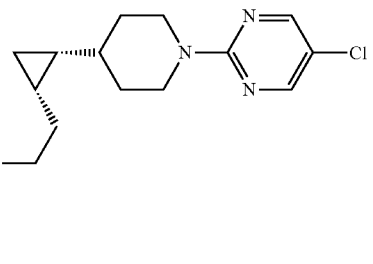 | N-(2-{(1S,2S)-2-[1-(5-chloropyrimidin-2-yl)piperidin-4-yl]cyclopropyl}ethyl)-1H-indazol-5-amine |

TABLE A-continued

| No. | Structure | Name |
|---|---|---|
| 19 | 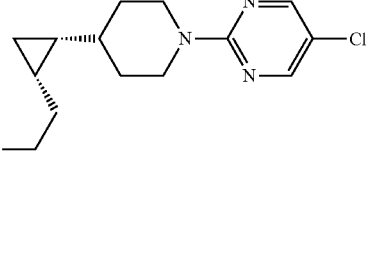 | 5-[(2-{(1S,2S)-2-[1-(5-chloropyrimidin-2-yl)piperidin-4-yl]cyclopropyl}ethyl)amino]isoindolin-1-one |
| 20 | 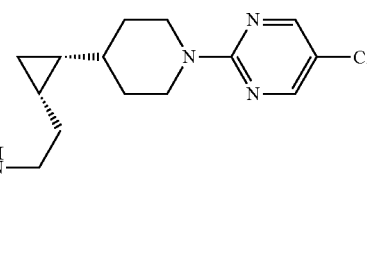 | 5-[(2-{(1S,2S)-2-[1-(5-chloropyrimidin-2-yl)piperidin-4-yl]cyclopropyl}ethyl)amino]-2-methylisoindolin-1-one |
| 21 | 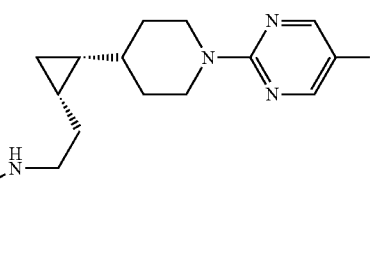 | 5-[(2-{(1S,2S)-2-[1-(5-chloropyrimidin-2-yl)piperidin-4-yl]cyclopropyl}ethyl)amino]-2-cyclopropylisoindolin-1-one |
| 22 | 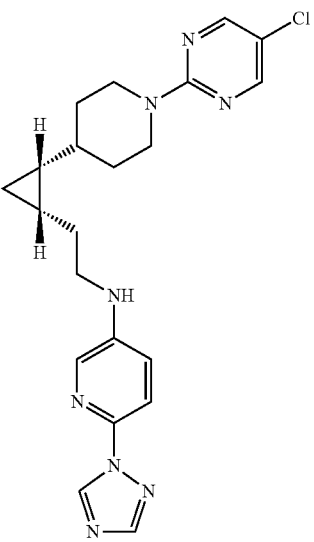 [SMILES: Clc1cnc(N2CCC([C@H]3C[C@H]3CCNc3ccc(-n4cncn4)nc3)CC2)nc1] | N-(2-{(1S,2S)-2-[1-(5-chloropyrimidin-2-yl)piperidin-4-yl]cyclopropyl}ethyl)-6-(1H-1,2,4-triazol-1-yl)pyridin-3-amine |

TABLE A-continued

| No. | Structure | Name |
|---|---|---|
| 23 | 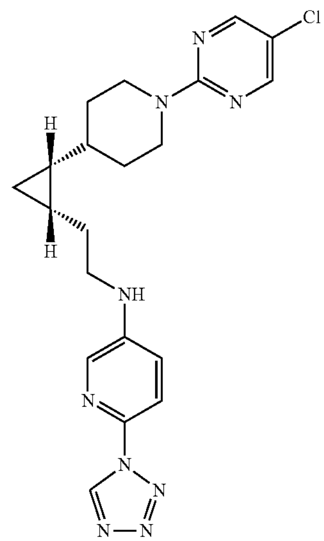 [SMILES: Clc1cnc(N2CCC([C@H]3C[C@H]3CCNc3ccc(-n4cnnn4)nc3)CC2)nc1] | N-(2-{(1S,2S)-2-[1-(5-1-(5-chloropyrimidin-2-yl)piperidin-4-yl]cyclopropyl}ethyl)-6-(1H-tetrazol-1-yl)pyridin-3-amine |
| 24 | 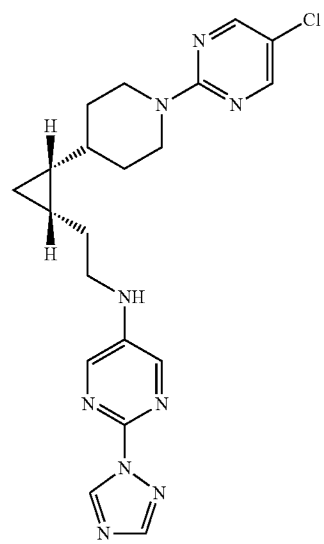 [SMILES: Clc1cnc(N2CCC([C@H]3C[C@H]3CCNc3cnc(-n4cncn4)nc3)CC2)nc1] | N-(2-{(1S,2S)-2-[1-(5-chloropyrimidin-2-yl)piperidin-4-yl]cyclopropyl}ethyl)-2-(1H-1,2,4-triazol-1-yl)pyrimidin-5-amine |
| 25 | 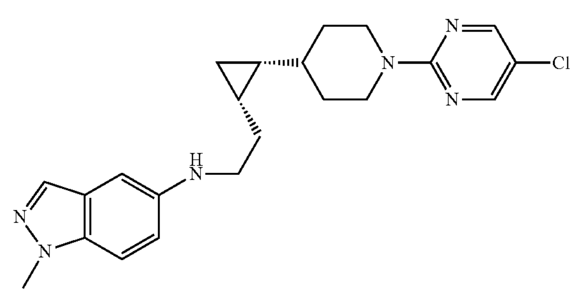 [SMILES: Cn1ncc2cc(NCC[C@@H]3C[C@@H]3C3CCN(c4ncc(Cl)cn4)CC3)ccc21] | N-(2-{(1S,2S)-2-[1-(5-chloropyrimidin-2-yl)piperidin-4-yl]cyclopropyl}ethyl)-1-methyl-1H-indazol-5-amine |
| 26 | 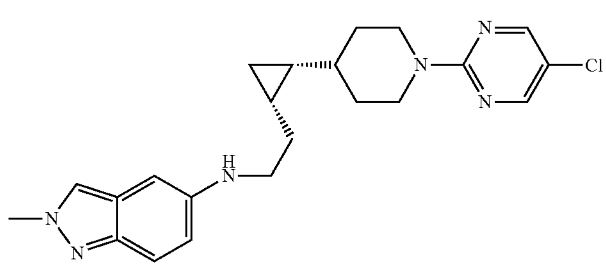 | N-(2-{(1S,2S)-2-[1-(5-chloropyrimidin-2-yl)piperidin-4-yl]cyclopropyl}ethyl)-2-methyl-2H-indazol-5-amine |

TABLE A-continued
| No. | Structure | Name |
|---|---|---|
| 27 | 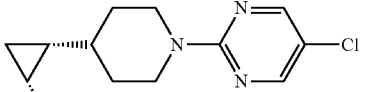 | N-(2-{(1S,2S)-2-[1-(5-chloropyrimidin-2-yl)piperidin-4-yl]cyclopropyl}ethyl)-3-methyl-1H-indazol-5-amine |
| 28 | 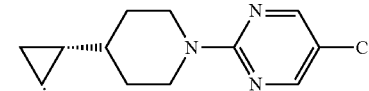 | 5-[(2-{(1S,2S)-2-[1-(5-chloropyrimidin-2-yl)piperidin-4-yl]cyclopropyl}ethyl)amino]-1,3-dihydro-2H-indol-2-one |
| 29 | 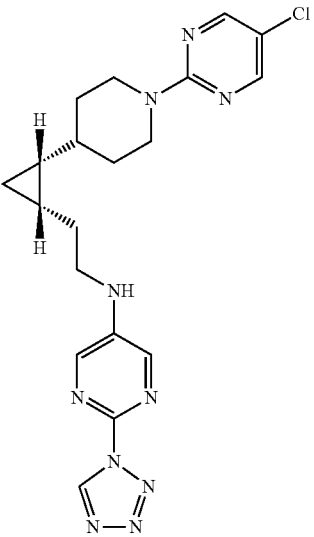 [SMILES: Clc1cnc(N2CCC([C@H]3C[C@H]3CCNc3cnc(-n4cnnn4)nc3)CC2)nc1] | N-(2-{(1S,2S)-2-[1-(5-chloropyrimidin-2-yl)piperidin-4-yl]cyclopropyl}ethyl)-2-(1H-tetrazol-1-yl)pyrimidin-5-amine |

TABLE A-continued
| No. | Structure | Name |
|---|---|---|
| 30 | 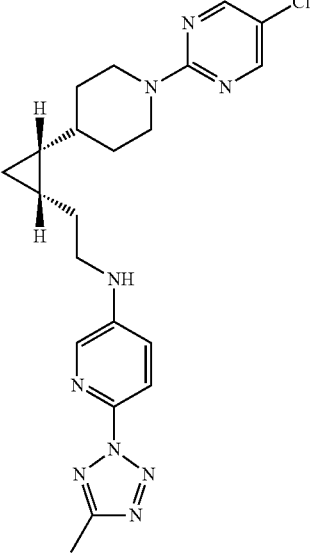 | N-(2-{(1S,2S)-2-[1-(5-chloropyrimidin-2-yl)piperidin-4-yl]cyclopropyl}ethyl)-6-(5-methyl-2H-tetrazol-2-yl)pyridin-3-amine |
| 31 | 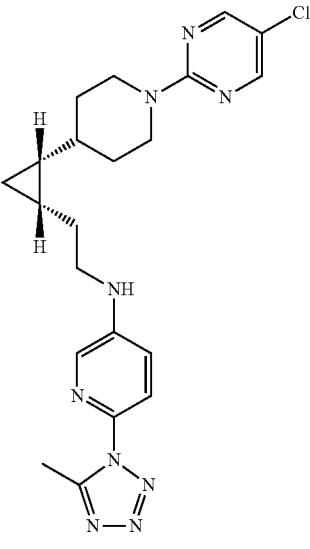 [SMILES: Cc1nnnn1-c1ccc(NCC[C@@H]2C[C@@H]2C2CCN(c3ncc(Cl)cn3)CC2)cn1] | N-(2-{(1S,2S)-2-[1-(5-chloropyrimidin-2-yl)piperidin-4-yl]cyclopropyl}ethyl)-6-(5-methyl-1H-tetrazol-1-yl)pyridin-3-amine |

TABLE A-continued

| No. | Structure | Name |
|---|---|---|
| 32 | 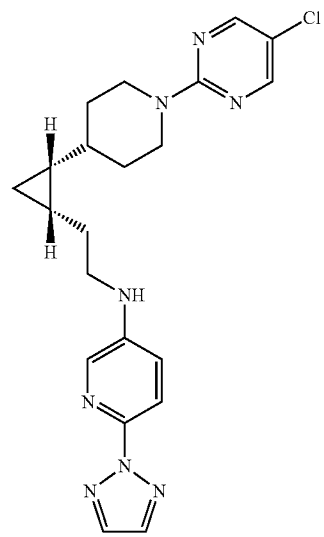 [SMILES: Clc1cnc(N2CCC([C@H]3C[C@H]3CCNc3ccc(-n4nccn4)nc3)CC2)nc1] | N-(2-{(1S,2S)-2-[1-(5-chloropyrimidin-2-yl)piperidin-4-yl]cyclopropyl}ethyl)-6-(2H-1,2,3-triazol-2-yl)pyridin-3-amine |
| 33 | 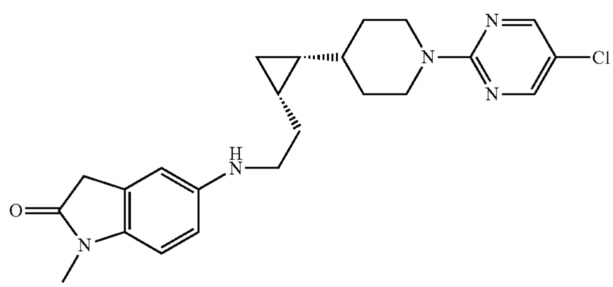 [SMILES: CN1C(=O)Cc2cc(NCC[C@@H]3C[C@@H]3C3CCN(c4ncc(Cl)cn4)CC3)ccc21] | 5-[(2-{(1S,2S)-2-[1-(5-chloropyrimidin-2-yl)piperidin-4-yl]cyclopropyl}ethyl)amino]-1-methyl-1,3-dihydro-2H-indol-2-one |
| 34 | 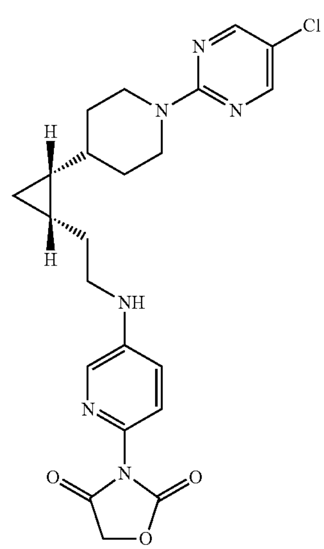 [SMILES: O=C1COC(=O)N1c1ccc(NCC[C@@H]2C[C@@H]2C2CCN(c3ncc(Cl)cn3)CC2)cn1] | 3-{5-[(2-{(1S,2S)-2-[1-(5-chloropyrimidin-2-yl)piperidin-4-yl]cyclopropyl}ethylamino]pyridin-2-yl}-1,3-oxazolidine-2,4-dione |

TABLE A-continued

| No. | Structure | Name |
|---|---|---|
| 35 | 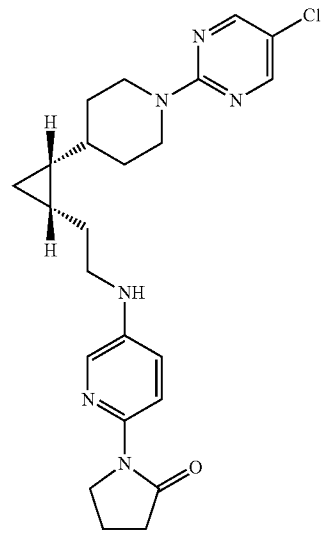 [SMILES: O=C1CCCN1c1ccc(NCC[C@@H]2C[C@@H]2C2CCN(c3ncc(Cl)cn3)CC2)cn1] | 1-{5-[(2-{(1S,2S)-2-[1-(5-chloropyrimidin-2-yl)piperidin-4-yl]cyclopropyl}ethyl)amino]pyridin-2-yl}pyrrolidin-2-one |
| 36 | 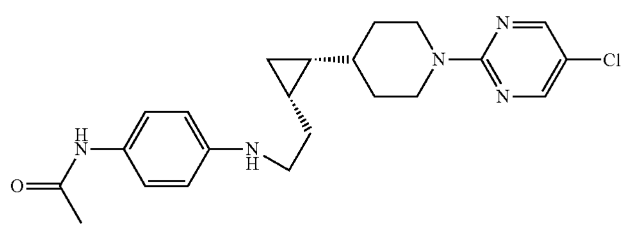 [SMILES: CC(=O)Nc1ccc(NCC[C@@H]2C[C@@H]2C2CCN(c3ncc(Cl)cn3)CC2)cc1] | N-{4-[(2-{(1S,2S)-2-[1-(5-chloropyrimidin-2-yl)piperidin-4-yl]cyclopropyl}ethyl)amino]phenyl}acetamide |
| 37 | 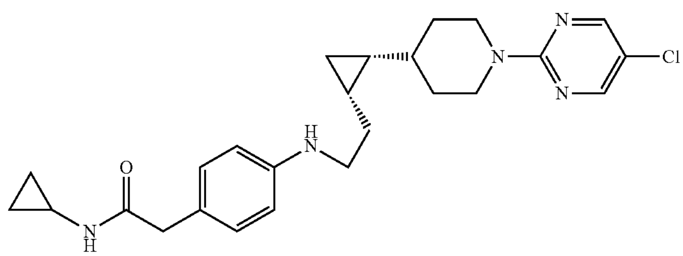 [SMILES: O=C(Cc1ccc(NCC[C@@H]2C[C@@H]2C2CCN(c3ncc(Cl)cn3)CC2)cc1)NC1CC1] | 2-{4-[(2-{(1S,2S)-2-[1-(5-chloropyrimidin-2-yl)piperidin-4-yl]cyclopropyl}ethyl)amino]phenyl}-N-cyclopropylacetamide |
| 38 | 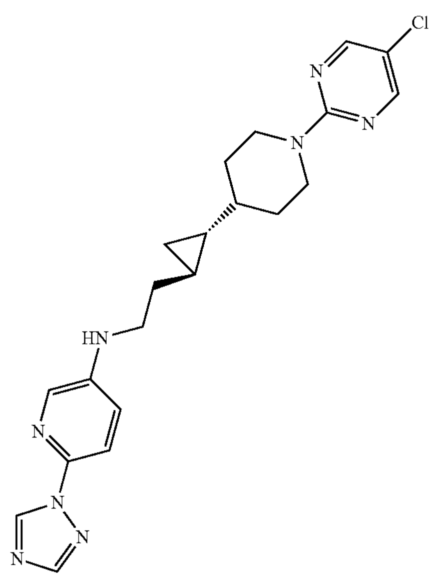 [SMILES: Clc1cnc(N2CCC([C@H]3C[C@@H]3CCNc3ccc(-n4cncn4)nc3)CC2)nc1] | N-(2-{(1R,2S)-2-[1-(5-chloropyrimidin-2-yl)piperidin-4-yl]cyclopropyl}ethyl)-6-(1H-1,2,4-triazol-1-yl)pyridin-3-amine |

TABLE A-continued

| No. | Structure | Name |
| --- | --- | --- |
| 39 | 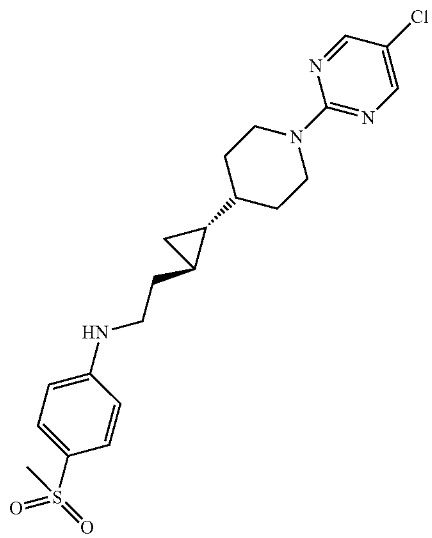 [SMILES: CS(=O)(=O)c1ccc(NCC[C@H]2C[C@@H]2C2CCN(c3ncc(Cl)cn3)CC2)cc1] | N-(2-{(1R,2S)-2-[1-(5-chloropyrimidin-2-yl)piperidin-4-yl]cyclopropyl}ethyl)-4-(methylsulfonyl)aniline |
| 40 | 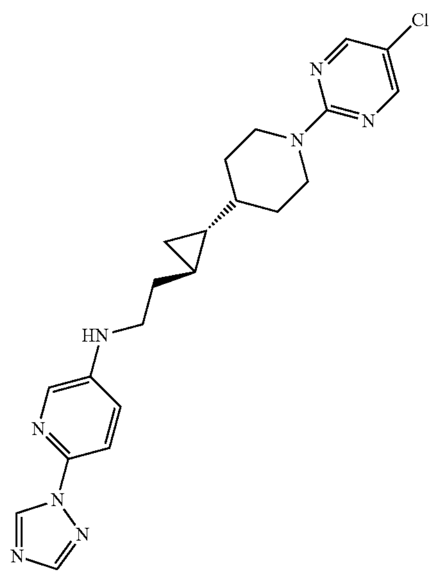 [SMILES: Clc1cnc(N2CCC([C@H]3C[C@@H]3CCNc3ccc(-n4cncn4)nc3)CC2)nc1] | N-(2-{(1R,2S)-2-[1-(5-chloropyrimidin-2-yl)piperidin-4-yl]cyclopropyl}ethyl)-6-(1H-1,2,4-triazol-1-yl)pyridin-3-amine |
| 41 | 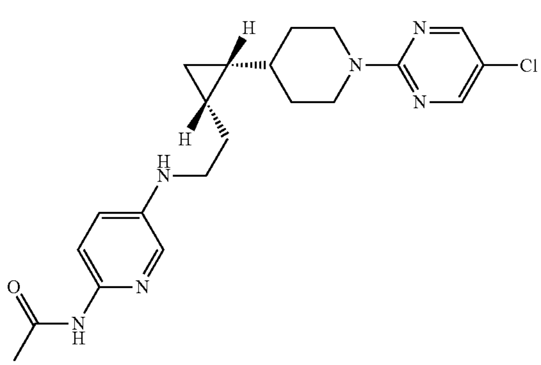 [SMILES: CC(=O)Nc1ccc(NCC[C@@H]2C[C@@H]2C2CCN(c3ncc(Cl)cn3)CC2)cn1] | N-{5-[(2-{(1S,2S)-2-[1-(5-chloropyrimidin-2-yl)piperidin-4-yl]cyclopropyl}ethyl)amino]pyridin-2-yl}acetamide |

TABLE A-continued
| No. | Structure | Name |
|---|---|---|
| 42 | 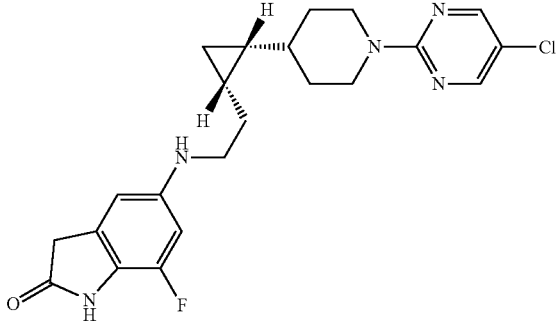 [SMILES: O=C1Cc2cc(NCC[C@@H]3C[C@@H]3C3CCN(c4ncc(Cl)cn4)CC3)cc(F)c2N1] | 5-[(2-{(1S,2S)-2-[1-(5-chloropyrimidin-2-yl)piperidin-4-yl]cyclopropyl}ethyl)amino]-7-fluoro-1,3-dihydro-2H-indol-2-one |
| 43 | 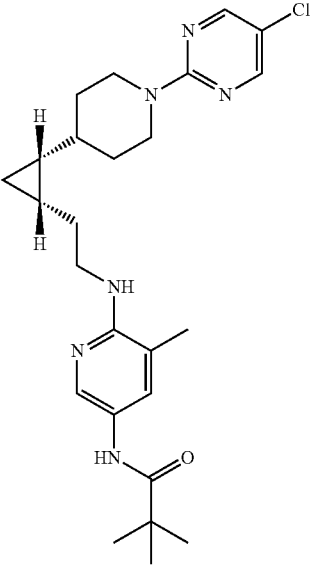 [SMILES: Cc1cc(NC(=O)C(C)(C)C)cnc1NCC[C@@H]1C[C@@H]1C1CCN(c2ncc(Cl)cn2)CC1] | N-{6-[(2-{(1S,2S)-2-[1-(5-chloropyrimidin-2-yl)piperidin-4-yl]cyclopropyl}ethyl)amino]-5-methylpryidin-3-yl}-2,2-dimethylpropanamide |
| 44 | 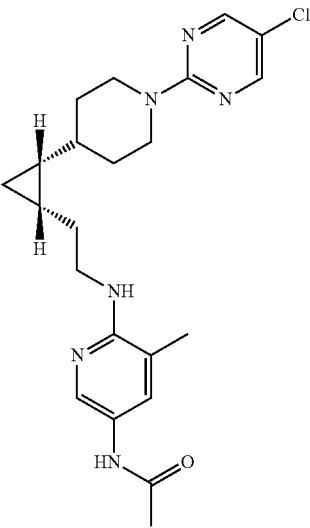 [SMILES: CC(=O)Nc1cnc(NCC[C@@H]2C[C@@H]2C2CCN(c3ncc(Cl)cn3)CC2)c(C)c1] | N-{6-[(2-{(1S,2S)-2-[1-(5-chloropyrimidin-2-yl)piperidin-4-yl]cyclopropyl}ethyl)amino]-5-methylpryidin-3-yl}acetamide |

TABLE A-continued
| No. | Structure | Name |
|---|---|---|
| 45 | 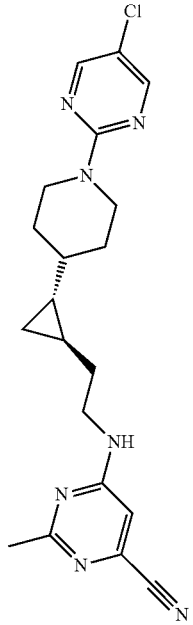 [SMILES: Cc1nc(C#N)cc(NCC[C@H]2C[C@@H]2C2CCN(c3ncc(Cl)cn3)CC2)n1] | 6-[(2-{(1R,2S)-2-[1-(5-chloropyrimidin-2-yl)piperidin-4-yl]cyclopropyl}ethyl)amino]-2-methylpyrimidine-4-carbonitrile |
| 46 | 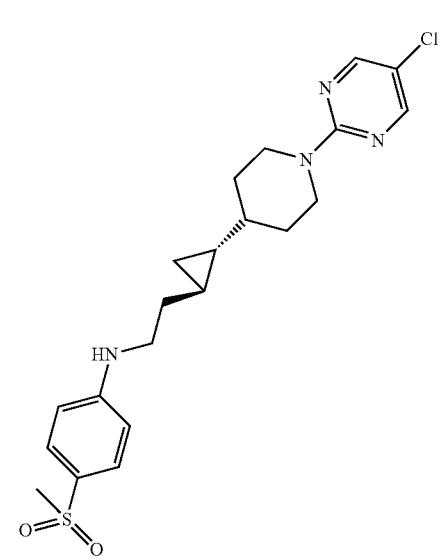 [SMILES: CS(=O)(=O)c1ccc(NCC[C@H]2C[C@@H]2C2CCN(c3ncc(Cl)cn3)CC2)cc1] | N-(2-{(1R,2S)-2-[1-(5-chloropyrimidin-2-yl)piperidin-4-yl]cyclopropyl}ethyl)-4-(methylsulfonyl)aniline |

TABLE A-continued

| No. | Structure | Name |
|---|---|---|
| 47 | 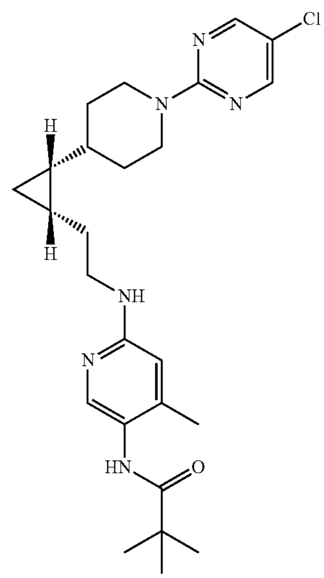 [SMILES: Cc1cc(NCC[C@@H]2C[C@@H]2C2CCN(c3ncc(Cl)cn3)CC2)ncc1NC(=O)C(C)(C)C] | N-{6-[(2-{(1S,2S)-2-[1-(5-chloropyrimidin-2-yl)piperidin-4-yl]cyclopropyl}ethyl)amino]-4-methylpyridin-3-yl}-2,2-dimethylpropanamide |
| 48 | 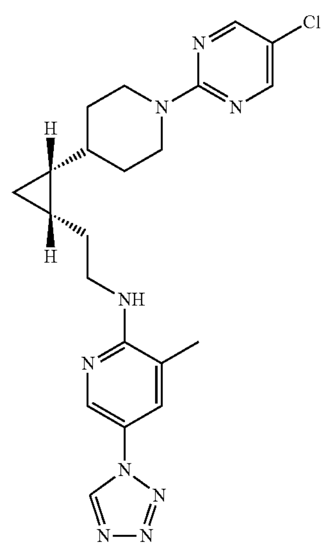 [SMILES: Cc1cc(-n2cnnn2)cnc1NCC[C@@H]1C[C@@H]1C1CCN(c2ncc(Cl)cn2)CC1] | N-(2-{(1S,2S)-2-[1-(5-chloropyrimidin-2-yl)piperidin-4-yl]cyclopropyl}ethyl)-3-methyl-5-(1H-tetrazol-1-yl)pyridin-2-amine |
| 49 | 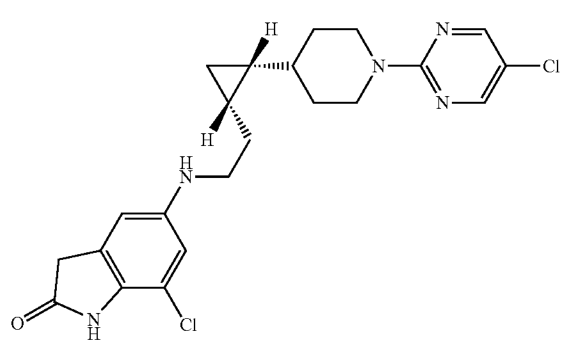 [SMILES: O=C1Cc2cc(NCC[C@@H]3C[C@@H]3C3CCN(c4ncc(Cl)cn4)CC3)cc(Cl)c2N1] | 7-chloro-5-[(2-{(1S,2S)-2-[1-(5-chloropyrimidin-2-yl)piperidin-4-yl]cyclopropyl}ethyl)amino]-1,3-dihydro-2H-indol-2-one |

TABLE A-continued

| No. | Structure | Name |
|---|---|---|
| 50 | 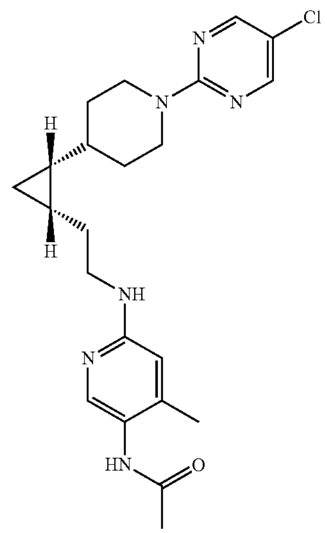 [SMILES: CC(=O)Nc1cnc(NCC[C@@H]2C[C@@H]2C2CCN(c3ncc(Cl)cn3)CC2)cc1C] | N-{6-[(2-{(1S,2S)-2-[1-(5-chloropyrimidin-2-yl)piperidin-4-yl]cyclopropyl}ethyl)amino]-4-methylpyridin-3-yl}acetamide |
| 51 | 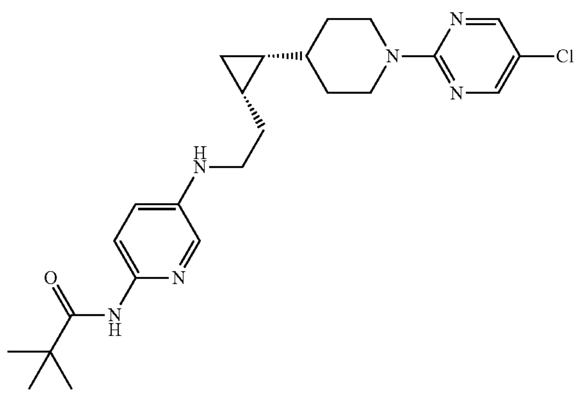 [SMILES: CC(C)(C)C(=O)Nc1ccc(NCC[C@@H]2C[C@@H]2C2CCN(c3ncc(Cl)cn3)CC2)cn1] | N-{5-[(2-{(1S,2S)-2-[1-(5-chloropyrimidin-2-yl)piperidin-4-yl]cyclopropyl}ethyl)amino]pyridin-2-yl}-2,2-dimethylpropanamide |
| 52 | 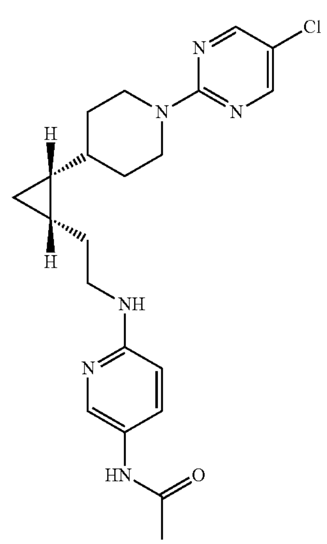 [SMILES: CC(=O)Nc1ccc(NCC[C@@H]2C[C@@H]2C2CCN(c3ncc(Cl)cn3)CC2)nc1] | N-{6-[(2-{(1S,2S)-2-[1-(5-chloropyrimidin-2-yl)piperidin-4-yl]cyclopropyl}ethyl)amino]pyridin-3-yl}acetamide |

TABLE A-continued
| No. | Structure | Name |
|---|---|---|
| 53 | 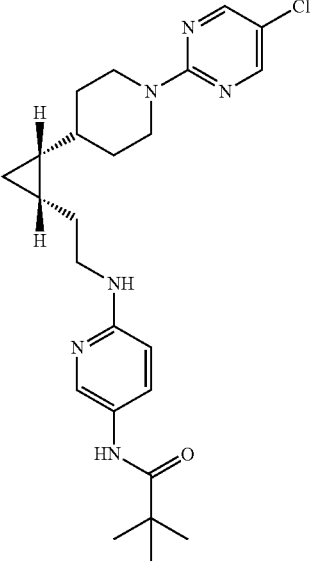 [SMILES: CC(C)(C)C(=O)Nc1ccc(NCC[C@@H]2C[C@@H]2C2CCN(c3ncc(Cl)cn3)CC2)nc1] | N-{6-[(2-{(1S,2S)-2-[1-(5-chloropyrimidin-2-yl)piperidin-4-yl]cyclopropyl}ethyl)amino]pyridin-3-yl}-2,2-dimethylpropanamide |
| 54 | 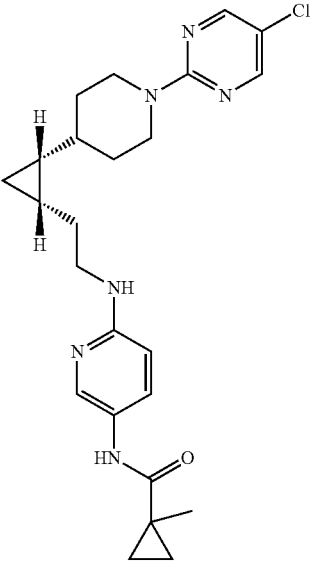 [SMILES: CC1(C(=O)Nc2ccc(NCC[C@@H]3C[C@@H]3C3CCN(c4ncc(Cl)cn4)CC3)nc2)CC1] | N-{6-[(2-{(1S,2S)-2-[1-(5-chloropyrimidin-2-yl)piperidin-4-yl]cyclopropyl}ethyl)amino]pyridin-3-yl}-1-methylcyclopropanecarboxamide |

TABLE A-continued

| No. | Structure | Name |
|---|---|---|
| 55 | 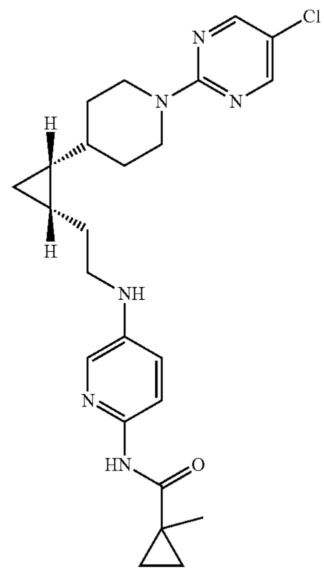 [SMILES: CC1(C(=O)Nc2ccc(NCC[C@@H]3C[C@@H]3C3CCN(c4ncc(Cl)cn4)CC3)cn2)CC1] | N-{5-[(2-{(1S,2S)-2-[1-(5-chloropyrimidin-2-yl)piperidin-4-yl]cyclopropyl}ethyl)amino]pyridin-2-yl}-1-methylcyclopropanecarboxamide |
| 56 | 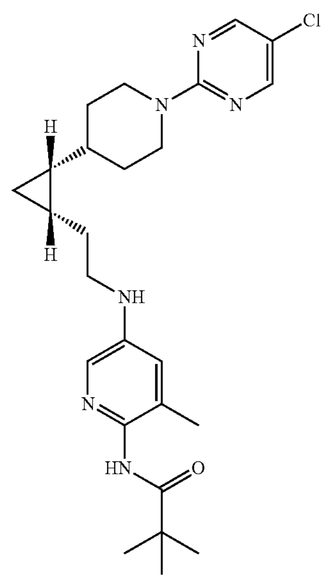 [SMILES: Cc1cc(NCC[C@@H]2C[C@@H]2C2CCN(c3ncc(Cl)cn3)CC2)cnc1NC(=O)C(C)(C)C] | N-{5-[(2-{(1S,2S)-2-[1-(5-chloropyrimidin-2-yl)piperidin-4-yl]cyclopropyl}ethyl)amino]-3-methylpyridin-2-yl}-2,2-dimethylpropanamide |
| 57 | 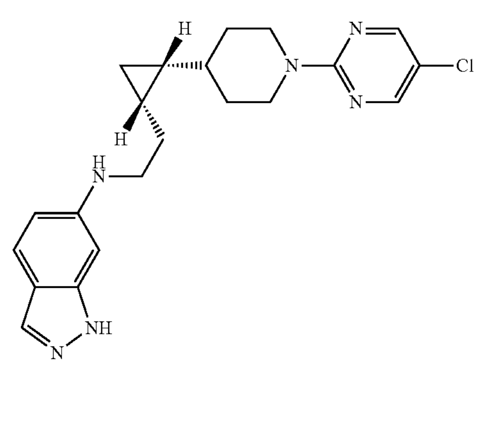 [SMILES: Clc1cnc(N2CCC([C@H]3C[C@H]3CCNc3ccc4cn[nH]c4c3)CC2)nc1] | N-(2-{(1S,2S)-2-[1-(5-chloropyrimidin-2-yl)piperidin-4-yl]cycloporpyl}ethyl)-1H-indazol-6-amine |

TABLE A-continued

| No. | Structure | Name |
|---|---|---|
| 58 | 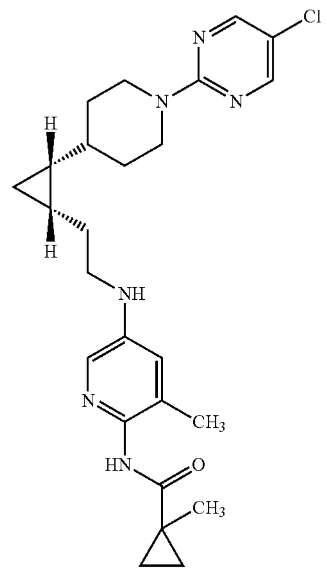 [SMILES: Cc1cc(NCC[C@@H]2C[C@@H]2C2CCN(c3ncc(Cl)cn3)CC2)cnc1NC(=O)C1(C)CC1] | N-{5-[(2-{(1S,2S)-2-[1-(5-chloropyrimidin-2-yl)piperidin-4-yl]cyclopropylethyl)amino]-3-methylpyridin-2-yl}-1-methylcyclopropanecarboxamide |
| 59 | | N-{3-chloro-5-[(2-{(1S,2S)-2-[1-(5-chloropyrimidin-2-yl)piperidin-4-yl]cyclopropyl}ethyl)amino]pyridin-2-yl}-2,2-dimethylpropanamide | as well as the pharmaceutically acceptable salts thereof.

Utilities

Compounds of the present invention are potent agonists of the GPR 119 receptor. The compounds of the invention, and pharmaceutically acceptable salts thereof are modulators of the receptor known as GPR 119, and are therefore useful in the treatment of diseases that are modulated by GPR119 ligands and agonists. Many of these diseases are summarized below.

Treatment and prevention of the following diseases and conditions are included in the present invention: Also, the compounds of the invention may be used for the manufacture of a medicament for treating one or more of these diseases or conditions:

(1) noninsulin dependent diabetes mellitus (type 2 diabetes);
(2) hyperglycemia;
(3) the metabolic syndrome;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapoBliproteinemia; and
(11) atherosclerosis.

More particularly, the following diseases and conditions can be treated using the compounds of the formulas described herein or a pharmaceutically acceptable salt thereof. The compounds may be used for manufacturing a medicament for the treatment or prevention of one or more of these diseases or conditions:

(1) Type 2 diabetes, and specifically hyperglycemia;
(2) Metabolic syndrome;
(3) Obesity; and
(4) Hypercholesterolemia or dyslipidemia.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

The compounds, compositions, and medicaments as described herein are useful for reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

The compounds generally are useful for treating the following diseases and conditions: (1) type 2 diabetes (also known as non-insulin dependent diabetes mellitus, or T2DM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure, (19) Alzheimer's disease, (20) schizophrenia, (21) multiple sclerosis, and (22) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and anacetrapib), niacin, bile acid sequestrants, microsomal triglyceride transport inhibitors, and bile acid reuptake inhibitors. These combination treatments are useful for the treatment or control of conditions selected from the group consisting of hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, particularly a lipase inhibitor such as orlistat, or a monoamine neurotransmitter uptake inhibitor such as sibutramine, phentetraine and the like. The compound may also be used advantageously in combination with CB-1 inverse agonists or antagonists such as rimonabant and taranabant.

Another aspect of the invention that is of interest relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

More particularly, another aspect of the invention that is of interest relates to a method of treating type 2 diabetes in a mammalian patient in need of such treatment comprising administering to the patient a compound in accordance with the formulas described herein or a pharmaceutically acceptable salt thereof in an amount that is effective to treat type 2 diabetes.

Yet another aspect of the invention that is of interest relates to a method of treating non-insulin dependent diabetes mellitus in a mammalian patient in need of such treatment comprising administering to the patient a compound in accordance with the formulas described herein or a pharmaceutically acceptable salt thereof in an amount that is effective to treat non-insulin dependent diabetes mellitus.

Yet another aspect of the invention that is of interest relates to a method of treating obesity in a mammalian patient in need of such treatment comprising administering to said patient a compound in accordance with the formulas described herein or a pharmaceutically acceptable salt thereof in an amount that is effective to treat obesity.

Yet another aspect of the invention that is of interest relates to a method of treating Syndrome X in a mammalian patient in need of such treatment, comprising administering to said patient a compound in accordance with the formulas described herein or a pharmaceutically acceptable salt thereof in an amount that is effective to treat Syndrome X.

Yet another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with the formulas described herein or a pharmaceutically acceptable salt thereof in an amount that is effective to treat said lipid disorder.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of treating a condition selected from the group consisting of: (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition.

Yet another aspect of the invention that is of interest relates to a method of delaying the onset of a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP,GIP mimetics, and GIP receptor agonists;
(i) PACAP, PACAP mimetics, and PACAP receptor 3 agonists;
(j) cholesterol lowering agents selected from the group consisting of
  (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
(k) PPARδ agonists;
(l) antiobesity compounds;
(m) ileal bile acid transporter inhibitors;
(n) anti-inflammatory agents excluding glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Yet another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with the formulas described herein or a pharmaceutically acceptable salt thereof and an HMG-CoA reductase inhibitor, in amounts that are effective to treat said condition.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with the formulas described herein or a pharmaceutically acceptable salt thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of the formulas described herein and an HMG-CoA reductase inhibitor.

More particularly, another aspect of the invention that is of interest relates to a method of delaying the onset or reducing the risk of developing atherosclerosis in a human patient in need of such treatment comprising administering to the patient a compound in accordance with the formulas described herein or a pharmaceutically acceptable salt thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

More particularly, another aspect of the invention that is of interest relates to a method of treating, delaying the onset or reducing the risk of developing atherosclerosis in a human patient in need of such treatment comprising administering to the patient a compound in accordance with the formulas described herein or a pharmaceutically acceptable salt thereof and a cholesterol absorption inhibitor, said compounds being administered in amounts that treat, delay the onset, or reduce the risk of developing atherosclerosis.

Even more particularly, another aspect of the invention that is of interest relates to a method of treating, delaying the onset or reducing the risk of developing atherosclerosis in a human patient in need of such treatment comprising administering to the patient a compound in accordance with the formulas described herein or a pharmaceutically acceptable salt thereof and a cholesterol absorption inhibitor, wherein the cholesterol absorption inhibitor is ezetimibe, said compounds being administered in amounts that treat, delay the onset, or reduce the risk of developing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the formulas described herein or a pharmaceutically acceptable salt thereof are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5, mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Pharmaceutical Compositions

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art of pharmacy.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethyleellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

Compounds of the formulas described herein may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;
(2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metfonuin hydrochloride, and extended-release formulations thereof, such as Glumetza™, Fortamet™, and GlucophageXR™; (iii) protein tyrosine phosphatase-1B (PTP-1B) inhibitors;
(3) insulin or insulin analogs, such as insulin lispro, insulin detemir, insulin glargine, insulin glulisine, and inhalable formulations of each thereof;
(4) leptin and leptin derivatives and agonists;
(5) amylin and amylin analogs, such as pramlintide;
(6) sulfonylurea and non-sulfonylurea insulin secretagogues, such as tolbutamide, glyburide, glipizide, glimepiride, mitiglinide, and meglitinides, such as nateglinide and repaglinide;

(7) α-glucosidase inhibitors (such as acarbose, voglibose and miglitol);

(8) glucagon receptor antagonists, such as those disclosed in WO 98/04528, WO 99/01423, WO 00/39088, and WO 00/69810;

(9) incretin mimetics, such as GLP-1, GLP-1 analogs, derivatives, and mimetics; and GLP-1 receptor agonists, such as exenatide, liraglutide, taspoglutide, AVE0010, CJC-1131, and BIM-51077, including intranasal, transdermal, and once-weekly formulations thereof;

(10) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(11) HDL-raising drugs, such as niacin or a salt thereof and extended-release versions thereof; Tredaptive™, which is a combination of niacin extended-release and the DP-1 antagonist LAROPIPRANT; and nicotinic acid receptor agonists;

(12) antiobesity compounds;

(13) agents intended for use in inflammatory conditions, such as aspirin, non-steroidal anti-inflammatory drugs (NSAIDs), glucocorticoids, and selective cyclooxygenase-2 (COX-2) inhibitors;

(14) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(15) glucokinase activators (GKAs), such as LY2599506;

(16) inhibitors of 11β-hydroxysteroid dehydrogenase type 1, such as those disclosed in U.S. Pat. No. 6,730,690; WO 03/104207; and WO 04/058741;

(17) inhibitors of cholesteryl ester transfer protein (CETP), such as torcetrapib and anacetrapib;

(18) inhibitors of fructose 1,6-bisphosphatase, such as those disclosed in U.S. Pat. Nos. 6,054,587; 6,110,903; 6,284,748; 6,399,782; and 6,489,476;

(19) inhibitors of acetyl CoA carboxylase-1 or 2 (ACC1 or ACC2);

(20) AMP-activated Protein Kinase (AMPK) activators;

(21) agonists of the G-protein-coupled receptors: GPR-109, GPR-119, and GPR-40;

(22) SSTR3 antagonists, such as those disclosed in WO 2009/011836;

(23) neuromedin U receptor agonists, such as those disclosed in WO2009/042053, including, but not limited to, neuromedin S (NMS);

(24) inhibitors of stearoyl-coenzyme A delta-9 desaturase (SCD);

(25) GPR-105 antagonists, such as those disclosed in WO 2009/000087;

(26) inhibitors of glucose uptake, such as sodium-glucose transporter (SGLT) inhibitors and its various isoforms, such as SGLT-1; SGLT-2, such as dapagliflozin and remogliflozin; and SGLT-3;

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR);

(32) ileal bile acid transporter inhibitors;

(33) PACAP, PACAP mimetics, and PACAP receptor 3 agonists;

(34) PPARδ agonists;

(35) protein tyrosine phosphatase-1B (PTP-1B) inhibitors; and

(36) bromocriptine mesylate and rapid-release formulations thereof.

Dipeptidyl peptidase-IV (DPP-4) inhibitors that can be used in combination with compounds of the formulas described herein include, but are not limited to, sitagliptin (disclosed in U.S. Pat. No. 6,699,871), vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein 1 include, but are not limited to:

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro-5-(4,6-dihydropyrrolo[3,4-c]pyrazol-5(1H)-yl) tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl]hexahydro-1-methyl-2H-1,4-diazepin-2-one hydrochloride; and (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Antiobesity compounds that can be combined with compounds of the formulas described herein include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); CB1 receptor inverse agonists and antagonists (such as rimonabant and taranabant); $β_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert*

*Opin. Emerging Drugs,* 8: 217-237 (2003); J. A. Fernandez-Lopez, et al., "Pharmacological Approaches for the Treatment of Obesity," *Drugs,* 62: 915-944 (2002); and K. M. Gadde, et al., "Combination pharmaceutical therapies for obesity," *Exp. Opin. Pharmacother.,* 10: 921-925 (2009).

Glucagon receptor antagonists that can be used in combination with the compounds of the formulas described herein include, but are not limited to:
N-[4-((1S)-1-{3-(3,5-dichlorophenyl)-5-[6-(trifluoromethoxy)-2-naphthyl]-1H-pyrazol-1-yl}ethyl)benzoyl]-β-alanine;
N-[4-((1R)-1-{3-(3,5-dichlorophenyl)-5-[6-(trifluoromethoxy)-2-naphthyl]-1H-pyrazol-1-yl}ethyl)benzoyl]-β-alanine;
N-(4-{1-[3-(2,5-dichlorophenyl)-5-(6-methoxy-2-naphthyl)-1H-pyrazol-1-yl]ethyl}benzoyl)-β-alanine;
N-(4-{(1S)-1-[3-(3,5-dichlorophenyl)-5-(6-methoxy-2-naphthyl)-1H-pyrazol-1-yl]ethyl}benzoyl)-β-alanine;
N-(4-{(1S)-1-[(R)-(4-chlorophenyl)(7-fluoro-5-methyl-1H-indol-3-yl)methyl]butyl}benzoyl)-β-alanine; and
N-(4-{(1S)-1-[(4-chlorophenyl)(6-chloro-8-methylquinolin-4-yl)methyl]butyl}benzoyl)-β-alanine; and pharmaceutically acceptable salts thereof.

Inhibitors of stearoyl-coenzyme A delta-9 desaturase (SCD) that can be used in combination with the compounds of the formulas described herein include, but are not limited to:
[5-(5-{4-[2-(trifluoromethyl)phenoxy]piperidin-1-yl}-1,3,4-thiadiazol-2-yl)-2H-tetrazol-2-yl]acetic acid;
(2-{4-[2-(trifluoromethyl)phenoxy]piperidin-1-yl}-2,5-bi-1,3-thiazol-4-yl)acetic acid;
(5-{3-[4-(2-bromo-5-fluorophenoxy)piperidin-1-yl]isoxazol-5-yl}-2H-tetrazol-2-yl)acetic acid;
(3-{3-[4-(2-bromo-5-fluorophenoxy)piperidin-1-yl]-1,2,4-oxadiazol-5-yl}-1H-pyrrol-1-yl)acetic acid;
(5-{5-[4-(2-bromo-5-fluorophenoxy)piperidin-1-yl]pyrazin-2-yl}-2H-tetrazol-2-yl)acetic acid; and
(5-{2-[4-(5-bromo-2-chlorophenoxy)piperidin-1-yl]pyrimidin-5-yl}-2H-tetrazol-2-yl)acetic acid; and pharmaceutically acceptable salts thereof.

Glucokinase activators that can be used in combination with the compounds of the formulas described herein include, but are not limited to:
3-(6-ethanesulfonylpyridin-3-yloxy)-5-(2-hydroxy-1-methyl-ethoxy)-N-(1-methyl-1H-pyrazol-3-yl)benzamide;
5-(2-hydroxy-1-methyl-ethoxy)-3-(6-methanesulfonylpyridin-3-yloxy)-N-(1-methyl-1H-pyrazol-3-yl)benzamide;
5-(1-hydroxymethyl-propoxy)-3-(6-methanesulfonylpyridin-3-yloxy)-N-(1-methyl-1H-pyrazol-3-yl)benzamide;
3-(6-methanesulfonylpyridin-3-yloxy)-5-(1-methoxymethyl-propoxy)-N-(1-methyl-1H-pyrazol-3-yl)benzamide;
5-isopropoxy-3-(6-methanesulfonylpyridin-3-yloxy)-N-(1-methyl-1H-pyrazol-3-yl)benzamide;
5-(2-fluoro-1-fluoromethyl-ethoxy)-3-(6-methanesulfonylpyridin-3-yloxy)-N-(1-methyl-1H-pyrazol-3-yl)benzamide;
3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;
3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;
N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide; and
3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide; and pharmaceutically acceptable salts thereof.

Agonists of the GPR-119 receptor that can be used in combination with the compounds of the formulas described herein include, but are not limited to:
rac-cis 5-chloro-2-{4-[2-(2-{[5-(methylsulfonyl)pyridin-2-yl]oxy}ethyl)cyclopropyl]piperidin-1-yl}pyrimidine;
5-chloro-2-{4-[(1R,2S)-2-(2-{[5-(methylsulfonyl)pyridin-2-yl]oxy}ethyl)cyclopropyl]piperidin-1-yl}pyrimidine;
rac cis-5-chloro-2-[4-(2-{2-[4-(methylsulfonyl)phenoxy]ethyl}cyclopropyl)piperidin-1-yl]pyrimidine;
5-chloro-2-[4-((1S,2R)-2-{2-[4-(methylsulfonyl)phenoxy]ethyl}cyclopropyl)piperidin-1-yl]pyrimidine;
5-chloro-2-[4-((1R,2S)-2-{2-[4-(methylsulfonyl)phenoxy]ethyl}cyclopropyl)piperidin-1-yl]pyrimidine;
rac cis-5-chloro-2-[4-(2-{2-[3-(methylsulfonyl)phenoxy]ethyl}cyclopropyl)piperidin-1-yl]pyrimidine; and
rac cis-5-chloro-2-[4-(2-{2-[3-(5-methyl-1,3,4-oxadiazol-2-yl)phenoxy]ethyl}cyclopropyl)piperidin-1-yl]pyrimidine; and pharmaceutically acceptable salts thereof.

Selective PPARγ modulators (SPPARγM's) that can be used in combination with the compounds of the formulas described herein include, but are not limited to:
(2S)-2-({6-chloro-3-[6-(4-chlorophenoxy)-2-propylpyridin-3-yl]-1,2-benzisoxazol-5-yl}oxy)propanoic acid;
(2S)-2-({6-chloro-3-[6-(4-fluorophenoxy)-2-propylpyridin-3-yl]-1,2-benzisoxazol-5-yl}oxy)propanoic acid;
(2S)-2-{[6-chloro-3-(6-phenoxy-2-propylpyridin-3-yl)-1,2-benzisoxazol-5-yl]oxy}propanoic acid;
(2R)-2-({6-chloro-3-[6-(4-chlorophenoxy)-2-propylpyridin-3-yl]-1,2-benzisoxazol-5-yl}oxy)propanoic acid;
(2R)-2-{3-[3-(4-methoxy)benzoyl-2-methyl-6-(trifluoromethoxy)-1H-indol-1-yl]phenoxy}butanoic acid;
(2S)-2-{3-[3-(4-methoxy)benzoyl-2-methyl-6-(trifluoromethoxy)-1H-indol-1-yl]phenoxy}butanoic acid;
2-{3-[3-(4-methoxy)benzoyl-2-methyl-6-(trifluoromethoxy)-1H-indol-1-yl]phenoxy}-2-methylpropanoic acid; and
(2R)-2-{3-[3-(4-chloro)benzoyl-2-methyl-6-(trifluoromethoxy)-1H-indol-1-yl]phenoxy}propanoic acid; and pharmaceutically acceptable salts thereof.

Inhibitors of 11β-hydroxysteroid dehydrogenase type 1 that can be used in combination with the compounds of the formulas described herein include, but are not limited to:
3-[1-(4-chlorophenyl)-trans-3-fluorocyclobutyl]-4,5-dicyclopropyl-r-4H-1,2,4-triazole;
3-[1-(4-chlorophenyl)-trans-3-fluorocyclobutyl]-4-cyclopropyl-5-(1-methylcyclopropyl)-r-4H-1,2,4-triazole;
3-[1-(4-chlorophenyl)-trans-3-fluorocyclobutyl]-4-methyl-5-[2-(trifluoromethoxy)phenyl]-r-4H-1,2,4-triazole;
3-[1-(4-chlorophenyl)cyclobutyl]-4-methyl-5-[2-(trifluoromethyl)phenyl]-4H-1,2,4-triazole;
3-{4-[3-(ethylsulfonyl)propyl]bicyclo[2.2.2]oct-1-yl}-4-methyl-5-[2-(trifluoromethyl)phenyl]-4H-1,2,4-triazole;
4-methyl-3-{4-[4-(methyl sulfonyl)phenyl]bicyclo[2.2.2]oct-1-yl}-5-[2-(trifluoromethyl)phenyl]-4H-1,2,4-triazole;
3-(4-{4-methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;
3-(4-{4-methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;
5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;

2-(,1-difluoroethyl)-5-(4-{4-methyl-5-[2-(trifluoromethyl)phenyl]-4,1-1,2,4-triazol-3-yl}bicyclo[2.2.2]oct-1-yl)-1,3,4-oxadiazole;

2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and 5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; and pharmaceutically acceptable salts thereof.

Somatostatin subtype receptor 3 (SSTR3) antagonists that can be used in combination with the compounds of the formulas described herein include, but are not limited to:

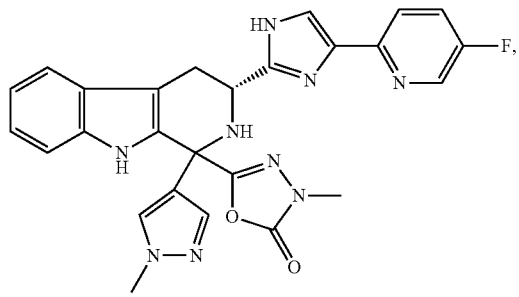

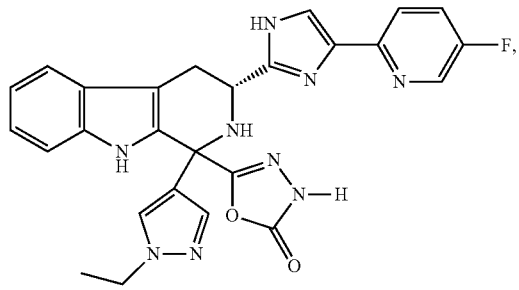

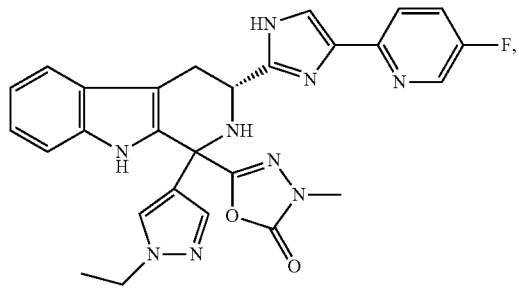

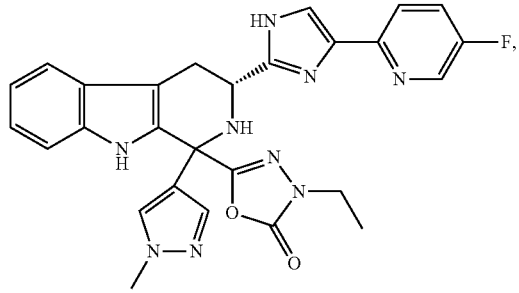

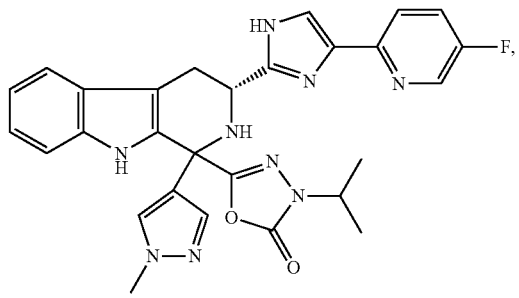

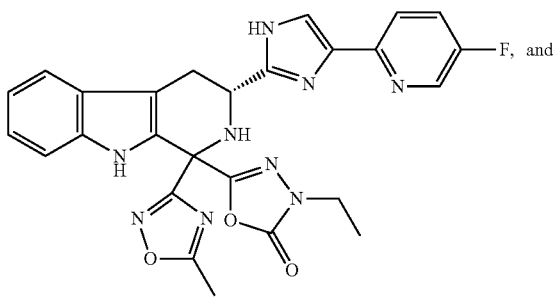

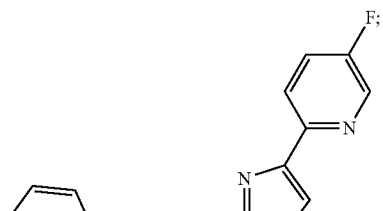

and pharmaceutically acceptable salts thereof.

AMP-activated Protein Kinase (AMPK) activators that can be used in combination with the compounds of the formulas described herein include, but are not limited to:

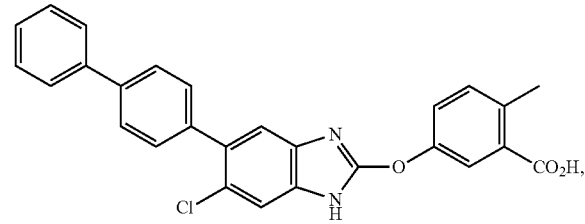

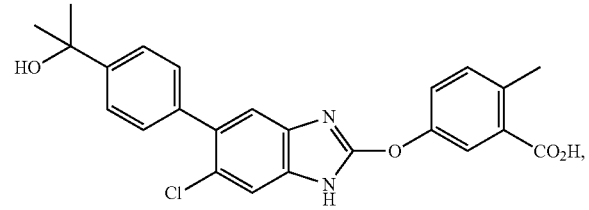

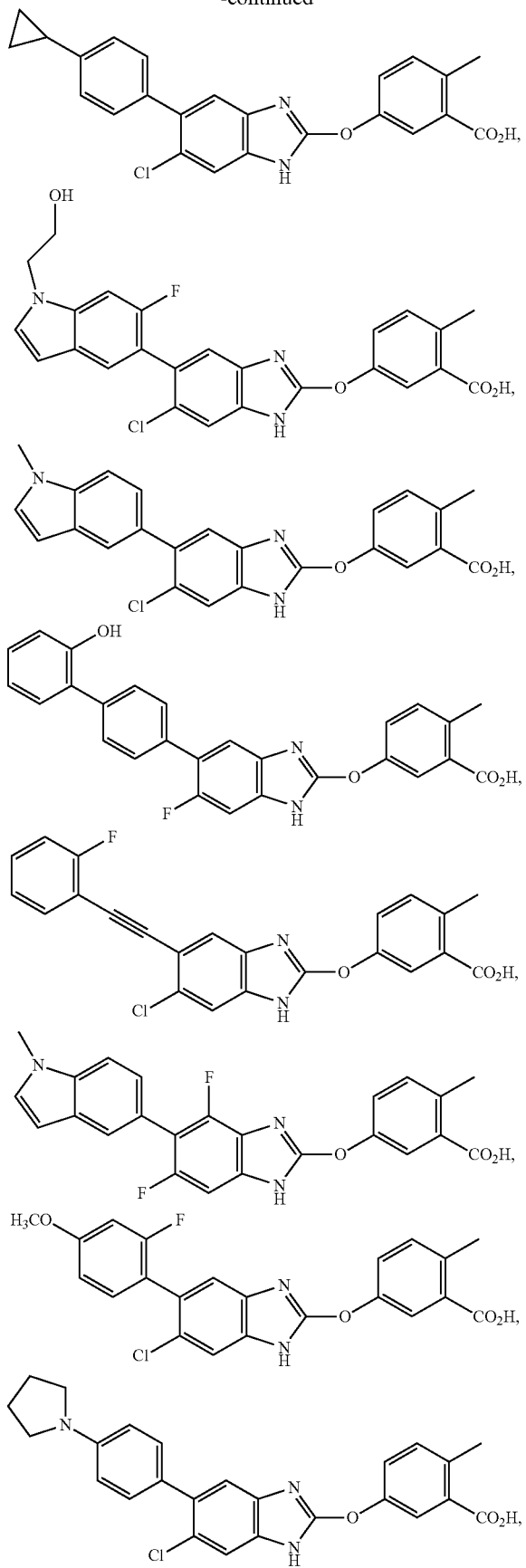

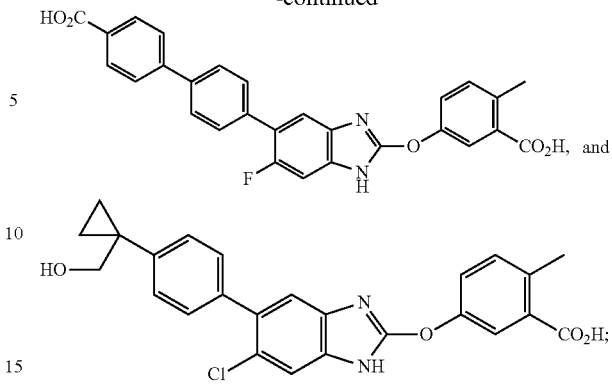

and pharmaceutically acceptable salts thereof.

Inhibitors of acetyl-CoA carboxylase-1 and 2 (ACC-1 and ACC-2) that can be used in combination with the compounds of the formulas described herein include, but are not limited to:

3-{1-[(1-cyclopropyl-4-methoxy-1H-indol-6-yl)carbonyl]-4-oxospiro[chroman-2,4-piperidin]-6-yl}benzoic acid;
5-{1-[(1-cyclopropyl-4-methoxy-1H-indol-6-yl)carbonyl]-4-oxospiro[chroman-2,4-piperidin]-6-yl}nicotinic acid;
1-[(1-cyclopropyl-4-methoxy-1H-indol-6-yl)carbonyl]-6-(1H-tetrazol-5-yl)spiro[chroman-2,4-piperidin]-4-one;
1-[(1-cyclopropyl-4-ethoxy-3-methyl-1H-indol-6-yl)carbonyl]-6-(1H-tetrazol-5-yl)spiro[chroman-2,4-piperidin]-4-one; and
5-{1-[(1-cyclopropyl-4-methoxy-3-methyl-1H-indol-6-yl)carbonyl]-4-oxo-spiro[chroman-2,4-piperidin]-6-yl}nicotinic acid; and pharmaceutically acceptable salts thereof.

In another aspect of the invention, a pharmaceutical composition is disclosed which comprises one or more of the following agents:

(a) a compound having the structure of the formulas described herein; and
(b) one or more compounds selected from the group consisting of:
  (1) dipeptidyl peptidase-IV (DPP-4) inhibitors;
  (2) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; (iii) protein tyrosine phosphatase-1B (PTP-1B) inhibitors;
  (3) sulfonylurea and non-sulfonylurea insulin secretagogues, such as tolbutamide, glyburide, glipizide, glimepiride, mitiglinide, and meglitinides, such as nateglinide and repaglinide;
  (4) α-glucosidase inhibitors (such as acarbose, voglibose and miglitol);
  (5) glucagon receptor antagonists;
  (6) LDL cholesterol lowering agents such as (i) HMG-CoA reductase inhibitors (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(7) HDL-raising drugs, such as niacin or a salt thereof and extended-release versions thereof; Tredaptive™, which is a combination of niacin extended-release and the DP-1 antagonist LAROPIPRANT; and nicotinic acid receptor agonists;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(11) glucokinase activators (GKAs), such as LY2599506;

(12) inhibitors of 11β-hydroxysteroid dehydrogenase type 1;

(13) inhibitors of cholesteryl ester transfer protein (CETP), such as torcetrapib and anacetrapib;

(14) inhibitors of fructose 1,6-bisphosphatase;

(15) inhibitors of acetyl CoA carboxylase-1 or 2 (ACC1 or ACC2);

(16) AMP-activated Protein Kinase (AMPK) activators;

(17) agonists of the G-protein-coupled receptors: GPR-109, GPR-119, and GPR-40;

(18) SSTR3 antagonists;

(19) neuromedin U receptor agonists, including, but not limited to, neuromedin S (NMS);

(20) inhibitors of stearoyl-coenzyme A delta-9 desaturase (SCD);

(21) GPR-105 antagonists;

(22) inhibitors of glucose uptake, such as sodium-glucose transporter (SGLT) inhibitors and its various isoforms, such as SGLT-1; SGLT-2, such as dapagliflozin and remogliflozin; and SGLT-3;

(23) inhibitors of acyl coenzyme A:diacylglycerol acyltransferase 1 and 2 (DGAT-1 and DGAT-2);

(24) inhibitors of fatty acid synthase;

(25) inhibitors of acetyl-CoA carboxylase-1 and 2 (ACC-1 and ACC-2);

(26) inhibitors of acyl coenzyme A:monoacylglycerol acyltransferase 1 and 2 (MGAT-1 and MGAT-2);

(27) agonists of the TGR5 receptor (also known as GPBAR1, BG37, GPCR19, GPR131, and M-BAR); and

(28) bromocriptine mesylate and rapid-release formulations thereat and (c) a pharmaceutically acceptable carrier.

The above combinations include combinations of a compound of the present invention not only with one other active compound, but also with two or more other active compounds. Non-limiting examples include combinations of compounds of the formulas described herein or a pharmaceutically acceptable salt thereof with two or more active compounds selected from biguanides, sulfonylureas, HMG-CoA reductase inhibitors, other PPAR agonists, PTP-1B inhibitors, DPP-4 inhibitors, and anti-obesity compounds.

Another aspect of the invention that is of interest relates to the use of a compound in accordance with the formulas described herein or a pharmaceutically acceptable salt thereof in the manufacture of a medicament for use in treating a disease or condition described herein.

The compounds of the invention can be prepared using the synthetic schemes described herein as well as any of several alternate methods which will be apparent to a chemist skilled in the art. The following abbreviations may be used in the synthetic schemes or Examples:

Ac is acetyl [CH$_3$C(O)—]; Ac$_2$O is acetic anhydride; AcAc is acetyl acetonoate; AIBN is azobisiobutyronitrile; Ar is Aryl; ArX is an aryl halide; 9-BBN is 9-borabicyclo[3.3.1]nonane; Bn is benzyl; BOc is tert Butyloxycarbonyl; BuTM-DOB is trans 2-butyl-N,N,N,N-tetramethyl-1,3,2-dioxaborolane-4,5-dicarboxamide, as specified R,R or S,S; DBU is diazabicycloundecane; DBAD is di-tert-butylazodicarboxylate; DCM is dichloromethane; DCE is dichloroethane; DIAD is diisopropylazodicarboxylate; DIBAL or DiBAl-H is diisobutylaluminum hydride; DMA is dimethylacetamide; DMAP is dimethylaminopyridine; DMF is N,N-dimethylformamide; DMSO is dimethyl sulfoxide; EDAC (or EDC) is 1-ethyl-3-[3-(dimethylamino)propyl]-carbodiimide HCl; Et$_3$N is triethylamine; Et is ethyl; EtOAc is ethyl acetate; EtOH is ethanol; HATU is 2-(1H-7-azabenzotriazol-1-yl)-1,1,3,3-tetramethyl uronium hexafluorophosphate methanaminium; HCl is hydrochloric acid; Het-X is heterocyclic halide; HOBt is 1-hydroxybenzotriazole; HPLC is high performance liquid chromatography; iPrOAc is isopropyl acetate; LG is leaving group; LRMS is low resolution mass spectrometry; M is molar; mmol is millimole; Me is methyl; MeOH is methanol; MsCl methanesulfonyl chloride; N is normal; NaHMDS is sodium hexamethyldisiliazide; NaOAc is sodium acetate; NaOtBu is sodium tert-butoxide; n-BuLi is n-butyllithium; NBS is n-bromosuccinimide; NMO is N-methylmorpholine N oxide; NMP is N-methylpyrrolidinone; Pd(dba)$_2$ is tris(dibenzylideneacetone)dipalladium; PdCl$_2$(Ph$_3$P)$_2$ is dichlorobis-(triphenylphosphene) palladium; PG Denotes an unspecified protecting group; Ph is phenyl; PhMe is toluene; PPh$_3$ is triphenylphosphine; PMB is para-methoxybenzyl; RT is room temperature; TBAF is tetrabutyl ammonium fluoride; TBS is tert-butyldimethylsilyl; tBu is tert-butyl; TEA is triethylamine; Tf is triflate; TFA is trifluoroacetic acid; THF is tetrahydrofuran; TLC is thin layer chromatography; TMEDA is tetramethylethylenediamine; TMS is trimethylsilyl; TPAP is tetrapropylammonium perruthenate, Ts or TsCl is tosyl or tosyl chloride.

General Schemes

Substituted aryl and heteroaryl coupling intermediates shown in the schemes are commercially available or may be prepared from readily accessible aryl, heterocyclic, or other congeners via a host of routes. Many intermediates are accessible through either modification of a pre-formed heteroaryl scaffold or through de novo ring synthesis.

The substituted alkyl piperidines of this invention can be prepared by any of several methods. The specific examples detailed below may employ some of the following general procedures. Many functionalized piperidines are commercially available. Where they are not, one of the most useful synthetic routes for their preparation utilizes a reduction of a suitable pyridine. Low pressure reductions with hydrogen and 5-10% Pd on charcoal or similar hydrogenation catalyst in acetic acid- or stepwise reduction of an activated pyridinium acyl by hydride followed by similar hydrogenation will lead to the appropriate piperidine. The side chain may be present in its desired final configuration, or it may be elaborated by well known methods after the piperidine ring is generated. (Scheme 1)

SCHEME 1

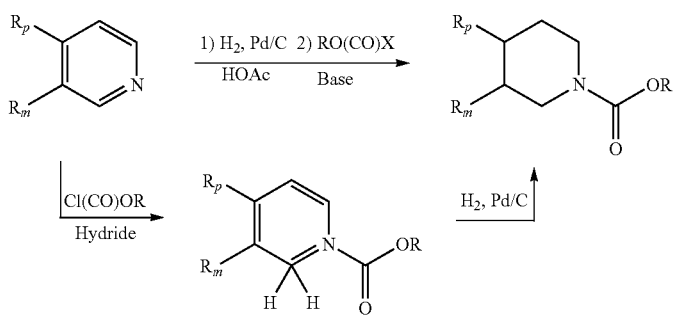

R represents lower alkyl, Rp and Rm represents para and meta substitution on ring A The cyclopropyl residue in the connecting chain of the present examples may be introduced by any of several methods. A particularly convenient method is outlined in Scheme 2 below. Conversion of the readily available hydroxymethyl piperidine to the acetylene by a multistep protocol allows ready access to the indicated cis olefins after Lindlar reduction. (See for example; Eymery, et al, *Synth* 2000, 185-213. Page 196 for a convenient protocol.) Homologation of the same intermediate through the Horner-Emmons modification of the Wittig reaction allows easy access to the trans olefins. Charette's $Et_2Zn/CH_2I_2$ cyclopropanation affords racemic, diasteromerically enriched or enantiomerically enriched cyclopropyl analogs. (Charette et al, *JACS* 1998, 120, 11943-11952; further details in Charette, et al, *JACS*, 2001, 123, 12160-12167.) In the absence of an auxiliary chiral Lewis acid the cis allylic olefin affords good yields of the desired racemic analog. Also in the absence of an auxiliary chiral Lewis acid, the chiral alcohol derived from the opening of R or S glycidyl epoxide affords reasonable ratios the chiral diasteromeric cyclopropanation products.

With the addition of the auxiliary chiral Lewis acid RR or SS trans-2-butyl-N,N,N,N-tetramethyl-1,3,2-dioxaborolane-4,5-dicarboxamide (BuTMDOB), the same cyclopropanation protocol leads to very good ratios of the desired enantiomer in either the allylic or homoallylic cyclopropanation. The depicted chiral homoallylic alcohol requires the "matched" dioxaborolane in the double diasteroselection protocol.

SCHEME 2

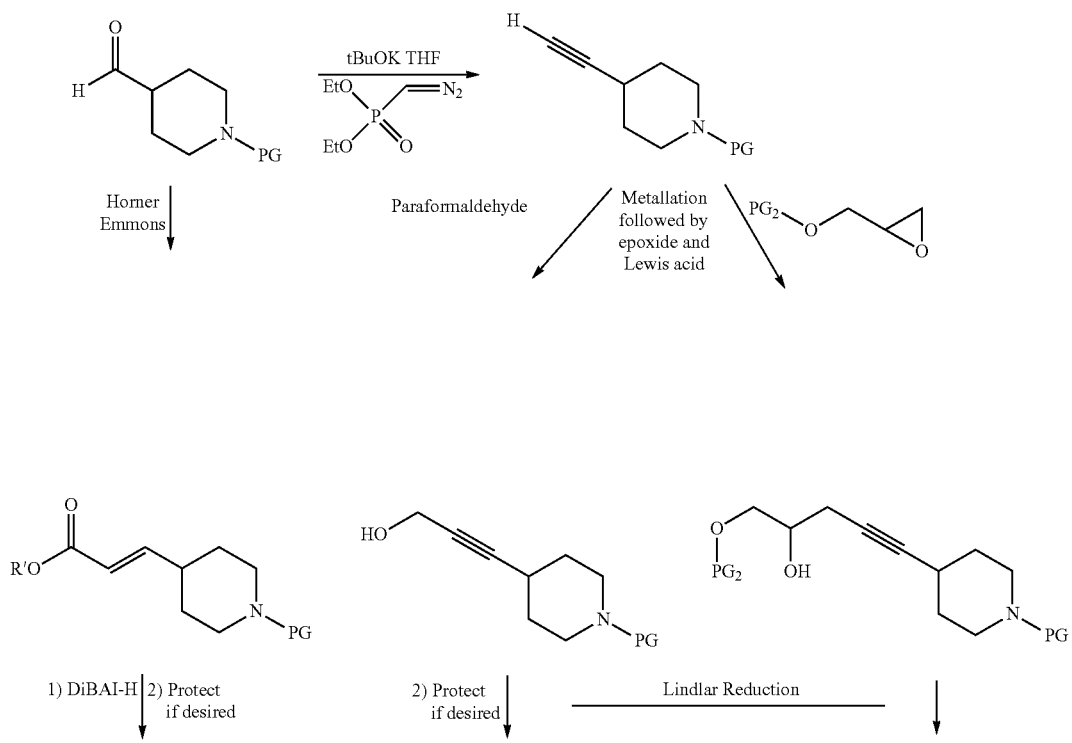

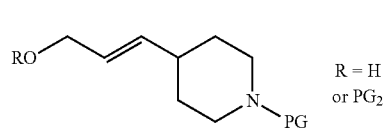
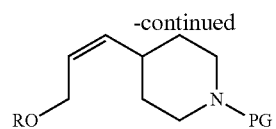
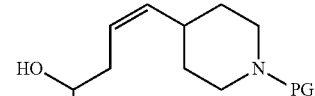

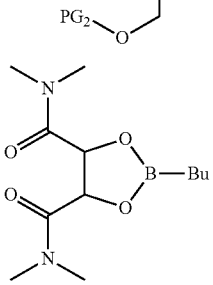

RR or SS

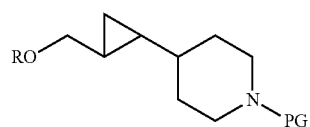
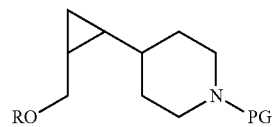
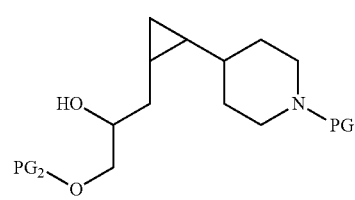

1) Deprotect if required
2) TPAP NMO
3) Ph₃PCH₂OMe Base
4) H⁺
5) NaBH₄

1) Deprotection
2) NaIO₄
3) NaBH₄

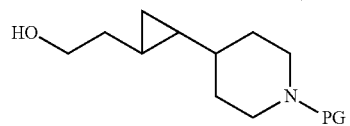
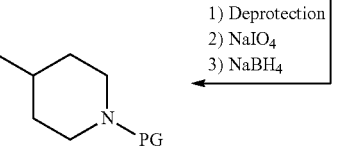

R' represents lower alkyl, R represents H or PG$_2$. PG$_2$ is a protection group, preferably benzyl Introduction of the piperidine nitrogen substituent can be accomplished by a particularly wide variety of routes. Some of the most versatile routes for the examples reported here are represented in scheme 3. Direct displacement of labile heteroaryl halides or similar leaving groups can often be used to introduce the nitrogen substituent directly. Subsequent functionalization of the aryl ether is similarly straightforward. Subsequent functionalization of the alcohol is similarly straightforward. Oxidation of the alcohol followed by reductive amination, conversion of the primary alcohol to an amine followed by displacement or direct displacement on heteroaryl systems are all well known to the practicing synthetic chemist.

SCHEME 3

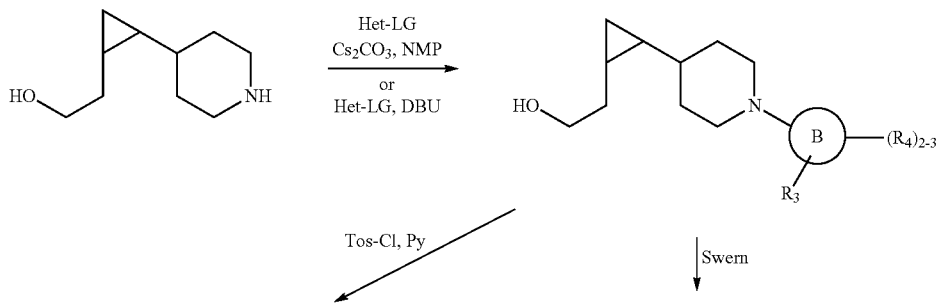

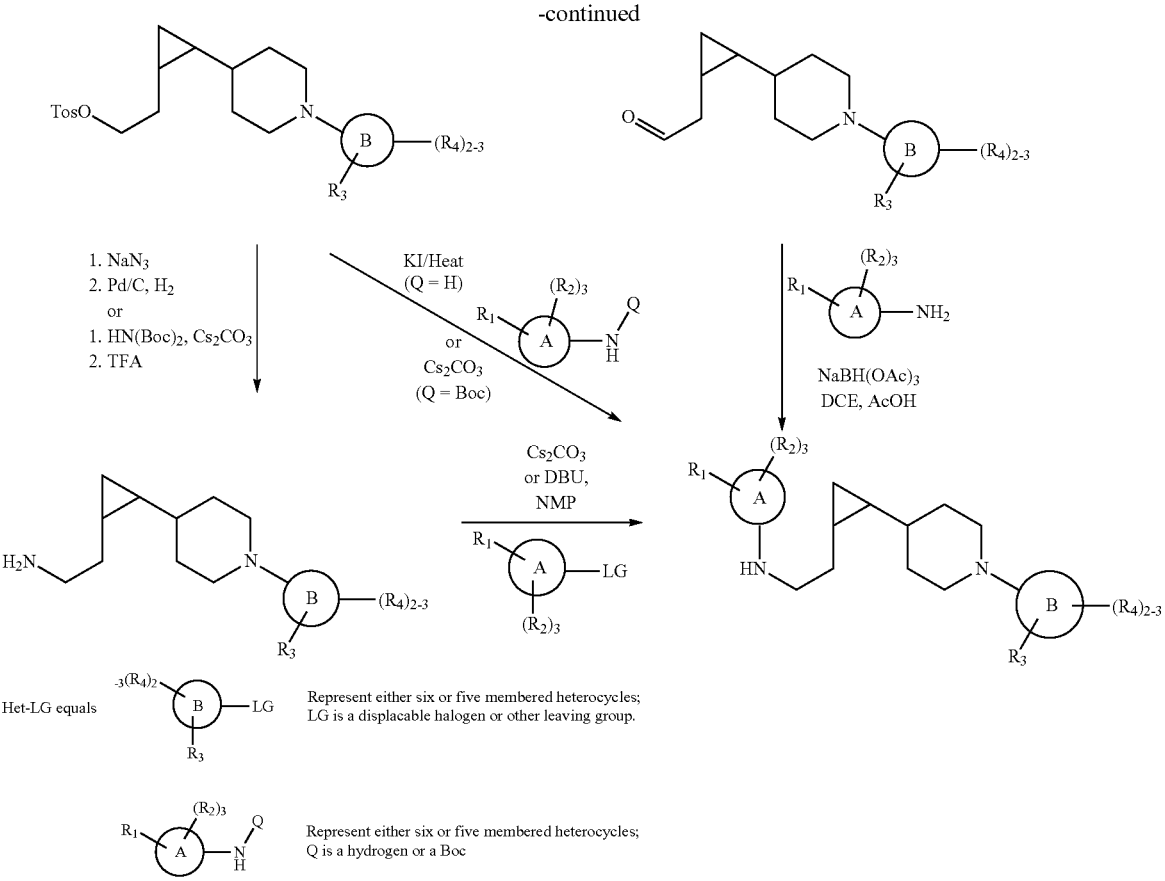
The order of introduction of the aryl amine and piperidine N substituents is easily inverted by use of nitrogen protecting groups such as Boc, FMOC, CBZ or other readily removed PG. Optional orthogonal protection of the aryl amine, followed by removal of the piperidine nitrogen protecting group generates a coupling partner for further elaboration.
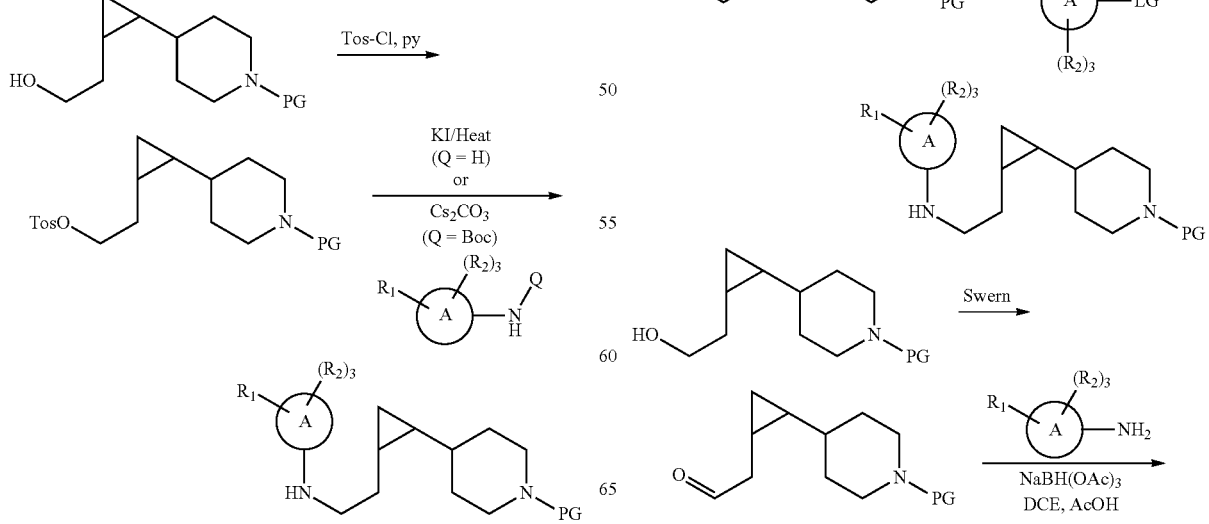

-continued

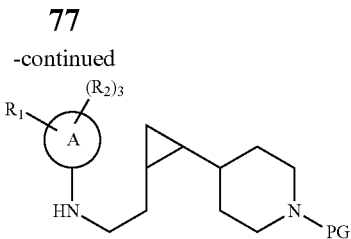

A particularly useful synthetic method for the mild final elaboration of the piperidine N substituent is the Buchwald coupling, as outlined in Scheme 3b and described in several literature reviews. (See for example B. Schlummer, U. Scholtz *Adv. Synth. Catal.* 2004, 346, 1599-1626.)

SCHEME 3b

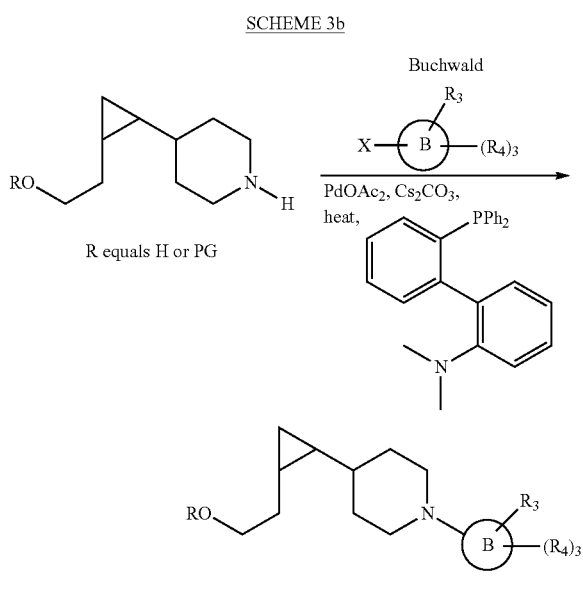

R equals H or PG

For some substitution patterns, it is more expedient to introduce the piperidine N substituent by de novo ring synthesis. The well known pyrimidine synthesis shown in Scheme 5 is one example of a broad variety of such methods.

SCHEME 5

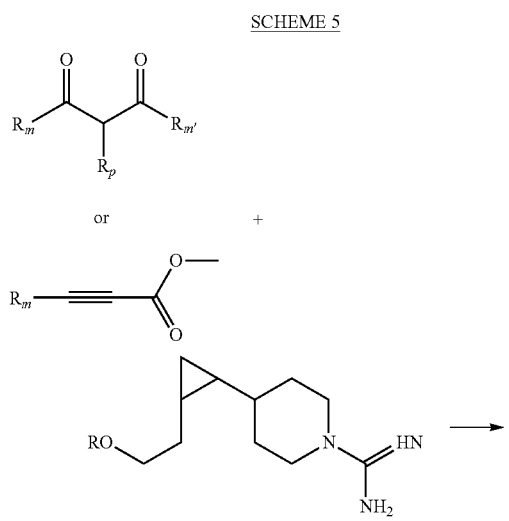

-continued

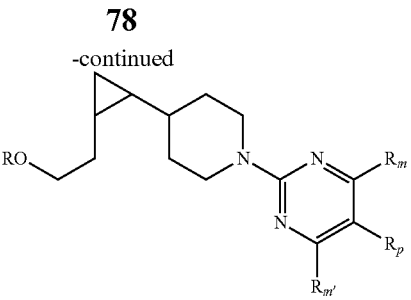

The meta and para substituents; $R_m$, $R_p$ and $R_{m'}$ are selected from $R_3$ and $R_4$
R is H or PG When the N-Aryl or N-heteroaryl residue is substituted with an X group (where X=Cl, Br, I or OTf) it is possible to further functionalize the residue utilizing iron or palladium organometallic mediated coupling reactions. Methods with extraordinarily broad applicability are metal mediated couplings outlined in Scheme 6.

SCHEME 6

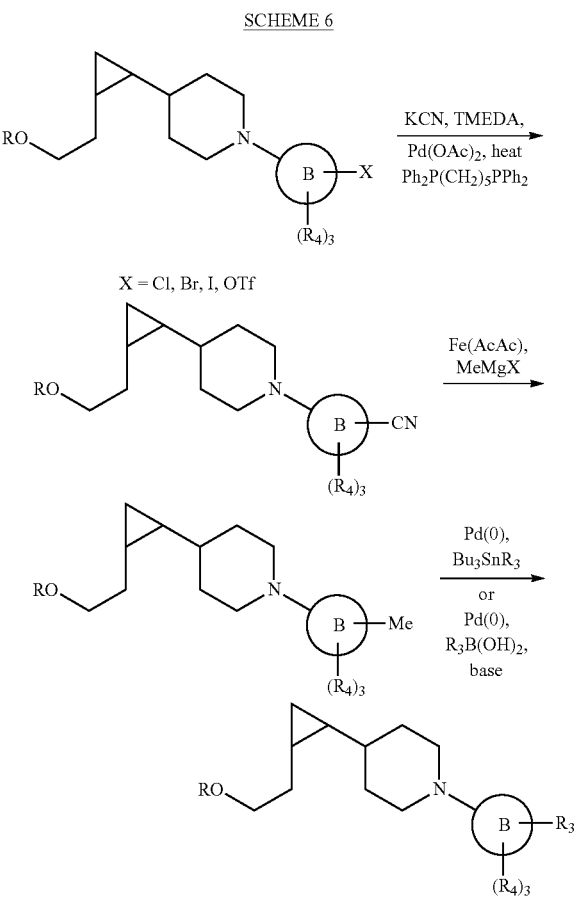

i and j vary from 0-2
R is H or PG

Solvents specified as "dry" or "anhydrous" may be commercial anhydrous solvent or solvent distilled from the appropriate drying agent under inert gas. (See *Purification of Laboratory Chemicals* D. D. Perrin, Elsevier Science.) Cyclopropanation reactions are run under rigorous exclusion of air in distilled solvent. Note the exotherm warning reported by A. B. Charette, et al in *JACS* 120, 46, 11943-11952, page 11945.

Many examples are prepared as the racemic mixture and separated by chromatography on chiral stationary phase. Several commercially available stationary phases are suitable for this purpose. Commercial Chiralpak IA 4.6×250 mm, 5µ columns are typically used for analytical work and semi-prep Chiralpak IA columns (20×250 mm, 5µ) for preparative separations. Heptane alcohol mixtures are typically used to elute the enantiomers.

PREPARATIVE EXAMPLE 1

Preparation of: 2-{(1S,2R)-2-[1-(5-chloropyrimidin-2-yl)piperidin-4-yl]cyclopropyl}ethanol Step 1 Preparation of tert-butyl 4-[(4R)-5-(benzyloxy)-4-hydroxypent-1-yn-1-yl]piperidine-1-carboxylate

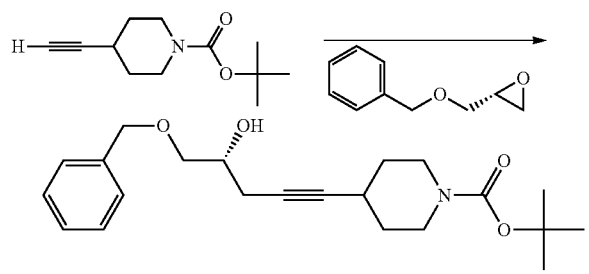

Commercially available tert-butyl 4-ethynylpiperidine-1-carboxylate was dissolved in 40 ml of THF and cooled to −78° C. forming a white slurry. Titrated n-BuLi (2.2 M in hexanes, 23.9 ml, 52.6 mmol) was added drop wise with stirring. The clear colorless solution was stirred at −78° C. for 5 minutes. A solution of the R-(+) benzyl glycidyl epoxide (8.63 g, 52.6 mmol) in THF (20 ml) was added drop wise. BF₃ etherate (8.43 g, 59.7 mmol) was then added drop wise with a syringe and the solution stirred at −78° C. for 1 hour. Saturated aqueous NH₄Cl was added (100 ml), the mixture warmed to RT, diluted with water to dissolve any remaining solids, and extracted with iPrOAc (3×100 ml). The organic fractions were combined, washed with brine, dried over MgSO₄, filtered and stripped. Crude product was purified by chromatography on SiO₂ eluting with 30% EtOAc:Hexanes. The alcohol was repurified by chromatography on a C18 reversed phase column (12-100% water:acetonitrile 0.1% TFA as two runs.). Product containing fractions were combined, reduced in volume by approximately 50%, made basic by addition of saturated aqueous NaHCO₃, water was added to dissolve some white solids, and the mixture extracted with iPrOAc (3×100). The organic fractions were combined, washed with brine, dried over MgSO₄, filtered, and stripped to give the titled compound.

Step 2 Preparation of tert-butyl 4-[(1Z,4R)-5-(benzyloxy)-4-hydroxypent-1-en-1-yl]piperidine-1-carboxylate

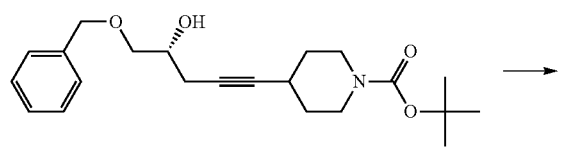

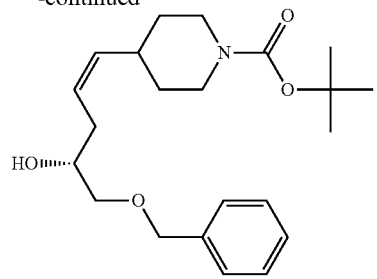

The alcohol from step 1 of this example (9.1 g, 24.4 mmol) was dissolved in EtOAc (100 ml) and quinoline (0.48 ml, 4.03 mmol) was added. Lindlar's catalyst (1.04 g) was added and the vessel evacuated and refilled three times with H₂. The slurry was stirred under a H₂ atmosphere for 40 min. The starting material was completely consumed. The mixture was filtered through CELITE and rinsed with EtOAc (4×50 ml). The volume of EtOAc was reduced ~80% in vacuum. The remaining solution was diluted with ether (100 ml) and washed with 2N HCl (100 ml). The aqueous fraction was re-extracted with ether (2×50 ml), organics combined and washed with 15 ml 2 N HCl. The organic fraction was washed with saturated aqueous NaHCO₃, brine, dried over MgSO₄, filtered, and stripped. The resulting oil was purified by chromatography on SiO₂ 30% eluting with EtOAc:Hexanes to give the titled compound.

Step 3: Preparation of tert-butyl 4-{(1R,2S)-2-[(2R)-3-(benzyloxy)-2-hydroxypropyl]cyclopropyl}piperidine-1-carboxylate

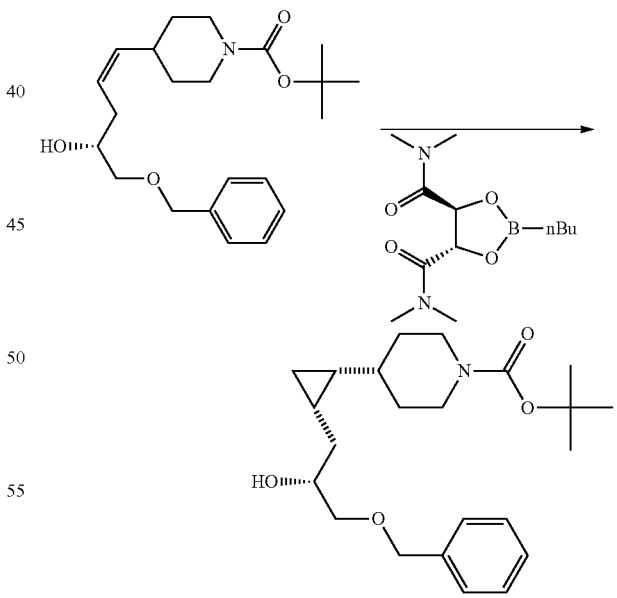

Dichloromethane stabilized with EtOH was distilled from CaH₂ under N₂ and sparged with N₂ to maintain oxygen free solvents.

A 500 ml 3N round bottom flask was equipped with an addition funnel topped with a 3 way stopcock and internal thermal couple. The apparatus was evacuated and backfilled with N₂ 4 times. To this degassed vessel was added 20 mL DCM, Diethyl Ether (5.06 g, transferred by weight) and a solution of Et$_2$Zn (8.43 g, 68.2 mmol, in 30 ml DCM) under a N$_2$ atmosphere. The solution was cooled to −20° C. and a solution of CH$_2$I$_2$ (36.5 g, 136 mmol, in 20 ml DCM) was added drop wise. The temperature is monitored with an internal temperature probe. The rate of addition was altered to maintain a constant −20° C. internal temperature. A fine precipitate forms after the addition is ~80% complete. The mixture was stirred for 10 minutes.

A solution of the commercially available (S,S) dioxaborolane ligand (7.37 g, 27.3 mmol) in DCM (20 mL) was added. The mixture was stirred for 10 minutes. The precipitate dissolved yielding a clear solution. A solution of the alkene from step 2 of this example (8.53 g, 22.7 mmol) in DCM (20 mL) was added. The solution was warmed to 0° C. and stirred for 24 hours. The solution remained clear after stirring for 24 hours. The reaction was quenched after 24 hr by addition of 50 ml of saturated aqueous NH$_4$Cl. The mixture was placed in a separatory funnel, 250 ml DCM and 200 ml 10% HCl (aq) added, shaken, and the layers separated. The aqueous layer was re-extracted with DCM (2×150 ml), the organic layers combined, transferred to a Morton flask. 2N NaOH (300 ml) and 50 ml of 30% H$_2$O$_2$ were added. The biphasic solution was stirred vigorously for 12 hours. The layers were separated and the aqueous phase was re-extracted with DCM (2×150 ml), the organic phases were combined, washed with 10% HCl (aq, 250 ml), 1N Na$_2$S$_2$O$_3$ (250 ml), saturated NaHCO$_3$ (250 ml), brine (250 ml), dried over MgSO$_4$, filtered and stripped. The material was purified by chromatography on SiO$_2$ eluting with 30% EtOAc: Hexanes. The desired product is obtained as a mixture with the minor diastereomer and the residual starting material. The desired diastereomer was isolated by chromatography on Chiralpak IA stationary phase to give the titled compound. The minor diastereomer was also isolated by this method.

Step 4 Preparation of tert-butyl 4-[(1R,2S)-2-(2-hydroxyethyl)cyclopropyl]piperidine-1-carboxylate

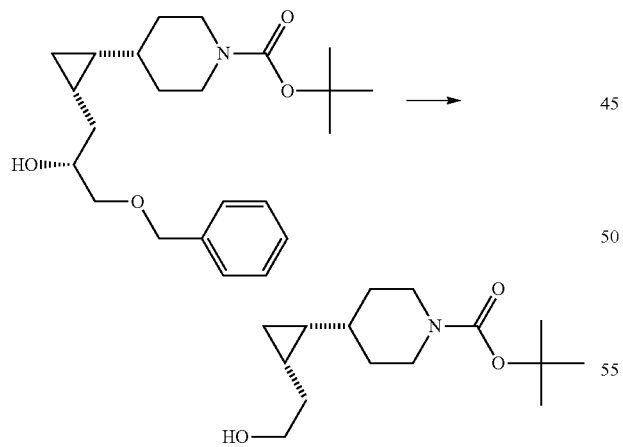

The tert-butyl 4-{(1R,2S)-2-[(2R)-3-(benzyloxy)-2-hydroxypropyl]cyclopropyl}piperidine-1-carboxylate from step 3 of this example (4.3 g, 11 mmol) was transferred to a Parr shaker pressure tube in 55 ml 1:1 EtOAc/Ethanol with 0.88 mgs Aldrich palladium hydroxide (20% wt on carbon-Degussa type E101). The mixture was shaken at 50 psi (345 kPa) hydrogen on a Parr shaker. HPLC check at 30 min. indicated complete conversion. The product was filtered through CELITE (which is diatomaceous earth), washed with ethanol, and reduced to an oil in vacuum.

The crude debenzylation product was dissolved in CH$_2$Cl$_2$ (56 ml) and cooled in ice. Sodium periodate (4.77 g, 22.3 mmol) was dissolved in water (56 ml) and added slowly drop wise. The milky mixture was stirred vigorously at 0° C. HPLC indicated complete cleavage at 30 min. at 0° C. The reaction mixture was diluted with brine and CH$_2$Cl$_2$. The mixture was extracted three times with CH$_2$Cl$_2$, dried over MgSO$_4$ and reduced in vacuum.

The crude aldehyde was redissolved in EtOH (56 ml), sodium borohydride (0.422 g, 11.2 mmol) was added as a solid and the mixture stirred at RT. The reduction is complete in 30 min. Saturated aqueous NH$_4$Cl (70 ml) was added to quench, and the mixture reduced to a paste in vacuum. The result was diluted with water (350 ml), and iPrOAc. The mixture was extracted with iPrOAc (3×), washed with brine, dried over MgSO$_4$, filtered and reduced in vacuum. The crude product was purified by chromatography on SiO$_2$ eluting with 40% EtOAc: Hexanes to give the titled compound.

Step 5, Preparation of 2,5-dichloropyrimidine

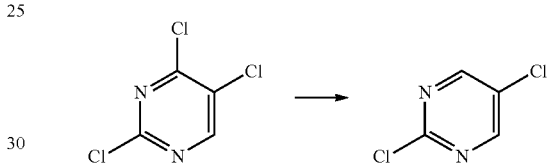

2,4,5-Trichloropyrimidine (25 g, 136 mmol) and zinc (26.7 g, 409 mmol, granular) were combined and THF (100 ml) added. The slurry was stirred at RT, glacial acetic acid was added (11.7 ml, 204 mmol) and the mixture heated at reflux for 2 hours. The mixture was cooled to RT, diluted with DCM (100 ml) and filtered through CELITE. The solution was then concentrated in vacuum. The crude material was dissolved in DCM (100 ml), saturated NaHCO$_3$ was added in small portions and shaken until the pH of the aqueous phase was 8. Then the pH was adjusted to 10 using 1N NaOH (aq), shaken and the layers separated. The organic fraction was dried over MgSO$_4$, filtered, and the volatiles removed in vacuum. The material was purified by chromatography on SiO$_2$ eluting with 2% EtOAc: Hexanes to give the titled compound.

Step 6: 2-{(1S,2R)-2-[1-(5-chloropyrimidin-2-yl)piperidin-4-yl]cyclopropyl}ethanol

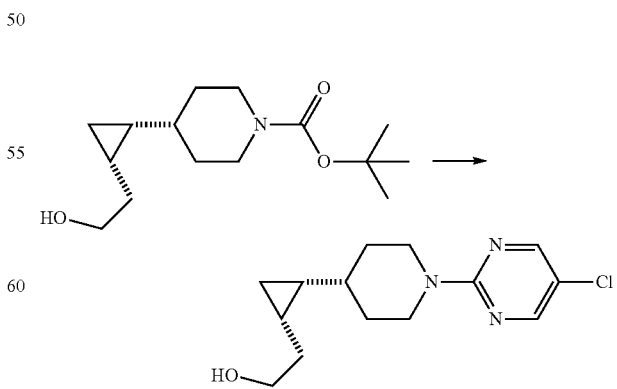

tert-butyl 4-[(1R,2S)-2-(2-hydroxyethyl)cyclopropyl]piperidine-1-carboxylate from step 4 of this example (1.07 g, 3.95 mmol) was dissolved in DCM (20 ml) and cooled to 0° C. Excess TFA (20 ml) was added drop wise and the solution was stirred at 0° C. for 30 minutes. The volatiles were removed under vacuum. Residual TFA was further removed by stripping twice from DCM followed by drying in vacuum. The resulting material was transferred to a pear-shaped flask in DCM and the volatiles removed in vacuum.

The crude piperidine was dissolved in DMF (9 ml, 0.44 M) with the dichloropyrimidine from step 5 of this example (0.59 g, 3.95 mmol) and cesium carbonate (7.08 g, 21.7 mmol, 5.5 eq) was added. The mixture was stirred at RT for 6.0 hrs. The mixture was poured into 150 ml water and extracted with iPrOAc (3×100 ml). The organic phases were washed with brine, dried over Na$_2$SO$_4$, filtered and stripped. Crude material was purified by column chromatography on SiO$_2$ eluting with 40% EtOAc: Hexanes to give the titled compound. LRMS calc: 281.1; obs: 282.2 (M+1).

PREPARATIVE EXAMPLE 1b

Preparation of rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

Step. 1. Preparation of tert-Butyl 4-[(1Z)-4-(benzyloxy)but-1-en-1-yl]piperidine-1-carboxylate

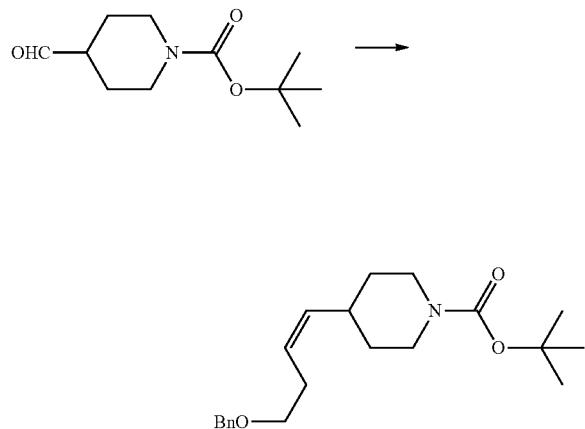

(3-Benzyloxypropyl)triphenylphosphonium bromide (2.88 g, 5.86 mmol) was suspended in 15 mL THF and cooled to 0° C. Sodium bis(trimethylsily)amide (1M in THF, 5.63 mL, 5.63 mmol) was added drop wise. The mixture turned deep orange. tert-Butyl 4-formylpiperidine-1-carboxylate (1 g, 4.69 mmol) in 3 mL THF was added after 5 minutes. Color faded to slight yellow. The reaction was stirred at room temperature for 1.5 hours, before quenching with saturated aqueous ammonium chloride solution. The aqueous layer was extracted twice with ethyl acetate. The organic layers were combined, washed with water and brine, dried over sodium sulfate, filtered, concentrated and purified by passing through a 40 gram Biotage™ silica gel cartridge using 20% EtOAc/hexanes to afford the product as colorless oil. NMR integration indicated >20:1 Z/E selectivity. LRMS calc: 345.2; obs: 346.5 (M+1).

Step 2. rac-tert-butyl 4-{2-[2-(benzyloxy)ethyl]cyclopropyl}piperidine-1-carboxylate, i.e. (tert-butyl 4-{(1S,2R)-2-[2-(benzyloxy)ethyl]cyclopropyl}piperidine-1-carboxylate and tert-butyl 4-{(1R,2S)-2-[2-(benzyloxy)ethyl]cyclopropyl}piperidine-1-carboxylate)

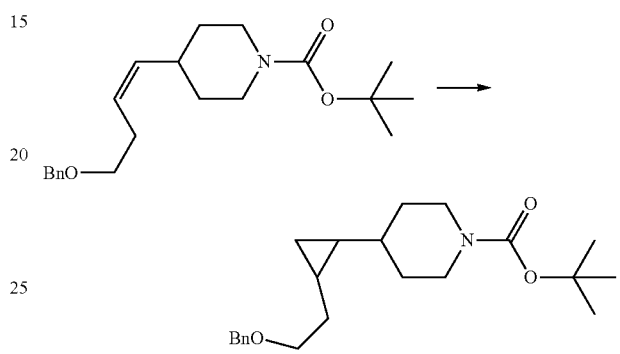

Dichloroethane (5 mL) was degassed and purged with argon three times before diethylzinc solution (1M in hexanes, 1.74 mL, 1.74 mmol) was added. The solution was cooled to −20° C. Chloroiodomethane (613 mg, 3.47 mmol) was added drop wise while maintaining internal temperature below −15° C. After stirring for 10 minutes at −20° C., tert-butyl 4-[(1Z)-4-(benzyloxy)but-1-en-1-yl]piperidine-1-carboxylate (from step 1, this Example 200 mg, 0.579 mmol) in degassed dichloroethane (1 mL) was added drop wise. The reaction was stirred at −20° for 10 minutes before slowly warming to RT. The reaction mixture was cooled to −10° C. after 1 hour. A 1:4 mixture of saturated aqueous ammonium chloride and aqueous ammonium hydroxide (28% w/w) was slowly introduced to quench excess reagents. The mixture was stirred at room temperature for 3 hours. The aqueous layer was separated and extracted twice with dichloromethane. The combined organic layers were washed with brine, dried over sodium sulfate, concentrated and purified by column chromatography eluting with 25% EtOAc/hexanes to give the product as colorless oil. LRMS calc: 359.25; obs: 360.5 (M+1).

Step 3. rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

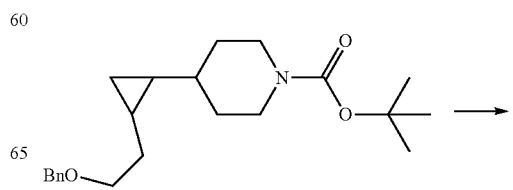

-continued

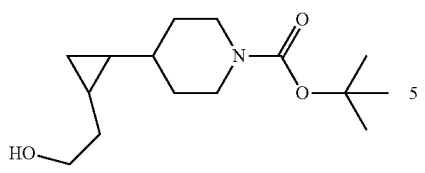

Racemic-cis tert-butyl 4-{2-[2-(benzyloxy)ethyl] cyclopropyl}piperidine-1-carboxylate from step 2 (140 mg, 0.39 mmol) was dissolved in 5 mL ethyl acetate and ethanol (1:1). The solution was degassed and purged with nitrogen 3 times, before palladium hydroxide (20% on carbon, 54.6 mg, 0.08 mmol) was added. The mixture was degassed and purged with hydrogen three times. The reaction was stirred under a hydrogen balloon at room temperature for 1 hour and filtered through a small plug of silica gel to remove catalyst. The silica gel plug was thoroughly washed with acetone. The eluent was concentrated to give the crude product, which was used without further purification. LRMS calc: 269.2; obs: 270.2 (M+1).

PREPARATIVE EXAMPLE 2

Preparation of rac-trans-2-{2-[1-(5-chloropyrimidin-2-yl)piperidin-4-yl]cyclopropyl}ethanol Step 1: tert-Butyl 4-[(1E)-3-methoxy-3-oxoprop-1-en-1-yl]piperidine-1-carboxylate

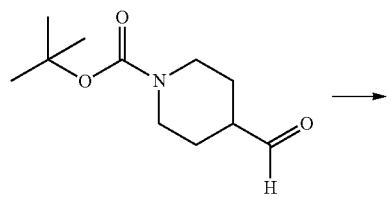

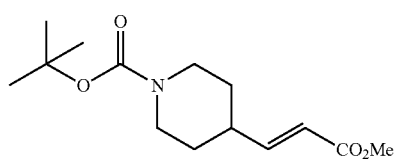

Lithium chloride (1.013 gram, 1.23 eq.) was suspended in 100 mL HPLC grade acetonitrile. Methyl (diethoxyphosphoryl) acetate (4.33 gram, 1.06 eq.) was added slowly at room temperature, followed by DBU (3.14 gram, 1.06 eq.) and the indicated commercially available aldehyde (4.14 gram, 1 eq.) in acetonitrile (10 mL). The mixture was stirred at room temperature for 3 hours. Excess solvent was removed in vacuum. The residue was diluted with water (100 mL) and was extracted with ether (50 mL×3). The combined organic layers were dried over sodium sulfate, filtered, and concentrated to give the crude ester as pale yellow oil, which was used in the next step without further purification.

Step 2: rac-trans-tert-Butyl 4-[(1E)-3-hydroxyprop-1-en-1-yl]piperidine-1-carboxylate

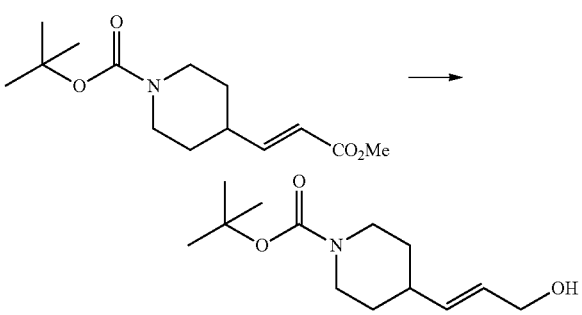

1 M DiBAl-H in dichloromethane (42 mL, 2.2 eq.) was added slowly, via an addition funnel, over 20 min to a well stirred solution of the α,β-unsaturated ester from step 1 of this example (5.14 gram, 1 eq.) in anhydrous DCM (100 mL) under argon atmosphere at −78° C. The resulting solution was warmed to 0° C. after completion of addition and was kept at that temperature for 30 min. The reaction was cooled back to −78° C. and 4 mL MeOH was added slowly to quench the excess DiBAl-H. The cold solution was further stirred at −78° C. for 10 min before pouring into 150 mL saturated aqueous Rochelle (sodium potassium tartrate) salts solution. The mixture was vigorously stirred at room temperature for 3 hours until it turned clear. The organic layer was separated, dried over sodium sulfate, filtered and concentrated in vacuum. The residue was further purified by column chromatography using acetone/hexanes (20%, isocratic) to give the desired product as colorless oil.

Step 3: rac-trans-tert-Butyl 4-[(1E)-3-(benzyloxy) prop-1-en-1-yl]piperidine-1-carboxylate

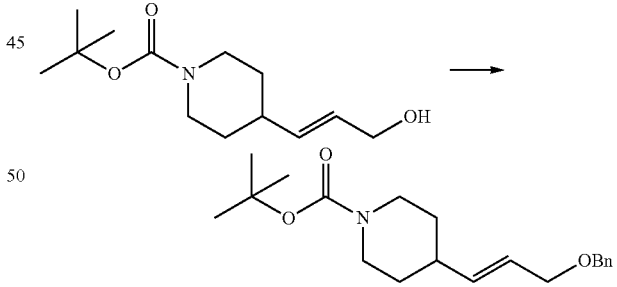

Sodium hydride (60% in mineral oil, 2.73 g, 1.1 eq.) was suspended in anhydrous DMF (180 mL) and cooled to 0° C. The allylic alcohol from step 2 of this example (15 g, 1 eq.) in anhydrous DMF (20 mL) was added slowly. The mixture was stirred at room temperature for 15 min under nitrogen atmosphere. Benzyl bromide (8.13 mL, 1.1 eq.) was then added drop wise. The mixture was stirred at room temperature for 2 hours. The reaction was diluted with 300 mL water and 200 mL EtOAc. The aqueous layer was separated and extracted twice using EtOAc (50 mL×2). The combined organic layers were dried over sodium sulfate, concentrated and purified by column chromatography eluting with EtOAc/hexanes (15%, isocratic) to give the desired benzyl ether as colorless oil.

Step 4: rac trans tert-Butyl 4-{2-[(benzyloxy)methyl]
cyclopropyl}piperidine-1-carboxylate, i.e. tert-butyl
4-{(1S,2R)-2-[(benzyloxy)methyl]cyclopropyl} piperidine-1-carboxylate and tert-butyl 4-{(1R,2S)-2-
[(benzyloxy)methyl]cyclopropyl}-piperidine-1-carboxylate)

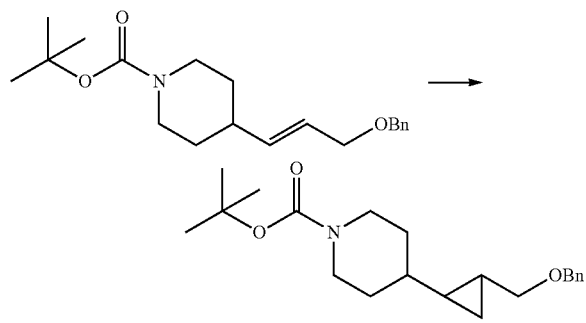

Anhydrous dichloroethane (130 mL) in a 500 mL round bottom flask was degassed and backfilled with argon three times. Diethylzinc (1 M in DCM, 87 mL, 5 eq.) was added rapidly via a syringe under argon. The solution was cooled to –18° C. Chloroiodomethane (12.61 mL, 10 eq.) was added, via a syringe, at a rate such that the internal temperature remained below –10° C. The reaction mixture was stirred at –18° C. for 10 min. A white precipitate was observed. The benzyl protected allylic alcohol from step 3 of this example (6 g, 1 eq.) in anhydrous DCE (30 mL) was added slowly while maintaining internal temperature below –5° C. The reaction was stirred at –18° C. and was monitored by LC-MS. The reaction generally finished within 10-30 min. Upon completion the reaction was quenched, while cold, with 100 mL aqueous saturated ammonium chloride solution and 50 mL 28% aqueous ammonium hydroxide. The mixture was warmed to room temperature and stirred vigorously until both phases became clear. The organic phase was separated, dried over sodium sulfate, concentrated and purified by column chromatography eluting with EtOAc/hexanes (15%, isocratic) to give the product as a colorless oil.

Step 5: rac trans tert-Butyl 4-[2-(hydroxymethyl)
cyclopropyl]piperidine-1-carboxylate, i.e. tert-butyl
4-[(1S,2R)-2-(hydroxymethyl)cyclopropyl]piperidine-1-carboxylate and tert-butyl 4-[(1R,2S)-2-(hydroxymethyl)cyclopropyl]piperidine-1-carboxylate

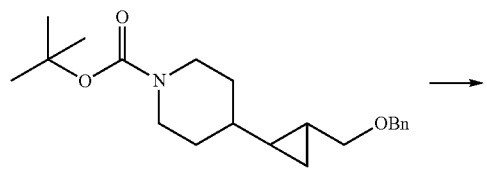

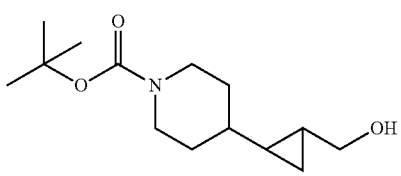

The benzyl protected hydroxyethylcyclopropane from step 4 of this example (6 g, 1 eq.) was dissolved in a mixture of HPLC grade EtOAc (75 mL) and ethanol (75 mL). The solution was degassed and backfilled with nitrogen, before Pd(OH)$_2$ (20w % on carbon, 2.34 g, 0.2 eq.) was added. The reaction vessel was degassed and backfill with hydrogen three times. The reaction mixture was rigorously stirred under a 1 L hydrogen balloon and was monitored by LC-MS. The deprotection is typically complete within 2 hours. The mixture was then filtered through a plug of silica gel (100 g) and was washed thoroughly with 50% EtOAc/hexanes (1 L). Concentration gave the cyclopropanol as colorless oil.

Step 6: trans rac-tert-Butyl 4-(2-formylcyclopropyl)
piperidine-1-carboxylate, i.e. tert-butyl 4-[(1S,2R)-2-
formylcyclopropyl]piperidine-1-carboxylate and
tert-butyl 4-[(1R,2S)-2-formylcyclopropyl]piperidine-1-carboxylate

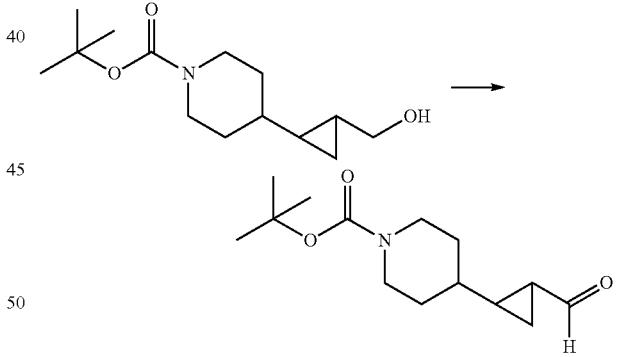

A mixture of the hydroxyethylcyclopropane from step 5 of this example (9 g, 1 eq.), powdered 4Å activated molecular sieves (18 g) and N-methylmorpholine oxide (6.19 g, 1.5 eq.) was stirred in anhydrous DCM (200 mL) under nitrogen for 15 min at room temperature. TPAP (1.24 g, 0.1 eq.) was added in one portion. The reaction was exothermic and ice-bath was used occasionally to maintain internal temperature around room temperature. The mixture was stirred at room temperature for 1 hour. The reaction was diluted with 500 mL ether and stirred for 10 min. The mixture was filtered through a plug of silica gel (200 g) which was washed thoroughly with 50% acetone/hexanes (2 L). Concentration afforded the aldehyde as colorless oil.

Step 7: trans rac trans tert-Butyl 4-(2-vinylcyclopropyl)piperidine-1-carboxylate, i.e. tert-butyl 4-[(1S,2S)-2-vinylcyclopropyl]piperidine-1-carboxylate and tert-butyl 4-[(1R,2R)-2-vinylcyclopropyl]piperidine-1-carboxylate

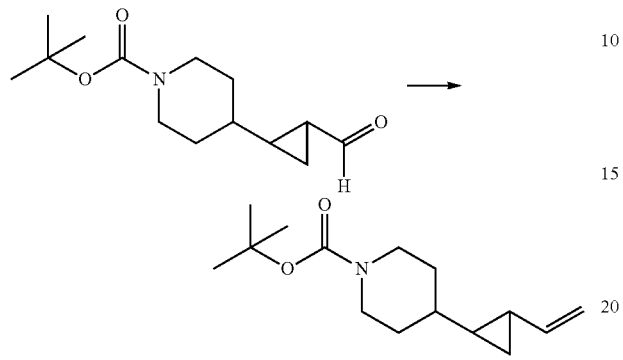

Triphenylmethyl phosphonium iodide (1.92 g, 1.2 eq.) was suspended in anhydrous THF (7 mL) under nitrogen and cooled to −78° C. n-BuLi (1.6 M, 2.84 mL, 1.15 eq.) was added slowly and the mixture was stirred for 15 min. The suspension turned yellow. The aldehyde from step 6 of this example (1 g, 1 eq.) in anhydrous THF (3 mL) was added slowly. The reaction was warmed to room temperature and stirred for 30 min. Saturated aqueous ammonium chloride was added. The aqueous layer was extracted twice with EtOAc. The combined extracts were dried over sodium sulfate, concentrated and purified by column chromatography eluting with EtOAc/hexanes (15%, isocratic) to give the desired olefin as colorless oil.

Step 8: rac-trans-tert-butyl 4-[2-(2-hydroxyethyl)cyclopropyl]piperidine-1-carboxylate, i.e. tert-butyl 4-[(1R,2R)-2-(2-hydroxyethyl)cyclopropyl]piperidine-1-carboxylate and tert-butyl 4-[(1S,2S)-2-(2-hydroxyethyl)cyclopropyl]piperidine-1-carboxylate

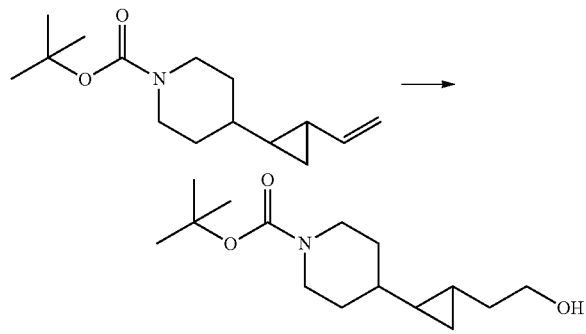

Borane dimethylsufide complex (1.0 M in THF, 0.7 mL, 0.5 eq.) was dissolved in anhydrous THF (2 mL) and cooled in 0° C. The olefin from step 7 of this example (350 mg, 1 eq.) in anhydrous THF (0.8 mL) was added slowly. The mixture was stirred at room temperature for 2 hours. Aqueous sodium hydroxide solution (5 M, 1.5 mL) was added very slowly. Significant gas evolution was observed. The reaction vessel was cooled using an ice-bath as necessary. Hydrogen peroxide solution (30%, 1.39 mL) was added slowly. The mixture was stirred at room temperature for 2 hours. Water (3 mL) was added. The mixture was extracted three times with EtOAc. The combined organic layers were washed with brine, dried over sodium sulfate, concentrated and purified by column chromatography using EtOAc/hexanes (40%, isocratic) to give the desired final product as colorless oil.

Step 9: Preparation of rac-trans-2-{2-[1-(5-chloropyrimidin-2-yl)piperidin-4-yl]cyclopropyl}ethanol

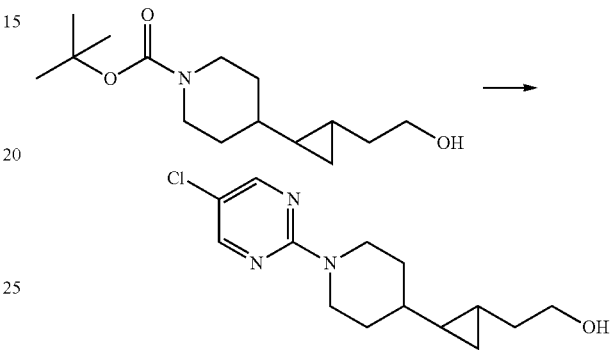

The title compound was prepared from trans rac-trans-tert-butyl 4-[2-(2-hydroxyethyl)cyclopropyl]piperidine-1-carboxylate prepared in step 8 of this example by a general procedure analogous to that reported in step 6, Example 1. Racemic: LRMS: 281.78; obs: 282.07 (M+1).

PREPARATIVE EXAMPLE 2b

F (Fast) and S (Slow)

Preparation of pure enantiomers; 2-{(1S,2S)-2-[1-(5-chloropyrimidin-2-yl)piperidin-4-yl]cyclopropyl}ethanol and 2-{(1R,2R)-2-[1-(5-chloropyrimidin-2-yl)piperidin-4-yl]cyclopropyl}ethanol

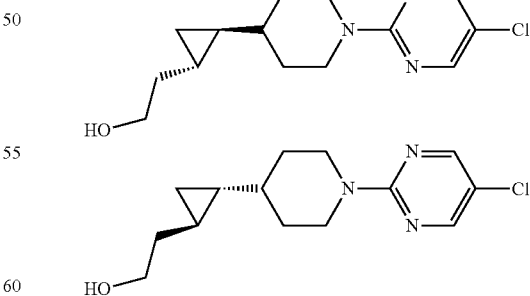

rac trans 2-{2-[1-(5-chloropyrimidin-2-yl)piperidin-4-yl]cyclopropyl}ethanol from step 9 Example 2 (650 mg) was dissolved in 7 mL methanol, The solution was subjected to HPLC separation on a semi-prep chiralpak AD column (20× 250 mm, 5 under isocratic elution with 15% ethanol/heptanes at 9 mL/min, 7 injections. The enantiomers were baseline separated. Retention time (analytical ChiralPak AD-H 4.6× 250 mm, 5μ under isocratic elution with 15% ethanol/heptanes at 0.75 mL/min)-2F (faster enantiomer): 61 F, T=9.72 min; 2S (slower enantiomer): 61S, T=14.31 min. Faster enantiomer LRMS: 281.78; obs: 282.08 (M÷1). Slower enantiomer LRMS: 281.78; obs: 282.08 (M+1).

PREPARATIVE EXAMPLE 3

Preparation of: {(1S,2R)-2-[1-(5-chloropyrimidin-2-yl)piperidin-4-yl]cyclopropyl}acetaldehyde

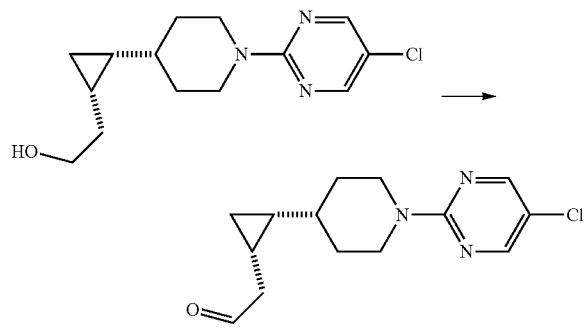

A flame dried flask was charged with DCM (20 ml) and oxalyl chloride (0.90 g, 0.62 mmol) under $N_2$. The vessel was cooled to −50° C. in an acetorntrile:dry ice bath. DMSO (1.1 g, 14.2 mmol) was added drop wise after which the solution was stirred for 2 minutes. A solution of 2-{(1S,2R)-2-[1-(5-chloropyrimidin-2-yl)piperidin-4-yl]cyclopropyl}ethanol from step 6 of Example 1 (1 g, 3.55 mmol) in DCM (15 ml) was added drop wise and the mixture was stirred for 15 minutes. TEA (2.88 g, 28.4 mmol) was added, the mixture stirred for 15 minutes at −50° C. and then allowed to warm to RT for 1 hour. Water (15 ml) was then added drop wise, the mixture diluted with an additional 50 ml water. The mixture was then place in a separatory funnel, shaken and the layers separated. The aqueous phase was extracted with DCM (2×35 ml), the organic fractions combined, washed with brine, dried over $Na_2SO_4$, filtered, and the volatiles removed in vacuum strip. The product was purified by chromatography on $SiO_2$ eluting with 30% acetone:hexanes. LRMS calc: 279.11; obs: 280.05 (M+1).

EXAMPLE 4

Preparation of: rac-cis-6-[(2-{2-[1-(5-chloropyrimidin-2-yl)piperidin-4-yl]cyclopropyl}ethyl)amino]-2-methylpyrimidine-4-carbonitrile Step 1: 6-chloro-N-(4-methoxybenzyl)-2-methylpyrimidin-4-amine

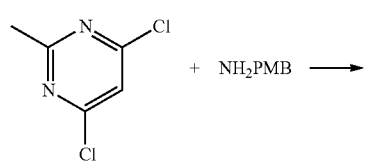

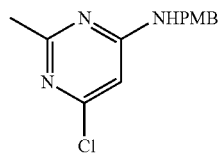

1-(4-methoxyphenyl)methanamine (1.51 g, 11 mmol) was added in DMF (15 mL), potassium hydroxide was added and stirred at room temperature for 10 minutes. The reaction was cooled to −2° C., 4,6-dichloro-2-methylpyrimidine (1.63 g, 10 mmol) in DMF (5 mL) was added drop-wise at a speed the internal temperature was controlled <0° C. After 30 minutes, the reaction was added ethyl acetate (50 mL), washed with brine (20 mL×2). The organic phase was dried by magnesium sulfate, filter, concentrated and purified by column chromatography through a 110 gram AnaLogix™ silica gel cartridge eluting with 30% ethyl acetate/hexanes to give the title compound as a pale yellow solid.

LRMS calc: 263.72; obs: 264.52 (M+1).

Step 2: 6-[(4-hydroxybenzyl)amino]-2-methylpyrimidine-4-carbonitrile

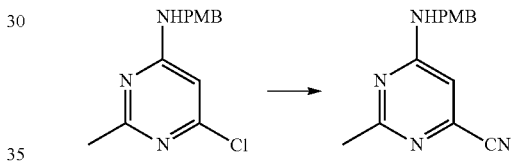

6-chloro-N-(4-methoxybenzyl)-2-methylpyrimidin-4-amine (500 mg, 01.90 mmol) from Step 1 from this example, palladium (II) trifluoroacetate (27.1 mg, 0.082 mmol), zinc dust (23.6 mg, 0.36 mmol), rac-2-(di-t-butylphosphino)-1,1-binaphthyl (66.5 mg, 0.17 mmol), zinc cyanide (125 mg, 1.1 mmol) was added dimethylacetamide (10 mL) in a flask (flame-dried) and evacuated and back-filled with $N_2$ (3×). The reaction was heated to 95° C. for 30 min, cooled to room temperature. Water (20 mL) was added, extracted with ethyl acetate (20 mL), second wash with brine (20 mL). The organic phase was dried by magnesium sulfate and filtered through silica gel pad (1 inch deep), concentrated and purified by column chromatography through a 40 gram RediSep Rf™ silica gel cartridge eluting with 18% ethyl acetate/hexanes to give the title compounds as a pale yellow oil.

LRMS calc: 254.29; obs: 255.52 (M+1).

Step 3: rac-cis-tert-butyl 4-[2-(2-iodoethyl)cyclopropyl]piperidine-1-carboxylate

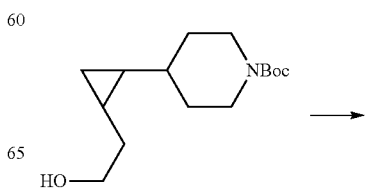

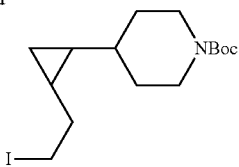

rac-cis-tert-butyl 4-[2-(2-hydroxyethyl)cyclopropyl]piperidine-1-carboxylate (100 mg, 0.37 mmol) from step 2 of this example was dissolved in dichloromethane (3.7 mL), triphenylphosphine (195 mg, 0.74 mmol), iodine (94 mg, 0.37 mmol) and imidazole (51 mg, 0.74 mmol) were added. After 20 minutes, diethyl ether (10 mL) was added, filtered through a silica gel pad (0.5 inch), concentrated and purified by column chromatography through a 24 gram AnaLogix™ silica gel cartridge eluting with 10% ethyl acetate/hexanes to give the title compound as a white solid.

LRMS calc: 379.28; obs: 379.98 (M+1), 323.96 (M−55).

Step 4: rac-cis-tert-butyl 4-(2-{2-[(6-cyano-2-methylpyrimidin-4-yl)(4-methoxybenzyl)amino]ethyl}cyclopropyl)piperidine-1-carboxylate

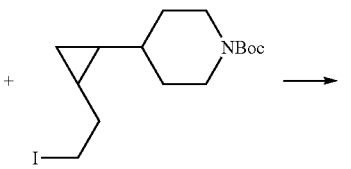

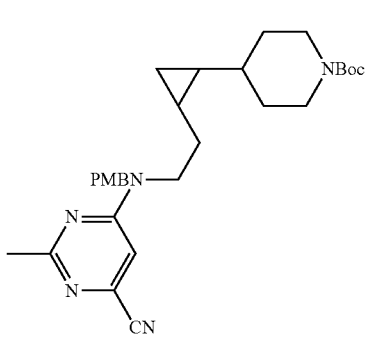

Rac-cis-tert-butyl 4-[2-(2-iodoethyl)cyclopropyl]piperidine-1-carboxylate (86 mg, 0.23 mmol) from Step 3 of this example and 6-[(4-hydroxybenzyl)amino]-2-methylpyrimidine-4-carbonitrile (63.4 mg, 0.25 mmol) from Step 2 of this example were dissolved in DMF (2.3 mL), sodium hydride (18 mg, 0.45 mmol) was added. After 10 minutes, the reaction was quenched with saturated ammonia chloride solution (5 mL), extracted with ethyl acetate (10 mL), second washed with brine (5 mL). The organic phase was dried by magnesium sulfate, filtered, concentrated and purified by preparative-TLC (Analtech Silica Gel GF 1500 µM, 20×20 cm) using 30% ethyl acetate/hexane to give the title compound as a white solid.

LRMS calc: 505.65; obs: 506.78 (M+1), 450.67 (M−55).

Step 5: rac-cis-6-[(2-{2-[1-(5-chloropyrimidin-2-yl)piperidin-4-yl]cyclopropyl}ethyl)amino]-2-methylpyrimidine-4-carbonitrile

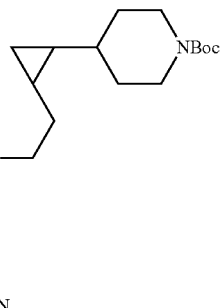

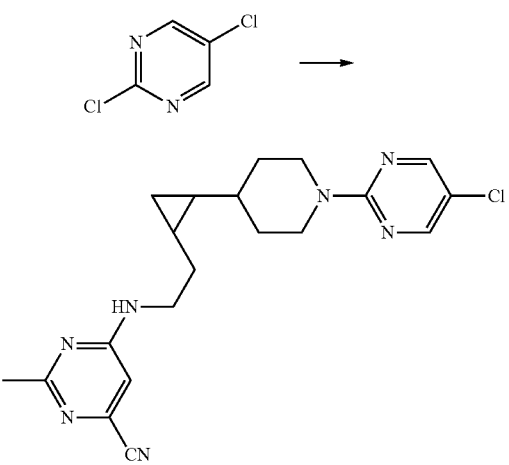

rac-cis-tert-butyl 4-(2-{2-[(6-cyano-2-methylpyrimidin-4-yl)(4-methoxybenzyl)amino]ethyl}cyclopropyl)piperidine-1-carboxylate (74 mg, 0.15 mmol) from Step 4 of this example was dissolved in trifluoroacetic acid (3 mL) at room temperature for 20 minutes. It was concentrated without heating and pumped overnight.

The crude amine was dissolved in NMP (0.7 mL), cesium carbonate (146 mg, 0.45 mmol) was added and stirred for 5 minutes at room temperature. 2,5-di-chloropyrimidine (24.6 mg, 0.16 mmol) from step 5, Example 1 was added and heated to 70° C. for 30 minutes. The reaction was cooled down to room temperature, ethyl acetate (1.0 mL) was added, washed with brine (5 mL×2). The organic phase was dried by magnesium sulfate, filter, concentrated and purified by column chromatography through a 24 gram AnaLogix™ silica gel cartridge eluting with 10% ethyl acetate/hexanes to compound with the PMB protection group as a white solid.

The solid was added in a microwave tube with neat trifluoroacetic acid (3 mL), and heated to 100° C. in microwave for 20 min. After cooling, the reaction was concentrated, ethyl acetate (10 mL) was added, washed with saturated sodium bicarbonate (5 mL×2). The organic phase was dried by magnesium sulfate, filter, concentrated and purified by preparative-TLC (Analtech Silica Gel GF 1500 µM, 20×20 cm) using 30% ethyl acetate/hexane to give the titled compound as a white solid.

LRMS calc: 397.90; obs: 398.58 (M+1).

EXAMPLE 5

Preparation of 6-[(2-{(1S,2S)-2-[1-(5-chloropyrimidin-2-yl)piperidin-4-yl]cyclopropyl}ethyl)amino]-2-methylpyrimidine-4-carbonitrile Step 1: 2-{(1S,2R)-2-[1-(5-chloropyrimidin-2-yl)piperidin-4-yl]cyclopropyl}ethyl 4-methylbenzenesulfonate

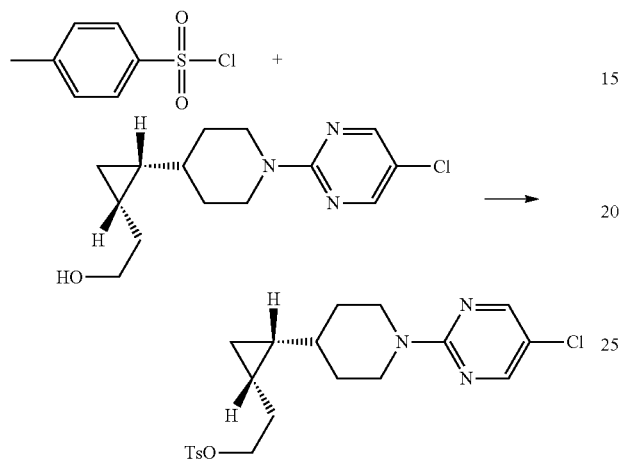

2-{(1S,2R)-2-[1-(5-chloropyrimidin-2-yl)piperidin-4-yl]cyclopropyl}ethanol (176 mg, 0.63 mmol) from. Step 6, Example 2 was dissolved in dichloromethane (3 mL), then added triethylamine (190 mg, 1.87 mmol), 4-dimethylaminopyridine (15.3 mg, 0.13 mmol), last tosylchloride (167 mg, 0.87 mmol), stirred under $N_2$ for 1.5 hours. The reaction solution was poured into ice water (10 mL), extracted with dichloromethane (10 mL×2). The organic phase was combined and dried by magnesium sulfate, filtered, then concentrated and purified by column chromatography through a 24 gram RediSep Rf™ silica gel cartridge eluting with 10% ethyl acetate/hexanes to give the title compound as a white solid.

LRMS calc: 435.97; obs: 436.07 (M+1).

Step 2: 2-{-4-[(1S,2S)-2-(2-azidoethyl)cyclopropyl]piperidin-1-yl}-5-chloropyrimidine

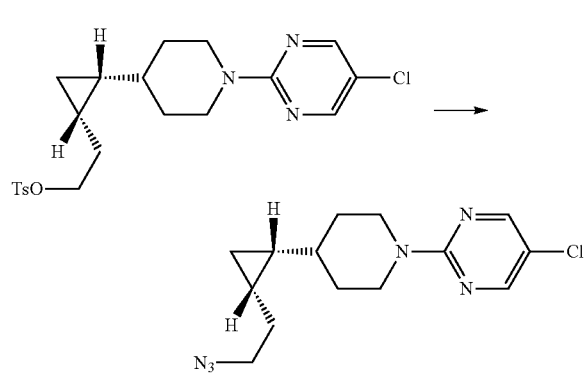

2-{(1S,2R)-2-[1-(5-chloropyrimidin-2-yl)piperidin-4-yl]cyclopropyl}ethyl 4-methylbenzenesulfonate (65 mg, 0.15 mmol) from step 1 of this example was dissolved in dioxane (1.2mL). Sodium azide (22.3 mg, 0.34 mmol) was added, then water (0.3 mL). The reaction was heated to 100° C. to reflux for 2 hours. The reaction was cooled to room temperature, water (10 mL) was added and extracted with EtOAc (10 mL×2). The combined organic phase was dried by magnesium sulfate, filter, concentrated and purified by column chromatography through a 12 gram RediSep Rf™ silica gel cartridge eluting with 5% ethyl acetate/hexanes to give the title compound as a white solid.

LRMS calc: 306.79; obs: 307.04 (M+1).

Step 3: 2-{(1S,2S)-2-[1-(5-chloropyrimidin-2-yl)piperidin-4-yl]cyclopropyl}ethanamine

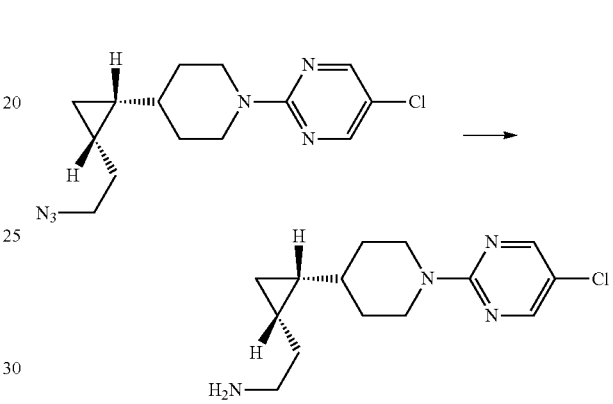

2-{4-[(1S,2S)-2-(2-azidoethyl)cyclopropyl]piperidin-1-yl}-5-chloropyrimidine (34 mg, 0.11 mmol) from step 2 of this example was dissolved in THF (1 mL), triphenylphosphine (58.1 mg, 0.22 mmol) was added, then water (0.085 mL). The reaction was run at room temperature for 1 hour, then 40° C. 1 hour. The reaction was cooled down to room temperature, concentrated to dryness and purified by column chromatography through a 12 gram RediSep Rf™ silica gel cartridge eluting with 10% methanol/dichloromethane to give the title compound as a white solid.

LRMS calc: 280.80; obs: 281.08 (M+1).

Step 4: Preparation of 6-chloro-2-methylpyrimidine-4-carbonitrile

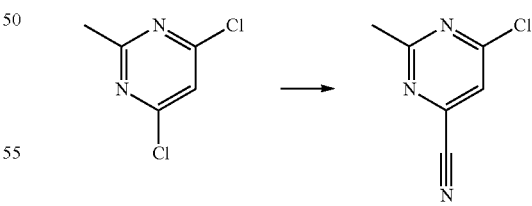

The 4,6-dichloro-2-methyl-pyrimidine (10 g, 60 mmol), palladium (II) trifluoroacetate (0.86 g, 2.6 mmol), zinc dust (65.3 g, 11.4 mmol), rac-2-(di-t-butylphosphino)-1,1-binaphthyl (2.1 g, 5.3 mmol), zinc cyanide (3.95 g, 33.7 mmol) and dimethyl acetamide (316 ml) were added to a 500 mL, flame-dried flask. The vessel was evacuated and back-filled with $N_2$ (3×). The mixture was stirred under $N_2$ for 30 min. at RT, then heated to 95° C. After 2.5 hours the mixture was diluted with EtOAc (300mL), and washed with water (300 mL×3). The organic fractions were combined, dried over MgSO₄, filtered, and the volatiles removed in vacuum. The residue was dissolved in EtOAc (100 mL), washed with water (50 ml), and the layers separated. The aqueous phase was then extracted with EtOAc (50 mL), the organic fractions combined, dried over MgSO₄, filtered, and the volatiles removed in vacuum. The crude mixture was purified by chromatography on silica gel (eluting 1:19 ethyl acetate:hexane) to yield the titled compound as a colorless oil. ¹H NMR (CD₃OD): 8.235 (s, 1H), 2.816 (s, 3H).

Step 5: 6-[(2-{(1S,2S)-2-[1-(5-chloropyrimidin-2-yl)piperidin-4-yl]cyclopropyl}ethyl)amino]-2-methylpyrimidine-4-carbonitrile

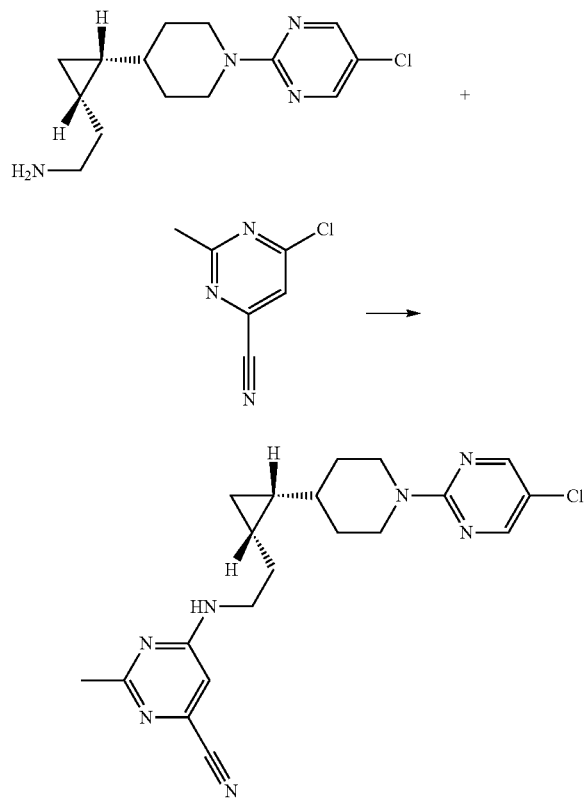

2-{(1S,2S)-2-[1-(5-chloropyrimidin-2-yl)piperidin-4-yl]cyclopropyl}ethanamine (29 mg, 0.10 mmol) from step 3 of this example was dissolved in DMF (0.4 mL), cesium carbonate (168 mg, 0.52 mmol) was added, stirred at room temperature for 10 minutes, then cooled down to 0° C. 6-chloro-2-methylpyrimidine-4-carbonitrile (17.5 mg, 0.114 mmol; from step 4 of this example) was added in DMF (0.1 mL) via syringe. Reaction was kept at 0° C. for 30 minutes, then warmed up to room temperature for 1 hour. Water (50 mL) was added, extracted with EtOAc (50 mL×2), second wash with Brine (20 mL). The combined organic phase was dried by magnesium sulfate, filter, concentrated and purified by column chromatography through a 40 gram RediSep Rf™ silica gel cartridge eluting with 17% acetone/hexanes to give the title compound as a pale yellow solid.

LRMS calc: 397.90; obs: 398.07 (M+1).

EXAMPLE 6

Preparation of N-(2-{(1S,2S)-2-[1-(5-chloropyrimidin-2-yl)piperidin-4-yl]cyclopropyl}ethyl)-5-(methylsulfonyl)pyridin-2-amine

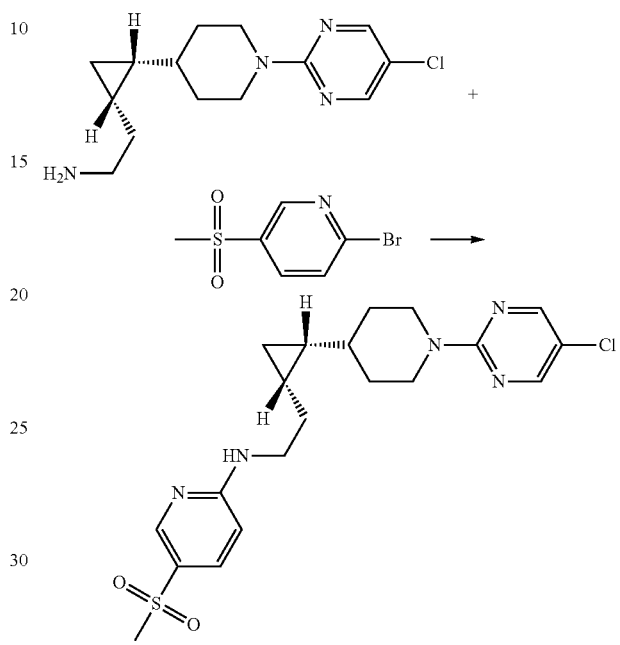

2-{(1S,2S)-2-[1-(5-chloropyrimidin-2-yl)piperidin-4-yl]cyclopropyl}ethanamine (35 mg, 0.125 mmol) from Example 5 step 3 was dissolved in DMF (0.62 mL), cesium carbonate (203 mg, 0.62 mmol) was added, stirred at room temperature for 10 minutes. 2-bromo-5-(methylsulfonyl)pyridine (32.4 mg, 0.137 mmol) was added. Reaction was run at room temperature for 1 hour, then heated to 50° C. for 5 hours. Water (10 mL) was added, extracted with EtOAc (10 mL×2), second wash with brine (10 mL). The organic phase was dried by magnesium sulfate, filter, concentrated and purified by preparative-TLC (Analtech Silica Gel GF 1500 μM, 20×20 cm) using 30% acetone/hexane to give the title compound as a white solid.

LRMS calc: 435.97; obs: 436.08 (M+1).

EXAMPLE 7

Preparation of N-(2-{(1S,2S)-2-[1-(5-chloropyrimidin-2-yl)piperidin-4-yl]cyclopropyl}ethyl)-4-(methylsulfonyl)aniline

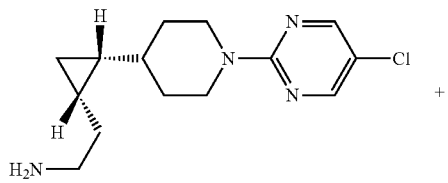

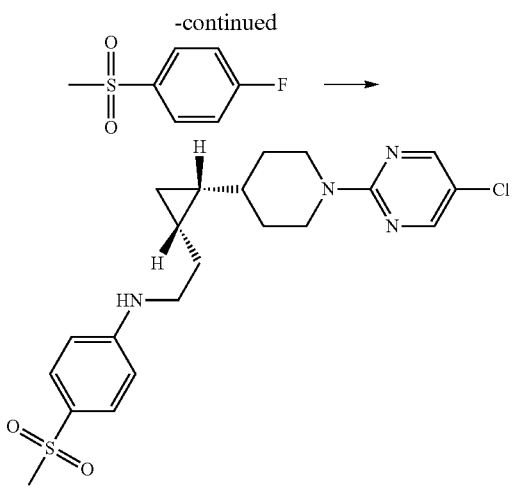

2-{(1S,2S)-2-[1-(5-chloropyrimidin-2-yl)piperidin-4-yl]cyclopropyl}ethanamine (30 mg, 0.11 mmol) from Example 5 step 3 was dissolved in NMP (0.21 mL), DBU (24.4 mg, 0.16 mmol) was added, stirred at room temperature for 5 minutes. 1-fluoro-4-(methylsulfonyl)benzene (22.3 mg, 0.13 mmol) was added. Reaction was heated to 110° C. for 17 hours. The reaction was cooled down to room temperature, water (10 mL) was added, extracted with EtOAc (10 mL×2), second wash with Brine (10 mL). The organic phase was dried by magnesium sulfate, filter, concentrated and purified by purified by column chromatography through a 12 gram RediSep Rf™ silica gel cartridge eluting with 30% acetone/hexanes to give the title compound as a white solid.

LRMS calc: 434.98; obs: 435.10 (M+1).

EXAMPLE 8

Preparation of N-(2-{(1S,2S)-2-[1-(5-chloropyrimidin-2-yl)piperidin-4-yl]cyclopropyl}ethyl)-5-(1H-1,2,3-triazol-1-yl)pyridin-2-amine

Step 1: 5-Azido-2-fluoropyridine

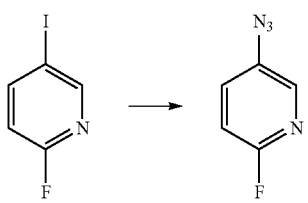 [SMILES: Fc1ccc(I)cn1 ; [N-]=[N+]=Nc1ccc(F)nc1]

2-Fluoro-5-iodopyridine (1.12 g, 5 mmol), sodium azide (390 mg, 6.00 mmol), copper(I) iodide (95 mg, 0.500 mmol) and L-ascorbic acid sodium salt (49.5 mg, 0.250 mmol) were added to a flame dried sealable reaction vessel. The vessel was evacuated and purged with nitrogen. Ethanol (7 mL) and water (3 ml) were added to the reaction vessel, which was then evacuated and purged again with nitrogen. N,N-Dimethylethylenediamine (80 μl, 0.750 mmol) was added to the vessel via microliter syringe. The top was screwed on and the reaction heated to 100° C.

A safety shield was placed in front of the reaction as a precaution. The reaction was monitored by TLC, which indicated consumption of starting material after 45 minutes. The reaction was diluted with water and extracted with ethyl acetate twice. The combined organics were washed three times with water and once with brine. The organic was dried over sodium sulfate, filtered and evaporated to give 630 mg of crude material, which contains azide, starting material, and another impurity. This was carried on to the next step without purification. ¹H NMR (CDCl3): δ 7.95 (d, 1H), 7.45 (m, 1H), 7.26 (s, CDCl3), 6.95 (dd, 1H).

Step 2: 5-(1H-1,2,3-triazol-1-yl)-2-fluoropyridine

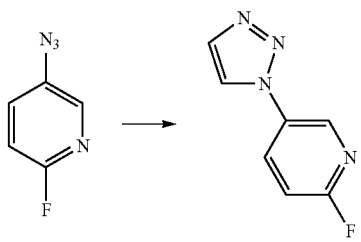 [SMILES: [N-]=[N+]=Nc1ccc(F)nc1 ; Fc1ccc(-n2ccnn2)cn1]

5-Azido-2-fluoropyridine (262 mg, 1.9 mmol) step 1 of this example and vinyl acetate (4.0 mL, 43 mmol) were mixed in a flame dried high pressure sealable vessel. The reaction vessel was evacuated and charged with nitrogen, sealed, and heated to 100° C. for 15 hours. The reaction was cooled to room temperature and TLC indicated that the reaction was complete. Minimal dichloromethane was added to the reaction (just enough to dissolve solids that formed upon cooling) and the solution directly chromatographed on silica gel (Biotage™ size 40S column), eluting with 20-50% ethyl acetate/heptane to give the title compound as a white solid.

Step 3: Preparation of N-(2-{(1S,2S)-2-[1-(5-chloropyrimidin-2-yl)piperidin-4-yl]cyclopropyl}ethyl)-5-(1H-1,2,3-triazol-1-yl)pyridin-2-amine

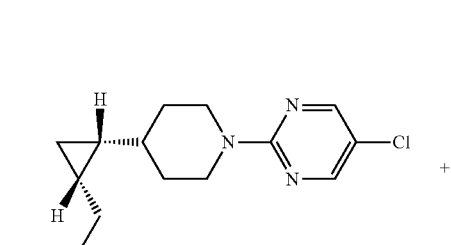

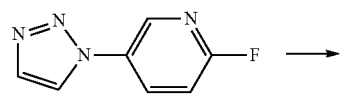

101

-continued

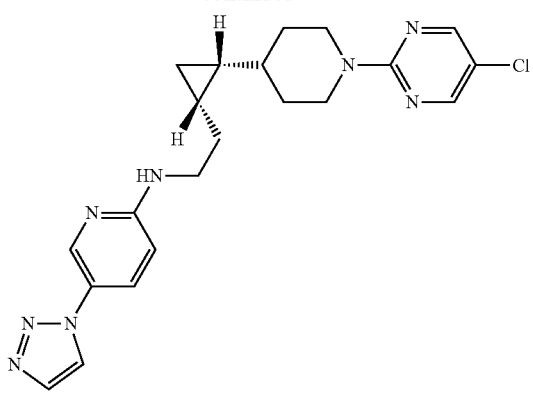

2-{(1S,2S)-2-[1-(5-chloropyrimidin-2-yl)piperidin-4-yl] cyclopropyl}ethanamine (30 mg, 0.11 mmol) from Example 2 step 3 was dissolved in NMP (0.21 mL), DBU (24.4 mg, 0.16 mmol) was added, stirred at room temperature for 10 minutes. 2-fluoro-5-(1H-1,2,3-triazol-1-yl)pyridine (21 mg, 0.13 mmol; from step 2 of this example) was added. Reaction was heated to 110° C. for 3 hours. The reaction was cooled down to room temperature, water (10 mL) was added, extracted with EtOAc (10 mL×2), second wash with Brine (10 mL). The organic phase was dried by magnesium sulfate, filter, concentrated and purified by column chromatography through a 12 gram RediSep Rf™ silica gel cartridge eluting with 30% ethylacetate/hexanes to give the title compound as a white solid.

LRMS calc: 424.93; obs: 425.13 (M+1).

102

-continued

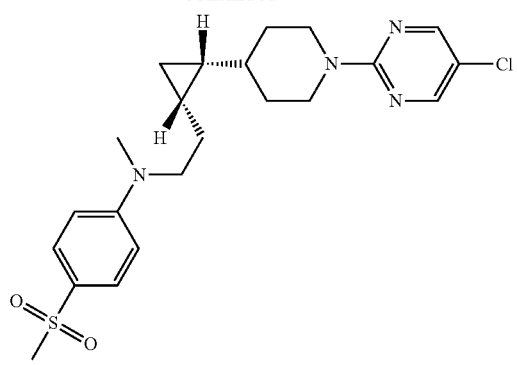

N-(2-{(1S,2S)-2-[1-(5-chloropyrimidin-2-yl)piperidin-4-yl] cyclopropyl}ethyl)-4-(methylsulfonyl)aniline (6 mg, 0.014 mmol) from Example 7 and paraformaldehyde were added to dichloroethane (0.2 mL), then sodium triacetoxyborohydride (10.1 mg, 0.041 mmol) was added and stirred overnight at room temperature. The reaction was quenched with sodium bicarbonate saturated solution (10 mL), extracted with EtOAc (10 mL), second wash with Brine (10 mL). The organic phase was dried by magnesium sulfate, filtered, concentrated and purified by purified by preparative-TLC (Analtech Silica Gel GF 1500 μM, 20×20 cm) using 50% ethyl acetate/hexane to give the title compound as a white solid.

LRMS calc: 449.01; obs: 449.07 (M+1).

EXAMPLE 9

Preparation of N-(2-{(1S,2S)-2-[1-(5-chloropyrimidin-2-yl)piperidin-4-yl]cyclopropyl}ethyl)-N-methyl-4-(methylsulfonyl)aniline

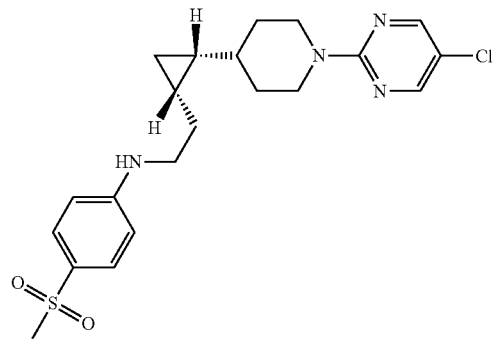

EXAMPLE 10

2-{4-[(1S,2S)-2-(2-azidoethyl)cyclopropyl]piperidin-1-yl}-5-chloropyrimidine

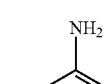

+

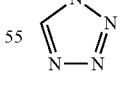

⟶

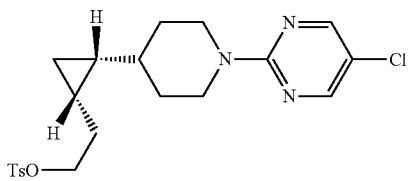

⟶

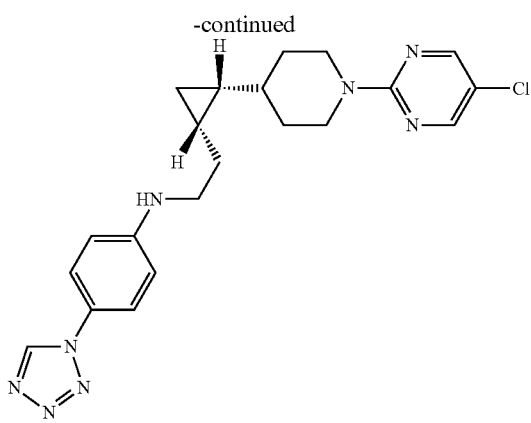

2-{(1S,2R)-2-[1-(5-chloropyrimidin-2-yl)piperidin-4-yl]cyclopropyl}ethyl 4-methylbenzenesulfonate (80 mg, 0.18 mmol) from Example 5 step 1,4-(1H-tetrazol-1-yl)aniline (32.5 mg, 0.20 mmol) and potassium iodide (3.1 mg, 0.018 mmol) were added in a microwave tube and were dissolved in acetonitrile (0.37 mL). The mixture was set to 170° C. for 30 min in microwave. The reaction was cooled to room temperature, concentrated and purified by column chromatography through a 25 gram Biotage SNAP KP-Sil™ silica gel cartridge eluting with 13% acetone/hexanes to give the title compound as a white-solid.

LRMS calc: 424.93; obs: 425.04 (M+1).

EXAMPLE 11

Preparation of N-(2-{(1S,2S)-2-[1-(5-chloropyrimidin-2-yl)piperidin-4-yl]cyclopropyl}ethyl)-4-(1H-1,2,4-triazol-1-yl)aniline Step 1: tert-butyl [4-(1H-1,2,4-triazol-1-yl)phenyl]carbamate

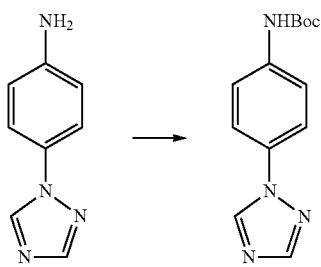 [SMILES: Nc1ccc(-n2cncn2)cc1 ; CC(C)(C)OC(=O)Nc1ccc(-n2cncn2)cc1]

4-(1H-1,2,4-triazol-1-yl)aniline (250 mg, 1.51 mmol) and di-tert-butyl dicarbonate (409 mg, 1.82 mmol) were added in toluene (7.6 mL). The reaction was heated to 70° C. for over the weekend. The reaction was cooled to room temperature, concentrated and purified by column chromatography through a 50 gram Biotage SNAP KP-Sil™ silica gel cartridge eluting with 50% ethyl acetate/hexanes to give the title compound as a white solid.

LRMS calc: 260.29; obs: 160.92 (M−100).

Step 2: N-(2-{(1S,2S)-2-[1-(5-chloropyrimidin-2-yl)piperidin-4-yl]cyclopropyl}ethyl)-4-(1H-1,2,4-triazol-1-yl)aniline

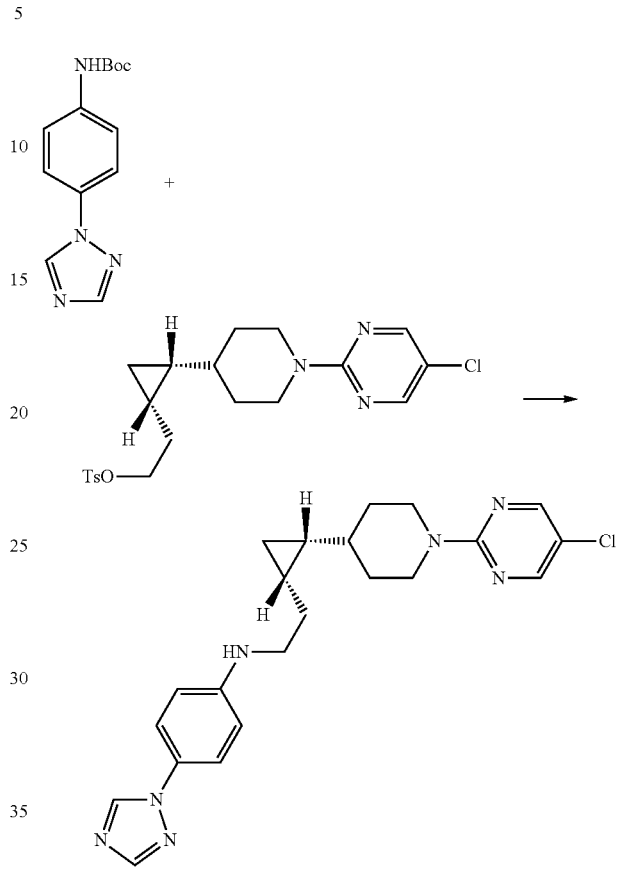

2-{(1S,2R)-2-[1-(5-chloropyrimidin-2-yl)piperidin-4-yl]cyclopropyl}ethyl 4-methylbenzenesulfonate (60 mg, 0.14 mmol) from Example 5 step 1 and tert-butyl [4-(1H-1,2,4-triazol-1-yl)phenyl]carbamate (39.4 mg, 0.15 mmol) from step 1 of this example were added in DMF (0.7 mL), then cesium carbonate (224 mg, 0.69 mmol) was added and the reaction was heated to 50° C. overnight. The reaction was cooled to room temperature, water (5 mL) was added and extracted with ethyl acetate (10 mL), second wash with brine (5 mL). The organic phase was dried by magnesium sulfate, filtered and concentrated.

The crude solid was treated with neat trifluoroacetic acid (2 mL) at room temperature for 20 minutes, and was concentrated without heating. Saturated sodium bicarbonate solution (10 mL) was added to the crude, extracted with ethyl acetate (10 mL×2). The organic phase was dried by magnesium sulfate, filtered, concentrated and purified by column chromatography through a 25 gram Biotage SNAP KP-Sil™ silica gel cartridge eluting with 26% acetone/hexanes to give the title compound as a white solid.

LRMS calc: 423.94; obs: 424.00 (M+1).

Compounds reported in Table 1 are prepared by a general procedure analogous to that described in Example 11 Step 2 above.

TABLE 1

| Examples | Chemical name | Chemical Structure | (M + 1) |
|---|---|---|---|
| Example 12 | N-(2-{(1S,2S)-2-[1-(5-chloropyrimidin-2-yl)piperidin-4-yl]cyclopropyl}ethyl)-4-(1H-pyrazol-5-yl)aniline | 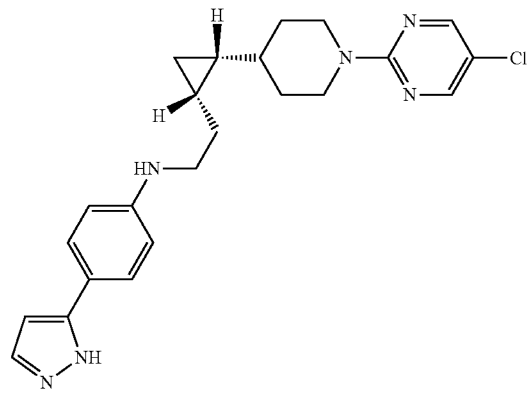 [SMILES: Clc1cnc(N2CCC([C@H]3C[C@H]3CCNc3ccc(-c4ccn[nH]4)cc3)CC2)nc1] | 423.06 |
| Example 13 | N-(2-{(1S,2S)-2-[1-(5-chloropyrimidin-2-yl)piperidin-4-yl]cyclopropyl}ethyl)-4-(4-methyl-4H-1,2,4-triazol-3-yl)aniline | 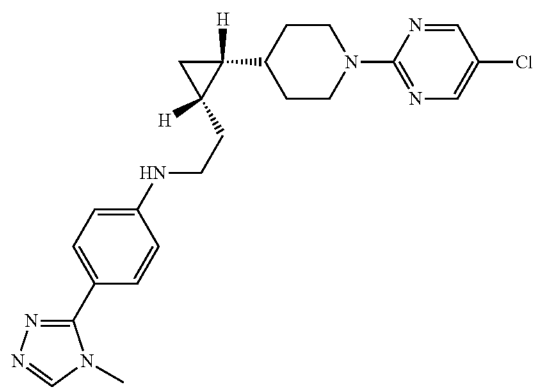 [SMILES: Cn1cnnc1-c1ccc(NCC[C@@H]2C[C@@H]2C2CCN(c3ncc(Cl)cn3)CC2)cc1] | 438.02 |
| Example 14 | N-(2-{(1S,2S)-2-[1-(5-chloropyrimidin-2-yl)piperidin-4-yl]cyclopropyl}ethyl)-6-(1H-1,2,4-triazol-1-yl)pyridin-3-amine | 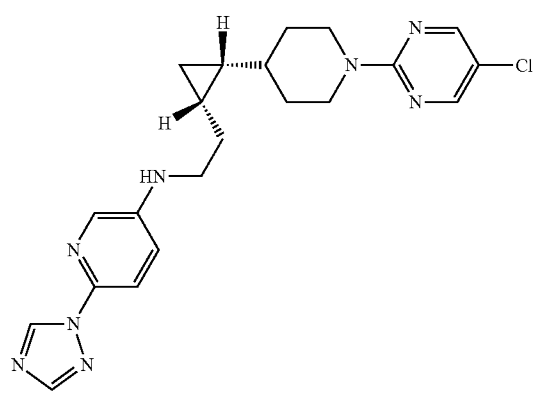 [SMILES: Clc1cnc(N2CCC([C@H]3C[C@H]3CCNc3ccc(-n4cncn4)nc3)CC2)nc1] | 424.97 |
| Example 15 | N-(2-{(1S,2S)-2-[1-(5-chloropyrimidin-2-yl)piperidin-4-yl]cyclopropyl}ethyl)-6-(1H-tetrazol-1-yl)pyridin-3-amine | 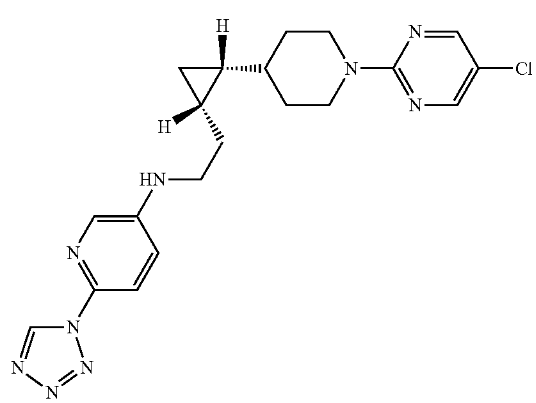 [SMILES: Clc1cnc(N2CCC([C@H]3C[C@H]3CCNc3ccc(-n4cnnn4)nc3)CC2)nc1] | 398.93 (M + 1 − 28) |

TABLE 1-continued

| Examples | Chemical name | Chemical Structure | (M + 1) |
|---|---|---|---|
| Example 16 | N-(2-{(1S,2S)-2-[1-(5-chloropyrimidin-2-yl)piperidin-4-yl]cyclopropyl}ethyl)-2-(1H-1,2,4-triazol-1-yl)pyrimidin-5-amine | 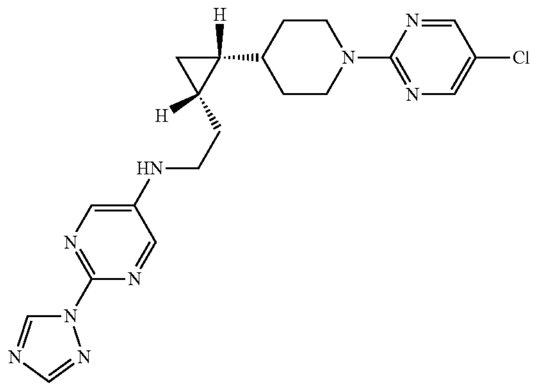 [SMILES: Clc1cnc(N2CCC([C@H]3C[C@H]3CCNc3cnc(-n4cncn4)nc3)CC2)nc1] | 425.86 |
| Example 17 | N-(2-{(1S,2S)-2-[1-(5-chloropyrimidin-2-yl)piperidin-4-yl]cyclopropyl}ethyl)-6-(5-methyl-2H-tetrazol-2-yl)pyridin-3-amine | 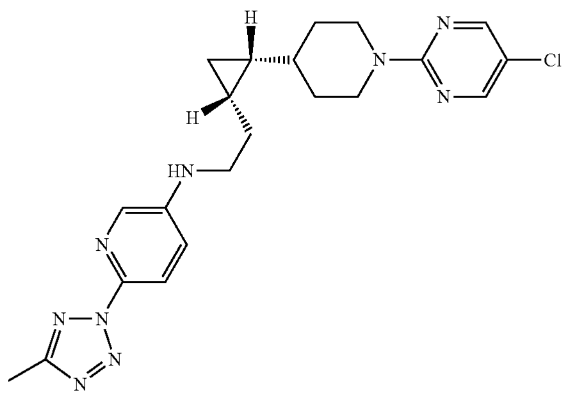 | 412.00 (M + 1 − 28) |
| Example 18 | N-(2-{(1S,2S)-2-[1-(5-chloropyrimidin-2-yl)piperidin-4-yl]cyclopropyl}ethyl)-6-(5-methyl-1H-tetrazol-1-yl)pyridin-3-amine | 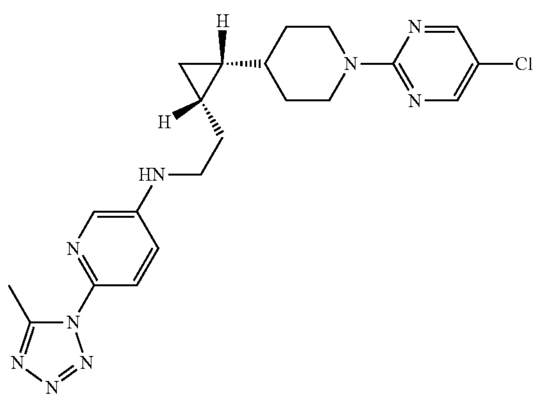 | 411.94 (M + 1 − 28) |
| Example 19 | N-(2-{(1S,2S)-2-[1-(5-chloropyrimidin-2-yl)piperidin-4-yl]cyclopropyl}ethyl)-6-(2H-1,2,3-triazol-2-yl)pyridin-3-amine | 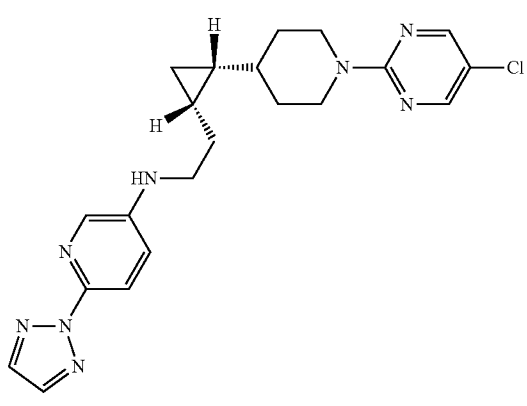 [SMILES: Clc1cnc(N2CCC([C@H]3C[C@H]3CCNc3ccc(-n4nccn4)nc3)CC2)nc1] | 424.97 |

TABLE 1-continued

| Examples | Chemical name | Chemical Structure | (M + 1) |
| --- | --- | --- | --- |
| Example 20 | 1-{5-[(2-{(1S,2S)-2-[1-(5-chloropyrimidin-2-yl)piperidin-4-yl]cyclopropyl}ethyl)amino]pyridin-2-yl}pyrrolidin-2-one | 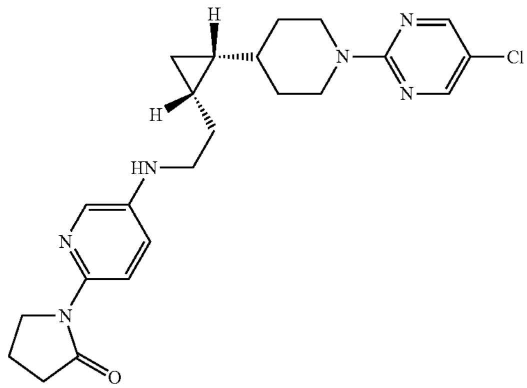 [SMILES: O=C1CCCN1c1ccc(NCC[C@@H]2C[C@@H]2C2CCN(c3ncc(Cl)cn3)CC2)cn1] | 440.98 |
| Example 21 | N-(2-{(1S,2S)-2-[1-(5-chloropyrimidin-2-yl)piperidin-4-yl]cyclopropyl}ethyl)-4-(1H-1,2,3-triazol-1-yl)aniline | 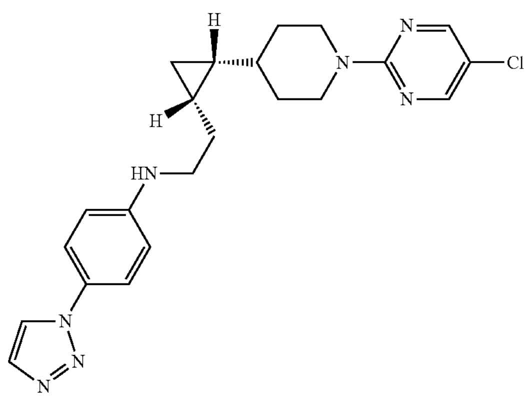 [SMILES: Clc1cnc(N2CCC([C@H]3C[C@H]3CCNc3ccc(-n4ccnn4)cc3)CC2)nc1] | 424.10 |
| Example 22 | 4-[(2-{(1S,2S)-2-[1-(5-chloropyrimidin-2-yl)piperidin-4-yl]cyclopropyl}ethyl)amino]-6-methylpyridine-2-carbonitrile | 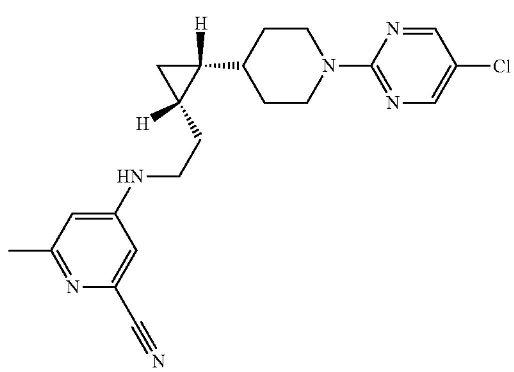 [SMILES: Cc1cc(NCC[C@@H]2C[C@@H]2C2CCN(c3ncc(Cl)cn3)CC2)cc(C#N)n1] | 397.08 |

Preparation of non-commercial phenyl carbamates for examples in Table 1 are reported below.

PREPARATIVE EXAMPLE 12a

Preparation of tert-butyl 5-{4-[(tert-butoxycarbonyl)amino]phenyl}-1H-pyrazole-1-carboxylate

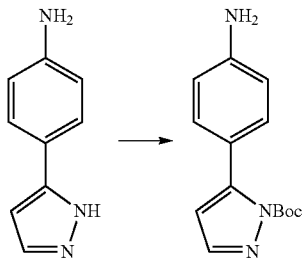 [SMILES: Nc1ccc(-c2ccn[nH]2)cc1 ; CC(C)(C)OC(=O)n1nccc1-c1ccc(N)cc1]

The title compound was synthesized by procedure analogous to Example 11, step 1 from commercially available 4-(1H-pyrazol-5-yl)aniline.

LRMS calc: 359.42; obs: 159.93 (M−200), 303.99 (M−55).

PREPARATIVE EXAMPLE 13a

Preparation of tert-butyl [4-(4-methyl-4H-1,2,4-triazol-3-yl)phenyl]carbamate

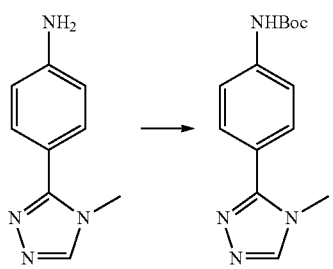 [SMILES: Cn1cnnc1-c1ccc(N)cc1 ; Cn1cnnc1-c1ccc(NC(=O)OC(C)(C)C)cc1]

4-(4-methyl-4H-1,2,4-triazol-3-yl)aniline (250 mg, 1.29 mmol) and di-tert-butyl dicarbonate (592 mg, 2.71 mmol) were added in DMF (6.5 mL), then cesium carbonate (1.26 g, 3.87 mmol). The reaction was heated to 50° C. for over night, then 70° C. for 5 hours. The reaction was cooled to room temperature, water (20 mL) was added, extracted with ethyl acetate (20 mL), second wash with brine (20 mL). The organic phase was dried by magnesium sulfate, filtered, concentrated and purified by column chromatography through a 25 gram Biotage SNAP KP-Sil™ silica gel cartridge eluting with 75% acetone/hexanes to give the title compound as a white solid.

LRMS calc: 274.32; obs: 174.89 (M−100), 274.97 (M+1).

PREPARATIVE EXAMPLE 14a

Preparation of tert-butyl [6-(1H-1,2,4-triazol-1-yl)pyridin-3-yl]carbamate

Step 1: 5-nitro-2-(1H-1,2,4-triazol-1-yl)pyridine.

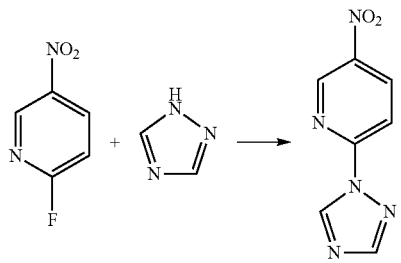

2-fluoro-5-nitropyridine (0.5 g, 3.38 mmol), 1,2,4-triazole (0.22 g, 3.22 mmol) were added in DMF (6.4 mL), then cesium carbonate (3.14 g, 9.65 mmol) was added. The reaction was run at room temperature for 30 minutes. Water (50 mL) was added and product fell out of the solution. The solution was filtered and the solid was rinsed with ethyl acetate/water (1:1, 20 mL×2), hot hexane (20 mL) to give the title compound as a white solid.

LRMS calc: 191.15; obs: 192.15 (M+1).

Step 2: 6-(1H-1,2,4-triazol-1-yl)pyridin-3-amine

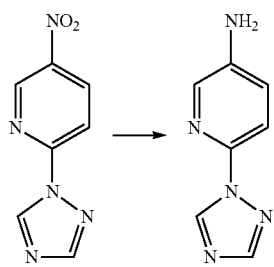 [SMILES: O=[N+]([O-])c1ccc(-n2cncn2)nc1 ; Nc1ccc(-n2cncn2)nc1]

5-nitro-2-(1H-1,2,4-triazol-1-yl)pyridine (100 mg, 0.523 mmol) from step 1 of this example was added Pd/C (111 mg, 0.105 mmol) and methanol (5.2 mL). Set the reaction on Parr Shaker at 50 psi (345 kPa) for overnight. The solution was filtered through CELITE and rinsed with methanol to give the title compound as a white solid.

LRMS calc: 161.16; obs: 162.01 (M+1).

Step 3: tert-butyl [6-(1H-1,2,4-triazol-1-yl)pyridin-3-yl]carbamate

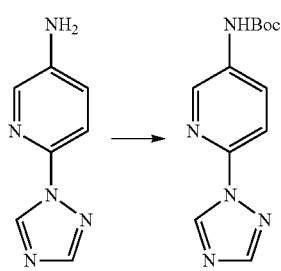 [SMILES: Nc1ccc(-n2cncn2)nc1 ; CC(C)(C)OC(=O)Nc1ccc(-n2cncn2)nc1]

The title compound was synthesized by procedure analogous to Example 11, step 1 except using t-butanol as the solvent from 6-(1H-1,2,4-triazol-1-yl)pyridin-3-amine from Step 2 of this example.

LRMS calc: 261.28; obs: 161.82 (M−100).

PREPARATIVE EXAMPLE 15a

Preparation of text-butyl [6-(1H-tetrazol-1-yl)pyridin-3-yl]carbamate

Step 1: 5-nitro-2-(1H-tetrazol-1-yl)pyridine

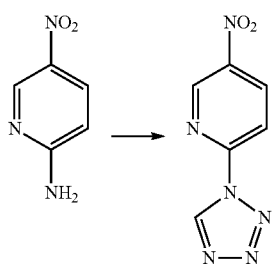 [SMILES: Nc1ccc([N+](=O)[O-])cn1 ; O=[N+]([O-])c1ccc(-n2cnnn2)nc1]

The title compound was synthesized using 5-nitropyridin-2-amine (1 g, 6.97 mmol), sodium azide (0.68 g, 10.5 mmol), trimethylorthoformate (1.2 g, 11.2 mmol) and acetic acid (14 mL) and stirred at room temperature over night. The reaction was heated to 120° C. reflux for 7 hours. The reaction was cooled down to room temperature, concentrated to take off acetic acid. Ice water (50 mL) was added, extracted with ethyl acetate (50 mL), second wash with sodium hydroxide (1N, 20 mL). The organic phase was dried by magnesium sulfate, filtered, concentrated and purified by column chromatography through a 50 gram Biotage SNAP KP-Sil™ silica gel cartridge eluting with 30% ethyl acetate/hexanes to give the title compound as a pale yellow solid.

LRMS calc: 192.13; obs: 165.14 (M+1-28), 206.15 (M+1+23).

Step 2: 6-(1H-tetrazol-1-yl)pyridin-3-amine

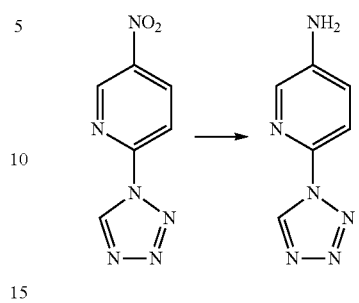

The title compound was synthesized by procedure analogous to Step 2 of Example 14a from 5-nitro-2-(1H-tetrazol-1-yl)pyridine from Step 1.

LRMS calc: 162.15; obs: 163.04 (M+1), 134.95 (M+1-28).

Step 3: tert-butyl [6-(1H-tetrazol-1-yl)pyridin-3-yl]carbamate

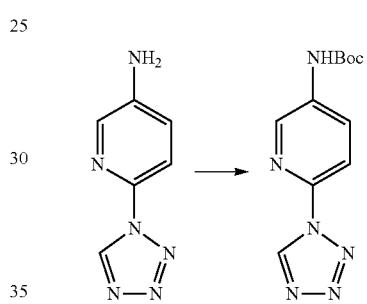

The title compound was synthesized by procedure analogous to Step 3 of Example 14a using 6-(1H-tetrazol-1-yl)pyridin-3-amine from Step 2.

LRMS calc: 262.27; obs: 134.97 (M−100-28), 179.01 (M−28-55).

PREPARATIVE EXAMPLE 18a

Preparation of text-butyl [2-(1H-1,2,4-triazol-1-yl)pyrimidin-5-yl]carbamate

Step 1: 5-nitro-2-(1H-1,2,4-triazol-1-yl)pyrimidine

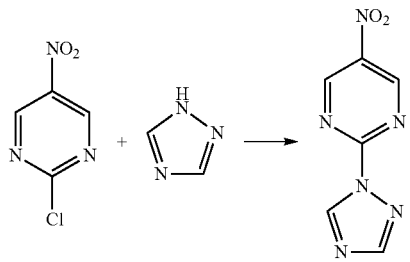 [SMILES: O=[N+]([O-])c1cnc(Cl)nc1 ; c1nc[nH]n1 ; O=[N+]([O-])c1cnc(-n2cncn2)nc1]

The title compound was synthesized by procedure analogous to Step 1 of Example 14a using commercially available 2-chloro-5-nitropyrimidine (1 g, 6.3 mmol)

LRMS calc: 192.13; obs: 193.01 (M+1).

Step 2: 2-(1H-1,2,4-triazol-1-yl)pyrimidin-5-amine

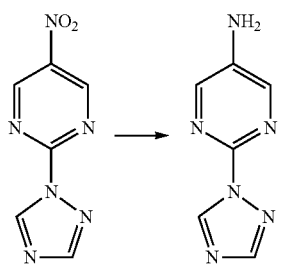 [SMILES: O=[N+]([O-])c1cnc(-n2cncn2)nc1 ; Nc1cnc(-n2cncn2)nc1]

The title compound was synthesized by procedure analogous to Step 2 of Example 14a using 5-nitro-2-(1H-1,2,4-triazol-1-yl)pyrimidine from Step 1.

LRMS calc: 162.15; obs: 163.03 (M+1).

Step 3: tert-butyl [2-(1H-1,2,4-triazol-1-yl)pyrimidin-5-yl]carbamate

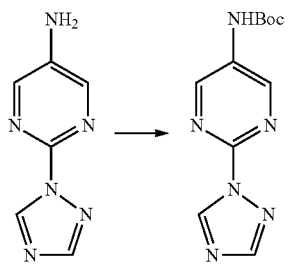 [SMILES: Nc1cnc(-n2cncn2)nc1 ; CC(C)(C)OC(=O)Nc1cnc(-n2cncn2)nc1]

The title compound was synthesized by procedure analogous to Step 3 of Example 14a using 2-(1H-1,2,4-triazol-1-yl)pyrimidin-5-amine from Step 2.

LRMS calc: 262.27; obs: 162.84 (M−100), 206.85 (M+1−55).

PREPARATIVE EXAMPLE 17a and 18a

Preparation of tert-butyl [6-(5-methyl-2H-tetrazol-2-yl)pyridin-3-yl]carbamate (20a) and tert-butyl [6-(5-methyl-1H-tetrazol-1-yl)pyridin-3-yl]carbamate (21a)

Step 1: 2-(5-methyl-2H-tetrazol-2-yl)-5-nitropyridine and 2-(5-methyl-1H-tetrazol-1-yl)-5-nitropyridine

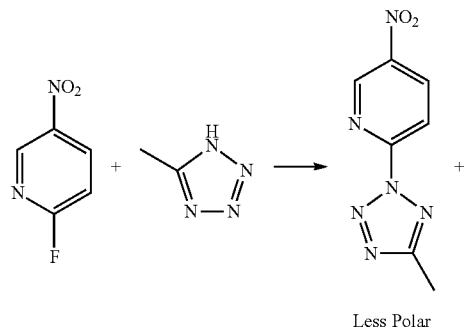

Less Polar

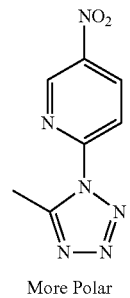

More Polar 2-fluoro-5-nitropyridine (142, 1 mmol), 1,2,4-triazole (100.8 mg, 1.2 mmol) were added in DMF (5 mL), then cesium carbonate (977 g, 3 mmol) was added. The reaction was run at room temperature for 2 hours. Water (50 mL) was added, extracted with ethyl acetate (50 mL), second wash with brine (20 mL). The organic phase was dried by magnesium sulfate, filtered, concentrated and purified by column chromatography through a 25 gram Biotage SNAP KP-Sil™ silica gel cartridge eluting with 22% ethyl acetate/hexanes to give the title compounds as a mixture, white solid. Several milligram of mixtures were separated by preparative-TLC (Analtech Silica Gel GF 1500 µM, 20×20 cm) using 30% ethyl acetate/hexane, NOE studies show that 2-(5-methyl-2H-tetrazol-2-yl)-5-nitropyridine is the less polar product LRMS calc: 206.16; obs: 206.87 (M+1).

2-(5-methyl-1H-tetrazol-1-yl)-5-nitropyridine is the more polar product.

LRMS calc: 206.16; obs: 206.99 (M+1).

Step 2: 6-(5-methyl-2H-tetrazol-2-yl)pyridin-3-amine and 6-(5-methyl-1H-tetrazol-1-yl)pyridin-3-amine

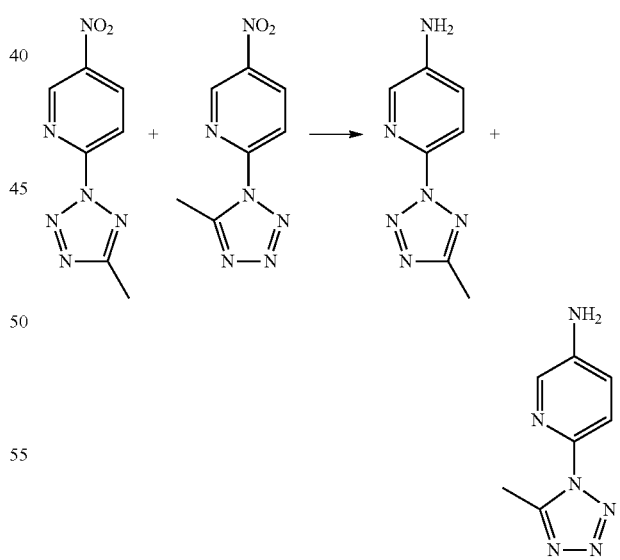

2-(5-methyl-2H-tetrazol-2-yl)-5-nitropyridine and 2-(5-methyl-1H-tetrazol-1-yl)-5-nitropyridine (120 mg, 0.87 mmol) from step 1 was added Pd/C (47 mg, 0.044 mmol) and methanol (4.4 mL) under balloon hydrogen (1 atm) for 30 min. The solution was filtered through CELITE and rinsed with methanol to give the title compounds as a mixture white solid.

LRMS calc: 176.18; obs: 177.06 (M+1), 149 (M−28).

Step 3: tert-butyl [6-(5-methyl-2H-tetrazol-2-yl)pyridin-3-yl]carbamate and tert-butyl [6-(5-methyl-1H-tetrazol-1-yl)pyridin-3-yl]carbamate

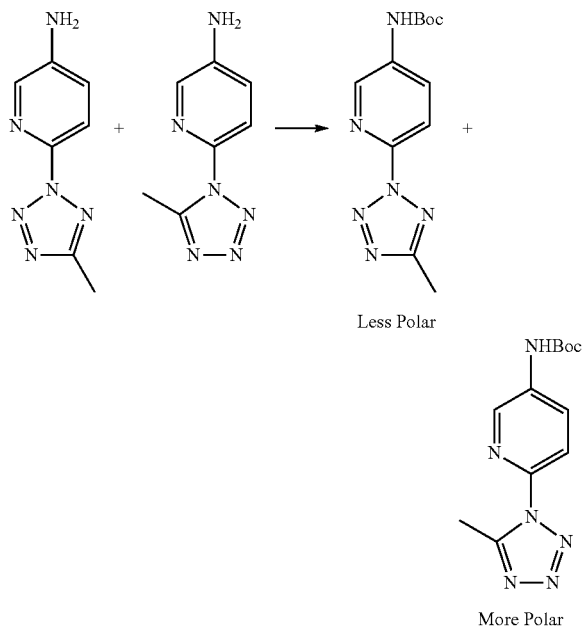

6-(5-methyl-2H-tetrazol-2-yl)pyridin-3-amine and 6-(5-methyl-1H-tetrazol-1-yl)pyridin-3-amine (120 mg, 0.68=01) from Step 2, di-tert-butyl dicarbonate (268 mg, 1.23 mmol) were added t-BuOH (10 mL). The reaction was heated 70° C. one night then 80° C. for 2 days. The reaction was cooled to room temperature, concentrated and purified by column chromatography through a 25 gram Biotage SNAP KP-Sil™ silica gel cartridge eluting with 30% ethyl acetate/hexanes to give the title compounds as a mixture, white solid. The mixture were separated by preparative-TLC (Analtech Silica Gel GF 1500 μM, 20×20 cm) using 30% acetone/hexane (developed twice) to give tert-butyl [6(5-methyl-2H-tetrazol-2-yl)pyridin-3-yl]carbamate (20a) as the less polar product.

LRMS calc: 276.29; obs: 299.00 (M+23), 193.01 (M−73). and to give tert-butyl [6(5-methyl-1H-tetrazol-1-yl)pyridin-3-yl]carbamate (21a) as the more polar product.

LRMS calc: 276.29; obs: 221.03 (M−55), 193.02 (M−73).

PREPARATIVE EXAMPLE 19a

Preparation of tert-butyl [6-(1H-1,2,4-triazol-1-yl)pyridin-3-yl]carbamate

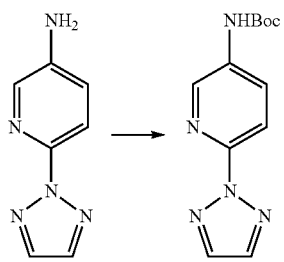 [SMILES: Nc1ccc(-n2nccn2)nc1 ; CC(C)(C)OC(=O)Nc1ccc(-n2nccn2)nc1]

The title compound was synthesized by procedure analogous to Step 3 of Example 14a using commercially available 6-(2H-1,2,3-triazol-2-yl)pyridin-3-amine.

LRMS calc: 261.28; obs: 161.87 (M−100), 205.89 (M+1-55).

Preparation of tert-butyl [6-(2-oxopyrrolidin-1-yl)pyridin-3-yl]carbamate

PREPARATIVE EXAMPLE 20a

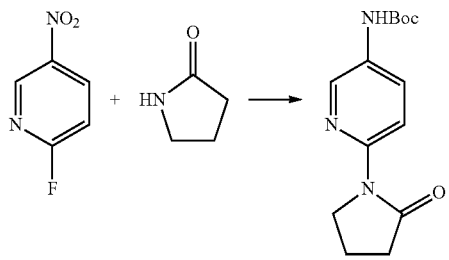 [SMILES: O=[N+]([O-])c1ccc(F)nc1 ; O=C1CCCN1 ; CC(C)(C)OC(=O)Nc1ccc(N2CCCC2=O)nc1]

The title compound was synthesized by procedure analogous to Example 14a from commercially available 2-fluoro-5-nitopyridine and 2-pyrrolidone.

LRMS calc: 277.32; obs: 177.93 (M−100), 221.88 (M+1-55).

PREPARATIVE EXAMPLE 21a

Preparation of tert-butyl [4-(1H-1,2,3-triazol-1-yl)phenyl]carbamate

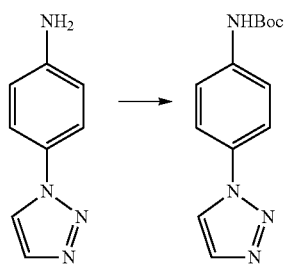 [SMILES: Nc1ccc(-n2ccnn2)cc1 ; CC(C)(C)OC(=O)Nc1ccc(-n2ccnn2)cc1]

The title compound was synthesized by procedure analogous to Step 1 of Example 11 from commercially available 4-(1H-1,2,3-triazol-1-yl)aniline LRMS calc: 260.29; obs: 261.14 (M+1), 205.14 (M+1-55).

PREPARATIVE EXAMPLE 22a

Preparation of tert-butyl (2-cyano-6-methylpyridin-4-yl)carbamate

Step 1: tert-butyl (2,6-dichloropyridin-4-yl)carbamate

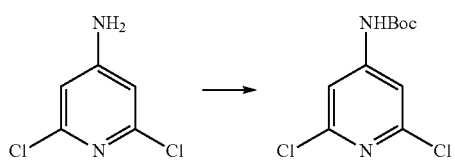 [SMILES: Nc1cc(Cl)nc(Cl)c1 ; CC(C)(C)OC(=O)Nc1cc(Cl)nc(Cl)c1]

The title compound was synthesized by procedure analogous to Example 13a from commercially available 2,6-dichloropyridin-4-amine.

LRMS calc: 263.82; obs: 162.77 (M−100), 206.82 (M+1-55).

Step 2: tert-butyl (2-chloro-6-methylpyridin-4-yl)carbamate

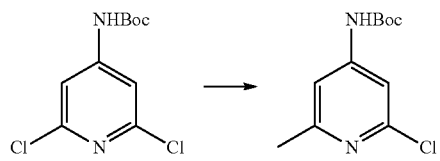 [SMILES: CC(C)(C)OC(=O)Nc1cc(Cl)nc(Cl)c1 ; Cc1cc(NC(=O)OC(C)(C)C)cc(Cl)n1]

tert-butyl (2,6-dichloropyridin-4-yl)carbamate (460 mg, 1.75 mmol) from Step 1 of this example, ferric acetylacetonate (309 mg, 0.87 mmol) was added in THF:NMP (1:1, 17.4 mL), methyl magnesium bromide (3 mL [3M], 8.9 mmol) was added drop-wise and stirred for 15 min. The reaction was quenched with ice-cold ammonia chloride saturated solution (100 mL), extracted with ethyl acetate (100 mL), second wash with brine (50 mL). The organic phase was dried by magnesium sulfate and filtered through silica gel (1 inch deep), concentrated and purified by column chromatography through a 50 gram Biotage SNAP KP-Sil™ silica gel cartridge eluting with 10% ethyl acetate/hexanes to give the title compounds as a white solid.

LRMS calc: 242.70; obs: 186.89 (M+1-55).

Step 3: tert-butyl (2-cyano-6-methylpyridin-4-yl)carbamate

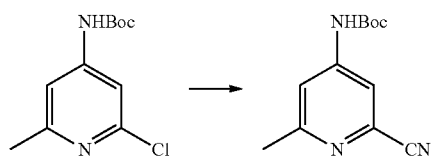 [SMILES: Cc1cc(NC(=O)OC(C)(C)C)cc(Cl)n1 ; Cc1cc(NC(=O)OC(C)(C)C)cc(C#N)n1]

tert-butyl (2-chloro-6-methylpyridin-4-yl)carbamate (220 mg, 0.91 mmol) from Step 2 of this example, palladium (II) trifluoroacetate (13 mg, 0.039 mmol), zinc dust (11.3 mg, 0.17 mmol), me-2-(di-t-butylphosphino)-1H-binaphthyl (32 mg, 0.08 mmol), zinc cyanide (59.6 mg, 0.51 mmol) was added dimethylacetamide (4.8 mL) in a flask (flame-dried) and evacuated and back-filled with $N_2$ (3×). The reaction was heated to 95° C. for 30 min, cooled to room temperature. Water (50 mL) was added, extracted with ethyl acetate (50 mL), second wash with brine (50 mL). The organic phase was dried by magnesium sulfate and filtered through silica gel pad (1 inch deep), concentrated and purified by column chromatography through a 40 gram RediSep Rf™ silica gel cartridge eluting with 18% ethyl acetate/hexanes to give the title compounds as a white solid.

LRMS calc: 233.27; obs: 177.92 (M+1-55).

EXAMPLE 23

Preparation of N-(2-{(1S,2S)-2-[1-(5-chloropyrimidin-2-yl)piperidin-4-yl]cyclopropyl}ethyl)-5-(1H-1,2,4-triazol-1-yl)pyrazin-2-amine

Step 1: 2-chloro-5-(1H-1,2,4-triazol-1-yl)pyrazine

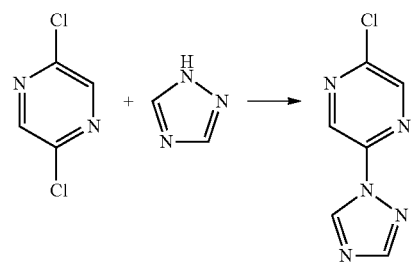 [SMILES: Clc1cnc(Cl)cn1 ; c1nc[nH]n1 ; Clc1cnc(-n2cncn2)cn1]

2,5-Dichloropyrazine (298 mg, 2.0 mmol) and 1,2,4-triazole (145 mg, 2.1 mmol) were added in DMF (10 mL), then cesium carbonate was added and the reaction was at room temperature over night. Water (20mL) was added, extracted with ethyl acetate (30 mL), second wash with brine (20 mL). The organic phase was dried by magnesium sulfate, filtered, concentrated and purified by column chromatography through a 25 gram Biotage SNAP KP-Sil™ silica gel cartridge eluting with 22% ethyl acetate/hexanes to give the title compound as a white solid.

LRMS calc: 181.58; obs: 182.21 (M+1).

Step 2: N-(2-{(1S,2S)-2-[1-(5-chloropyrimidin-2-yl)piperidin-4-yl]cyclopropyl}ethyl)-5-(1H-1,2,4-triazol-1-yl)pyrazin-2-amine

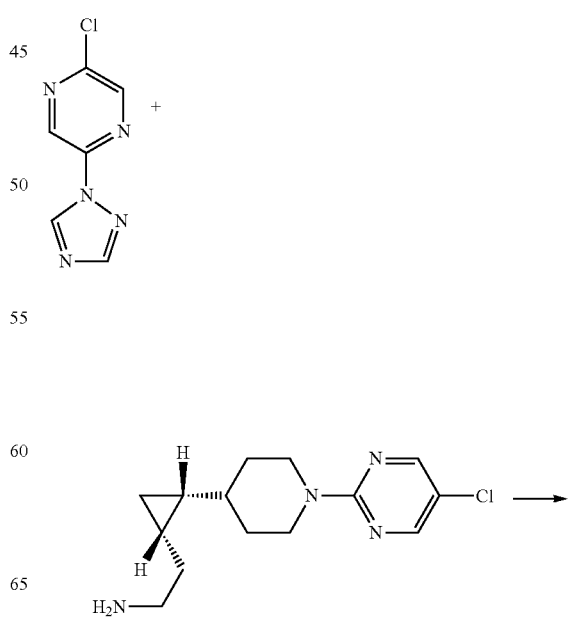

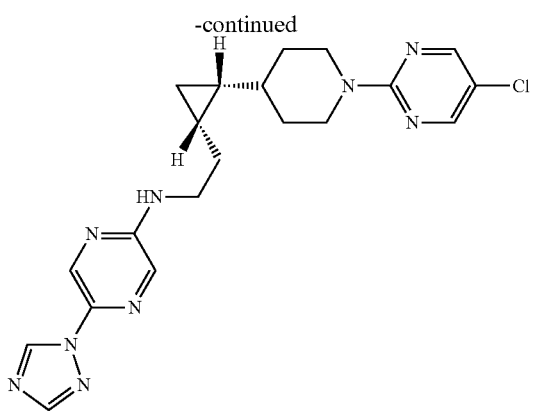

2-{(1S,2S)-2-[1-(5-chloropyrimidin-2-yl)piperidin-4-yl]cyclopropyl}ethanamine (50 mg, 0.18 mmol) from step 3, Example 5 and 2-chloro-5-(1H-1,2,4-triazol-1-yl)pyrazine (35.6 mg, 0.20 mmol) were added in NMP (0.89 mL), then potassium carbonate (73.8 mg, 0.53 mmol) was added and the reaction was heated to 90° C. overnight. The reaction was cooled to room temperature, water (10 mL) was added and drops of acetic acid were added to adjust pH value to ~4, extracted with ethyl acetate (20 mL), second wash with brine (10 mL). The water phase was back extracted with ethyl acetate (10 mL×2). The organic phase were combined and dried by magnesium sulfate, filtered and concentrated and purified by column chromatography through a 25 gram Biotage SNAP KP-Sil™ silica gel cartridge eluting with 30% ethyl acetate/hexane to give the title compound as a white solid.

LRMS calc: 425.92; obs: 426.00 (M+1).

EXAMPLE 24

Preparation of N-(2-{(1S,2S)-2-[1-(5-chloropyrimidin-2-yl)piperidin-4-yl]cyclopropyl}ethyl)-5-(1H-tetrazol-1-yl)pyridin-2-amine Step 1: 2-fluoro-5-(1H-tetrazol-1-yl)pyridine

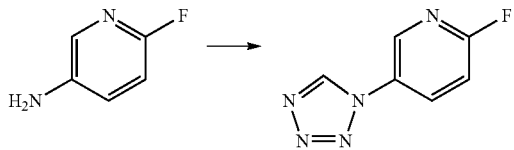 [SMILES: Nc1ccc(F)nc1 ; Fc1ccc(-n2cnnn2)cn1]

6-fluoropyridin-3-amine (1.12 g, 10 mmol), sodium azide (0.98 g, 15 mmol) and trimethylorthoformate (1.7 g, 16 mmol) were added to acetic acid (20 mL), and stirred at room temperature over night. The reaction was heated to 120° C. reflux for 7 hours. The reaction was cooled down to room temperature, poured into ice water (50 mL), extracted with ethyl acetate (50 mL), second wash with sodium hydroxide (1N, 20 mL). The organic phase was dried by magnesium sulfate, filtered, concentrated and purified by column chromatography through a 80 gram Analogix™ silica gel cartridge eluting with 50% ethyl acetate/hexanes to give the title compound as a white solid.

LRMS calc: 165.13; obs: 165.91 (M+1), 137.82 (M−28).

Step 2: N-(2-{(1S,2S)-241-(5-chloropyrimidin-2-yl)piperidin-4-yl]cyclopropyl}ethyl)-54/H-tetrazol-1-yl)pyridin-2-amine

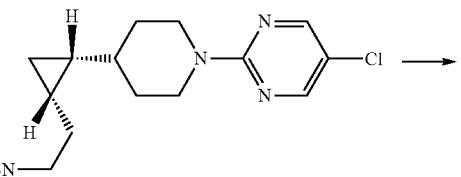

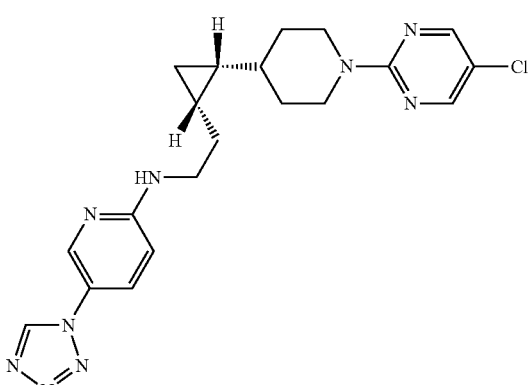

2-{(1S,2S)-2-[1-(5-chloropyrimidin-2-yl)piperidin-4-yl]cyclopropyl}ethanamine (50 mg, 0.18 mmol) from Example 5 step 3 and 2-fluoro-5-(1H-tetrazol-1-yl)pyridine (35.6 mg, 0.20 mmol) from step 1 were added in NMP (0.89 mL), then potassium carbonate (73.8 mg, 0.53 mmol) was added and the reaction was heated to 70° C. 6.5 hours. The reaction was cooled to room temperature, water (10 mL) was added, extracted with ethyl acetate (20 mL), second wash with brine (10 mL). The organic phase was dried by magnesium sulfate, filtered and concentrated and purified by column chromatography through a 25 gram Biotage SNAP KP-Sil™ silica gel cartridge eluting with 40% ethyl acetate/hexane to give the title compound as a white-solid.

LRMS calc: 425.92; obs: 426.26 (M+1).

EXAMPLE 25

Preparation of N-(2-{(1S,2S)-2-[1-(5-chloropyrimidin-2-yl)piperidin-4-yl]cyclopropyl}ethyl)-4-(4H-1,2,4-triazol-4-yl)aniline Step 1: N-(2-{(1S,2S)-2-[1-(5-chloropyrimidin-2-yl)piperidin-4-yl]cyclopropyl}ethyl)-N-[4-(4H-1,2,4-triazol-4-yl)phenyl]acetamide

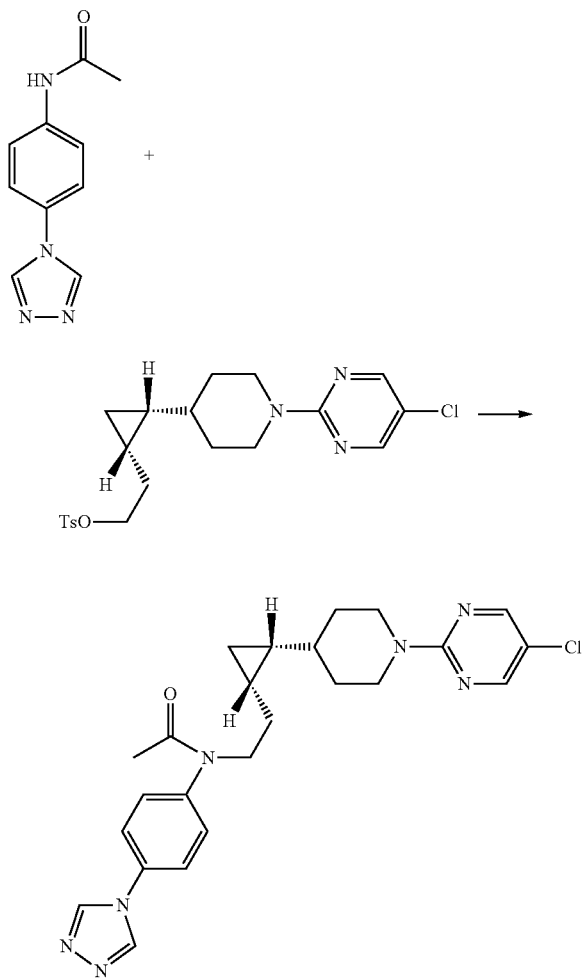

2-{(1S,2R)-2-[1-(5-chloropyrimidin-2-yl)piperidin-4-yl]cyclopropyl}ethyl 4-methylbenzenesulfonate (60 mg, 0.14 mmol) from Example 5 step 1 and N-[4-(4H-1,2,4-triazol-4-yl)phenyl]acetamide (30.6 mg, 0.15 mmol) were added in DMF (0.7 mL), then cesium carbonate (224 mg, 0.69 mmol) was added and the reaction was heated to 50° C. overnight. The reaction was cooled to room temperature, water (10 mL) was added and extracted with ethyl acetate (20 mL), second wash with brine (10 mL). The organic phase was dried by magnesium sulfate, filtered, concentrated and purified by column chromatography through a 25 gram Biotage SNAP KP-Sil™ silica gel cartridge eluting with 50% acetone/hexanes to give the title compound as a white solid.

LRMS calc: 465.99; obs: 466.03 (M+1).

Step 2: N-(2-{(1S,2S)-2-[1-(5-chloropyrimidin-2-yl)piperidin-4-yl]cyclopropyl}ethyl)-4-(4H-1,2,4-triazol-4-yl)aniline

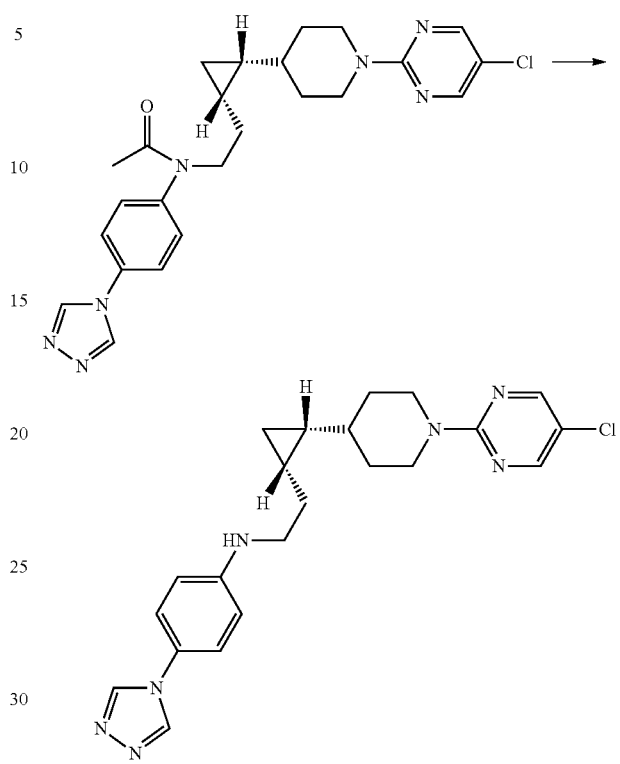

N-(2-{(1S,2S)-2-[1-(5-chloropyrimidin-2-yl)piperidin-4-yl]cyclopropyl}ethyl)-N-[4-(4H-1,2,4-triazol-4-yl)phenyl]acetamide from step 1 of this example was dissolved in ethanol (0.5 mL), added sodium hydroxide (60% w/w, 0.3 mL) and heated to 80° C. for 5.5 hours. The reaction was cooled to room temperature, water (10 mL) was added and extracted with ethyl acetate (20 mL). The organic phase was dried by magnesium sulfate, filtered, concentrated and purified by column chromatography through a 25 gram Biotage SNAP KP-Sil™ silica gel cartridge eluting with 50% acetone/hexanes to give the title compound as a white-solid.

LRMS calc: 423.94; obs: 424.03 (M+1).

EXAMPLE 26

Preparation of N-(2-{(1S,2S)-2-[1-(5-chloropyrimidin-2-yl)piperidin-4-yl]cyclopropyl}ethyl)-2-(1H-tetrazol-1-yl)pyrimidin-5-amine Step 1: 5-nitro-2-(1H-tetrazol-1-yl)pyrimidine

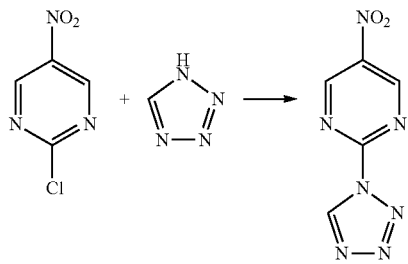 [SMILES: O=[N+]([O-])c1cnc(Cl)nc1 ; c1nnn[nH]1 ; O=[N+]([O-])c1cnc(-n2cnnn2)nc1]

2-chloro-5-nitropyrimidine (1.6 g, 10 mmol), 1H-tetrazole (24.44 mL, 11 mmol, 0.45M in MeCN) were added in DMF (20 mL), cooled to 0° C., then triethylamine (1.67 mL, 12 mmol) was added drop-wise. After 15 minutes, water (100 mL) was added, extracted with ethyl acetate (100 mL×1, 50 mL×6). The organic phase were combined and dried by magnesium sulfate, filtered, concentrated and purified by column chromatography through a 100 gram Biotage SNAP KP-Sil™silica gel cartridge eluting with 30% ethyl acetate/hexanes to give the title compound as a pale yellow solid.

LRMS calc: 193.12; obs: 166.91 (M+1-28).

Step 2: 2-(1H-tetrazol-1-yl)pyrimidin-5-amine

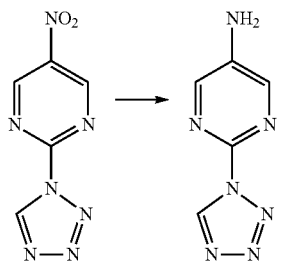 [SMILES: O=[N+]([O-])c1cnc(-n2cnnn2)nc1 ; Nc1cnc(-n2cnnn2)nc1]

5-nitro-2-(1H-tetrazol-1-yl)pyramidine (550 mg, 2.85 mmol) from step 1 of this example, added Pd/C (152 mg, 0.142 mmol) and methanol (3 mL) under balloon hydrogen (1 atm) for 1 h. The solution was filtered through CELITE and rinsed with methanol:dichloromethane (1:1, 20 mL) to give the title compound as a white solid.

LRMS calc: 163.14; obs: 164.00 (M+1), 135.89 (M+1-28).

Step 3: N-(2-{(1S,2S)-2-[1-(5-chloropyrimidin-2-yl)piperidin-4-yl]cyclopropyl}ethyl)-2-(1H-tetrazol-1-yl)pyrimidin-5-amine

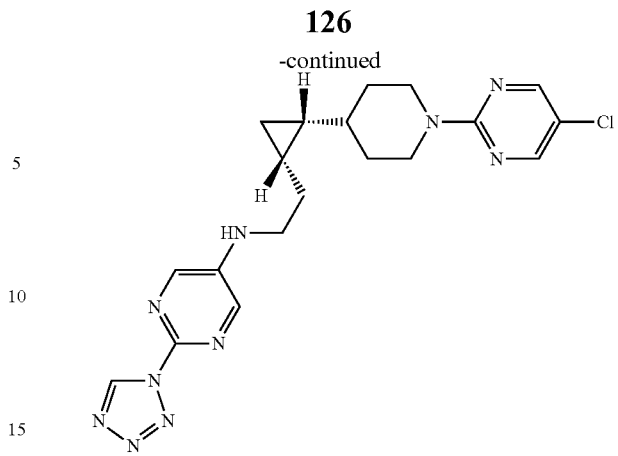

{(1S,2R)-2-[1-(5-chloropyrimidin-2-yl)piperidin-4-yl]cyclopropyl}acetaldehyde (20 mg, 0.068 mmol, from Example 3) and 2-(1H-tetrazol-1-yl)pyrimidin-5-amine (24.37 mg, 0.15 mmol) from example 2 of this example were added in methanol (1:1, 4 mL), heated to dissolve. Acetic acid was added 3 drops and stirred at room temperature for 20 minutes. Then sodium cyanoborohydride (12.8 mg, 0.2 mmol) was added. After 3 hours, saturated sodium bicarbonate solution (20 mL) was added, extracted with ethyl acetate (20 mL), second wash with brine (20 mL). The organic phase was dried by magnesium sulfate, filtered, concentrated and purified by column chromatography through a 25 gram Biotage SNAP KP-Sil™ silica gel cartridge eluting with 40% ethyl acetate/hexanes to give the title compound as a white-solid.

LRMS calc: 426.91; obs: 398.97 (M−28), 448.99 (M+23).

EXAMPLE 27

Preparation of 3-{5-[(2-(1S,2S)-2-[1-(5-chloropyrimidin-2-yl)piperidin-4-yl]cyclopropyl}ethyl)amino]pyridin-2-yl}-1,3-oxazolidine-2,4-dione Step 1: 3-(5-aminopyridin-2-yl)-1,3-oxazolidine-2,4-dione

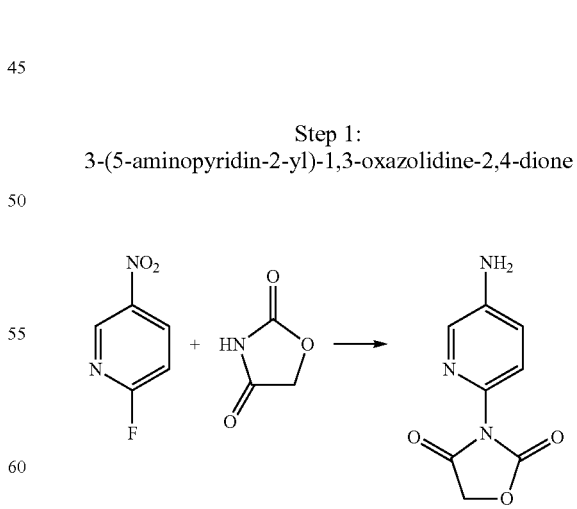

The title compound was synthesized by procedure analogous to Step 1 and 2 of Example 14a from commercially available 2-fluoro-5-nitropyridine and 1,2,4-Oxazolidinedione LRMS calc: 193.16; obs: 198.86 (M+1).

Step 2: 3-{5-(2-{(1S,2S)-2-[1-(5-chloropyrimidin-2-yl)piperidin-4-yl]cyclopropyl}ethyl)amino]pyridin-2-yl}-1,3-oxazolidine-2,4-dione

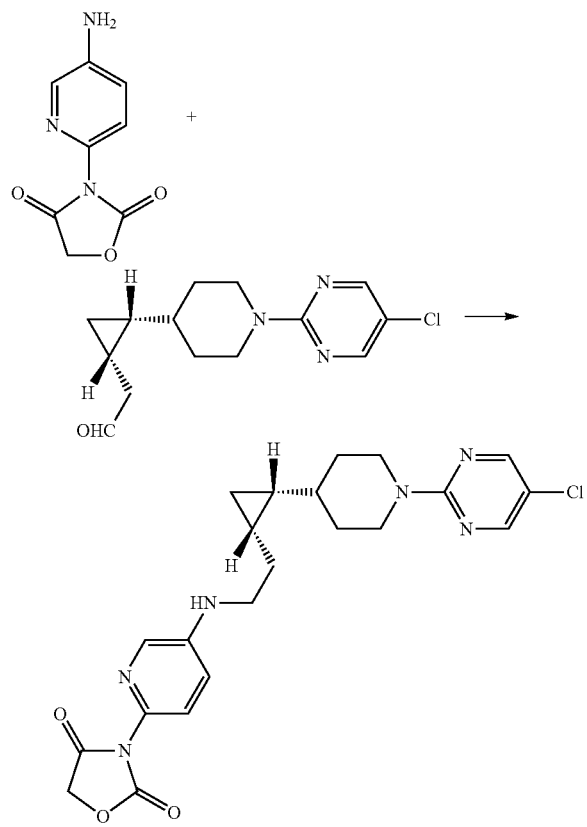

The title compound was synthesized by procedure analogous to Step 3 of Example 26 from {(1S,2R)-2-[1-(5-chloropyrimidin-2-yl)piperidin-4-yl]cyclopropyl}acetaldehyde from Example 63 and 3-(5-aminopyridin-2-yl)-1,3-oxazolidine-2,4-dione from step 1.

LRMS calc: 456.94; obs: 456.94 (M+1).

Example 28

Preparation of N-6-[(2-{(1S,2S)-2-[1-(5-chloropyrimidin-2-yl)piperidin-4-yl]cyclopropyl}ethyl)amino]-5-methylpyridin-3-yl}-2,2-dimethylpropanamide Step 1: tert-butyl (3-methyl-5-nitropyridin-2-yl)carbamate

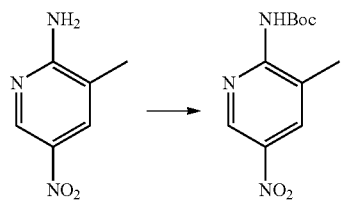 [SMILES: Cc1cc([N+](=O)[O-])cnc1N ; Cc1cc([N+](=O)[O-])cnc1NC(=O)OC(C)(C)C]

2-Amino-3-methyl-5-nitropyridine (1 g, 6.5 mmol) and di-tert-butyl Bicarbonate (2.2 g, 9.8 mmol) were added in DMF (33 mL), then cesium carbonate (6.4 g, 19.6 mmol) at room temperature for 6 hours. Water (200 mL) was added, extracted with ethyl acetate (200 mL), second wash with brine (100 mL). The organic phase was dried by magnesium sulfate, filtered, concentrated and purified by column chromatography through a 25 gram Biotage SNAP KP-Sil™ silica gel cartridge eluting with 13% ethyl acetate/hexanes to give the title compound as a pale yellow solid.

LRMS calc: 253.25; obs: 153.83 (M−100), 197.96 (M+1-55).

Step. 2: tert-butyl (2-{(1S,2S)-2-[1-(5-chloropyrimidin-2-yl)piperidin-4-yl]cyclopropyl}ethyl)(3-methyl-5-nitropyridin-2-yl)carbamate

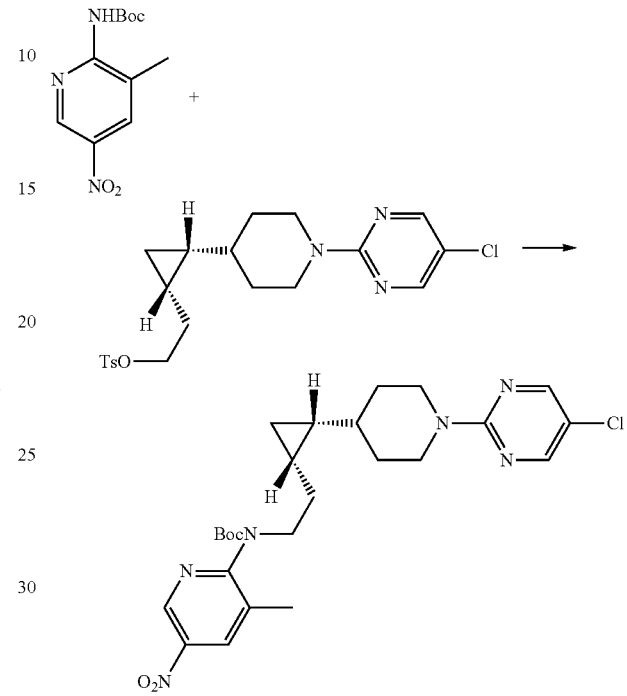

2-{(1S,2R)-2-[1-(5-chloropyrimidin-2-yl)piperidin-4-yl]cyclopropyl}ethyl 4-methylbenzenesulfonate (95 mg, 0.22 mmol) from Step 1 of Example 2 and tert-butyl (3-methyl-5-nitropyridin-2-yl)carbamate (55 mg, 0.22 mmol) were added in DMF (2.2 mL), then cesium carbonate (212 mg, 0.65=101) was added and the reaction was heated to 50° C. overnight. The reaction was cooled to room temperature, water (20 mL) was added and extracted with ethyl acetate (50 mL), second wash with brine (20 mL). The organic phase was dried by magnesium sulfate, filtered, concentrated and purified by column chromatography through a 25 gram Biotage SNAP KP-Sil™ silica gel cartridge eluting with 6.3% ethyl acetate/hexanes to give the title compound as a pale yellow sticky solid.

LRMS calc: 517.02; obs: 517.32 (M+1), 417.32 (M−100).

Step 3: tert-butyl (5-amino-3-methylpyridin-2-yl)(2-{(1S,2S)-2-[1-(5-chloropyrimidin-2-yl)piperidin-4-yl]cyclopropyl}ethyl)carbamate

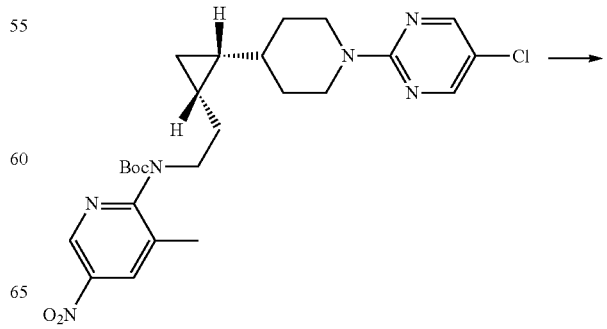

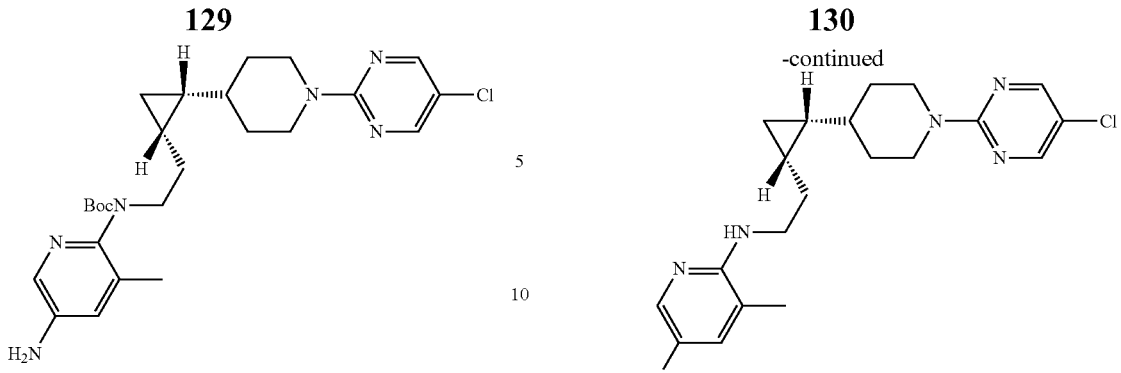

The title compound was synthesized by procedure analogous to Step 2 of Example 26 from tert-butyl (2-{(1S,2S)-2-[1-(5-chloropyrimidin-2-yl)piperidin-4-yl]cyclopropyl}ethyl)(3-methyl-5-nitropyridin-2-yl)carbamate from Step 2 of this example.

LRMS calc: 487.05; obs: 487.19 (M+1), 387.15 (M−100).

Step 4: N-{6-[(2-{(1S,2S)-2-[1-(5-chloropyrimidin-2-yl)piperidin-4-yl]cyclopropyl}ethyl)amino]-5-methylpyridin-3-yl}-2,2-dimethylpropanamide

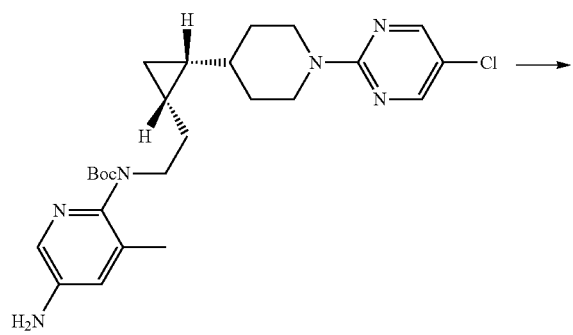

tert-butyl (5-amino-3-methylpyridin-2-yl)(2-{(1S,2S)-2-[1-(5-chloropyrimidin-2-yl)piperidin-4-yl]cyclopropyl}ethyl) carbamate (42 mg, 0.086 mmol) from Step 3 and triethylamine (9.6 mg, 0.095 mmol) were added in dichloromethane (0.86 mL) and cooled to 0° C. Pivaloyl chloride (11.4 mg, 0.095 mmol) was added drop-wise via syringe and the reaction was kept at 0° C. for 15 minutes. Dichloromethane (20 mL) was added, poured into ice-water (20 mL), extracted with dichloromethane (20 mL×3). The organic phase was combined, dried by magnesium sulfate, filtered and concentrated.

The crude solid was treated with neat trifluoroacetic acid (3 mL) at room temperature for 15 minutes, and was concentrated without heating. Saturated sodium bicarbonate solution (20 mL) was added to the crude, extracted with ethyl acetate (20 mL), second wash with Brine (10 mL). The organic phase was dried by magnesium sulfate, filtered, concentrated and purified by column chromatography through a 25 gram Biotage SNAP KP-Sil™ silica gel cartridge eluting with 13% acetone/hexanes to give the title compound as a white solid.

LRMS calc: 471.04; obs: 471.15 (M+1).

Compounds reported in Table 2 are prepared by a general procedure analogous to that described in Example 28 Step 4 above.

TABLE 2

| Example | Chemical name | Chemical Structure | (M + 1) |
| --- | --- | --- | --- |
| Example 29 | N-{6-[(2-{(1S,2S)-2-[1-(5-chloropyrimidin-2-yl)piperidin-4-yl]cyclopropyl}ethyl)amino]-4-methylpyridin-3-yl}-2,2-dimethyl propanamide | 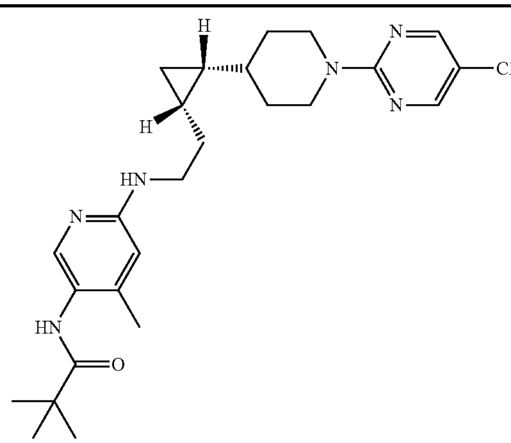 | 471.14 |

TABLE 2-continued

| Example | Chemical name | Chemical Structure | (M + 1) |
|---|---|---|---|
| Example 30 | N-{6-[(2-{(1S,2S)-2-[1-(5-chloropyrimidin-2-yl)piperidin-4-yl]cyclopropyl}ethyl)amino]pyridin-3-yl}-2,2-dimethyl propanamide | 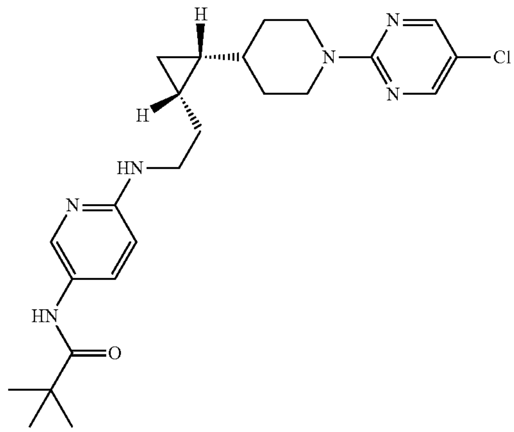 [SMILES: CC(C)(C)C(=O)Nc1ccc(NCC[C@@H]2C[C@@H]2C2CCN(c3ncc(Cl)cn3)CC2)nc1] | 457.43 |
| Example 31 | N-{5-[(2-{(1S,2S)-2-[1-(5-chloropyrimidin-2-yl)piperidin-4-yl]cyclopropyl}ethyl)amino]-3-methylpyridin-2-yl}-2,2-dimethyl propanamide | 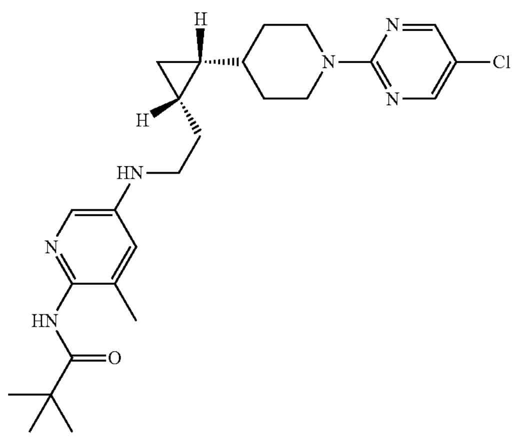 | 471.14 |
| Example 32 | N-{3-chloro-5-[(2-{(1S,2S)-2-[1-(5-chloropyrimidin-2-yl)piperidin-4-yl]cyclopropyl}ethyl)amino]pyridin-2-yl}-2,2-dimethyl propanamide | 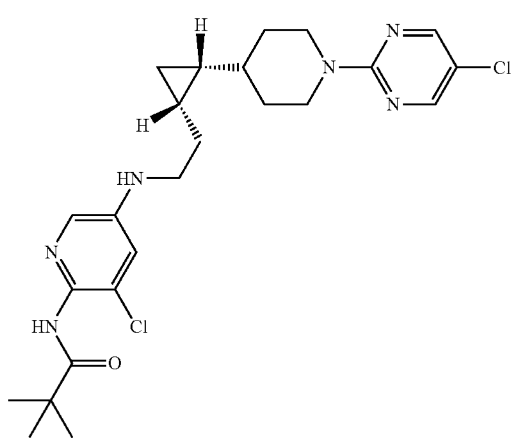 [SMILES: CC(C)(C)C(=O)Nc1ncc(NCC[C@@H]2C[C@@H]2C2CCN(c3ncc(Cl)cn3)CC2)cc1Cl] | 491.14 |

Preparation of non-commercial pyridine carbamates for examples in Table 2 are reported below.

PREPARATIVE EXAMPLE 29a

Preparation of tert-butyl (5-amino-4-methylpyridin-2-yl)(2-{(1S,2S)-2-[1-(5-chloropyrimidin-2-yl)piperidin-4-yl]cyclopropyl}ethyl)carbamate Step 1: tert-butyl (4-methyl-5-nitropyridin-2-yl)carbamate

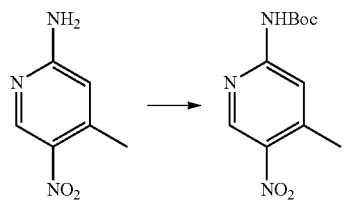 [SMILES: Cc1cc(N)ncc1[N+](=O)[O-] ; Cc1cc(NC(=O)OC(C)(C)C)ncc1[N+](=O)[O-]]

2-Amino-4-methyl-5-nitropyridine (1 g, 6.5 mmol) and di-tert-butyl Bicarbonate (2.4 g, 11.1 mmol) were added in DMSO:tBuOH (1:1, 20 mL), DMAP (80 mg, 0.65 mmol) was added and heated to 70° C. over night. The reaction was cooled to room temperature, concentrated and purified by column chromatography through a 100 gram Biotage SNAP KP-Sil™ silica gel cartridge eluting with 13% ethyl acetate/hexanes to give the title compound as a white solid.

LRMS calc: 253.25; obs: 154.22 (M+1-100), 276.24 (M+3).

Step 2: tert-butyl (5-amino-4-methylpyridin-2-yl)(2-{(1S,2S)-2-[1-(5-chloropyrimidin-2-yl)piperidin-4-yl]cyclopropyl}ethyl)carbamate

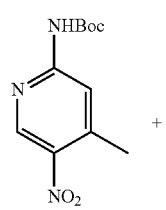

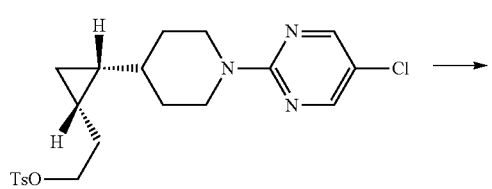

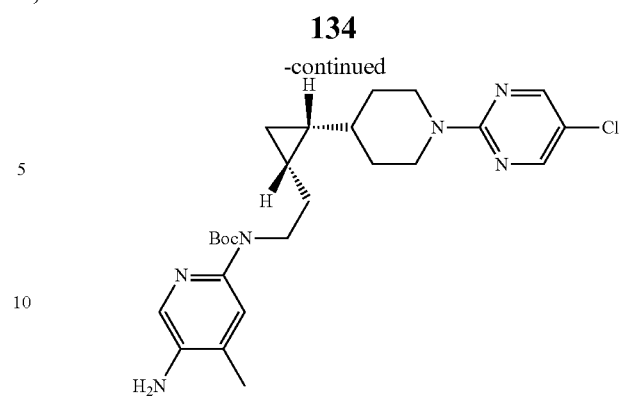

The title compound was synthesized by procedure analogous to Step 2 and 3 of Example 28 from 2-{(1S,2R)-2-[1-(5-chloropyrimidin-2-yl)piperidin-4-yl]cyclopropyl}ethyl 4-methylbenzenesulfonate from Step 1 of Example 5 and tert-butyl (4-methyl-5-nitropyridin-2-yl)carbamate from Step 1 of this example.

LRMS calc: 487.04; obs: 487.18 (M+1), 387.18 (M−100).

PREPARATIVE EXAMPLE 30a

Preparation of tert-butyl (5-amino-4-methylpyridin-2-yl)(2-{(1S,2S)-2-[1-(5-chloropyrimidin-2-yl)piperidin-4-yl]cyclopropyl}ethyl)carbamate Step 1: tert-butyl (5-nitropyridin-2-yl)carbamate

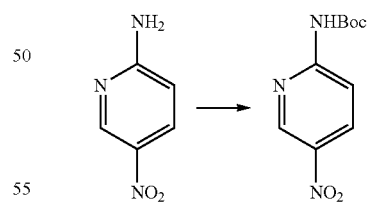

2-Amino-5-nitropyridine (1 g, 7.2=01) and di-tert-butyl dicarbonate (2.4 g, 10.8 mmol) were added in DMSO (10 mL), DMAP (170 mg, 1.4 mmol) was added and stirred at room temperature for 2 days. Water (50 mL) was added, extracted with ethyl acetate (100 mL), second wash with Brine (50 mL). The organic phase was dried by magnesium sulfate, filtered, concentrated and purified by column chromatography through a 50 gram Biotage SNAP KP-Sil™ silica gel cartridge eluting with 13% ethyl acetate/hexanes to give the title compound as a white solid.

LRMS calc: 239.23; obs: 262.34 (M+23), 184.14 (M−55), 166.11 (M−73).

Step 2: tert-butyl (5-amino-pyridin-2-yl)(2-{(1S,2S)-2-[1-(5-chloropyrimidin-2-yl)piperidin-4-yl]cyclopropyl}ethyl)carbamate

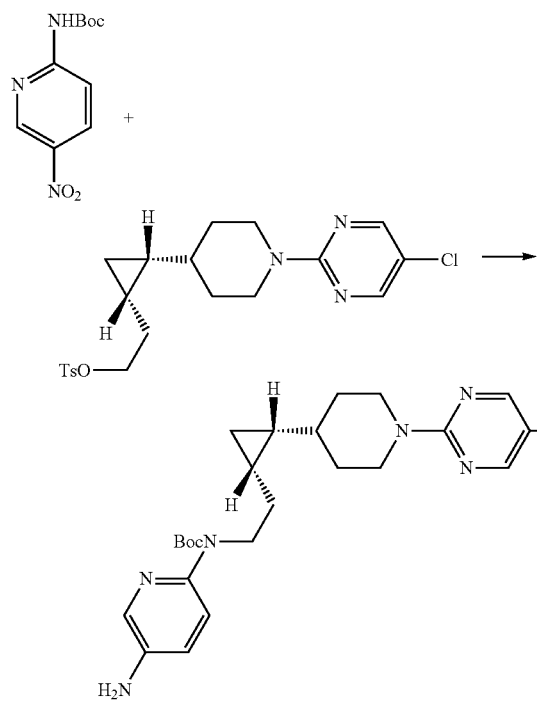

The title compound was synthesized by procedure analogous to Step 2 and 3 of Example 28 from 2-{(1S,2R)-2-[1-(5-chloropyrimidin-2-yl)piperidin-4-yl]cyclopropyl}ethyl 4-methylbenzenesulfonate from Step 1 of Example 5 and tert-butyl (5-nitropyridin-2-yl)carbamate from Step 1 of this example.

LRMS calc: 473.01; obs: 373.35 (M−100).

PREPARATIVE EXAMPLE 31a

Preparation of N-(2-{(1S,2S)-2-[1-(5-chloropyrimidin-2-yl)piperidin-4-yl]cyclopropyl}ethyl)-3-methylpyridine-2,5-diamine Step 1: di-tert-butyl (3-methyl-5-nitropyridin-2-yl)imidodicarbonate

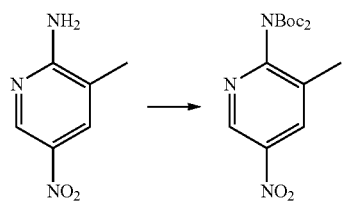

2-Amino-3-methyl-5-nitropyridine (0.5 g, 3.6 mmol) and di-tert-butyl dicarbonate (1.7 g, 7.8 mmol) were added in dichloromethane (8.9 mL), DMAP (87 mg, 0.71 mmol) was added and stirred at room temperature for 30 minutes. The reaction was directly loaded and purified by column chromatography through a 50 gram Biotage SNAP KP Sil™ silica gel cartridge eluting with 10% ethyl acetate/hexanes to give the title compound as a white solid.

LRMS calc: 339.34; obs: 340.11 (M+1).

Step. 2: di-tert-butyl {5-tert-butoxycarbonyl)amino-3-methylpyridin-2-yl}imidodicarbonate

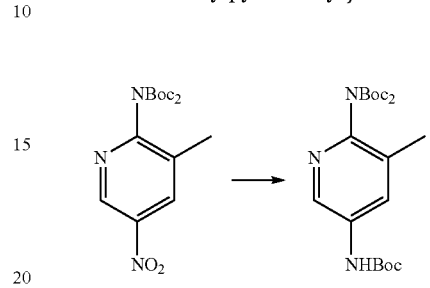

The title compound was synthesized by procedure analogous Step 2 of Example 26 and Step 3 of Example 14a using di-tert-butyl (3-methyl-5-nitropyridin-2-yl)imidodicarbonate from Step 1 of this example.

Step 3: N-(2-{(1S,2S)-2-[1-(5-chloropyrimidin-2-yl)piperidin-4-yl]cyclopropyl}ethyl)-3-methylpyridine-2,5-diamine

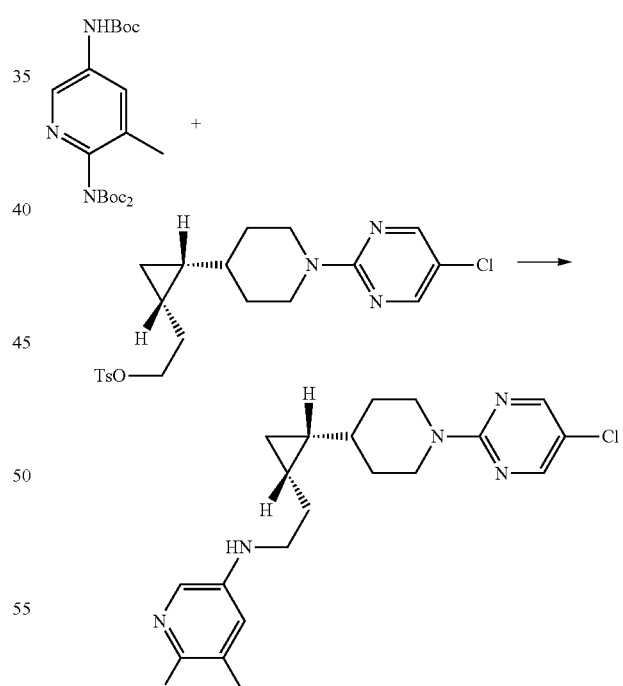

The title compound was synthesized by procedure analogous to Step 2 of Example 11 from 2-{(1S,2R)-2-[1-(5-chloropyrimidin-2-yl)piperidin-4-yl]cyclopropyl}ethyl 4-methylbenzenesulfonate from Step 1 of Example 5 and di-tert-butyl {5-[(tert-butoxycarbonyl)amino]-3-methylpyridin-2-yl}imidodicarbonate from Step 2 of this example LRMS calc: 386.92; obs: 387.14 (M−100). .

PREPARATIVE EXAMPLE 32a

Preparation of tert-butyl (6-amino-5-chloropyridin-3-yl)(2-{(1S,2S)-2-[1-(5-chloropyrimidin-2-yl)piperidin-4-yl]cyclopropyl}ethyl)carbamate Step 1: di-tert-butyl {5-11(tert-butoxycarbonyl)amino]-3-chloropyridin-2-yl}imidodicarbonate

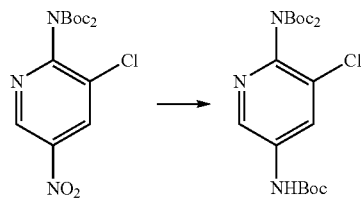

The title compound was synthesized by procedure analogous to Step 1 and 2 of Example 31a from 3-chloro-5-nitropyridin-2-amine.

LRMS calc: 443.92; obs: 444.03 (M+1), 344.02 (M−100), 466.01 (M+23).

Step 2: N-(2-{(1S,2S)-2-[1-(5-chloropyrimidin-2-yl)piperidin-4-yl]cyclopropyl}ethyl)-3-chloropyridine-2,5-diamine

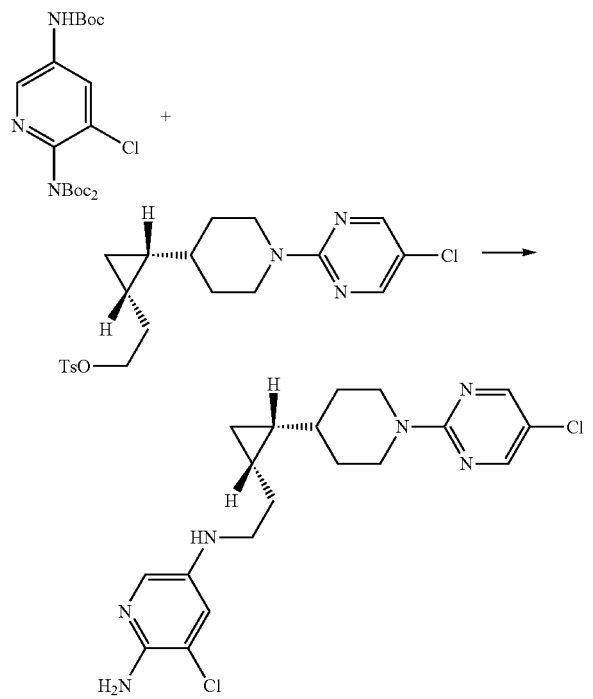

The title compound was synthesized by procedure analogous to Step 2 of Example 11 from cis-2-{(1S,2R)-2-[1-(5-chloropyrimidin-2-yl)piperidin-4-yl]cyclopropyl}ethyl 4-methylbenzenesulfonate from Step 1 of Example 5 and di-tert-butyl {5-[(tert-butoxycarbonyl)amino]-3-chloropyridin-2-yl}imidodicarbonate from Step 1 of this example.

LRMS calc: 407.36; obs: 407.06 (M+1).

Step 3: tert-butyl (6-amino-5-chloropyridin-3-yl)(2-{(1S,2S)-2-[1-(5-chloropyrimidin-2-yl)piperidin-4-yl]cyclopropyl}ethyl)carbamate

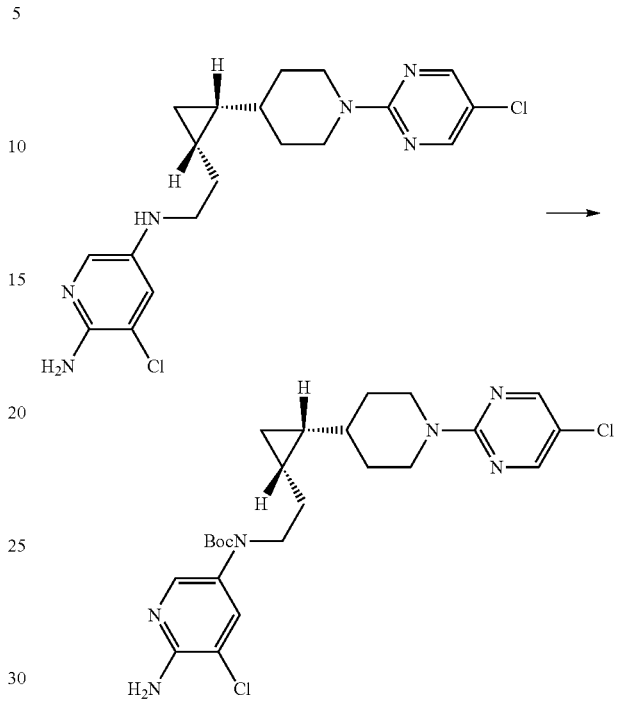

N-(2-{(1S,2S)-2-[1-(5-chloropyrimidin-2-yl)piperidin-4-yl]cyclopropyl}ethyl)-3-chloropyridine-2,5-diamine (480 mg, 1.2 mmol) from Step 2 of this example, di-tert-butyl dicarbonate (314 mg, 1.4 mmol) and pyridine (9.5 mg, 0.12 mmol) were added in tetrahydrofuran (12 mL) at room temperature for overnight. The reaction was concentrated and purified by column chromatography through a 25 gram Biotage SNAP KP-Sil™ silica gel cartridge eluting with 10% acetone/hexanes to give the title compound as a pale yellow solid.

LRMS calc: 507.46; obs: 507.14 (M+1), 451.07 (M+1-55), 407.11 (M−100).

EXAMPLE 33

Preparation of N-{6-[(2-{(1S,2S)-2-[1-(5-chloropyrimidin-2-yl)piperidin-4-yl]cyclopropyl}ethyl)amino]-5-methylpyridin-3-yl}acetamide

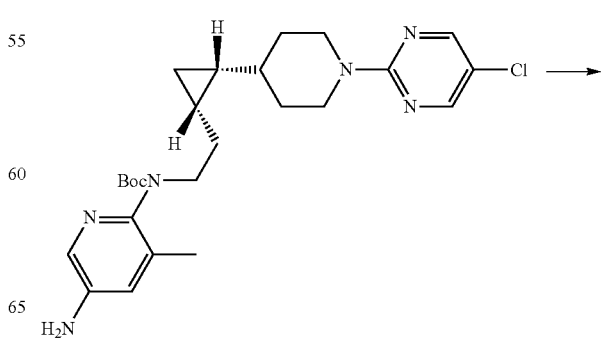

-continued

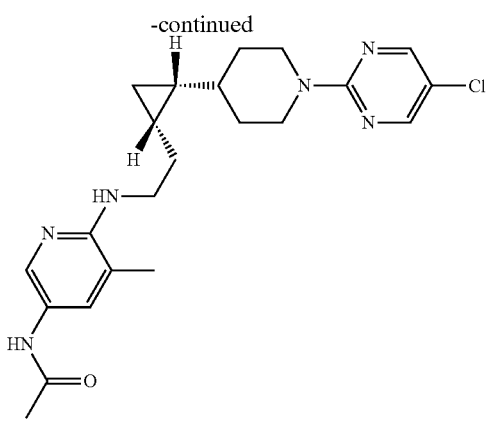

tert-butyl (5-amino-3-methylpyridin-2-yl)(2-{(1S,2S)-2-[1-(5-chloropyrimidin-2-yl)piperidin-4-yl]cyclopropyl}ethyl) carbamate (60 mg, 0.123 mmol) from Step 3 of Example 28, acetic anhydride (18.9 mg, 0.19 mmol) and pyridine (0.97 mg, 0012 mmol) were added in tetrahydrofuran (6 mL) at room temperature for 2 h. The reaction was concentrated to dryness, ethyl acetate (20 mL) was added, washed with water (20 mL), second wash with sodium bicarbonate saturated solution (10 mL). The organic phase was dried by magnesium sulfate, filtered and concentrated.

The crude solid was treated with neat trifluoroacetic acid (3 mL) at room temperature for 15 minutes, and was concentrated without heating. Saturated sodium bicarbonate solution (20 mL) was added to the crude, extracted with ethyl acetate (20 mL), second wash with Brine (10 mL). The organic phase was dried by magnesium sulfate, filtered, concentrated and purified by column chromatography through a 25 gram Biotage SNAP KP-Sil™ silica gel cartridge eluting with 22% acetone/hexanes to give the title compound as a white solid.

LRMS calc: 428.96; obs: 429.18 (M+1).

Compounds retorted in Table 3 are prepared by a general procedure analogous to that described in Example 33 above.

TABLE 3

| Examples | Chemical name | Chemical Structure | (M + 1) |
|---|---|---|---|
| Example 34 | N-{6-[(2-{(1S,2S)-2-[1-(5-chloropyrimidin-2-yl)piperidin-4-yl]cyclopropyl}ethyl)amino]-4-methylpyridin-3-yl}acetamide | 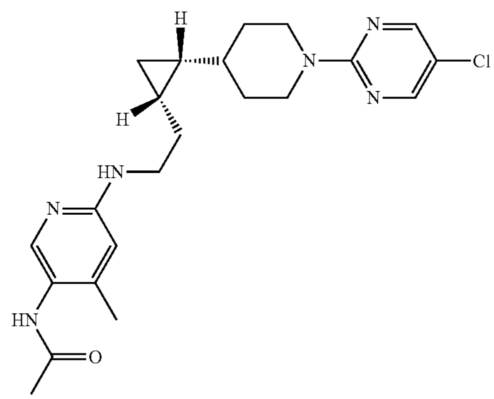 [SMILES: CC(=O)Nc1cnc(NCC[C@@H]2C[C@@H]2C2CCN(c3ncc(Cl)cn3)CC2)cc1C] | 429.41 |
| Example 35 | N-{6-[(2-{(1S,2S)-2-[1-(5-chloropyrimidin-2-yl)piperidin-4-yl]cyclopropyl}ethyl)amino]pyridin-3-yl}acetamide | 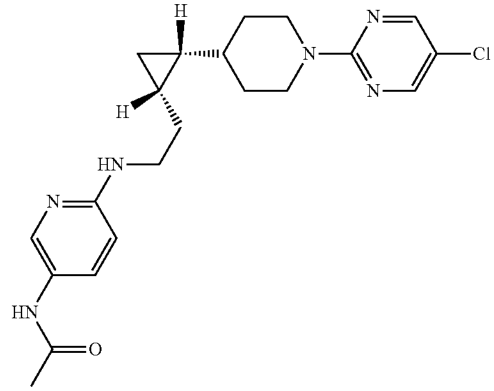 [SMILES: CC(=O)Nc1ccc(NCC[C@@H]2C[C@@H]2C2CCN(c3ncc(Cl)cn3)CC2)nc1] | 415.36 |

EXAMPLE 36

Preparation of N-(2-{(1S,2S)-2-[1-(5-chloropyrimidin-2-yl)piperidin-4-yl]cyclopropyl}ethyl)-3-methyl-5-(1H-tetrazol-1-yl)pyridin-2-amine

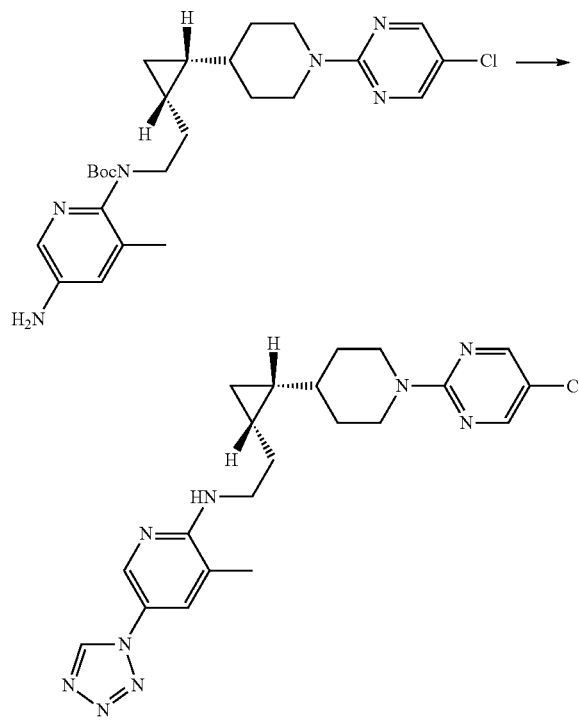

The title compound was synthesized by procedure analogous to Step 1 of Example 15a from tert-butyl (5-amino-3-methylpyridin-2-yl)(2-{(1S,2S)-2-[1-(5-chloropyrimidin-2-yl)piperidin-4-yl]cyclopropyl}ethyl)carbamate from Step 3 of Example 28.

LRMS calc: 439.94; obs: 440.03 (M+1), 412.10 (M+1-28).

EXAMPLE 37

Preparation of N-{6-[(2-{(1S,2S)-2-[1-(5-chloropyrimidin-2-yl)piperidin-4-yl]cyclopropyl}ethyl)amino]pyridin-3-yl}-1-methylcyclopropanecarboxamide Step 1: tert-butyl (2-{(1S,2S)-2-[1-(5-chloropyrimidin-2-yl)piperidin-4-yl]cyclopropyl}ethyl)(6-{[(1-methylcyclopropyl)carbonyl]amino}pyridin-3-yl)carbamate

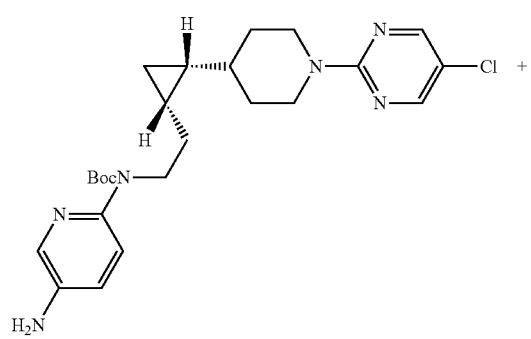

tert-butyl (5-amino-4-methylpyridin-2-yl)(2-{(1S,2S)-2-[1-(5-chloropyrimidin-2-yl)piperidin-4-yl]cyclopropyl}ethyl) carbamate (80 mg, 0.17 mmol) from Step 2 of Example 30a, 1-methylcyclopropane-1-carboxylic acid (19.2 mg, 0.19 mmol), HATU (84 mg, 0.22 mmol) and triethylamine (68.5 mg, 0.68 mmol) were added in DMF (1.7 mL) at room temperature for 2 days. The reaction was added ethyl acetate (20 mL, washed with sodium bicarbonate saturated solution (10 mL), second wash with brine (10 mL). The organic phase was dried by magnesium sulfate, filtered, concentrated and purified by column chromatography through a 25 gram Biotage SNAP KP-Sil™ silica gel cartridge eluting with 30% ethyl acetate/hexanes to give the title compound as a pale yellow oil.

LRMS calc: 554.99; obs: 455.08 (M+1-100), 577.16 (M+23).

Step 2: N-{6-[(2-{(1S,2S)-2-[1-(5-chloropyrimidin-2-yl)piperidin-4-yl]cyclopropyl}ethyl)amino]pyridin-3-yl}-1-methylcyclopropanecarboxamide -continued

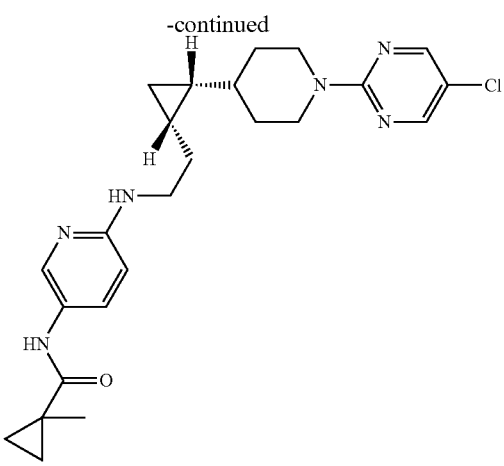

tert-butyl (2-{(1S,2S)-2-[1-(5-chloropyrimidin-2-yl)piperidin-4-yl]cyclopropyl}ethyl)(6-{[(1-methylcyclopropyl)carbonyl]amino}pyridin-3-yl)carbamate (90 mg) from step 1 of this example was dissolved in TFA:MeOH (1:1, 6 mL) at room temperature for 2 h. The reaction was concentrated without heating. Ethyl acetate (20 mL) was added, washed with sodium bicarbonate saturated solution (10 mL), second wash with brine (10 mL). The organic phase was dried by magnesium sulfate, filtered, concentrated and purified by column chromatography through a 25 gram Biotage SNAP KP-Sil™ silica gel cartridge eluting with 50% ethyl acetate/hexanes to give the title compound as a pale yellow solid.

LRMS calc: 454.99; obs: 455.11 (M+1).

Compounds reported in Table 4 are prepared by a general procedure analogous to that described in Example 37 above.

TABLE 4

| Examples | Chemical name | Chemical Structure | (M + 1) |
|---|---|---|---|
| Example 38 | N-{5-[(2-{(1S,2S)-2-[1-(5-chloropyrimidin-2-yl)piperidin-4-yl]cyclopropyl}ethyl)amino]pyridin-2-yl}-1-methylcyclopropanecarboxamide | 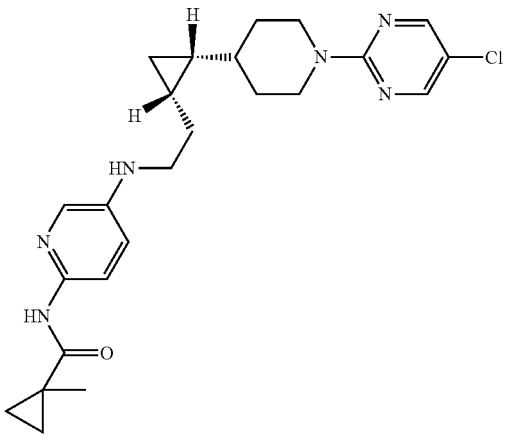 [SMILES: CC1(C(=O)Nc2ccc(NCC[C@@H]3C[C@@H]3C3CCN(c4ncc(Cl)cn4)CC3)cn2)CC1] | 455.11 |
| Example 39 | N-{6-[(2-{(1S,2S)-2-[1-(5-chloropyrimidin-2-yl)piperidin-4-yl]cyclopropyl}ethyl)amino]pyridin-3-yl}acetamide | 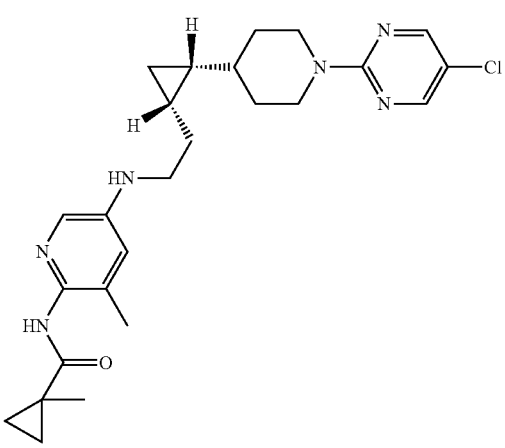 [SMILES: Cc1cc(NCC[C@@H]2C[C@@H]2C2CCN(c3ncc(Cl)cn3)CC2)cnc1NC(=O)C1(C)CC1] | 469.17 |

Preparation of non-commercial pyridine carbamates for examples in Table 4 are reported below.

PREPARATIVE EXAMPLE 32a

Preparation of N(2-{(1S,2S)-2-[1-(4-chlorophenyl)piperidin-4-yl]cyclopropyl}ethyl)pyridine-2,5-diamine

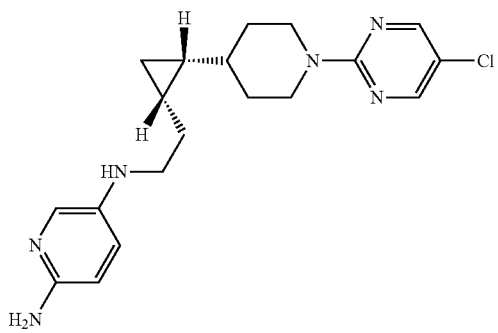 [SMILES: Nc1ccc(NCC[C@@H]2C[C@@H]2C2CCN(c3ncc(Cl)cn3)CC2)cn1]

The title compound was synthesized by procedure analogous to Example 31a from commercial 5-nitropyridin-2-amine. LRMS calc: 372.89; obs: 373.15 (M+1).

EXAMPLE 40

Preparation of 2-[(2-{(1S,2S)-2-[1-(5-chloropyrimidin-2-yl)piperidin-4-yl]cyclopropyl}ethyl)amino]-6-methylisonicotinonitrile Step 1: 2-chloro-6-methylisonicotinonitrile

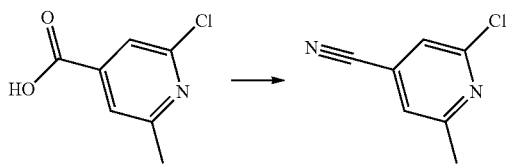

2-chloro-6-methylisonicotinonitrile (3.1 gram, 18.11 mmol) was dissolved in pyridine (90 ml), the mixture cooled to 0° C., and methanesulfonyl chloride (2.1 gram, 18.3 mmol) added drop wise. The mixture was stirred for 1 hour. Ammonia gas was passed through the mixture for 2 minutes. The excess ammonia was removed by placing the vessel on the rotary evaporator for 15 minutes. The mixture was cooled to 0° C., methanesulfonyl chloride added (11.66 g, 8.3 ml) drop wise and the mixture stirred for 72 hours. The mixture was poured into an solution of HCl(aq) (10 ml 1 N HCl in 100 ml water), the pH of the mixture adjusted to 7, and 100 ml of EtOAc added. The mixture was shaken, filtered through CELITE, the layers separated, the aqueous phase extracted with EtOAc (100 ml). The organic fractions were combined, dried over $Na_2SO_4$, filtered, and the volatiles removed in vacuum. The product was purified by chromatography on $SiO_2$ eluting with 40% EtOAc:Hexanes to give the titled compound.

Step 2: 2-[(2-{(1S,2S)-2-[1-(5-chloropyrimidin-2-yl)piperidin-4-yl]cyclopropyl}ethyl)amino]-6-methyl-isonicotinonitrile

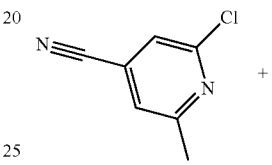

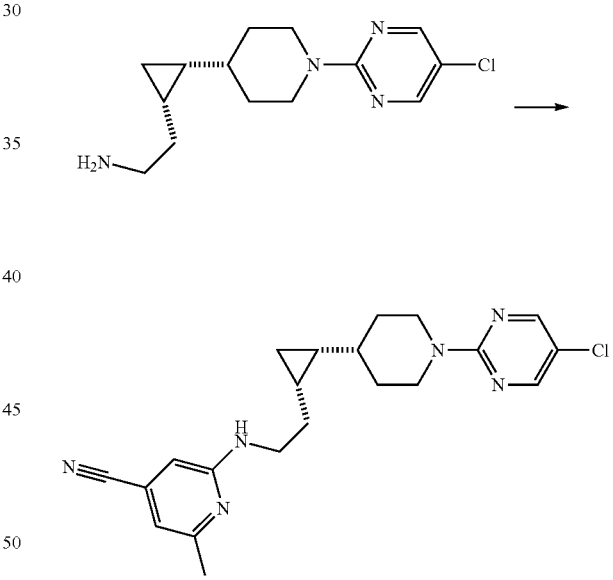

2-{(1S,2S)-2-[1-(5-chloropyrimidin-2-yl)piperidin-4-yl]cyclopropyl}ethanamine from step 3 of Example 5 (59 mg, 0.21 mmol) was dissolved in DMSO (1.0 ml). $K_2CO_3$ (86 mg, 0.62 mmol) and 2-chloro-6-methylisonicotinonitrile (31 mg, 0.21 mmol) from step 2 of this example were added and the mixture stirred at 150° C. overnight. The mixture was cooled to RT, diluted with water (30 ml), and extracted with EtOAc (3×30 ml). The organic fractions were combined, washed with brine, dried over $Na_2SO_4$, filtered and the volatiles removed in vacuum. The product was purified by chromatography on $SiO_2$ eluting with 20% EtOAc:Hexanes to give the titled compound. LRMS calc: 396.18; obs: 397.27 (M+1).

Compounds reported in Table 5 are prepared by a general procedure analogous to that described in Example 40 above.

TABLE 5

| Example | Chemical name | Chemical Structure | (M + 1) |
|---|---|---|---|
| Example 41 | 6-[(2-{(1S,2S)-2-[1-(5-chloropyrimidin-2-yl)piperidin-4-yl]cyclopropyl}ethyl)amino]-4-methylpyridine-2-carbonitrile | 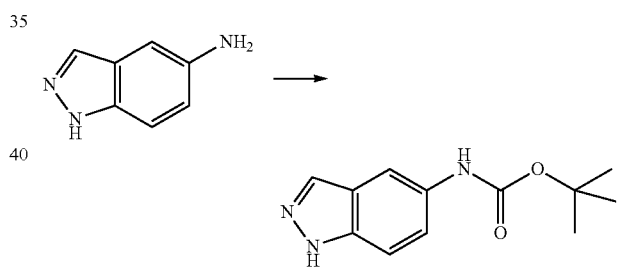 | 397.28 |

Preparations of non-commercial chloride starting materials for examples in Table 5 are reported below.

PREPARATIVE EXAMPLE 41a

Preparation of 6-chloro-4-methylpyridine-2-carbonitrile

Step 1: 2-chloro-4-methylpyridine 1-oxide

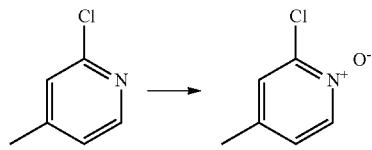

2-chloro-4-methylpyridine (10 g, 80 mmol) was dissolved in acetic acid (100 ml). Hydrogen peroxide (31%, 86.8 g, 80.7 ml, 790 mmol)) was added in 4 portions and the solution stirred under nitrogen at 65° C. for 18 hours. The mixture was poured into ice water (300 ml), and solid Na₂CO₃ added until the solution was alkaline. The mixture was extracted with DCM (3×300 ml), the organic fractions combined, washed with sodium thiosulfate (1M, 100 ml), brine, dried over Na₂SO₄, and the volatiles removed in vacuum to give the titled compound.

Step 2: 6-chloro-4-methylpyridine-2-carbonitrile

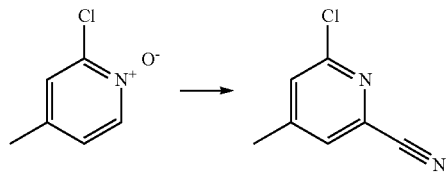

2-chloro-4-methylpyridine 1-oxide (8.5 g, 59.2 mmol) from step 1 of this example was added to the dimethyl sulfate (9.0 g, 71 mmol) and the mixture stirred overnight. Diethyl ether (40 ml) was added, the mixture stirred, and ether decanted (2×). The volatiles were removed in vacuum. The residue was dissolved in water (50 ml) and the solution added drop wise to a −15° C. solution of sodium cyanide (11.3 g, 231 mmol) in water (50 ml) under N₂. The mixture was stirred between −7 and −15° C. for 1.5 hours during which a solid precipitates. The crystals were filtered, washed with water followed by a small amount of cold ether to give the titled compound. LRMS calc: 152.01; obs: 153.56 (M+1).

EXAMPLE 42

Preparation of N-(2-{(1S,2S)-2-[1-(5-chloropyrimidin-2-yl)piperidin-4-yl]cyclopropyl}ethyl)-1H-indazol-5-amine Step 1: tert-butyl 1H-imidazol-5-ylcarbamate

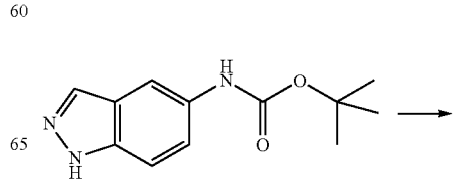

1H-indazol-5-amine (2 g, 15 mmol) was dissolved in toluene (75 ml), BOC anhydride added (33 g, 15 mmol) and the mixture heated at 70° C. overnight. The mixture was cooled to RT, diluted with water (200 ml), extracted with EtOAc (3×100 ml), the organic fractions combined, washed with brine, dried over Na₂SO₄, filtered and the volatiles removed in vacuum. The product was purified by chromatography on SiO₂ eluting with 30% ethyl acetate:hexanes to give the titled mixture.

Step 2: tert-butyl [1-(4-methoxybenzyl)-1H-indazol-5-yl]carbamate and tert-butyl [1-(4-methoxybenzyl)-2H-indazol-5-yl]carbamate

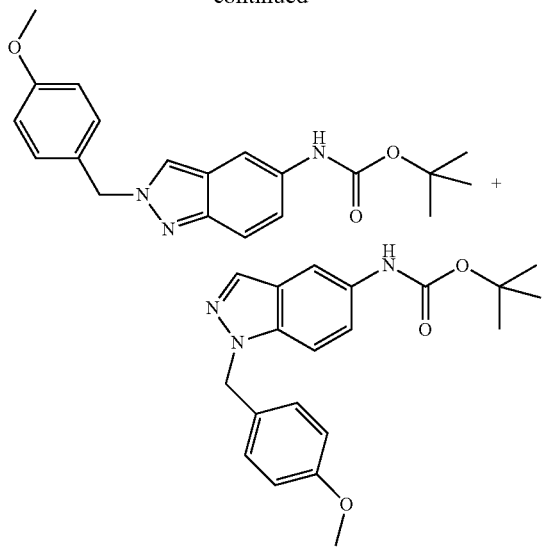

+ tert-butyl 1H-indazol-5-ylcarbamate (300 mg, 1.3 mol) from step 1 of this example was dissolved in DMF (2.5 ml) and cesium carbonate (419 mg, 1.3 mmol) added and the slurry stirred vigorously. p-methoxy benzyl bromide (259 mg, 1.3 mmol) was added at RT and the mixture stirred for 1 h. The mixture was diluted with water and extracted with EtOAc (3×30 ml), the organic fractions combined, washed with brine, dried over $Na_2SO_4$ filtered and the volatiles removed in vacuum. The product was purified by chromatography on $SiO_2$ eluting with 30% acetone:hexanes to give the titled mixture.

Step 3: N-(2-{(1S,2S)-2-[1-(5-chloropyrimidin-2-yl)piperidin-4-yl]cyclopropyl}ethyl)1H-indazol-5-amine

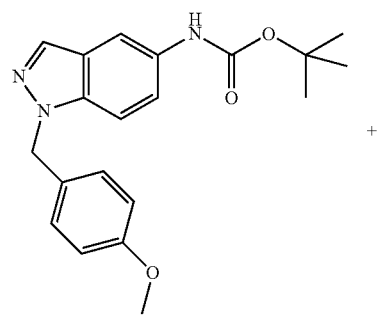

+

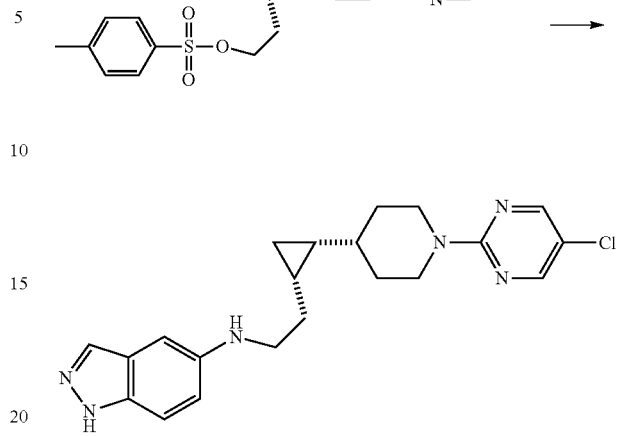

2-{(1S,2R)-2-[1-(5-chloropyrimidin-2-yl)piperidin-4-yl]cyclopropyl}ethyl 4-methylbenzenesulfonate from step 1 of Example 5 (100 mg, 0.23 mmol) was dissolved in NMP (1.1 ml). The mixture of tert-butyl [1-(4-methoxybenzyl)-1H-indazol-5-yl]carbamate and tert-butyl [1-(4-methoxybenzyl)-2H-indazol-5-yl]carbamate (81 mg, 0.23 mmol) from step 2 of this example and cesium carbonate (0.224 mg, 0.69 mmol) were added and the slurry stirred at 70° C. for 24 h. The mixture was diluted with 4:1 water:saturated sodium bicarbonate (30 ml), extracted with EtOAc (3×30 ml), the organic fractions combined, washed with brine, dried over $Na_2SO_4$, filtered, and the volatiles removed in vacuum. The material was dissolved in TPA at RT and the solution stirred for 5 minutes. The solution was heated to 70° C. for 2 hours. The volatiles were removed in vacuum. The residue was dissolved in DCM (30 ml), shaken with a solution of saturated bicarbonate (30 ml), the layers separated, and the aqueous phase extracted with DCM (2×30 ml). The organic fractions were combined, washed with brine, dried over $Na_2SO_4$, filtered, and the volatiles removed in vacuum. The product was purified by chromatography on $SiO_2$ eluting with 20% acetone: DCM to give the titled compound. LRMS calc: 396.18; obs: 397.27 (M+1).

Compounds reported in Table 6 are prepared by a general procedure analogous to that described in Example 42 above.

TABLE 6

| Examples | Chemical name | Chemical Structure | (M + 1) |
|---|---|---|---|
| Example 43 | 2-{4-[(2-{(1S,2S)-2-[1-(5-chloropyrimidin-2-yl)piperidin-4-yl]cyclopropyl}ethyl)amino]phenyl}-N-cyclopropylacetamide | 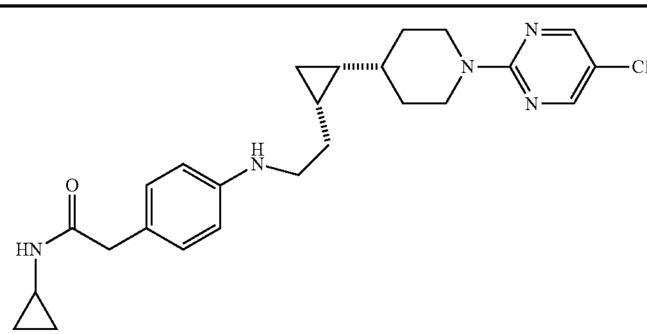 | 454.07 |

Preparations of non-commercial Boc starting materials for examples in Table 6 are reported below.

PREPARATIVE EXAMPLE 43a

Preparation of tert-butyl {4-[2-(cyclopropylamino)-2-oxoethyl]phenyl}carbamate

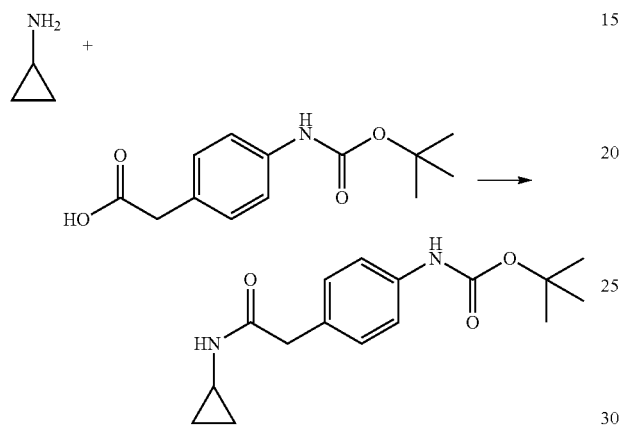

{4-[(tert-butoxycarbonyl)amino]phenyl}acetic acid (300 mg, 1.2 mmol) was dissolved in DMF (3 ml). EDC (275 mg, 1.4 mmol), HOBt (256 mg, 1.7 mmol), DIEA (450 mg, 3.6 mmol) and cyclopropyl amine (82 mg, 1.4) were added and the mixture stirred at RT for 2 hours. The mixture was diluted into a 10% solution of sodium bicarbonate (aq, 50 ml), extracted with EtOAc (3×30 ml), the organic fractions combined, dried over Na$_2$SO$_4$, filtered and the volatiles removed in vacuum to give the titled compound. LRMS calc: 290.16; obs: 397.27 (M+1).

EXAMPLE 44

Preparation of 5-[(2-{(1S,2S)-2-[1-(5-chloropyrimidin-2-yl)piperidin-4-yl]cyclopropyl}ethyl)amino]isoindolin-1-one Step 1: methyl 2-methyl-4-nitrobenzoate

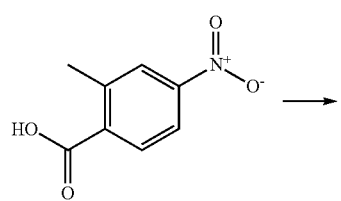

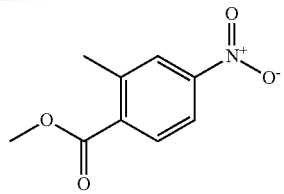

Sulfuric acid (6 ml, 113 mmol) was added to drop wise to a solution of the 2-methyl-4-nitrobenzoic acid (5 g, 27.6 mmol) in MeOH (138 ml) at RT. After the addition was complete the mixture was heated to 55° C. overnight. The volatiles were removed in vacuum and the residue partitioned between EtOAc (100 ml) and water (100 ml). The layers were separated and aqueous phase extracted with EtOAc (2×100 ml). The organic fractions were combined, washed with saturated sodium bicarbonate (aqueous, 100 ml), brine, dried over Na$_2$SO$_4$, filtered and the volatiles removed in vacuum to give the titled compound.

Step 2: 5-nitroisoindolin-1-one

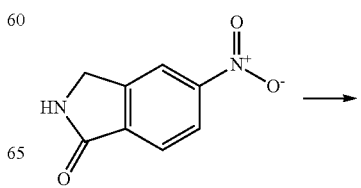

AIBN (84 mg, 0.51), NBS (1.1 gram, 6.4 mmol), and the methyl 2-methyl-4-nitrobenzoate (1 g, 5.1 mmol) from step 1 of this example were suspended in CCl$_4$ and the mixture heated under N$_2$ at 79 C overnight. The solution was filtered, and concentrated in vacuum. The residue was dissolved in 7 N ammonia in methanol (15 ml) and the solution stirred for 2 hours at RT. The mixture was concentrated in vacuum. and the resulting solid suspended in EtOAc (21.5 ml), heated at 80° C. for 30 minutes with stirring, cooled RT and aged at −20° C. for the 3 days. The solid was isolated by filtration to give the titled compound.

Step 3: 5-aminoisoindolin-1-one

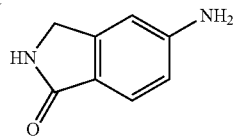

Iron powder (2.51 g, 45 mmol), water (0.97 ml) and HCl (37%, 0.74 ml), were added to a stirred suspension of the 5-nitroisoindolin-1-one (800 mg, 4.5 mmol) from step 2 of this example in EtOH (11.2 ml). The mixture was heated at 95° C. for 2 h. Ammonia (7N in MeOH) was added (1 mL) to make the pH of the mixture alkaline. The mixture was filtered to removed undissolved solids and the filter cake washed with EtOH (2×40 ml). The filtrate and organic washes were combined and concentrated in vacuum to give the titled compound.

Step 4: 5-[(2-{(1S,2S)-2-[1-(5-chloropyrimidin-2-yl)piperidin-4-yl]cyclopropyl}ethyl)amino]isoindolin-1-one

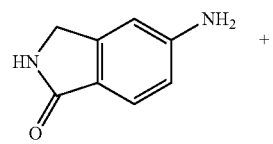

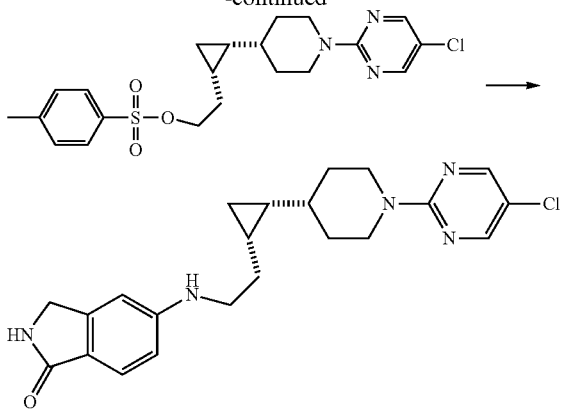

2-{(1S,2R)-2-[1-(5-chloropyrimidin-2-yl)piperidin-4-yl]cyclopropyl}ethyl 4-methylbenzenesulfonate from step 1 of Example 5 (100 mg, 0.23 mmol) was dissolved in sulfolane and 5-aminoisoindolin-1-one (68 mg, 0.46 mmol) from step 3 of this example added. The mixture was at stirred 110° C. for 3 and at 120° C. for 2 hours. The mixture was cooled to RT, diluted with 4:1 water:saturated sodium bicarbonate (40 ml), extracted with EtOAc (3×30 ml), the organic fractions combined, washed with brine, dried over Na$_2$SO$_4$, filtered, the volatiles removed in vacuum. The product was purified by chromatography on SiO$_2$ eluting with 80% acetone:hexanes to give the titled compound. LRMS calc: 411.18; obs: 412.08 (M+1).

Compounds reported in Table 7 are prepared by a general procedure analogous to that described in Example 44 above.

TABLE 7

| Examples | Chemical name | Chemical Structure | (M + 1) |
|---|---|---|---|
| Example 45 | 5-[(2-{(1S,2S)-2-[1-(5-chloropyrimidin-2-yl)piperidin-4-yl]cyclopropyl}ethyl)amino]-2-methylisoindolin-1-one | 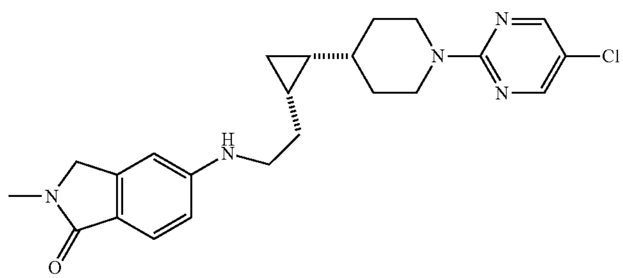 | 426.03 |
| Example 46 | 5-[(2-{(1S,2S)-2-[1-(5-chloropyrimidin-2-yl)piperidin-4-yl]cyclopropyl}ethyl)amino]-2-cyclopropylisoindolin-1-one | 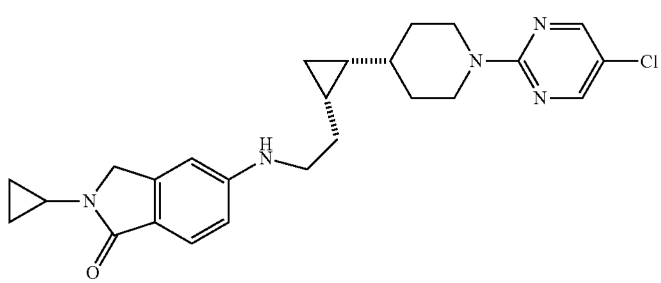 | 452.02 |

Preparations of non-commercial amino starting materials for examples in Table 7 are reported below.

PREPARATIVE EXAMPLE 45a

Preparation of 5-amino-2-methylisoindolin-1-one

Step 1: 2-methyl-5-nitroisoindolin-1-one

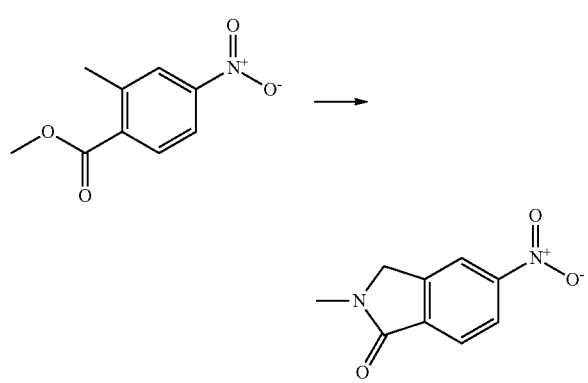

AIBN (84 mg, 0.51), NBS (1.1 gram, 6.4 mmol), and the methyl 2-methyl-4-nitrobenzoate (1 g, 5.1 mmol, as prepared in Step 1, Example 44) were suspended in $CCl_4$ (12.8 ml), the vessel evacuated and backfilled with $N_2$ (2×) and the mixture heated under $N_2$ at 79° C. overnight. The solution was filtered, and concentrated in vacuum. One third of the crude material was dissolved in 2 N methylamine in methanol (18 ml), 2N methylamine in THF added (18 ml) and the solution stirred for 2 hours at RT. The volatiles were removed in vacuum and the product was purified by chromatography on $SiO_2$ eluting with 10% acetone:DCM to give the titled compound.

Step 2: 5-amino-2-methylisoindolin-1-one

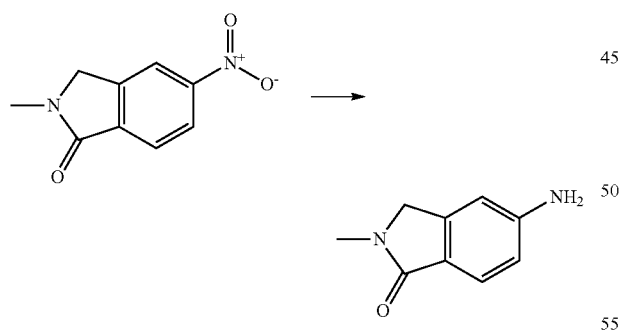

The 2-methyl-5-nitroisoindolin-1-one (50 mg, 0.26 mmol) was dissolved in EtOH (1.3 ml) with heating, and tin chloride (117 mg, 0.52 mmol) added. The solution was stirred at 79° C. for 2 hours. The mixture was cooled to RT, diluted with 4:1 water:saturated sodium bicarbonate (aq, 100 ml), extracted with EtOAc (3×100 ml), the organics combined, washed with brine, dried over $Na_2SO_4$, filtered and the volatiles removed in vacuum. The product was purified by chromatography on $SiO_2$ eluting with 5% MeOH:DCM+1% TEA to give the titled compound.

LRMS calc: 162.08; obs: 163.18 (M+1).

PREPARATIVE EXAMPLE 46a

Preparation of 5-amino-2-cyclopropylisoindolin-1-one

Step 1: 2-cyclopropyl-5-nitroisoindolin-1-one

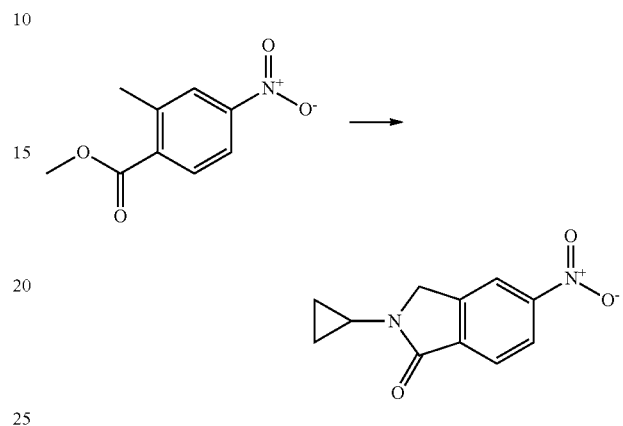

AIBN (28 mg, 0.17), NBS (0.37 gram, 2.1 mmol), and the methyl 2-methyl-4-nitrobenzoate (334 g, 1.7 mmol, as prepared in Step 1, Example 44) were suspended in $CCl_4$ (4.2 ml), the vessel evacuated and backfilled with $N_2$ (2×) and the mixture heated under $N_2$ at 79° C. overnight. The solution was filtered, and concentrated in vacuum. The residue was dissolved in 7 N cyclopropyl amine (2.1 g, 35.9 mmol, in methanol, 18 ml), and the solution stirred for 2 hours at RT. The volatiles were removed in vacuum and the product purified by chromatography on $SiO_2$ eluting with 10% acetone:DCM to give the titled compound.

Step 2: 5-amino-2-cyclopropylisoindolin-1-one

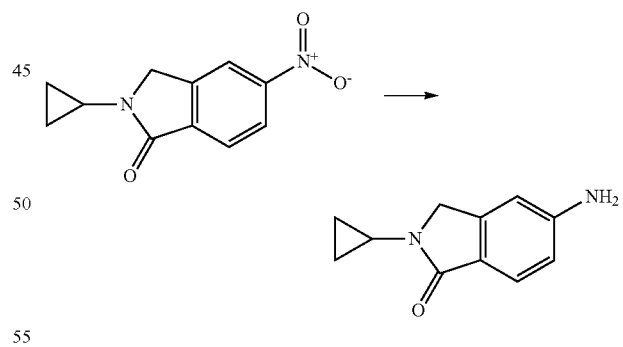

The 2-cyclopropyl-5-nitroisoindolin-1-one (50 mg, 0.23 mmol) was dissolved in EtOH (1.1 ml) with heating, and tin chloride (117 mg, 0.52 mmol) added. The solution was stirred at 79° C. for 2 hours. The mixture was cooled to RT, diluted with 4:1 water:saturated sodium bicarbonate (aq, 100 ml), extracted with EtOAc (3×100 ml), the organics combined, washed with brine, dried over $Na_2SO_4$, filtered and the volatiles removed in vacuum. The product was purified by chromatography on $SiO_2$ eluting with 5% MeOH:DCM+1% TEA to give the titled compound.

LRMS calc: 188.09; obs: 189.17 (M+1).

EXAMPLE 47

Preparation of N-(2-{(1S,2S)-2-[1-(5-chloropyrimidin-2-yl)piperidin-4-yl]cyclopropyl}ethyl)-3-methyl-1H-indazol-5-amine

Step 1:
1-(4-methoxybenzyl)-3-methyl-5-nitro-1H-indazole

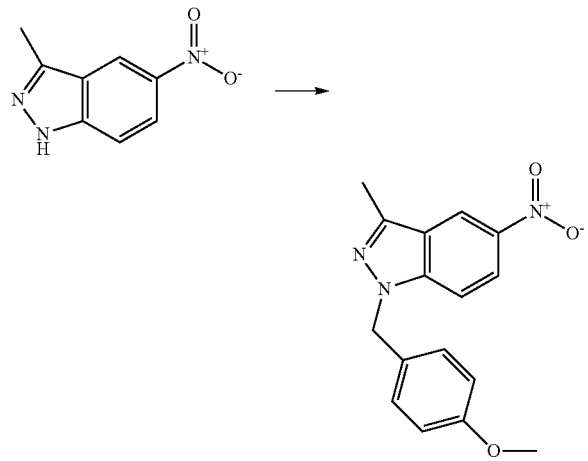

3-methyl-5-nitro-1H-indazole (1.0 g, 5.6 mmol) was dissolved in DMF (11.2 mmol) and cesium carbonate (2.0 g, 6.2 mmol) added. The slurry was cooled to 0° C. and p-methoxy benzyl chloride (0.97 g, 6.2 mmol) added to vigorously stirred slurry drop wise. The slurry was stirred at 0° C. for 1 hour, the cooling bath removed and the mixture stirred at RT for 3 h. The mixture was diluted with 4:1 water:saturated sodium bicarbonate (200 ml), extracted with EtOAc (3×50 ml), the organic fractions combined, washed with brine, dried over Na₂SO₄, filtered and the volatiles removed in vacuum. The product was purified by chromatography on SiO₂ eluting with 30% acetone:hexanes to give the titled compound.

Step 2:
1-(4-methoxybenzyl)-3-methyl-1H-indazol-5-amine

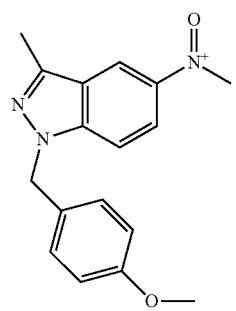

+

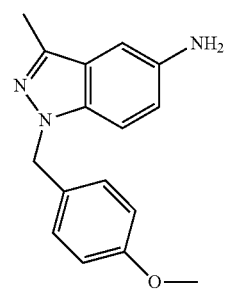

1-(4-methoxybenzyl)-3-methyl-5-nitro-1H-indazole (275 mg, 0.93 mmol) from Step 1 of this example was dissolved in MeOH (4.6 ml) and EtOAc (10 ml) to give a clear yellow solution. Pd/C (10%, 98 mg) was added, the vessel evacuated and backfilled with hydrogen (3×) and slurry stirred under a hydrogen atmosphere for 30 minutes. The mixture was filtered through CELITE, the filter cake washed with EtOAc (2×40 ml), the filtrates combined and the volatiles removed in vacuum to give the titled compound.

Step 3: N-(2-{(1S,2S)-2-[1-(5-chloropyrimidin-2-yl)piperidin-4-yl]cyclopropyl}ethyl)-1-(4-methoxybenzyl)-3-methyl-1H-indazol-5-amine

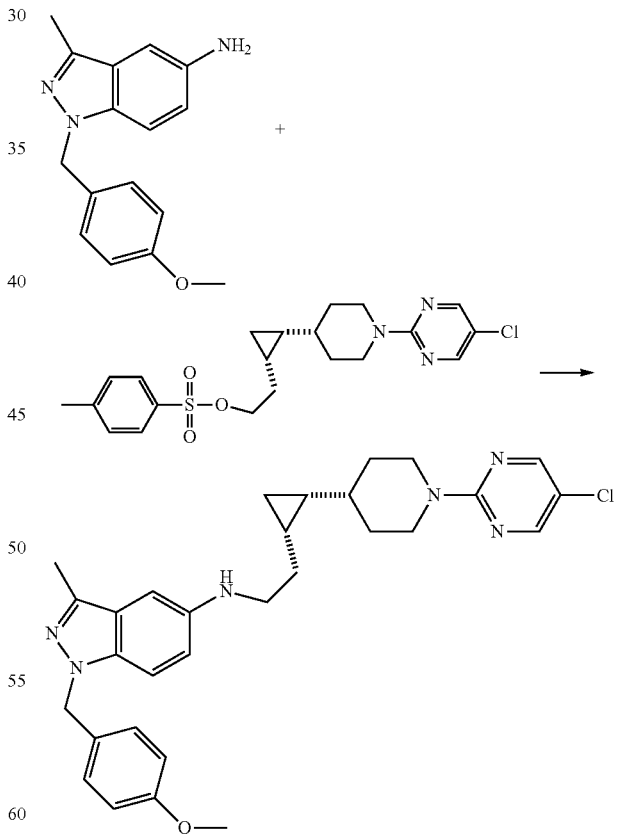

1-(4-methoxybenzyl)-3-methyl-1H-indazol-5-amine (51 mg, 0.34 mmol) from step 2 of this example, 2-{(1S,2R)-2-[1-(5-chloropyrimidin-2-yl)piperidin-4-yl]cyclopropyl}ethyl 4-methylbenzenesulfonate from step 1 of Example 5 (75 mg, 0.17 mmol) and potassium iodide (3 mg, 0.017 mmol) combined and the solids slurried in acetonitrile. The slurry was reacted in the microwave with stirring for 80 minutes at 110° C. using normal power. The mixture was cooled to RT, diluted with 4:1 water:saturated sodium bicarbonate (40 ml), extracted with EtOAc (3×40 ml), the organic fractions combined, washed with brine, dried over Na$_2$SO$_4$, filtered and the volatiles removed in vacuum. The product was purified by chromatography on SiO$_2$ eluting with 10% acetone:DCM to give the titled compound.

Step 4: N-(2-{(1S,2S)-2-[1-(5-chloropyrimidin-2-yl) piperidin-4-yl]cyclopropyl}ethyl)-3-methyl-1H-indazol-5-amine

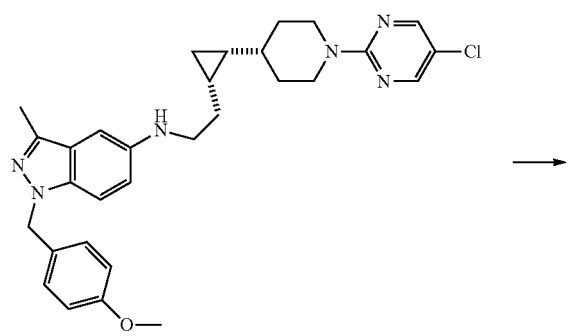

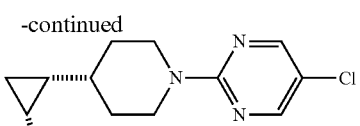

N-(2-{(1S,2S)-2-[1-(5-chloropyrimidin-2-yl)piperidin-4-yl] cyclopropyl}ethyl)-1-(4-methoxybenzyl)-3-methyl-1H-indazol-5-amine (22 mg, 0.041 mmol) from step 3 of this example was dissolved in TFA (200 uL) and stirred at 75° C. for 4.5 hours. The volatiles were removed in vacuum. The residue was then dissolved in MeOH, and the volatiles removed in vacuum. The residue was then dissolved in DCM, and the volatiles removed in vacuum. The product was purified by chromatography on KPNH$_2$™ SiO$_2$ (Biotage) eluting with 5% acetone:DCM to give the titled compound. LRMS calc: 410.20; obs: 411.05 (M+1).

Compounds reported in Table 8 are prepared by a general procedure analogous to that described in step 3, Example 48 above.

TABLE 8

| Examples | Chemical name | Chemical Structure | (M + 1) |
|---|---|---|---|
| Example 48 | N-(2-{(1S,2S)-2-[1-(5-chloropyrimidin-2-yl)piperidin-4-yl]cyclopropyl}ethyl)-1-methyl-1H-indazol-5-amine | 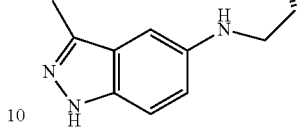 | 410.96 |
| Example 49 | N-(2-{(1S,2S)-2-[1-(5-chloropyrimidin-2-yl)piperidin-4-yl]cyclopropyl}ethyl)-2-methyl-2H-indazol-5-amine | 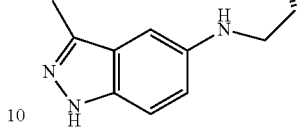 | 410.96 |
| Example 50 | 5-[(2-{(1S,2S)-2-[1-(5-chloropyrimidin-2-yl)piperidin-4-yl]cyclopropyl}ethyl)amino]-1,3-dihydro-2H-indol-2-one | 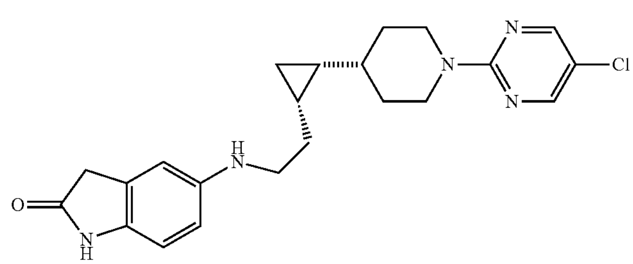 [SMILES: O=C1Cc2cc(NCC[C@@H]3C[C@@H]3C3CCN(c4ncc(Cl)cn4)CC3)ccc2N1] | 412.08 |

TABLE 8-continued

| Examples | Chemical name | Chemical Structure | (M + 1) |
|---|---|---|---|
| Example 51 | 5-[(2-{(1S,2S)-2-[1-(5-chloropyrimidin-2-yl)piperidin-4-yl]cyclopropyl}ethyl)amino]-1-methyl-1,3-dihydro-2H-indol-2-one | 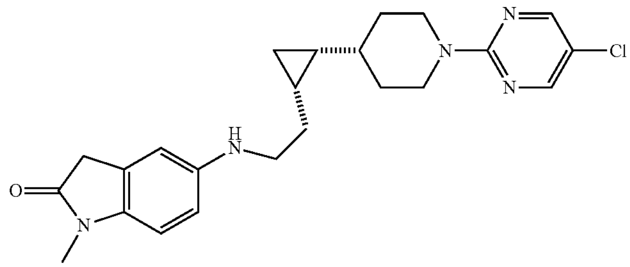 | 426.03 |
| Example 52 | N-{4-[(2-{(1S,2S)-2-[1-(5-chloropyrimidin-2-yl)piperidin-4-yl]cyclopropyl}ethyl)amino]phenyl}acetamide | 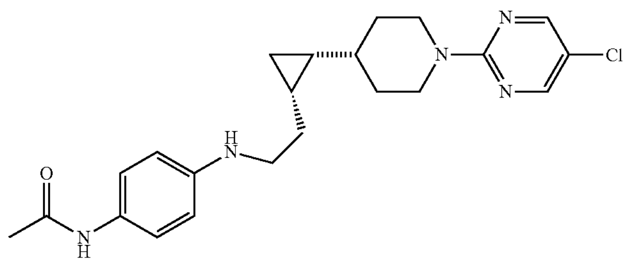 | 414.12 |

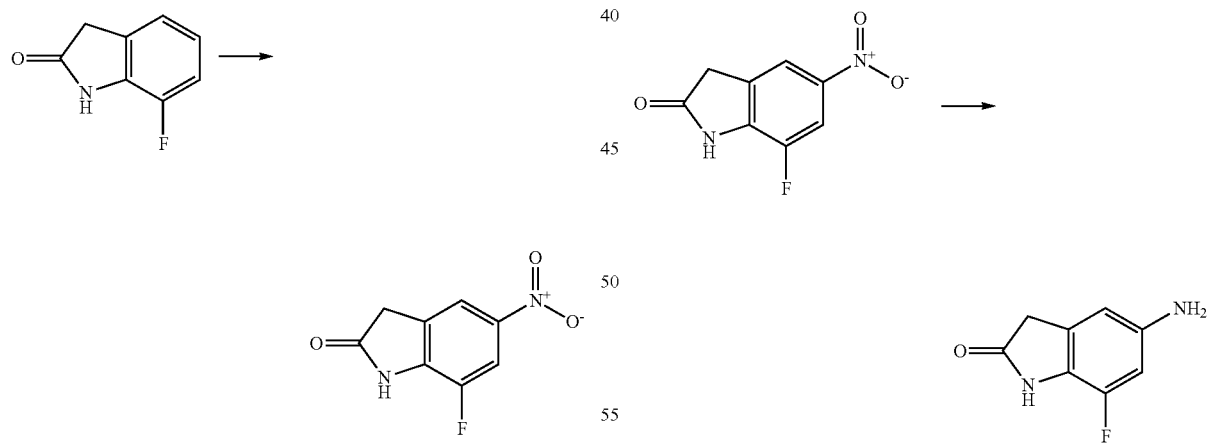

EXAMPLE 53

Preparation of 5(2-{(1S,2S)-2-[1-(5-chloropyrimidin-2-yl)piperidin-4-yl]cyclopropyl}ethyl)amino]-7-fluoro-1,3-dihydro-2H-indol-2-one Step 1: 7-fluoro-5-nitro-1,3-dihydro-2H-indol-2-one 7-fluoro-1,3-dihydro-2H-indol-2-one (8.0 g, 52.9 mmol) was slurried in $H_2SO_4$ (conc., 86 ml) and the mixture cooled to −45° C. A solution of fuming nitric acid (>90%, 3.34 g, 52.9 mmol) in $H_2SO_4$ (20 ml) was added drop wise, while maintaining the temperature at −45° C. throughout the addition. The mixture was allowed to slowly warm to RT and stirred overnight. The mixture was poured into stirred ice-cold water (1500 ml). A white precipitate resulted, and the slurry was aged at 0° C. for 1 hour. The solid was collected by filtration, triturated with cold water (2×), and dissolved into EtOAc (1 L). This solution was washed with basic brine (containing sodium bicarbonate), dried over $Na_2SO_4$, filtered, and the volatiles removed in vacuum to give the titled compound.

Step 2:
5-amino-7-fluoro-1,3-dihydro-2H-indol-2-one 7-fluoro-5-nitro-1,3-dihydro-2H-indol-2-one (8.5 g, 43.3 mmol) from Step 1 of this example was dissolved with stirring in 1:1 EtOH and EtOAc (433 ml). Palladium on carbon (10%, 2.55 g) was added and the slurry degassed and placed under an atmosphere of hydrogen (3×) and stirred at RT for 3 hours. The mixture was filtered through CELITE, the filter cake washed with EtOAc (3×100 ml), the filtrates combined and the volatiles removed in vacuum to give the titled compound.

Step. 3: 5-[(2-{(1S,2S)-2-[1-(5-chloropyrimidin-2-yl)piperidin-4-yl]cyclopropyl}ethyl)amino]-7-fluoro-1,3-dihydro-2H-indol-2-one

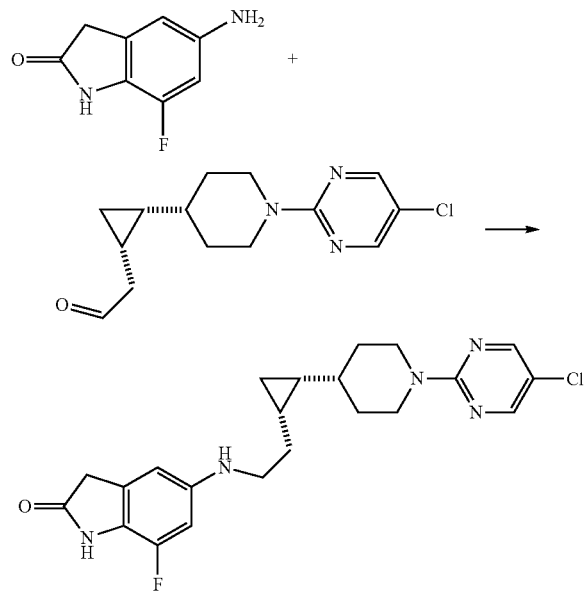

5-amino-7-fluoro-1,3-dihydro-2H-indol-2-one from step 2 of this example (33 mg, 0.20 mmol) was slurried in DCE (0.9 ml) and acetic acid (51 uL, 0.89 mmol) and NaBH(OAc)$_3$ (76 mg, 0.36 mmol) added. {(1S,2R)-2-[1-(5-chloropyrimidin-2-yl)piperidin-4-yl]cyclopropyl}acetaldehyde (50 mg, 0.18 mmol) from Example 3 was added and the mixture stirred at RT for 2 hours. The mixture was diluted with EtOAc (30 ml), and partitioned across 4:1 water:saturated sodium bicarbonate (50 ml). The layers were separated, the aqueous phase extracted with EtOAc (2×30 ml), the organic fractions combined, dried over Na$_2$SO$_4$, filtered, and the volatiles removed in vacuum. The product was purified by chromatography on SiO$_2$ eluting with 40% acetone:hexanes. This was followed by a second purification using chromatography on SiO$_2$ eluting with 30% acetone:hexanes to give the titled compound. LRMS calc: 429.17; obs: 430.19 (M+1).

EXAMPLE 54

Preparation of 7-chloro-5-[(2-{(1S,2S)-2-[1-(5-chloropyrimidin-2-yl)piperidin-4-yl]cyclopropyl}ethyl)amino]-1,3-dihydro-2H-indol-2-one Step 1: 7-chloro-5-nitro-1,3-dihydro-2H-indol-2-one

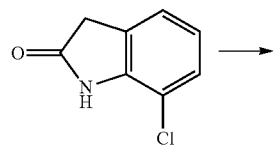

-continued

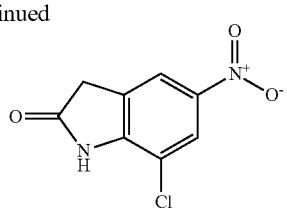

7-chloro-1,3-dihydro-2H-indol-2-one (8.0 g, 47.7 mmol) was slurried in H$_2$SO$_4$ (conc., 86 ml) and the mixture cooled to −45° C. A solution of fuming nitric acid (>90%, 3.34 g, 52.9 mmol) in H$_2$SO$_4$ (20 ml) was added drop wise, while maintaining the temperature at −45° C. throughout the addition. The mixture was allowed to slowly warm to RT and stirred overnight. The mixture was poured into stirred ice-cold water (1500 ml). A white precipitate resulted, and the slurry was aged at 0° C. for 1 hour. The solid was collected by filtration, triturated with cold water (2×), and dissolved into EtOAc (1 L). This mixture was filtered, washed with basic brine (containing sodium bicarbonate), dried over Na$_2$SO$_4$, filtered, and the volatiles removed in vacuum to give the titled compound.

Step 2:
5-amino-7-chloro-1,3-dihydro-2H-indol-2-one

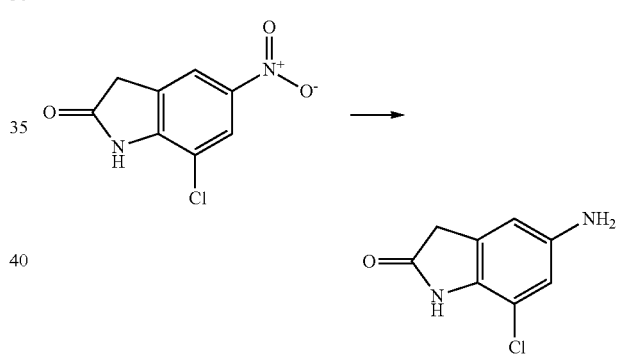

7-chloro-5-nitro-1,3-dihydro-2H-indol-2-one (6.1 g, 28.7 mmol) from Step 1 of this example was dissolved with stirring in 1:1 EtOH and EtOAc (287 ml). Palladium on carbon (10%, 1.8 g) was added and the slurry degassed, placed under an atmosphere of hydrogen (3×) and stirred at RT for 3 hours. The mixture was filtered through CELITE, the filter cake washed with EtOAc (3×100 ml), the filtrates combined and the volatiles removed in vacuum to give the titled compound.

Step 3: 7-chloro-5-[(2-{(1S,2S)-2-[1-(5-chloropyrimidin-2-yl)piperidin-4-yl]cyclopropyl}ethyl)amino]-1,3-dihydro-2,1-indol-2-one

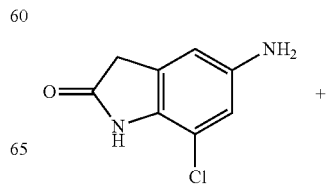

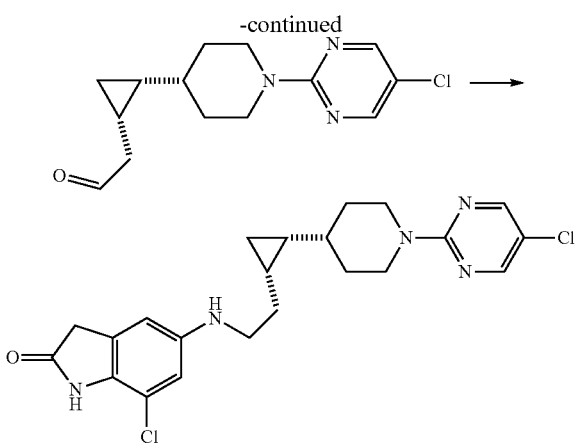

5-amino-7-chloro-1,3-dihydro-2H-indol-2-one from step 2 of this example (102 mg, 0.56 mmol) was slurried in DCE (2.1 ml) and acetic acid (32 uL, 0.56 mmol) and NaBH(OAc)$_3$ (273 mg, 1.29 mmol) added. {(1S,2R)-2-[1-(5-chloropyrimidin-2-yl)piperidin-4-yl]cyclopropyl}acetaldehyde (120 mg, 0.43 mmol) from Example 3 was added and the mixture stirred at RT for 2 hours. The mixture was diluted with EtOAc (50 ml), and partitioned across 4:1 water:saturated sodium bicarbonate (50 ml). The layers were separated, the aqueous phase extracted with EtOAc (2×35 ml), the organic fractions combined, dried over Na$_2$SO$_4$, filtered, and the volatiles removed in vacuum. The product was purified by chromatography on SiO$_2$ eluting with 50% EtOAc:hexanes. LRMS calc: 445.14; obs: 446.14 (M+1).

Compounds reported in Table 9 are prepared by a general procedure analogous to that described in step 3, Example 53 or 54 above.

TABLE 9

| Example | Chemical name | Chemical Structure | (M + 1) |
|---|---|---|---|
| Example 55 | N-{5-[(2-{(1S,2S)-2-[1-(5-chloropyrimidin-2-yl)piperidin-4-yl]cyclopropyl}ethyl)amino]pyridin-2-yl}acetamide | 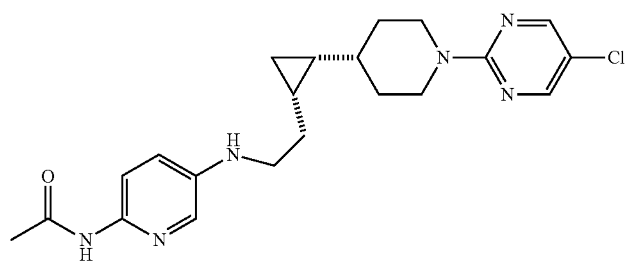 | 415.18 |
| Example 56 | N-{5-[(2-{(1S,2S)-2-[1-(5-chloropyrimidin-2-yl)piperidin-4-yl]cyclopropyl}ethyl)amino]pyridin-2-yl}-2,2-dimethyl propanamide | 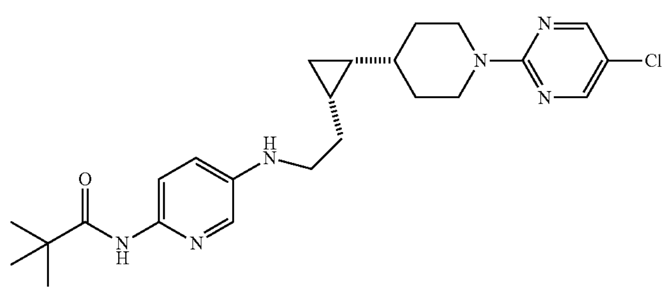 | 457.45 |
| Example 57 | N-(2-{(1S,2S)-2-[1-(5-chloropyrimidin-2-yl)piperidin-4-yl]cyclopropyl}ethyl)-1H-indazol-6-amine | 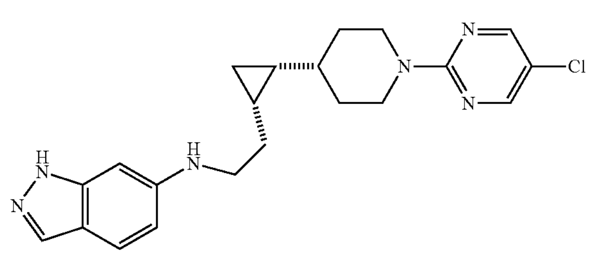 | 397.12 |

Preparations of non-commercial amino starting materials for examples in Table 9 are reported below.

PREPARATIVE EXAMPLE 56a

Preparation of N(5-aminopyridin-2-yl)-2,2-dimethylpropanamide

Step 1: 2,2-dimethyl-N-(5-nitropyridin-2-yl)propanamide

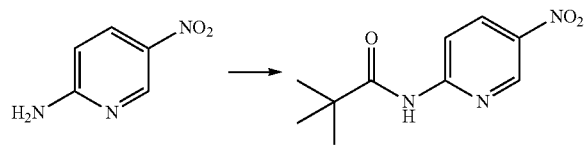 [SMILES: Nc1ccc([N+](=O)[O-])cn1 ; CC(C)(C)C(=O)Nc1ccc([N+](=O)[O-])cn1]

5-nitropyridin-2-amine (0.5 g, 3.59 mmol) was slurried in DCM (12 ml). TEA (2.5 ml, 18 mmol) and DMAP (88 mg, 0.72 mmol) were added. 2,2-dimethylpropanoyl chloride was added prop wise and the mixture stirred at RT overnight. The mixture was diluted into water (30 ml):saturated sodium bicarbonate (aq, 10 ml), extracted with DCM (3×30 ml), the organic fractions combined, washed with brine, dried over $Na_2SO_4$, filtered, and the volatiles removed in vacuum. The material was purified by chromatography on $SiO_2$ eluting with 10% acetone: hexanes to give the titled compound.

Step 2: N(5-aminopyridin-2-yl)-2,2-dimethylpropanamide

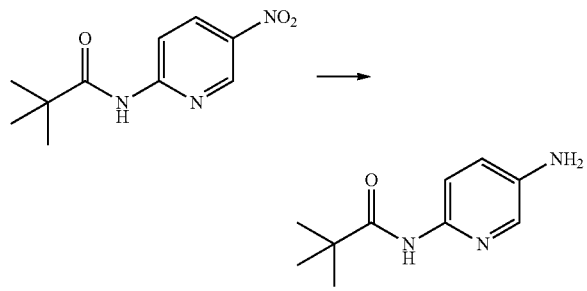

2,2-dimethyl-N-(5-nitropyridin-2-yl)propanamide (300 mg, 1.34 mmol) from Step 1 of this example was dissolved with stirring in MeOH (4.5 ml). Palladium on carbon (10%, 75 mg) was added and the slurry degassed, placed under an atmosphere of hydrogen (3×) and stirred at RT for 30 minutes. The mixture was filtered through CELITE, the filter cake washed with EtOAc (3×100 ml), the filtrates combined and the volatiles removed in vacuum to give the titled compound.

LRMS calc: 193.12; obs: 194.22 (M+1).

EXAMPLE 58

Preparation of chiral trans-N-(2-{2-[1-(5-chloropyrimidin-2-yl)piperidin-4-yl]cyclopropyl}ethyl)-4-(methylsulfonyl)aniline (from slow eluting enantiomer)

Step 1: 2-{(1R,2R)-2-[1-(5-chloropyrimidin-2-yl)piperidin-4-yl]cyclopropyl}ethyl 4-methylbenzenesulfonate

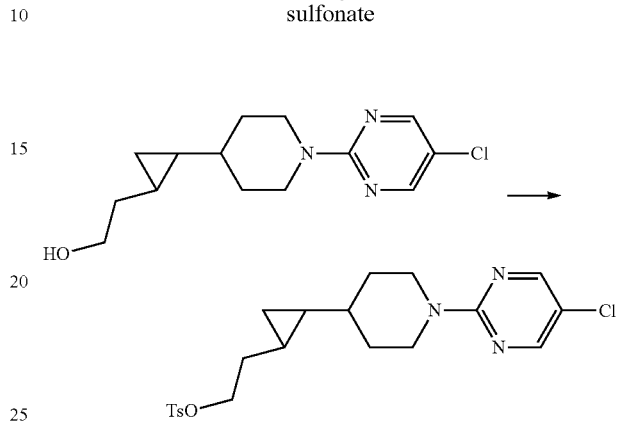

The title compound was synthesized using 2-{2-[1-(5-chloropyrimidin-2-yl)piperidin-4-yl]cyclopropyl}ethanol from Example 2b-S (slow) (41.2 mg, 0.146 mmol) was in 1.46 mL dichloromethane. TEA (0.0408 mL, 0.296 mol), DMAP (1.786 mg, 0.015 mmol) and TsCl (33.5 mg, 0.175 mmol) were sequentially added. The mixture was stirred at room temperature for 3 hour. Another 0.02 mL of TEA, 1 mg of DMAP and 14 mg of TsCl were added. Reaction mixture was stirred at room temperature for 30 min. The mixture was poured in to ice water. The aqueous phase was extracted with ethyl acetate for 3 times. The combined organic layers were washed with water and brine, then dried over $Na_2SO_4$ and concentrated. The residue was purified by column chromatography using gradient elution (0 to 50% ethyl acetate in hexane) to give the titled compound.

LRMS calc: 435.9; obs: 436.0 (M+1)

Step 2: 2-{4-[2-(2-azidoethyl)cyclopropyl]piperidin-1-yl}-5-chloropyrimidine

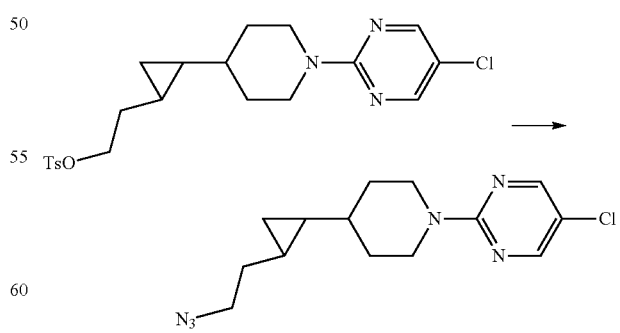

2-{2-[1-(5-chloropyrimidin-2-yl)piperidin-4-yl] cyclopropyl}ethyl 4-methylbenzenesulfonate from step 1 of this example (309 mg, 0.709 mmol) was in 5.67 mL dioxane. $NaN_3$ (106 mg, 1.63 mmol) was added, followed by addition of 1.418 mL water. Reaction mixture was stirred at 100° C. for 2.5 hours before cooled back to room temperature. The reaction mixture was diluted with water and aqueous phase was further extracted with ethyl acetate for 3 times. The combined organic layers were washed with water and brine, then dried over Na$_2$SO$_4$ and concentrated. The residue was purified by column chromatography using gradient elution (0 to 30% ethyl acetate in hexane) to give the titled compound.

LRMS calc: 306.8; obs: 307.1 (M+1).

Step 3: 2-{2-[1-(5-chloropyrimidin-2-yl)piperidin-4-yl]cyclopropyl}ethanamine

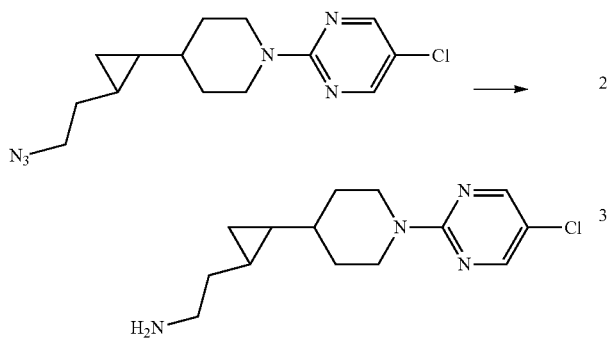

2-{4-[2-(2-azidoethyl)cyclopropyl]piperidin-1-yl}-5-chloropyrimidine from step 2 of this example (28 mg, 0,091 mmol) was dissolved in 0.821 mL THF. PPh$_3$ (47.9 mg, 0.182 mmol) was added, followed by addition of 0.091 mL water. The reaction mixture was stirred at room temperature for 1 hour then 40° C. for 3 hours before cooled back to room temperature. The solvent was evaporated in vacuum. The residue was purified by column chromatography eluting with 10% 2M NH$_3$-MeOH/ethyl acetate to give the titled compound. LRMS calc: 280.8; obs: 281.1 (M+1).

Step 4: N-(2-{2-[1-(5-chloropyrimidin-2-yl)piperidin-4-yl]cyclopropyl}ethyl)-4-(methylsulfonyl)aniline

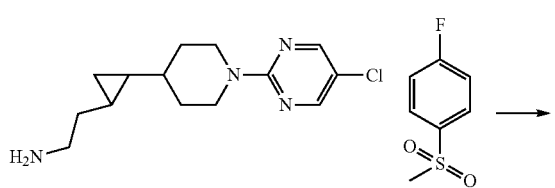

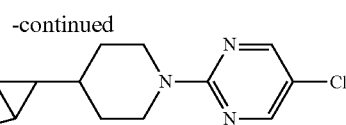

2-{2-[1-(5-chloropyrimidin-2-yl)piperidin-4-yl]cyclopropyl}ethanamine from step 3 of this example (50 mg, 0.178 mmol) was in 0.594 mL NMP. 1-fluoro-4-(methylsulfonyl)benzene (37.2 mg, 0.2141 mol) and DBU (0.040 mL, 0.267 mmol) were sequentially added. The reaction mixture was stirred at 110° C. overnight before cooled back to room temperature. The reaction mixture was diluted with water and aqueous phase was further extracted with ethyl acetate for 3 times. The combined organic layers were washed with water and brine, then dried over Na$_2$SO$_4$ and concentrated. The residue was purified by column chromatography using gradient elution (0 to 65% ethyl acetate in hexane) to give the titled compound. LRMS calc: 434.9; obs: 435 (M+1).

EXAMPLE 59

Preparation of chiral trans-N-(2-{2-[1-(5-chloropyrimidin-2-yl)piperidin-4-yl]cyclopropyl}ethyl)-6-1H-1,2,4-triazol-1-yl)pyridin-3-amine (from slow eluting enantiomer)

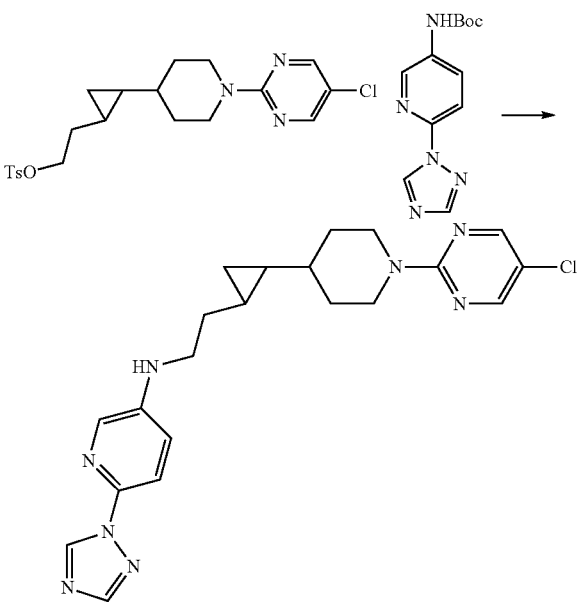

2-{2-[1-(5-chloropyrimidin-2-yl)piperidin-4-yl]cyclopropyl}ethyl 4-methlbenzenesulfonate from Step 1, Example 58 (60 mg, 0.138 mmol) was in 1.376 mL DMF. tert-butyl [6-(1H-1,2,4-triazol-1-yl)pyridin-3-yl]carbamate from Preparative Example 14a (39.6 mg, 0.151 mmol) and Cs$_2$CO$_3$ (224 mg, 0.688 mmol) was sequentially added. Reaction mixture was stirred at 50° C. for overnight before cooled back to room temperature. The reaction mixture was diluted with water and aqueous phase was further extracted with ethyl acetate for 3 times. The combined organic layers were washed with water and brine, then dried over Na$_2$SO$_4$ and concentrated. The resulting crude Boc amine was dissolved in 0.460 mL CH$_2$Cl$_2$. TFA (0.180 mL) was added. Stirred at room temperature for 30 min, upon which the volatile TFA was removed in vacuum. The residue was purified by column chromatography eluting with 50% ethyl acetate/hexane with 1% 2M NH$_3$-MeOH to give the titled compound. LRMS calc: 424.9; obs: 425.1 (M+1).

EXAMPLE 60

Preparation of chiral trans N-(2-{2-[1-(5-chloropyrimidin-2-yl)piperidin-4-yl]cyclopropyl}ethyl)-4-(methylsulfonyl)aniline (from fast eluting enantiomer)

Step 1: 2-{(1S,2R)-2-[1-(5-chloropyrimidin-2-yl)piperidin-4-yl]cyclopropyl}ethanamine

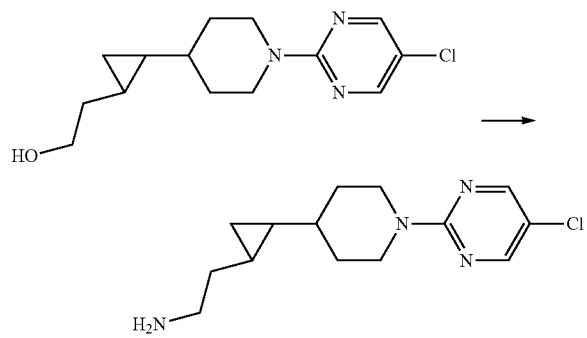

The title compound was synthesized using 2-{2-[1-(5-chloropyrimidin-2-yl)piperidin-4-yl]cyclopropyl}ethanol from Example 2b F (fast) by a general procedure analogous that described in Example 58 Step 1, 2, and 3.

Step 2: N-(2-{(1S,2R)-2-[1-(5-chloropyrimidin-2-yl)piperidin-4-yl]cyclopropyl}ethyl)-4-(methylsulfonyl)aniline

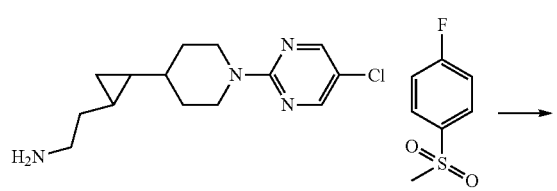

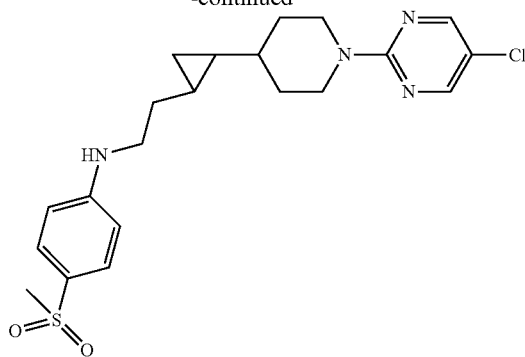

The title compound was synthesized using 2-{2-[1-(5-chloropyrimidin-2-yl)piperidin-4-yl]cyclopropyl}ethanamine from Step 1 of this example by a general procedure analogous to that describe in Example 58 Step 4 to give the titled compound. LRMS calc: 434.98; obs 435.1 (M+1).

EXAMPLE 61

Preparation of chiral trans 6-[(2-{2-[1-(5-chloropyrimidin-2-yl)piperidin-4-yl]cyclopropyl}ethyl)amino]-2-methylpyrimidine-4-carbonitrile (from fast eluting enantiomer)

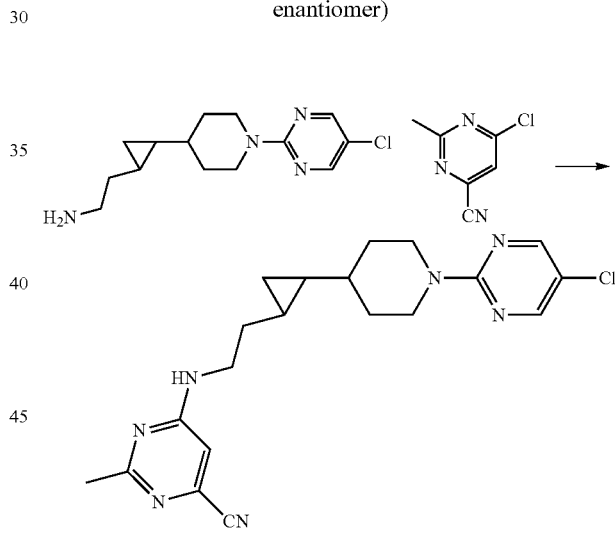

2-{2-[1-(5-chloropyrimidin-2-yl)piperidin-4-yl]cyclopropyl}ethanamine from Example 60 Step 1 (50 mg, 0.178 mmol) was in 0.5 mL DMF. Cs$_2$CO$_3$ (290 mg, 0.890 mmol) was added. Reaction mixture was stirred at room temperature for 10 min before cooled to 0° C. in ice bath. 6-chloro-2-methylpyrimidine-4-carbonitrile from Example 5 step 4 (30.1 mg, 0.196 mmol) in 0.3 mL DMF was added via syringe. Reaction was stirred at 0° C. in ice bath for 2 hours. The mixture was quenched with ice water and aqueous phase was further extracted with ethyl acetate for 3 times. The combined organic layers were washed with water and brine, then dried over Na$_2$SO$_4$ and concentrated. The residue was purified by column chromatography eluting with 30% Ethyl acetate/hexane with 0.5% 2M NH$_3$-MeOH to give the titled compound LRMS calc: 397.9; obs: 398.1 (M+1). .

EXAMPLE 62

Preparation of chiral trans N-(2-{2-[1-(5-chloropyrimidin-2-yl)piperidin-4-yl]cyclopropyl}ethyl)-6-(1H-1,2,4-triazol-1-yl)pyridin-3-amine (from fast eluting enantiomer)

Step 1: 2-{2-[1-(5-chloropyrimidin-2-yl)piperidin-4-yl]cyclopropyl}ethyl 4-methylbenzenesulfonate

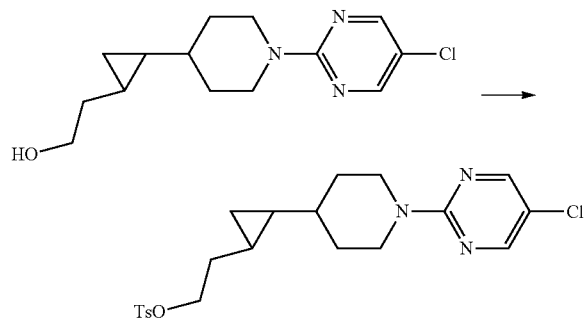

The title compound was synthesized using 2-{2-[1-(5-chloropyrimidin-2-yl)piperidin-4-yl]cyclopropyl}ethanol from Example 2b-F (fast) by a general procedure analogous that described in Example 59 Step 1.

Step 2: N-(2-(2-[1-(5-chloropyrimidin-2-yl)piperidin-4-yl]cyclopropyl}ethyl)-6-(1H-1,2,4-triazol-1-yl)pyridin-3-amine

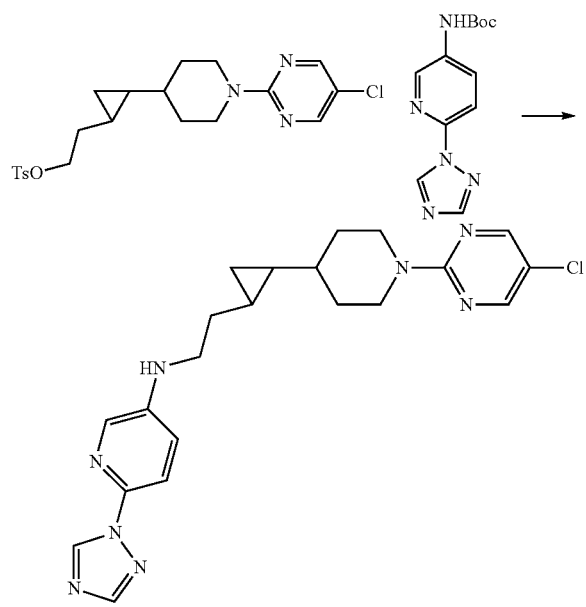

The title compound was synthesized using 2-{2-[1-(5-chloropyrimidin-2-yl)piperidin-4-yl]cyclopropyl}ethyl 4-methylbenzenesulfonate from step 1 of this example by a general procedure analogous that described in Example 59. LRMS calc: 424.9; obs: 425.01 (M+1).

Measurement of GPR119Signaling Using a Cyclic AMP (cAMP) Homogenous Time Resolved Fluorescence (HTRF) Assay Chinese hamster ovary (CHO) cell lines stably transfected with the permissive guanine nucleotide binding protein alpha 15 (Gα15) and murine GPR119 were maintained in DMEM media containing FBS, penicillin-streptomycin, puromycin, and G418 (geneticin). Alternatively, human embryonic kidney (HEK)293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at room temperature for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists will exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.

The Examples of this case show inflection points, denoted as $EC_{50}$ values, less than 1000 nM when tested in the above assays, as noted in the table below.

Activity is denoted as; $EC_{50}$<10 nM #, 10 nM <$EC_{50}$<50 nM ##, 50 nM <$EC_{50}$<200 nM ###, 200 nM <$EC_{50}$ ####

| | |
|---|---|
| Ex 4 | # |
| Ex 5 | ## |
| Ex 6 | ## |
| Ex 7 | # |
| Ex 8 | # |
| Ex 9 | ### |
| Ex 10 | # |
| Ex 11 | # |
| Ex 12 | # |
| Ex 13 | ## |
| Ex 14 | # |
| Ex 15 | # |
| Ex 16 | ## |
| Ex 17 | # |
| Ex 18 | ## |
| Ex 19 | ## |
| Ex 20 | ## |
| Ex 21 | # |
| Ex 22 | # |
| Ex 23 | # |
| Ex 24 | # |
| Ex 25 | # |
| Ex 26 | ## |
| Ex 27 | ## |
| Ex 28 | # |
| Ex 29 | # |
| Ex 30 | # |
| Ex 31 | # |
| Ex 32 | # |
| Ex 33 | ## |
| Ex 34 | ## |
| Ex 35 | ## |

-continued

| | |
|---|---|
| Ex 36 | # |
| Ex 37 | # |
| Ex 38 | # |
| Ex 39 | # |
| Ex 40 | ## |
| Ex 41 | ## |
| Ex 42 | # |
| Ex 43 | ## |
| Ex 44 | # |
| Ex 45 | ## |
| Ex 46 | # |
| Ex 47 | # |
| Ex 48 | ## |
| Ex 49 | ## |
| Ex 50 | ## |
| Ex 51 | # |
| Ex 52 | ## |
| Ex 53 | # |
| Ex 54 | # |
| Ex 55 | # |
| Ex 56 | # |
| Ex 57 | # |
| Ex 58 | ### |
| Ex 59 | ## |
| Ex 60 | ### |
| Ex 61 | # |
| Ex 62 | ## |
| Ex 63 | ### |

The compounds of the present application are surprisingly potent as GPR119 agonists.

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound represented by the formula:

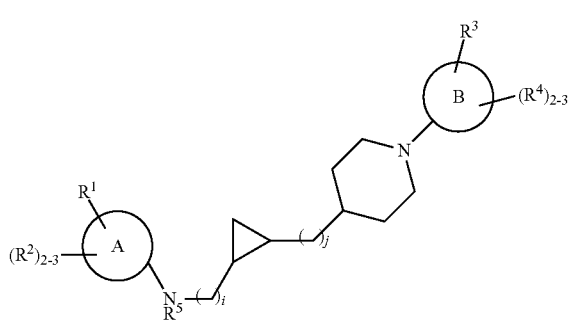

I or a pharmaceutically acceptable salt thereof, wherein:
ring A represents an aryl or heteroaryl group containing 1 nitrogen atom, and optionally 1-3 additional nitrogen atoms and optionally 0-1 oxygen or sulfur atoms;
ring B represents a heteroaryl ring containing 1-2 nitrogen atoms;
i and j independently represent integers selected from 0, 1 and 2, such that i plus j is 1 or 2;
$R^1$ represents a member selected from the group consisting of H, oxo, halo, $C_{1-6}$alkyl, $C_{1-6}$alkylhalo, $C_{1-6}$alkoxy, $C_{1-6}$alkoxyhalo, $C(O)C_{1-6}$alkyl, $C(O)—C_{1-6}$alkylhalo, $C(O)—NH—C_{1-6}$alkyl, $NH—C(O)—C_{1-6}$alkyl optionally substituted with $C_{1-6}$alkyl, $C_{1-6}$alkyl-$C(O)—NH—C_{1-6}$alkyl optionally substituted with $C_{1-6}$alkyl, $S(O)—C_{1-6}$alkyl, $SC_{1-6}$alkyl, $SO_2\_C_{1-6}$alkyl, $SO_2\_NH_2$, $SO_2\_NH—C_{1-6}$alkyl, $SO_2N—(C_{1-6}$alkyl$)_2$, CN, and heteroaryl ring or heteroalkyl ring optionally substituted with 1-3$C_{1-6}$alkyl, oxo, halo or $C_{1-6}$alkylhalo groups;
each $R^2$, $R^3$ and $R^4$ is independently selected from H, oxo, halo, $C_{1-6}$alkyl and $C_{1-6}$alkylhalo, wherein the total number of oxo groups does not exceed two; and
$R^5$ is selected from H, $C_{1-6}$alkylhalo and $C_{1-6}$alkyl.

2. The compound of claim 1, or a pharmaceutically acceptable salt thereof, wherein i and j represent 0, 1 or 2, such that the sum of i and j is 2.

3. The compound of claim 1, or a pharmaceutically acceptable salt thereof, wherein:
ring A is selected from the group consisting of phenyl, indole, pyridine, pyrimidine and pyrazine;
ring B is selected from the group consisting of pyridine, pyrimidine and pyrazine;
i is 2 and j is 0;
$R^1$ is selected from the group consisting of: H, oxo, halo which is F or Cl, $C_{1-3}$alkylhalo, $C(O)—NH—C_{2-4}$alkyl, $S(O)—C_{1-3}$alkyl, $SO_2\_C_{1-3}$alkyl, $SO_2\_NH—C_{1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with one $C_{1-3}$alkyl group;
$R^2$ represents H, halo selected from F and Cl, $CH_3$ and $CF_3$;
$R^3$ and $R^4$ represent H, halo selected from F and Cl, $CH_3$ and $CF_3$; and
$R^5$ represents H.

4. A compound represented by the formula:

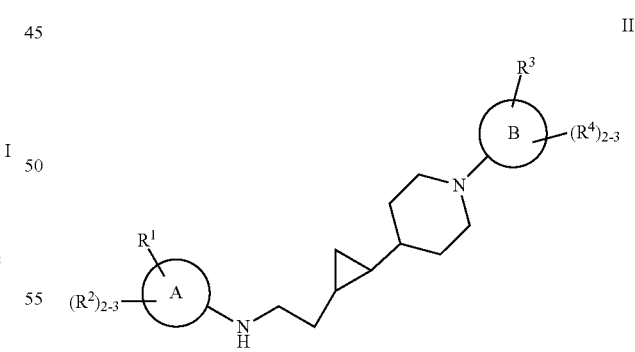

II or a pharmaceutically acceptable salt thereof, wherein:
ring A represents an aryl or heteroaryl group containing 1 nitrogen atom, and optionally 1-3 additional nitrogen atoms and optionally 0-1 oxygen or sulfur atoms;
ring B represents a heteroaryl ring containing 1-2 nitrogen atoms;
$R^1$ represents a member selected from the group consisting of H, oxo, halo, $C^{1-6}$alkyl, $C_{1-6}$alkylhalo, $C(O)—C_{1-6}$alkyl, $C(O)—C_{1-6}$alkylhalo, $C(O)—NH—C_{1-6}$alkyl, NH—C(O)—C$_{1-6}$alkyl optionally substituted with C$_{1-6}$alkyl, C$_{1-6}$alkyl-C(O)—NH—C$_{1-6}$alkyl optionally substituted with C$_{1-6}$alkyl, S(O)—C$_{1-6}$alkyl, SC$_{1-6}$alkyl, SO$_2$C$_{1-6}$alkyl, SO$_2$NH—C$_{1-6}$alkyl, SO$_2$N(C$_{1-6}$alkyl)$_2$, CN, and heteroaryl ring or heteroalkyl optionally substituted with 1-3, C$_{1-6}$alkyl, oxo, halo or C$_{1-6}$alkylhalo groups;

and each R$^2$, R$^3$ and R$^4$ is independently selected from H, oxo, halo, C$_{1-6}$alkyl, and C$_{1-6}$alkylhalo, wherein the total number of oxo groups does not exceed two.

5. The compound of claim 1, or a pharmaceutically acceptable salt thereof, wherein ring A is selected from the group consisting of phenyl, pyrrole, pyrazine, pyrazole, pyridine, pyrimidine, imidazole, triazole, tetrazole, triazine, indoline, pyridazine, indazole, isoindole, indolizine, cinnoline, phthalazine, quinazoline, naphthyridine, quinoxaline, purine, benzimidazole, quinolone, indole, oxindole, oxo-dihydroquinoline, and isoquinoline.

6. The compound of claim 1, or a pharmaceutically acceptable salt thereof, wherein ring A is selected from the group consisting of phenyl, indole, oxindole, pryidine and pyrimidine.

7. The compound of claim 1, or a pharmaceutically acceptable salt thereof, wherein ring A is a pyrimidine ring.

8. The compound of claim 1, or a pharmaceutically acceptable salt thereof, wherein ring A is an oxindole ring.

9. The compound of claim 1, or a pharmaceutically acceptable salt thereof, wherein ring B is selected from the group consisting of pyridine, pyrimidine, thiazole, oxadiazole and pyrazine.

10. The compound of claim 1, or a pharmaceutically acceptable salt thereof, wherein ring B is represents pyrimidine.

11. The compound of claim 1, or a pharmaceutically acceptable salt thereof, wherein R$^1$ is selected from the group consisting of: H, oxo, halo which is F or Cl, CF$_3$, NH—C(O)-cyclopropyl, S(O)—CH$_3$, SO$_2$CH$_3$, SO$_2$NH-cyclopropyl, CN and heteroaryl ring which is selected from the group consisting of: oxadiazole, pyrazole, triazole and tetrazole, said group being optionally substituted with methyl, oxo or cyclopropyl.

12. The compound of claim 1, or a pharmaceutically acceptable salt thereof, wherein ring A represents a phenyl ring and R$^1$ represents a five membered heteroaryl ring selected from the group consisting of oxadiazole, pyrazole, triazole and tetrazole, said ring being optionally substituted with methyl or cyclopropyl.

13. The compound of claim 1, or a pharmaceutically acceptable salt thereof, wherein ring A represents a pyridine or pyrimidine ring and R$^1$ represents CN, CF$_3$, SO$_2$C$_{1-3}$alkyl, NH—C(O)—C$_{1-6}$alkyl, or a five membered heteroaryl ring selected from the group consisting of oxadiazole, triazole and tetrazole, said ring being optionally substituted with methyl or cyclopropyl.

14. The compound of claim 1, or a pharmaceutically acceptable salt thereof, wherein R$^2$ represents H, halo selected from F and Cl, CH$_3$ or CF$_3$.

15. The compound of claim 1, or a pharmaceutically acceptable salt thereof, wherein R$^3$ is selected from the group consisting of: H, halo selected from F and Cl, oxo, CH$_3$ and CF$_3$.

16. The compound of claim 1, or a pharmaceutically acceptable salt thereof, wherein the cyclopropyl ring is the cis cyclopropyl isomer.

17. The compound of claim 1, or a pharmaceutically acceptable salt thereof, wherein:

ring A is selected from the group consisting of phenyl, indole, pyridine, pyrimidine and pyrazine;

ring B is selected from the group consisting of pyridine, pyrimidine and pyrazine;

R$^1$ is selected from the group consisting of: H, oxo, halo which is F or Cl, C$_{1-3}$alkylhalo, NH—C(O)—C$_{2-4}$alkyl, S(O)—C$_{1-3}$alkyl, SO$_2$C$_{1-3}$alkyl, SO$_{2-NH—C1-3}$alkyl, CN and heteroaryl ring which is a 5 membered heteroaromatic ring containing one nitrogen atom, optionally 1-3 additional nitrogen atoms, and optionally one oxygen atom, said heteroaryl being optionally substituted with one C$_{1-3}$alkyl group;

R$^2$ represents H, halo selected from F and Cl, CH$_3$ and CF$_3$;

and R$^3$ and R$^4$ represent H, halo selected from F and Cl, CH$_3$ and CF$_3$.

18. The compound of claim 1 which is:

6-[(2-{2-[1-(5-chloropyrimidin-2-yl)piperidin-4-yl]cyclopropyl}ethyl)amino]-2-methylpyrimidine-4-carbonitrile;

6-[(2-{(1S,2S)-2-[1-(5-chloropyrimidin-2-yl)piperidin-4-yl]cyclopropyl}ethyl)amino]-2-methylpyrimidine-4-carbonitrile;

N-(2-{(1S,2S)-2-[1-(5-chloropyrimidin-2-yl)piperidin-4-yl]cyclopropyl}ethyl)-5-(methylsulfonyl)pyridin-2-amine;

N-(2-{(1S,2S)-2-[1-(5-chloropyrimidin-2-yl)piperidin-4-yl]cyclopropyl}ethyl)-5-(methylsulfonyl)aniline;

N-(2-{(1S,2S)-2-[1-chloropyrimidin-2-yl)piperidin-4-yl]cyclopropyl}ethyl)-5-(1H-1,2,3-triazol-1-yl)pyridin-2-amine;

N-(2-{(1S,2S)-2-[1(5-chloropyrimidin-2-yl)piperidin-4-yl]cyclopropyl}ethyl)-N-methyl-4-(methylsulfonyl)aniline;

N-(2-{(1S,2S)-2-[1-(5-chloropyrimidin-2-yl)piperidin-4-yl]cyclopropyl}ethyl)-4-(1H-1,2,3-triazol-1-yl)aniline;

4-[(2-{(1S,2S)-2-[1-(5-chloropyrimidin-2-yl)piperidin-4-yl]cyclopropyl}ethyl)amino]-6-methylpyrimidine-2-carbonitrile;

N-(2-{(1S,2S)-2-[1-(5-chloropyrimidin-2-yl)piperidin-4-yl]cyclopropyl}ethyl)-4-(1H-tetrazol-1-yl)aniline;

2-[(2-{(1S,2S)-2-[1-(5-chloropyrimidin-2-yl)piperidin-4-yl]cyclopropyl}ethyl)amino]-6-methylisonicotinonitrile;

6-[(2-{(1S,2S)-2-[1-(5-chloropyrimidin-2-yl)piperidin-4-yl]cyclopropyl}ethyl)amino]-4-methylpyridine-2-carbonitrile;

N-(2-{(1S,2S)-2-[1-(5-chloropyrimidin-2-yl)piperidin-4-yl]cyclopropyl}ethyl)-4-(1H-1,2,4-triazol-1-yl)aniline;

N-(2-{(1S,2S)-2-[1-(5-chloropyrimidin-2-yl)piperidin-4-yl]cyclopropyl}ethyl)-4-(1H-pyrazol-5-yl) aniline;

N-(2-{(1S,2S)-2-[1-(5-chloropyrimidin-2-yl)piperidin-4-yl]cyclopropyl}ethyl)-5-(1H-1,2,4-triazol-1-yl) pyrazin-2-amine;

N-(2-{(1S,2S)-2-[1(5-chloropyrimidin-2-yl)piperidin-4-yl]cyclopropyl}ethyl)-5-(1H-tetrazol-1-yl)pyridin-2-amine;

N-(2-{(1S,2S)-2-[1-(5-chloropyrimidin-2-yl)piperidin-4-yl]cyclopropyl}ethyl)-4-(4-methyl-4H-1,2,4-triazol-3-yl)aniline;

N-(2-{(1S,2S)-2-[1-(5-chloropyrimidin-2-yl)piperidin-4-yl]cyclopropyl}ethyl)-4-(4H-1,2,4-triazol-4-yl)aniline;

N-(2-{(1S,2S)-2-[1-(5-chloropyrimidin-2-yl)piperidin-4-yl]cyclopropyl}ethyl)-1H-indazol-5-amine;

5-[(2-{(1S,2S)-2-[1-(5-chloropyrimidin-2-yl)piperidin-4-yl]cyclopropyl}ethyl)amino]isoindolin-1-one;

5-[(2-{(1S,2S)-2-[1-(5-chloropyrimidin-2-yl)piperidin-4-yl]cyclopropyl}ethyl)amino]-2-methylisoindolin-1-one;
5-[(2-{(1S,2S)-2-[1-(5-chloropyrimidin-2-yl)piperidin-4-yl]cyclopropyl}ethyl)amino]-2-cyclopropylisoindolin-1-one;
N-(2-{(1S,2S)-2-[1-(5-chloropyrimidin-2-yl)piperidin-4-yl]cyclopropyl}ethyl)-6-(1H-1,2,4-triazol-1-yl)pyridin-3-amine;
N-(2-{(1S,2S)-2-[1-(5-1-(5-chloropyrimidin-2-yl)piperidin-4-yl]cyclopropyl}ethyl)-6-(1H-tetrazol-1-yl) pyridin-3-amine;
N-(2-{(1S,2S)-2-[1-(5-chloropyrimidin-2-yl)piperidin-4-yl]cyclopropyl}ethyl)-2-(1H-1,2,4-triazol-1-yl) pyridin-5-amine;
N-(2-{(1S,2S)-2-[1-(5-chloropyrimidin-2-yl)piperidin-4-yl]cyclopropyl}ethyl)-1-methyl-1H-indazol-5-amine;
N-(2-{(1S,2S)-2-[1-(5-chloropyrimidin-2-yl)piperidin-4-yl]cyclopropyl}ethyl)-2-methyl-2H-indazol-5-amine;
N-(2-{(1S,2S)-2-[1-(5-chloropyrimidin-2-yl)piperidin-4-yl]cyclopropyl}ethyl)-3-methyl-1H-indazol-5-amine;
5-[(2-{(1S,2S)-2-[1-(5-chloropyrimidin-2-yl)piperidin-4-yl]cyclopropyl}ethyl)amino]-1,3-dihydro-2H-indol-2-one;
N-(2-{(1S,2S)-2-[1-(5-chloropyrimidin-2-yl)piperidin-4-yl]cyclopropyl}ethyl)-2-(1H-tetrazol-1-yl)pyrimidin-5-amine;
1-(2-{(1S,2S)-2-[1-(5-chloropyrimidin-2-yl)piperidin-4-yl]cyclopropyl}ethyl)-5-(methylsulfonyl)indoline;
N-(2-{(1S,2S)-2-[1-(5-chloropyrimidin-2-yl)piperidin-4-yl]cyclopropyl}ethyl)-6-(5-methyl-2H-tetrazol-2-yl)pyridin-3-amine;
N-(2-{(1S,2S)-2-[1-(5-chloropyrimidin-2-yl)piperidin-4-yl]cyclopropyl}ethyl)-6-(5-methyl -1H-tetrazol 1-yl) pyridin-3-amine;
N-(2-{(1S,2S)-2-[1-(5-chloropyrimidin-2-yl)piperidin-4-yl]cyclopropyl}ethyl)-6-(2H-1,2,3-triazol-2-yl)pyridin-3-amine;
5-[(2-{(1S,2S)-2-[1-(5-chloropyrimidin-2-yl)piperidin-4-yl]cyclopropyl}ethyl)amino]-1-methyl-1,3-dihydro-2H-indol-2-one;
3-{5-[(2-{(1S,2S)-2-[1-(5-chloropyrimidin-2-yl)piperidin-4-yl]cyclopropyl}ethyl)amino]pyridin-2-yl}-1,3-oxazolidine-2,4-dione;
1-{5-[(2-{(1S,2S)-2-[1-(5-chloropyrimidin-2-yl)piperidin-4-yl]cyclopropyl}ethyl)amino]pyridin-2-yl }pyrrolidin-2-one;
N-{4-[(2-{(1S,2S)-2-[1-(5-chloropyrimidin-2-yl)piperidin-4-yl]cyclopropyl}ethyl)amino]phenyl}acetamide;
2-{4-[(2-{(1S,2S)-2-[1-(5-chloropyrimidin-2-yl)piperidin-4-yl]cyclopropyl}ethyl)amino]phenyl}-N-cyclopropylacetamide;
N-(2-{(1R,2S)-2-[1-(5-chloropyrimidin-2-yl)piperidin-4-yl]cyclopropyl}ethyl)-6-(1H-1,2,4-triazol-1-yl)pyridin-3-amine;
N-(2-{(1R,2S)-2-[1-(5-chloropyrimidin-2-yl)piperidin-4-yl]cyclopropyl}ethyl)-4-(methylsulfonyl)aniline;
N-(2-{(1R,2S)-2-[1-(5-chloropyrimidin-2-yl)piperidin-4-yl]cyclopropyl}ethyl)-6-(1H-1,2,4-triazol-1-yl)pyridin-3-amine;
N-{5-[(2-{(1S,2S)-2-[1-(5-chloropyrimidin-2-yl)piperidin-4-yl]cyclopropyl}ethyl)amino]pyridin-2-yl}acetamide;
5-[(2-{(1S,2S)-2-[1-(5-chloropyrimidin-2-yl)piperidin-4-yl]cyclopropyl}ethyl)amino]-7-fluoro-1,3-dihydro-2H-indol-2-one;
N-{6-[(2-{(1S,2S)-2-[1-(5-chloropyrimidin-2-yl)piperidin-4-yl]cyclopropyl}ethyl)amino]-5-methylpryidin-3-yl}-2,2-dimethylpropanamide;
N-{6-[(2-{(1S,2S)-2-[1-(5-chloropyrimidin-2-yl)piperidin-4-yl]cyclopropyl}ethyl)amino]-5-methylpryidin-3-yl}acetamide;
6-[(2-{(1R,2S)-2-[1-(5-chloropyrimidin-2-yl)piperidin-4-yl]cyclopropyl}ethyl)amino]-2-methylpyrimidine-4-carbonitrile;
N-(2-{(1R,2S)-2-[1-(5-chloropyrimidin-2-yl)piperidin-4-yl]cyclopropyl}ethyl)-4-(methylsulfonyl)aniline;
N-{6-[(2-{(1S,2S)-2-[1-(5-chloropyrimidin-2-yl)piperidin-4-yl]cyclopropyl}ethyl)amino]-4-methylpryidin-3-yl}-2,2-dimethylpropanamide;
N-(2-{(1S,2S)-2-[1-(5-chloropyrimidin-2-yl)piperidin-4-yl]cyclopropyl }ethyl)-3-methyl-5-(1H-tetrazol-1-yl) pyridin-2-amine;
7-chloro-5-[(2-{(1S,2S)-2-[1-(5-chloropyrimidin-2-yl)piperidin-4-yl]cyclopropyl}ethyl)amino]-1,3-dihydro-2H-indol-2-one;
N-{6-[(2-{(1S,2S)-2-[1-(5-chloropyrimidin-2-yl)piperidin-4-yl]cyclopropyl }ethyl)amino]-4-methylpyridin-3-yl}acetamide;
N-{5-[(2-{(1S,2S)-2-[1-(5-chloropyrimidin-2-yl)piperidin-4-yl]cyclopropyl}ethyl)amino]pyridin-2-yl}-2,2-dimethylpropanamide;
N-{6-[(2-{(1S,2S)-2-[1-(5-chloropyrimidin-2-yl)piperidin-4-yl]cyclopropyl }ethyl)amino]pyridin-3-yl}acetamide;
N-{6-[(2-{(1S,2S)-2-[1-(5-chloropyrimidin-2-yl)piperidin-4-yl]cyclopropyl}ethyl)amino]pyridin-3-yl }-2,2-dimethylpropanamide;
N-{6-[(2-{(1S,2S)-2-[1-(5-chloropyrimidin-2-yl)piperidin-4-yl]cyclopropyl}ethyl)amino]pyridin-3-yl}-1-methylcyclopropanecarboxamide;
N-{5-[(2-{(1S,2S)-2-[1-(5-chloropyrimidin-2-yl)piperidin-4-yl]cyclopropyl}ethyl)amino]pyridin-2-yl}-1-methylcyclopropanecarboxamide;
N-{5-[(2-{(1S,2S)-2-[1-(5-chloropyrimidin-2-yl)piperidin-4-yl]cyclopropyl}ethyl)amino]-3-methylpyridin-2-yl}-2,2-dimethylpropanamide;
N-(2-{(1S,2S)-2-[1-(5-chloropyrimidin-2-yl)piperidin-4-yl]cyclopropyl }ethyl)-1H-indazol-6-amine;
N-{5-[(2-{(1S,2S)-2-[1-(5-chloropyrimidin-2-yl)piperidin-4-yl]cyclopropylethyl)amino]-3-methylpyridin-2-yl }-1-methylcyclopropanecarboxamide;
N-{3-chloro-5-[(2-{(1S,2S)-2-[1-(5-chloropyrimidin-2-yl)piperidin-4-yl]cyclopropyl}ethyl)amino]pyridin-2-yl}-2,2-dimethylpropanamide;
or a pharmaceutically acceptable salt thereof.

19. A pharmaceutical composition comprised of a compound of claim 1, or a pharmaceutically acceptable salt thereof, in combination with a pharmaceutically acceptable carrier.

20. A method of treating type 2 diabetes in a mammalian patient in need of such treatment comprising administering to the patient a compound of claim 1, or a pharmaceutically acceptable salt thereof, in an amount that is effective to treat type 2 diabetes.

* * * * *